US006960431B2

(12) United States Patent
Morham et al.

(10) Patent No.: US 6,960,431 B2
(45) Date of Patent: Nov. 1, 2005

(54) THERAPEUTIC COMPOSITIONS AND METHODS FOR TREATING VIRAL INFECTION

(75) Inventors: Scott Morham, Salt Lake City, UT (US); Kenton Zavitz, Salt Lake City, UT (US); Adrian Hobden, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 213 days.

(21) Appl. No.: 10/226,629

(22) Filed: Aug. 22, 2002

(65) Prior Publication Data

US 2003/0166504 A1 Sep. 4, 2003

Related U.S. Application Data

(60) Provisional application No. 60/314,182, filed on Aug. 22, 2001.

(51) Int. Cl.$^7$ ............................ C12Q 1/70; C12P 21/04; C12N 5/00; A61K 39/42

(52) U.S. Cl. ........................ 435/5; 4358/6; 4358/69.7; 4358/325; 4358/320.1; 424/159.1

(58) Field of Search .............................. 435/5, 6, 69.7, 435/325, 320.1; 424/159.1

(56) References Cited

U.S. PATENT DOCUMENTS

| 5,807,995 | A | 9/1998 | Cohen et al. |
| 5,891,668 | A | 4/1999 | Li et al. |
| 5,892,016 | A | 4/1999 | Brie et al. |
| 6,248,523 | B1 | 6/2001 | Cohen et al. |
| 6,251,629 | B1 | 6/2001 | Warren |
| 6,274,312 | B1 | 8/2001 | Gish et al. |
| 2003/0049607 | A1 | 3/2003 | Greener et al. |

FOREIGN PATENT DOCUMENTS

| WO | WO 02/094314 | 11/2002 |
| WO | WO 03/033646 | 4/2003 |
| WO | WO 03/046176 | 6/2003 |
| WO | WO 03/051835 | 6/2003 |

OTHER PUBLICATIONS

Parent, Leslie J., et al., "Positionally Independent and Exchangeable Late Budding Functions of the Rous Sarcoma Virus and Human Immunodeficiency Virus Gag Proteins", *Journal of Virology*, Sep. 1995; 69(9):5455–5460.
NCBI Entrez Protein Database Accession No.: AAB38034, Dec. 5, 1996.
Zhang, Yi–Ming, et al., "Drug Resistance during Indinavir Therapy Is Caused by Mutations in the Protease Gene and in Its Gag Substrate Cleavage Sites", *Journal of Virology*, Sep. 1997; 71(9):6662–6670.

Puffer, Bridget A., et al., "Equine Infectious Anemia Virus Utilizes a YXXL Motif within the Late Assembly Domain of the Gag p9 Protein", *Journal of Virology*, Sep. 1997; 71(9):6541–6546.
NCBI Entrez Protein Database Accession No.: AAB83138, Nov. 6, 1997.
NCBI Entrez Protein Database Accession No.: AAB83216, Nov. 6, 1997.
NCBI Entrez Protein Database Accession No.: AAB83821, Nov. 6, 1997.
Yasuda, Jiro, et al., "A Proline–Rich Motiff (PPPY) in the Gag Polyprotein of Mason–Pfizer Monkey Virus Plays a Maturation–Independent Role in Virion Release", *Journal of Virology*, May 1998; 72(5):4095–4103.
NCBI Entrez Protein Database Accession No.: P35962, Jul. 15, 1998.
Crump, Colin M., et al., "Inhibition of the Interaction between Tyrosine–based Motifs and the Medium Chain Subunit of the AP–2 Adaptor Complex by Specific Tyrphostins", *The Journal of Biological Chemistry*, Oct. 23, 1998; 273(43):28073–28077.
Puffer, Bridget A., et al., "Equine Infectious Anemia Virus Gag Polyprotein Late Domain Specifically Recruits Cellular AP–2 Adapter Protein Complexes during Virion Assembly", *Journal of Virology*, Dec. 1998; 72(12):10218–10221.
Sorkina, Tatiana, et al., "Clathrin, adaptors and eps15 in endosomes containing activated epidermal growth factor receptors", *Journal of Cell Science*, 1999; 112:317–327.
Yuan, Bing, et al., "Mutations altering the Moloney murine leukemia virus p12 Gag protein affect virion production and early events of the virus life cycle", *The EMBO Journal*, 1999; 18(17):4700–4710.
NCBI Entrez Protein Database Accession No.: AAD03232, Jan. 6, 1999.
NCBI Entrez Protein Database Accession No.: AAD03240, Jan. 6, 1999.
Garnier, Laurence, et al., "Identification of Retroviral Late Domains as Determinants of Particle Size", *Journal of Virology*, Mar. 1999; 73(3):2309–2320.
Harty, Ronald N., et al., "A Proline–Rich Motif within the Matrix Protein of Vesicular Stomatitis Virus and Rabies Virus Interacts with WW Domains of Cellular Proteins: Implications for Viral Budding", *Journal of Virology*, Apr. 1999; 73(4):2921–2929.
Craven, Rebecca C. et al., "Late Domain Function Identified in the Vesicular Stomatitis Virus M Protein by Use of Rhabdovirus–Retrovirus Chimeras", *Journal of Virology*, Apr. 1999; 73(4):3359–3365.

(Continued)

*Primary Examiner*—Hankyel T. Park
(74) *Attorney, Agent, or Firm*—Jay Z. Zhang; Andrew Gibbs; Myriad IP Dept.

(57) ABSTRACT

Methods for inhibiting viral propagation and treating viral infection are provided which include administering to cells infected with viruses a therapeutic peptide or a derivative thereof.

59 Claims, No Drawings

OTHER PUBLICATIONS

Harvey, Kieran F., et al., "Nedd4–like proteins: an emerging family of ubiquitin–protein ligases implicated in diverse cellular functions", *Trends in Cell Biology*, May 1999; 9:166–169.

Deschambeault, Julie, et al., "Polarized Human Immunodeficiency Virus Budding in Lymphocytes Involves a Tyrosine–Based Signal and Favors Cell–to–Cell Viral Transmission", *Journal of Virology*, Jun. 1999; 73(6):5010–5017.

NCBI Entrez Protein Database Accession No: AAF35354, Feb. 23, 2000.

Alexander, Louis, et al., "Unusual Polymorphisms in Human Immunodeficiency Virus Type 1 Associated with Nonprogressive Infection", *Journal of Virology*, May 2000; 74(9):4361–4376.

Butkiewicz, Nancy, et al., "Virus–Specific Cofactor Requirement and Chimeric Hepatitis C Virus/GB Virus B Nonstructural Protein 3" *Journal of Virology*, May 2000; 74(9):4291–4301.

Accola, Molly A., et al., "Efficient Particle Production by Minimal Gag Constructs Which Retain the Carboxy–Terminal Domain of Human Immunodeficiency Virus Type 1 Capsid–p2 and a Late Assembly Domain", *Journal of Virology*, Jun. 2000; 74(12):5395–5402.

Yuan, Bing, et al., "Infectivity of Moloney Murine Leukemia Virus Defective in Late Assembly Events Is Restored by Late Assembly Domains of Other Retroviruses", *Journal of Virology*, Aug. 2000; 74(16):7250–7260.

NCBI Entrez Protein Database Accession No.: CAB92786, Sep. 20, 2000.

Jayakar, Himangi R., et al., "Mutations in the PPPY Motif of Vesicular Stomatitis Virus Matrix Protein Reduce Virus Budding by Inhibiting a Late Step in Virion Release", *Journal of Virology*, Nov. 2000; 74(21):9818–9827.

Strack, Bettina, et al., "A role for ubiquitin ligase recruitment in retrovirus release", *PNAS*, Nov. 21, 2000; 97(24):13063–13068.

Schubert, Ulrich, et al., "Proteasome inhibition interferes with Gag polyprotein processing, release, and maturation of HIV–1 and HIV–2", *PNAS*, Nov. 21, 2000; 97(24):13057–13062.

Patnaik, Akash, et al., "Ubiquitin is part of the retrovirus budding machinery", *PNAS*, Nov. 21, 2000; 97(24):13069–13074.

Vogt, Volker M., "Ubiquitin in retrovirus assembly: Actor or bystander?", *PNAS*, Nov. 21, 2000; 97(24):12945–12947.

Harty, Ronald N., et al., "A PPxY motif within the VP40 protein of Ebola virus interacts physically and functionally with a ubiquitin ligase: Implications for filovirus budding", *PNAS*, Dec. 5, 2000; 97(25):13871–13876.

Ikeda, Masato, et al., "PY Motifs of Epstein–Barr Virus LMP2A Regulated Protein Stability and Phosphorylation of LMP2A–Associated Proteins", *Journal of Virology*, Jun. 2001; 75(12):5711–5718.

NCBI Entrez Protein Database Accession No.: AAD17020, Jun. 1, 2001.

Verplank, Lynn, et al., "Tsg101, a homologue of ubiquitin–conjugating (E2) enzymes, binds the L domain in HIV type 1 Pr55$^{Gag}$", *PNAS*, Jul. 3, 2001; 98(14):7724–7729.

Garrus, Jennifer E., et al., "Tsg101 and the Vacuolar Protein Sorting Pathway Are Essential for HIV–1 Budding", *Cell*, Oct. 5, 2001; 107:55–65.

Li, Feng, et al., "Functional Replacement and Positional Dependence of Homologous and Heterologous L Domains in Equine Infectious Anemia Virus Replication", *Journal of Virology*, Feb. 2002; 76(4):1569–1577.

Strack, Bettina, et al., "AIP/ALIX is a Binding Partner for HIV–1 p6 an EIAV p9 Functioning in Virus Budding", *Cell*, Sep. 19, 2003; 114:1–20.

SEQUENCE LISTING

<160> NUMBER OF SEQ ID NOS: 736

<210> SEQ ID NO 1
<211> LENGTH: 4
<212> TYPE: PRT
<213> ORGANISM: Equine infectious anemia virus

<400> SEQUENCE: 1

Tyr Pro Asp Leu
1

<210> SEQ ID NO 2
<211> LENGTH: 4
<212> TYPE: PRT
<213> ORGANISM: Artificial Sequence
<220> FEATURE:
<223> OTHER INFORMATION: Modified equine infectious anemia virus peptide

<400> SEQUENCE: 2

Tyr Pro Glu Leu
1

<210> SEQ ID NO 3
<211> LENGTH: 5
<212> TYPE: PRT
<213> ORGANISM: Hepatitis C virus

<400> SEQUENCE: 3

Tyr Pro Asp Leu Gly
1               5

<210> SEQ ID NO 4
<211> LENGTH: 5
<212> TYPE: PRT
<213> ORGANISM: human herpesvirus 2

<400> SEQUENCE: 4

Tyr Pro Asp Leu Arg
1               5

<210> SEQ ID NO 5
<211> LENGTH: 5
<212> TYPE: PRT
<213> ORGANISM: Variola virus

<400> SEQUENCE: 5

Tyr Pro Asp Leu Asn
1               5

<210> SEQ ID NO 6
<211> LENGTH: 5
<212> TYPE: PRT
<213> ORGANISM: Equine infectious anemia virus

<400> SEQUENCE: 6

Tyr Pro Asp Leu Ser
1               5

<210> SEQ ID NO 7
<211> LENGTH: 5
<212> TYPE: PRT
<213> ORGANISM: Hepatitis C virus

<400> SEQUENCE: 7

-continued

```
Val Tyr Pro Asp Leu
1               5

<210> SEQ ID NO 8
<211> LENGTH: 5
<212> TYPE: PRT
<213> ORGANISM: human herpesvirus 2

<400> SEQUENCE: 8

Gln Tyr Pro Asp Leu
1               5

<210> SEQ ID NO 9
<211> LENGTH: 5
<212> TYPE: PRT
<213> ORGANISM: Variola virus

<400> SEQUENCE: 9

Lys Tyr Pro Asp Leu
1               5

<210> SEQ ID NO 10
<211> LENGTH: 5
<212> TYPE: PRT
<213> ORGANISM: Human parainfluenza virus 1

<400> SEQUENCE: 10

Met Tyr Pro Asp Leu
1               5

<210> SEQ ID NO 11
<211> LENGTH: 5
<212> TYPE: PRT
<213> ORGANISM: Equine infectious anemia virus

<400> SEQUENCE: 11

Leu Tyr Pro Asp Leu
1               5

<210> SEQ ID NO 12
<211> LENGTH: 512
<212> TYPE: PRT
<213> ORGANISM: Equine infectious anemia virus

<400> SEQUENCE: 12

Asp Pro Arg Asp Ser Arg Gly Glu Leu Thr Glu Val Phe Trp Arg Cys
1               5                   10                  15

Ser Trp Pro Glu His Arg Arg Thr Gly Lys Met Gly Asp Pro Leu Thr
            20                  25                  30

Trp Ser Lys Ala Leu Lys Lys Leu Glu Lys Val Thr Val Gln Gly Ser
        35                  40                  45

Gln Lys Leu Thr Thr Gly Asn Cys Asn Trp Ala Leu Ser Leu Val Asp
    50                  55                  60

Leu Phe His Asp Thr Asn Phe Val Lys Glu Lys Asp Trp Gln Leu Arg
65                  70                  75                  80

Asp Val Ile Pro Leu Leu Glu Asp Val Thr Gln Thr Leu Ser Gly Gln
                85                  90                  95

Glu Arg Glu Ala Phe Glu Arg Thr Trp Trp Ala Ile Ser Ala Val Lys
            100                 105                 110

Met Gly Leu Gln Ile Asn Asn Val Val Asp Gly Lys Ala Ser Phe Gln
        115                 120                 125

```
Leu Leu Arg Ala Lys Tyr Glu Lys Thr Ala Asn Lys Lys Gln Ser
    130                 135                 140

Glu Pro Ser Glu Glu Tyr Pro Ile Met Ile Asp Gly Ala Gly Asn Arg
145                 150                 155                 160

Asn Phe Arg Pro Leu Thr Pro Arg Gly Tyr Thr Thr Trp Val Asn Thr
                165                 170                 175

Ile Gln Thr Asn Gly Leu Leu Asn Glu Ala Ser Gln Asn Leu Phe Gly
            180                 185                 190

Ile Leu Ser Val Asp Cys Thr Ser Glu Glu Met Asn Ala Phe Leu Asp
        195                 200                 205

Val Val Pro Gly Gln Ala Gly Gln Lys Gln Ile Leu Leu Asp Ala Ile
    210                 215                 220

Asp Lys Ile Ala Asp Asp Trp Asp Asn Arg His Pro Leu Pro Asn Ala
225                 230                 235                 240

Pro Leu Val Ala Pro Pro Gln Gly Pro Ile Pro Met Thr Ala Arg Phe
                245                 250                 255

Ile Arg Gly Leu Gly Val Pro Arg Glu Arg Gln Met Glu Pro Ala Phe
            260                 265                 270

Asp Gln Phe Arg Gln Thr Tyr Arg Gln Trp Ile Ile Glu Ala Met Ser
        275                 280                 285

Glu Gly Ile Lys Val Met Ile Gly Lys Pro Lys Ala Gln Asn Ile Arg
    290                 295                 300

Gln Gly Ala Lys Glu Pro Tyr Pro Glu Phe Val Asp Arg Leu Leu Ser
305                 310                 315                 320

Gln Ile Lys Ser Glu Gly His Pro Gln Glu Ile Ser Lys Phe Leu Thr
                325                 330                 335

Asp Thr Leu Thr Ile Gln Asn Ala Asn Glu Glu Cys Arg Asn Ala Met
            340                 345                 350

Arg His Leu Arg Pro Glu Asp Thr Leu Glu Glu Lys Met Tyr Ala Cys
        355                 360                 365

Arg Asp Ile Gly Thr Thr Lys Gln Lys Met Met Leu Leu Ala Lys Ala
    370                 375                 380

Leu Gln Thr Gly Leu Ala Gly Pro Phe Lys Gly Gly Ala Leu Lys Gly
385                 390                 395                 400

Gly Pro Leu Lys Ala Ala Gln Thr Cys Tyr Asn Cys Gly Lys Pro Gly
                405                 410                 415

His Leu Ser Ser Gln Cys Arg Ala Pro Lys Val Cys Phe Lys Cys Lys
            420                 425                 430

Gln Pro Gly His Phe Ser Lys Gln Cys Arg Ser Val Pro Lys Asn Gly
        435                 440                 445

Lys Gln Gly Ala Gln Gly Arg Pro Gln Lys Gln Thr Phe Pro Ile Gln
    450                 455                 460

Gln Lys Ser Gln His Asn Lys Ser Val Val Gln Glu Thr Pro Gln Thr
465                 470                 475                 480

Gln Asn Leu Tyr Pro Asp Leu Ser Glu Ile Lys Lys Glu Tyr Asn Val
                485                 490                 495

Lys Glu Lys Asp Gln Val Glu Asp Leu Asn Leu Asp Ser Leu Trp Glu
            500                 505                 510

<210> SEQ ID NO 13
<211> LENGTH: 2940
<212> TYPE: PRT
<213> ORGANISM: Hepatitis C virus
```

-continued

```
<400> SEQUENCE: 13

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
                100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
            195                 200                 205

Asn Asp Ser Ile Thr Trp Gln Leu Gln Ala Ala Val Leu His Val Pro
210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
            275                 280                 285

Gln Met Phe Ile Val Ser Pro Gln His His Trp Phe Val Gln Asp Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
            355                 360                 365

Ala Lys Val Val Ile Leu Leu Leu Ala Ala Gly Val Asp Ala Arg
370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
            405                 410                 415
```

```
Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
        435                 440                 445

Ser Ser Gly Cys Pro Glu Arg Met Ser Ala Cys Arg Ser Ile Glu Ala
    450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
                485                 490                 495

Gly Val Val Ser Ala Lys Thr Val Cys Gly Pro Val Tyr Cys Phe Thr
                500                 505                 510

Pro Ser Pro Val Val Gly Thr Asp Arg Leu Gly Ala Pro Thr
            515                 520                 525

Tyr Thr Trp Gly Glu Asn Glu Thr Asp Val Phe Leu Leu Asn Ser Thr
        530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
        595                 600                 605

Pro Arg Cys Leu Ile Asp Tyr Pro Tyr Arg Leu Trp His Tyr Pro Cys
        610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
                660                 665                 670

Thr Thr Glu Trp Ala Ile Leu Pro Cys Ser Tyr Ser Asp Leu Pro Ala
        675                 680                 685

Leu Ser Thr Gly Leu Leu His Leu His Gln Asn Ile Val Asp Val Gln
    690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Ile Leu His Ala Ala Ser Ala Ser Cys Asn Gly
            755                 760                 765

Phe Leu Tyr Phe Val Ile Phe Phe Val Ala Ala Trp Tyr Ile Lys Gly
    770                 775                 780

Arg Val Val Pro Leu Ala Thr Tyr Ser Leu Thr Gly Leu Trp Ser Phe
785                 790                 795                 800

Ser Leu Leu Leu Leu Ala Leu Pro Gln Gln Ala Tyr Ala Tyr Asp Ala
                805                 810                 815

Ser Val His Gly Gln Ile Gly Ala Ala Leu Leu Val Met Ile Thr Leu
            820                 825                 830
```

-continued

Phe Thr Leu Thr Pro Gly Tyr Lys Thr Leu Leu Ser Arg Phe Leu Trp
        835                 840                 845

Trp Leu Cys Tyr Leu Leu Thr Leu Gly Glu Ala Met Val Gln Glu Trp
        850                 855                 860

Ala Pro Pro Met Gln Val Arg Gly Gly Arg Asp Gly Ile Ile Trp Ala
865                 870                 875                 880

Val Ala Ile Phe Tyr Pro Gly Val Val Phe Asp Ile Thr Lys Trp Leu
                885                 890                 895

Leu Ala Val Leu Gly Pro Ala Tyr Leu Leu Lys Gly Ala Leu Thr Arg
            900                 905                 910

Val Pro Tyr Phe Val Arg Ala His Ala Leu Leu Arg Met Cys Thr Met
        915                 920                 925

Ala Arg His Leu Ala Gly Gly Arg Tyr Val Gln Met Ala Leu Leu Ala
    930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
        995                 1000                1005

Arg Leu Gly Arg Glu Val Leu Leu Gly Pro Ala Asp Gly Tyr Thr
    1010                1015                1020

Ser Lys Gly Trp Ser Leu Leu Ala Pro Ile Thr Ala Tyr Ala Gln
    1025                1030                1035

Gln Thr Arg Gly Leu Leu Gly Thr Ile Val Val Ser Met Thr Gly
    1040                1045                1050

Arg Asp Lys Thr Glu Gln Ala Gly Glu Ile Gln Val Leu Ser Thr
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Ser Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Thr
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Pro Arg Gly His Ala Val Gly Val Phe Arg Ala Ala Val
    1175                1180                1185

Cys Ser Arg Gly Val Ala Lys Ser Ile Asp Phe Ile Pro Val Glu
    1190                1195                1200

Thr Leu Asp Ile Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr

-continued

```
                1235                1240                1245
Ala Ala Gln Gly Tyr Lys Val Leu Val Leu Asn Pro Ser Val Ala
    1250                1255                1260
Ala Thr Leu Gly Phe Gly Ala Tyr Leu Ser Lys Ala His Gly Ile
    1265                1270                1275
Asn Pro Asn Ile Arg Thr Gly Val Arg Thr Val Thr Thr Gly Ala
    1280                1285                1290
Pro Ile Thr Tyr Ser Thr Tyr Gly Lys Phe Leu Ala Asp Gly Gly
    1295                1300                1305
Cys Ala Gly Gly Ala Tyr Asp Ile Ile Ile Cys Asp Glu Cys His
    1310                1315                1320
Ala Val Asp Ser Thr Thr Ile Leu Gly Ile Gly Thr Val Leu Asp
    1325                1330                1335
Gln Ala Glu Thr Ala Gly Val Arg Leu Thr Val Leu Ala Thr Ala
    1340                1345                1350
Thr Pro Pro Gly Ser Val Thr Thr Pro His Pro Asn Ile Glu Glu
    1355                1360                1365
Val Ala Leu Gly Gln Glu Gly Glu Ile Pro Phe Tyr Gly Arg Ala
    1370                1375                1380
Ile Pro Leu Ser Tyr Ile Lys Gly Gly Arg His Leu Ile Phe Cys
    1385                1390                1395
His Ser Lys Lys Lys Cys Asp Glu Leu Ala Ala Ala Leu Arg Gly
    1400                1405                1410
Met Gly Leu Asn Ser Val Ala Tyr Tyr Arg Gly Leu Asp Val Ser
    1415                1420                1425
Val Ile Pro Thr Gln Gly Asp Val Val Val Ala Thr Asp Ala
    1430                1435                1440
Leu Met Thr Gly Tyr Thr Gly Asp Phe Asp Ser Val Ile Asp Cys
    1445                1450                1455
Asn Val Ala Val Thr Gln Val Val Asp Phe Ser Leu Asp Pro Thr
    1460                1465                1470
Phe Thr Ile Thr Thr Gln Ile Val Pro Gln Asp Ala Val Ser Arg
    1475                1480                1485
Ser Gln Arg Arg Gly Arg Thr Gly Arg Gly Arg Leu Gly Ile Tyr
    1490                1495                1500
Arg Tyr Val Ser Thr Gly Glu Arg Ala Ser Gly Met Phe Asp Ser
    1505                1510                1515
Val Val Leu Cys Glu Cys Tyr Asp Ala Gly Ala Ala Trp Tyr Glu
    1520                1525                1530
Leu Thr Pro Ser Glu Thr Thr Val Arg Leu Arg Ala Tyr Phe Asn
    1535                1540                1545
Thr Pro Gly Leu Pro Val Cys Gln Asp His Leu Glu Phe Trp Glu
    1550                1555                1560
Ala Val Phe Thr Gly Leu Thr His Ile Asp Ala His Phe Leu Ser
    1565                1570                1575
Gln Thr Lys Gln Ser Gly Glu Asn Phe Ala Tyr Leu Thr Ala Tyr
    1580                1585                1590
Gln Ala Thr Val Cys Ala Arg Ala Lys Ala Pro Pro Pro Ser Trp
    1595                1600                1605
Asp Val Met Trp Lys Cys Leu Thr Arg Leu Lys Pro Thr Leu Val
    1610                1615                1620
Gly Pro Thr Pro Leu Leu Tyr Arg Leu Gly Ser Val Thr Asn Glu
    1625                1630                1635
```

-continued

Val Thr Leu Thr His Pro Val Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Val Cys Ile Ile Gly Arg Leu His Ile Asn Gln Arg Ala Val Val
1685                1690                1695

Ala Pro Asp Lys Glu Val Leu Tyr Glu Ala Phe Asp Glu Met Glu
1700                1705                1710

Glu Cys Ala Ser Arg Ala Ala Leu Ile Glu Glu Gly Gln Arg Ile
1715                1720                1725

Ala Glu Met Leu Lys Ser Lys Ile Gln Gly Leu Leu Gln Gln Ala
1730                1735                1740

Ser Lys Gln Ala Gln Asp Ile Gln Pro Thr Val Gln Ala Ser Trp
1745                1750                1755

Pro Lys Val Glu Gln Phe Trp Ala Lys His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Ser Thr Ser Thr Thr Ile Leu Leu Asn Ile Leu Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Val Leu Val Asp Ile Leu Ala Gly Tyr Gly Ala Gly Ile
1850                1855                1860

Ser Gly Ala Leu Val Ala Phe Lys Ile Met Ser Gly Glu Lys Pro
1865                1870                1875

Ser Met Glu Asp Val Val Asn Leu Leu Pro Gly Ile Leu Ser Pro
1880                1885                1890

Gly Ala Leu Val Val Gly Val Ile Cys Ala Ala Ile Leu Arg Arg
1895                1900                1905

His Val Gly Pro Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

Val Thr Glu Ser Asp Ala Ser Gln Arg Val Thr Gln Leu Leu Gly
1940                1945                1950

Ser Leu Thr Ile Thr Ser Leu Leu Arg Arg Leu His Asn Trp Ile
1955                1960                1965

Thr Glu Asp Cys Pro Ile Pro Cys Gly Gly Ser Trp Leu Arg Asp
1970                1975                1980

Val Trp Asp Trp Val Cys Thr Ile Leu Thr Asp Phe Lys Asn Trp
1985                1990                1995

Leu Thr Ser Lys Leu Phe Pro Lys Met Pro Gly Leu Pro Phe Val
2000                2005                2010

Ser Cys Gln Lys Gly Tyr Lys Gly Val Trp Ala Gly Thr Gly Ile
2015                2020                2025

-continued

```
Met Thr Thr Arg Cys Pro Cys Gly Ala Asn Ile Ser Gly Asn Val
    2030            2035                2040

Arg Leu Gly Ser Met Arg Ile Thr Gly Pro Lys Thr Cys Met Asn
    2045            2050                2055

Ile Trp Gln Gly Thr Phe Pro Ile Asn Cys Tyr Thr Glu Gly Gln
    2060            2065                2070

Cys Val Pro Lys Pro Ala Pro Asn Phe Lys Val Ala Ile Trp Arg
    2075            2080                2085

Val Ala Ala Ser Glu Tyr Ala Glu Val Thr Gln His Gly Ser Tyr
    2090            2095                2100

His Tyr Ile Thr Gly Leu Thr Thr Asp Asn Leu Lys Val Pro Cys
    2105            2110                2115

Gln Leu Pro Ser Pro Glu Phe Phe Ser Trp Val Asp Gly Val Gln
    2120            2125                2130

Ile His Arg Phe Ala Pro Thr Pro Lys Pro Phe Phe Arg Asp Glu
    2135            2140                2145

Val Ser Phe Cys Val Gly Leu Asn Ser Phe Val Val Gly Ser Gln
    2150            2155                2160

Leu Pro Cys Asp Pro Glu Pro Asp Thr Asp Val Leu Met Ser Met
    2165            2170                2175

Leu Thr Asp Pro Ser His Ile Thr Ala Glu Thr Ala Ala Arg Arg
    2180            2185                2190

Leu Ala Arg Gly Ser Pro Pro Ser Glu Ala Ser Ser Ser Ala Ser
    2195            2200                2205

Gln Leu Ser Ala Pro Ser Leu Arg Ala Thr Cys Thr Thr His Gly
    2210            2215                2220

Lys Ala Tyr Asp Val Asp Met Val Asp Ala Asn Leu Phe Met Gly
    2225            2230                2235

Gly Asp Val Thr Arg Ile Glu Ser Gly Ser Lys Val Val Val Leu
    2240            2245                2250

Asp Ser Leu Asp Pro Met Val Glu Glu Arg Ser Asp Leu Glu Pro
    2255            2260                2265

Ser Ile Pro Ser Glu Tyr Met Leu Pro Lys Lys Arg Phe Pro Pro
    2270            2275                2280

Ala Leu Pro Ala Trp Ala Arg Pro Asp Tyr Asn Pro Pro Leu Val
    2285            2290                2295

Glu Ser Trp Lys Arg Pro Asp Tyr Gln Pro Ala Thr Val Ala Gly
    2300            2305                2310

Cys Ala Leu Pro Pro Pro Arg Lys Thr Pro Thr Pro Pro Pro Arg
    2315            2320                2325

Arg Arg Arg Thr Val Gly Leu Ser Glu Asp Ser Ile Gly Asp Ala
    2330            2335                2340

Leu Gln Gln Leu Ala Ile Lys Ser Phe Gly Gln Pro Pro Pro Ser
    2345            2350                2355

Gly Asp Ser Gly Leu Ser Thr Gly Ala Gly Ala Ala Asp Ser Gly
    2360            2365                2370

Ser Gln Thr Pro Pro Asp Glu Leu Ala Leu Ser Glu Thr Gly Ser
    2375            2380                2385

Ile Ser Ser Met Pro Pro Leu Glu Gly Glu Leu Gly Asp Pro Asp
    2390            2395                2400

Leu Glu Pro Glu Gln Val Glu Pro Gln Pro Pro Gln Gly Gly
    2405            2410                2415

Val Ala Ala Pro Gly Ser Asp Ser Gly Ser Trp Ser Thr Cys Ser
```

-continued

```
             2420           2425                  2430
Glu Glu Asp Asp Ser Val Val Cys Cys Ser Met Ser Tyr Ser Trp
    2435                2440                2445
Thr Gly Ala Leu Ile Thr Pro Cys Ser Pro Glu Glu Lys Leu
    2450                2455                2460
Pro Ile Asn Pro Leu Ser Asn Ser Leu Leu Arg Tyr His Asn Lys
    2465                2470                2475
Val Tyr Cys Thr Thr Thr Lys Ser Ala Ser Leu Arg Ala Lys Lys
    2480                2485                2490
Val Thr Phe Asp Arg Met Gln Val Leu Asp Ser Tyr Tyr Asp Ser
    2495                2500                2505
Val Leu Lys Asp Ile Lys Leu Ala Ala Ser Lys Val Thr Ala Arg
    2510                2515                2520
Leu Leu Thr Met Glu Glu Ala Cys Gln Leu Thr Pro Pro His Ser
    2525                2530                2535
Ala Arg Ser Lys Tyr Gly Phe Gly Ala Lys Glu Val Arg Ser Leu
    2540                2545                2550
Ser Gly Arg Ala Val Asn His Ile Lys Ser Val Trp Lys Asp Leu
    2555                2560                2565
Leu Glu Asp Ser Glu Thr Pro Ile Pro Thr Thr Ile Met Ala Lys
    2570                2575                2580
Asn Glu Val Phe Cys Val Asp Pro Thr Lys Gly Gly Lys Lys Ala
    2585                2590                2595
Ala Arg Leu Ile Val Tyr Pro Asp Leu Gly Val Arg Val Cys Glu
    2600                2605                2610
Lys Met Ala Leu Tyr Asp Ile Thr Gln Lys Leu Pro Gln Ala Val
    2615                2620                2625
Met Gly Ala Ser Tyr Gly Phe Gln Tyr Ser Pro Ala Gln Arg Val
    2630                2635                2640
Glu Phe Leu Leu Lys Ala Trp Ala Glu Lys Lys Asp Pro Met Gly
    2645                2650                2655
Phe Ser Tyr Asp Thr Arg Cys Phe Asp Ser Thr Val Thr Glu Arg
    2660                2665                2670
Asp Ile Arg Thr Glu Glu Ser Ile Tyr Arg Ala Cys Ser Leu Pro
    2675                2680                2685
Glu Glu Ala His Thr Ala Ile His Ser Leu Thr Glu Arg Leu Tyr
    2690                2695                2700
Val Gly Gly Pro Met Phe Asn Ser Lys Gly Gln Thr Cys Gly Tyr
    2705                2710                2715
Arg Arg Cys Arg Ala Ser Gly Val Leu Thr Thr Ser Met Gly Asn
    2720                2725                2730
Thr Ile Thr Cys Tyr Val Lys Ala Leu Ala Ala Cys Lys Ala Ala
    2735                2740                2745
Gly Ile Ile Ala Pro Thr Met Leu Val Cys Gly Asp Asp Leu Val
    2750                2755                2760
Val Ile Ser Glu Ser Gln Gly Thr Glu Glu Asp Glu Arg Asn Leu
    2765                2770                2775
Arg Ala Phe Thr Glu Ala Met Thr Arg Tyr Ser Ala Pro Pro Gly
    2780                2785                2790
Asp Pro Pro Arg Pro Glu Tyr Asp Leu Glu Leu Ile Thr Ser Cys
    2795                2800                2805
Ser Ser Asn Val Ser Val Ala Leu Gly Pro Gln Gly Arg Arg Arg
    2810                2815                2820
```

```
Tyr Tyr Leu Thr Arg Asp Pro Thr Thr Pro Ile Ala Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Ala Arg Met Val Leu Met
    2855                2860                2865

Thr His Phe Phe Ser Ile Leu Met Ala Gln Asp Thr Leu Asp Gln
    2870                2875                2880

Asn Leu Asn Phe Glu Met Tyr Gly Ala Val Tyr Ser Val Ser Pro
    2885                2890                2895

Leu Asp Leu Pro Ala Ile Ile Glu Arg Leu His Gly Leu Asp Ala
    2900                2905                2910

Phe Ser Leu His Thr Tyr Thr Pro His Glu Leu Thr Arg Val Ala
    2915                2920                2925

Ser Ala Leu Arg Lys Leu Gly Ala Pro Pro Leu Arg
    2930                2935                2940

<210> SEQ ID NO 14
<211> LENGTH: 204
<212> TYPE: PRT
<213> ORGANISM: human herpesvirus 2

<400> SEQUENCE: 14

Met Ala His Leu Pro Gly Gly Ala Ala Ala Pro Leu Ser Glu Asp
1               5                   10                  15

Ala Ile Pro Ser Pro Arg Glu Arg Thr Glu Asp Trp Pro Pro Cys Gln
                20                  25                  30

Ile Val Leu Gln Gly Ala Glu Leu Asn Gly Ile Leu Gln Ala Phe Ala
            35                  40                  45

Pro Leu Arg Thr Ser Leu Leu Asp Ser Leu Leu Val Val Gly Asp Arg
        50                  55                  60

Gly Ile Leu Val His Asn Ala Ile Phe Gly Glu Gln Val Phe Leu Pro
65                  70                  75                  80

Leu Asp His Ser Gln Phe Ser Arg Tyr Arg Trp Gly Gly Pro Thr Ala
                85                  90                  95

Ala Phe Leu Ser Leu Val Asp Gln Lys Arg Ser Leu Leu Ser Val Phe
            100                 105                 110

Arg Ala Asn Gln Tyr Pro Asp Leu Arg Arg Val Glu Leu Thr Val Thr
        115                 120                 125

Gly Gln Ala Pro Phe Arg Thr Leu Val Gln Arg Ile Trp Thr Thr Ala
    130                 135                 140

Ser Asp Gly Glu Ala Val Glu Leu Ala Ser Glu Thr Leu Met Lys Arg
145                 150                 155                 160

Glu Leu Thr Ser Phe Ala Val Leu Leu Pro Gln Gly Asp Pro Asp Val
                165                 170                 175

Gln Leu Arg Leu Thr Lys Pro Gln Leu Thr Lys Val Val Asn Ala Val
            180                 185                 190

Gly Asp Glu Thr Ala Lys Pro Thr Thr Phe Glu Leu
        195                 200

<210> SEQ ID NO 15
<211> LENGTH: 892
<212> TYPE: PRT
<213> ORGANISM: Variola virus

<400> SEQUENCE: 15
```

-continued

```
Met Met Pro Ile Lys Ser Ile Val Thr Leu Asp Gln Leu Glu Asp Ser
1               5                   10                  15

Glu Tyr Leu Phe Arg Ile Val Ser Thr Val Leu Pro His Leu Cys Leu
            20                  25                  30

Asp Tyr Lys Val Cys Asp Gln Leu Lys Thr Thr Phe Val His Pro Phe
        35                  40                  45

Asp Val Phe Leu Asn Asn Ser Leu Gly Ser Val Thr Lys Gln Asp Glu
    50                  55                  60

Leu Gln Ala Ala Ile Ser Lys Leu Gly Ile Asn Tyr Leu Ile Asp Thr
65                  70                  75                  80

Thr Ser Arg Glu Leu Lys Leu Phe Asn Val Thr Leu Asn Ala Gly Asn
                85                  90                  95

Ile Asp Ile Ile Asn Thr Pro Ile Asn Ile Ser Ser Glu Thr Asn Pro
            100                 105                 110

Ile Ile Asn Thr His Ser Phe Tyr Asp Leu Pro Pro Phe Thr Gln His
        115                 120                 125

Leu Leu Asn Ile Arg Leu Thr Asp Thr Glu Tyr Arg Ala Arg Phe Ile
130                 135                 140

Gly Gly Tyr Ile Lys Pro Asp Gly Ser Asp Ser Met Asp Val Leu Ala
145                 150                 155                 160

Glu Lys Lys Tyr Pro Asp Leu Asn Phe Asp Asn Thr Tyr Leu Phe Asn
                165                 170                 175

Ile Leu Tyr Lys Asp Val Ile Asn Ala Pro Ile Lys Glu Phe Lys Ala
            180                 185                 190

Lys Ile Val Asn Gly Val Leu Ser Arg Gln Asp Phe Asp Asn Leu Ile
        195                 200                 205

Gly Val Arg Gln Tyr Ile Thr Ala Gln Asp Gln Pro Arg Phe Asp Asn
    210                 215                 220

Thr Tyr Ala Ile Ala Asp Ala Ala Arg His Tyr Gly Val Asn Leu Asn
225                 230                 235                 240

Thr Leu Pro Leu Pro Asn Val Asp Leu Thr Thr Met Pro Thr Tyr Lys
                245                 250                 255

His Leu Ile Met Tyr Glu Gln Tyr Phe Val Asp Asp Tyr Asp Arg Val
            260                 265                 270

Pro Ile Tyr Tyr Asn Gly Asn Arg Val Ile Phe Asp Asp Glu Ile Ile
        275                 280                 285

Asn Phe Cys Ile Ser Met Arg Tyr Gln Ser Leu Ile Pro Arg Leu Val
    290                 295                 300

Glu Phe Phe Pro Asp Ile Pro Val Asn Asn Ile Val Leu His Thr
305                 310                 315                 320

Arg Asp Pro Gln Asn Ala Ala Val Asn Val Thr Val Gly Leu Pro Asn
                325                 330                 335

Met Gln Phe Val Asp Ile Asn Arg Asn Asn Lys Phe Phe Ile Asn Phe
            340                 345                 350

Phe Asn Leu Leu Ala Lys Glu Gln Arg Ser Thr Ala Ile Lys Val Thr
        355                 360                 365

Lys Ser Met Phe Trp Asp Gly Met Asp Tyr Glu Glu Tyr Lys Ser Lys
    370                 375                 380

Asn Leu Gln Asp Met Met Phe Ile Asn Ser Thr Cys Tyr Val Phe Gly
385                 390                 395                 400

Leu Tyr Asn His Asn Asn Thr Thr Tyr Cys Ser Ile Leu Ser Asp Ile
                405                 410                 415
```

```
Ile Ser Ala Glu Lys Thr Pro Ile Arg Val Cys Leu Leu Pro Arg Val
            420                 425                 430

Val Gly Gly Lys Thr Val Thr Asp Leu Ile Ser Glu Thr Leu Lys Ser
            435                 440                 445

Ile Ser Ser Met Thr Ile Arg Glu Phe Pro Lys Asp Lys Ser Ser
450                 455                 460

Ile Met His Ile Gly Leu Ser Glu Thr Gly Phe Met Arg Phe Gln
465                 470                 475                 480

Leu Leu Arg Leu Met Ala Asp Lys Pro His Glu Thr Ala Ile Lys Glu
            485                 490                 495

Val Val Met Ala Tyr Val Gly Ile Lys Leu Gly Asp Lys Gly Ser Pro
            500                 505                 510

Tyr Tyr Ile Arg Lys Glu Ser Tyr Gln Asp Phe Ile Tyr Leu Leu Phe
            515                 520                 525

Ala Ser Met Gly Phe Lys Val Thr Thr Arg Arg Ser Ile Met Gly Ser
            530                 535                 540

Asn Asn Ile Ser Ile Ile Ser Ile Arg Pro Arg Val Thr Lys Gln Tyr
545                 550                 555                 560

Ile Val Thr Thr Leu Met Lys Thr Ser Cys Ser Lys Asn Glu Ala Glu
            565                 570                 575

Lys Leu Ile Thr Ser Ala Phe Asp Leu Leu Asn Phe Met Val Ser Val
            580                 585                 590

Ser Asp Phe Arg Asp Tyr Gln Ser Tyr Arg Gln Tyr Arg Asn Tyr Cys
            595                 600                 605

Pro Arg Tyr Phe Tyr Ala Gly Ser Pro Glu Gly Glu Glu Thr Ile Ile
            610                 615                 620

Cys Asp Ser Glu Pro Ile Ser Ile Leu Asp Arg Ile Asp Thr Arg Gly
625                 630                 635                 640

Ile Phe Ser Ala Tyr Thr Ile Asn Glu Met Met Asp Thr Asp Ile Phe
            645                 650                 655

Ser Pro Glu Asn Lys Ala Phe Lys Asn Asn Leu Ser Arg Phe Ile Glu
            660                 665                 670

Ser Gly Asp Ile Thr Gly Glu Asp Ile Phe Cys Ala Met Pro Tyr Asn
            675                 680                 685

Ile Leu Asp Arg Ile Ile Thr Asn Ala Gly Thr Cys Thr Val Ser Ile
            690                 695                 700

Gly Asp Met Leu Asp Asn Ile Thr Thr Gln Ser Asp Cys Asn Met Thr
705                 710                 715                 720

Asn Glu Ile Thr Asp Met Ile Asn Ala Ser Leu Lys Asn Thr Ile Ser
                    725                 730                 735

Lys Asp Asn Asn Met Leu Val Ser Gln Ala Leu Asp Ser Val Ala Asn
            740                 745                 750

His Ser Lys Gln Lys Ile Gly Asp Leu Arg Gln Ser Ser Cys Lys Met
            755                 760                 765

Ala Leu Leu Phe Lys Asn Leu Ala Thr Ser Ile Tyr Thr Ile Glu Arg
            770                 775                 780

Ile Phe Asn Ala Lys Val Gly Asp Val Lys Ala Ser Met Leu Glu
785                 790                 795                 800

Lys Tyr Lys Val Phe Thr Asp Ile Ser Met Ser Leu Tyr Lys Asp Leu
                805                 810                 815

Ile Ala Met Glu Asn Leu Lys Ala Met Leu Tyr Ile Ile Arg Arg Ser
            820                 825                 830

Gly Cys Arg Ile Asp Asp Ala Gln Ile Thr Thr Asp Asp Leu Val Lys
```

```
                    835                 840                 845
Ser Tyr Ser Leu Ile Arg Pro Lys Ile Leu Ser Met Ile Asn Tyr Tyr
            850                 855                 860

Asn Glu Met Ser Arg Gly Tyr Phe Glu His Met Lys Lys Asn Leu Asn
865                 870                 875                 880

Met Thr Asp Gly Asp Ser Val Ser Phe Asp Glu
                885                 890

<210> SEQ ID NO 16
<211> LENGTH: 891
<212> TYPE: PRT
<213> ORGANISM: Vaccinia virus

<400> SEQUENCE: 16

Met Met Pro Ile Lys Ser Ile Val Thr Leu Asp Gln Leu Glu Asp Ser
1               5                   10                  15

Glu Tyr Leu Phe Arg Ile Val Ser Thr Val Leu Pro His Leu Cys Leu
            20                  25                  30

Asp Tyr Lys Val Cys Asp Gln Leu Lys Thr Thr Phe Val His Pro Phe
        35                  40                  45

Asp Ile Leu Leu Asn Asn Ser Leu Gly Ser Val Thr Lys Gln Asp Glu
    50                  55                  60

Leu Gln Ala Ala Ile Ser Lys Leu Gly Ile Asn Tyr Leu Ile Asp Thr
65                  70                  75                  80

Thr Ser Arg Glu Leu Lys Leu Phe Asn Val Thr Leu Asn Ala Gly Asn
                85                  90                  95

Ile Asp Ile Ile Asn Thr Pro Ile Asn Ile Ser Ser Glu Thr Asn Pro
            100                 105                 110

Ile Ile Asn Thr His Ser Phe Tyr Asp Leu Pro Pro Phe Thr Gln His
        115                 120                 125

Leu Leu Asn Ile Arg Leu Thr Asp Thr Glu Tyr Arg Ala Arg Phe Ile
    130                 135                 140

Gly Gly Tyr Ile Lys Pro Asp Gly Ser Asp Ser Met Asp Val Leu Ala
145                 150                 155                 160

Glu Lys Lys Tyr Pro Asp Leu Asn Phe Asp Asn Thr Tyr Leu Phe Asn
                165                 170                 175

Ile Leu Tyr Lys Asp Val Ile Asn Ala Pro Ile Lys Glu Phe Lys Ala
            180                 185                 190

Lys Ile Val Asn Gly Val Leu Ser Arg Gln Asp Phe Asp Asn Leu Ile
        195                 200                 205

Gly Val Arg Gln Tyr Ile Thr Ile Gln Asp Arg Pro Arg Phe Asp Asp
    210                 215                 220

Ala Tyr Asn Ile Ala Asp Ala Ala Arg His Tyr Gly Val Asn Leu Asn
225                 230                 235                 240

Thr Leu Pro Leu Pro Asn Val Asp Leu Thr Thr Met Pro Thr Tyr Lys
                245                 250                 255

His Leu Ile Met Phe Glu Gln Tyr Phe Ile Tyr Thr Tyr Asp Arg Val
            260                 265                 270

Asp Ile Tyr Tyr Asn Gly Asn Lys Met Leu Phe Asp Asp Glu Ile Ile
        275                 280                 285

Asn Phe Thr Ile Ser Met Arg Tyr Gln Ser Leu Ile Pro Arg Leu Val
    290                 295                 300

Asp Phe Phe Pro Asp Ile Pro Val Asn Asn Ile Val Leu His Thr
305                 310                 315                 320
```

```
Arg Asp Pro Gln Asn Ala Ala Val Asn Val Thr Val Ala Leu Pro Asn
                325                 330                 335

Val Gln Phe Val Asp Ile Asn Arg Asn Asn Lys Phe Phe Ile Asn Phe
            340                 345                 350

Phe Asn Leu Leu Ala Lys Glu Gln Arg Ser Thr Ala Ile Lys Val Thr
        355                 360                 365

Lys Ser Met Phe Trp Asp Gly Met Asp Tyr Glu Glu Tyr Lys Ser Lys
370                 375                 380

Asn Leu Gln Asp Met Met Phe Ile Asn Ser Thr Cys Tyr Val Phe Gly
385                 390                 395                 400

Leu Tyr Asn His Asn Asn Thr Thr Tyr Cys Ser Ile Leu Ser Asp Ile
                405                 410                 415

Ile Ser Ala Glu Lys Thr Pro Ile Arg Val Cys Leu Leu Pro Arg Val
            420                 425                 430

Val Gly Gly Lys Thr Val Thr Asn Leu Ile Ser Glu Thr Leu Lys Ser
        435                 440                 445

Ile Ser Ser Met Thr Ile Arg Glu Phe Pro Arg Lys Asp Lys Ser Ile
450                 455                 460

Met His Ile Gly Leu Ser Glu Thr Gly Phe Met Arg Phe Phe Gln Leu
465                 470                 475                 480

Leu Arg Leu Met Ala Asp Lys Pro His Glu Thr Ala Ile Lys Glu Val
                485                 490                 495

Val Met Ala Tyr Val Gly Ile Lys Leu Gly Asp Lys Gly Ser Pro Tyr
            500                 505                 510

Tyr Ile Arg Lys Glu Ser Tyr Gln Asp Phe Ile Tyr Leu Leu Phe Ala
        515                 520                 525

Ser Met Gly Phe Lys Val Thr Thr Arg Ser Ile Met Gly Ser Asn
530                 535                 540

Asn Ile Ser Ile Ile Ser Ile Arg Pro Arg Val Thr Lys Gln Tyr Ile
545                 550                 555                 560

Val Ala Thr Leu Met Lys Thr Ser Cys Ser Lys Asn Glu Ala Glu Lys
                565                 570                 575

Leu Ile Thr Ser Ala Phe Asp Leu Leu Asn Phe Met Val Ser Val Ser
            580                 585                 590

Asp Phe Arg Asp Tyr Gln Ser Tyr Arg Gln Tyr Arg Asn Tyr Cys Pro
        595                 600                 605

Arg Tyr Phe Tyr Ala Gly Ser Pro Glu Gly Glu Thr Ile Ile Cys
610                 615                 620

Asp Ser Glu Pro Ile Ser Ile Leu Asp Arg Ile Asp Thr Arg Gly Ile
625                 630                 635                 640

Phe Ser Ala Tyr Thr Ile Asn Glu Met Met Asp Thr Asp Ile Phe Ser
                645                 650                 655

Pro Glu Asn Lys Ala Phe Lys Asn Asn Leu Ser Arg Phe Ile Glu Ser
            660                 665                 670

Gly Asp Ile Thr Gly Glu Asp Ile Phe Cys Ala Met Pro Tyr Asn Ile
        675                 680                 685

Leu Asp Arg Ile Ile Thr Asn Ala Gly Thr Cys Thr Val Ser Ile Gly
690                 695                 700

Asp Met Leu Asp Asn Ile Thr Thr Gln Ser Asp Cys Asn Met Thr Asn
705                 710                 715                 720

Glu Ile Thr Asp Met Ile Asn Ala Ser Leu Lys Asn Thr Ile Ser Lys
                725                 730                 735

Asp Asn Asn Met Leu Val Ser Gln Ala Leu Asn Ser Val Ala Asn Arg
```

```
                    740                 745                 750
Ser Lys Gln Lys Ile Gly Asp Leu Arg Gln Ser Ser Cys Lys Met Ala
                755                 760                 765

Leu Leu Phe Lys Asn Leu Ala Thr Ser Ile Tyr Thr Ile Glu Arg Ile
            770                 775                 780

Phe Asn Ala Lys Val Gly Asp Val Lys Ala Ser Met Leu Glu Lys
785                 790                 795                 800

Tyr Lys Val Phe Thr Asp Ile Ser Met Ser Leu Tyr Lys Asp Leu Ile
                805                 810                 815

Ala Met Glu Asn Leu Lys Ala Met Leu Tyr Ile Ile Arg Arg Ser Gly
                820                 825                 830

Cys Arg Ile Asp Asp Ala Gln Ile Thr Thr Asp Asp Leu Val Lys Ser
                835                 840                 845

Tyr Ser Leu Ile Arg Pro Lys Ile Leu Ser Met Ile Asn Tyr Tyr Asn
            850                 855                 860

Glu Met Ser Arg Gly Tyr Phe Glu His Met Lys Lys Asn Leu Asn Met
865                 870                 875                 880

Thr Asp Gly Asp Ser Val Ser Phe Asp Asp Glu
                    885                 890

<210> SEQ ID NO 17
<211> LENGTH: 575
<212> TYPE: PRT
<213> ORGANISM: Human parainfluenza virus 1

<400> SEQUENCE: 17

Met Ala Asp Lys Gly Lys Thr Ile Ser Ser Tyr Trp Ser Thr Thr Arg
1               5                   10                  15

Asn Asp Asn Ser Thr Val Asn Thr His Ile Asn Thr Pro Ala Gly Arg
                20                  25                  30

Ile His Ile Trp Leu Leu Ile Ala Thr Thr Met His Thr Val Leu Ser
            35                  40                  45

Phe Ile Ile Met Ile Leu Cys Ile Asp Leu Ile Ile Lys Gln Asp Thr
        50                  55                  60

Cys Met Lys Thr Asn Ile Met Thr Val Ser Ser Met Asn Glu Ser Ala
65                  70                  75                  80

Lys Thr Ile Lys Glu Thr Ile Thr Glu Leu Ile Arg Gln Glu Val Ile
                85                  90                  95

Ser Arg Thr Ile Asn Ile Gln Ser Ser Val Gln Ser Gly Ile Pro Ile
                100                 105                 110

Leu Leu Asn Lys Gln Ser Arg Asp Leu Thr Gln Leu Ile Glu Lys Ser
            115                 120                 125

Cys Asn Arg Gln Glu Leu Ala Gln Ile Cys Glu Asn Thr Ile Ala Ile
            130                 135                 140

His His Ala Asp Gly Ile Ser Pro Leu Asp Pro His Asp Phe Trp Arg
145                 150                 155                 160

Cys Pro Val Gly Glu Pro Leu Leu Ser Asn Asn Pro Asn Ile Ser Leu
                165                 170                 175

Leu Pro Gly Pro Ser Leu Leu Ser Gly Ser Thr Thr Ile Ser Gly Cys
            180                 185                 190

Val Arg Leu Pro Ser Leu Ser Ile Gly Asp Ala Ile Tyr Ala Tyr Ser
            195                 200                 205

Ser Asn Leu Ile Thr Gln Gly Cys Ala Asp Ile Gly Lys Ser Tyr Gln
        210                 215                 220
```

-continued

```
Val Leu Gln Leu Gly Tyr Ile Ser Leu Asn Ser Asp Met Tyr Pro Asp
225                 230                 235                 240

Leu Asn Pro Val Ile Ser His Thr Tyr Asp Ile Asn Asp Asn Arg Lys
            245                 250                 255

Ser Cys Ser Val Ile Ala Ala Gly Thr Arg Gly Tyr Gln Leu Cys Ser
            260                 265                 270

Leu Pro Thr Val Asn Glu Thr Thr Asp Tyr Ser Ser Glu Gly Ile Glu
        275                 280                 285

Asp Leu Val Phe Asp Ile Leu Asp Leu Lys Gly Lys Thr Lys Ser His
        290                 295                 300

Arg Tyr Lys Asn Glu Asp Ile Thr Phe Asp His Pro Phe Ser Ala Met
305                 310                 315                 320

Tyr Pro Ser Val Gly Ser Gly Ile Lys Ile Glu Asn Thr Leu Val Phe
                325                 330                 335

Leu Gly Tyr Gly Gly Leu Thr Thr Pro Leu Gln Gly Asp Thr Lys Cys
            340                 345                 350

Val Ile Asn Arg Cys Pro Asn Ile Asn Gln Ser Val Cys Asn Asp Ala
            355                 360                 365

Leu Lys Ile Thr Trp Leu Lys Lys Arg Gln Val Val Asn Val Leu Ile
370                 375                 380

Arg Ile Asn Asn Tyr Leu Ser Asp Arg Pro Lys Ile Val Val Glu Thr
385                 390                 395                 400

Ile Pro Ile Thr Gln Asn Tyr Leu Gly Ala Glu Gly Arg Leu Leu Lys
                405                 410                 415

Leu Gly Lys Lys Ile Tyr Ile Tyr Thr Arg Ser Ser Gly Trp His Ser
            420                 425                 430

Asn Leu Gln Ile Gly Ser Leu Asp Ile Asn Asn Pro Met Thr Ile Asn
            435                 440                 445

Trp Ala Pro His Lys Val Leu Ser Arg Pro Gly Asn Pro Asp Cys Asn
450                 455                 460

Trp Phe Asn Lys Cys Pro Arg Glu Cys Ile Ser Gly Val Tyr Thr Asp
465                 470                 475                 480

Ala Tyr Pro Leu Ser Pro Asp Ala Val Asn Val Ala Thr Thr Thr Leu
                485                 490                 495

Tyr Ala Asn Thr Ser Arg Val Asn Pro Thr Ile Met Tyr Ser Ser Thr
            500                 505                 510

Ser Lys Ile Ile Asn Met Leu Arg Leu Lys Asn Gly Gln Leu Glu Ala
            515                 520                 525

Ala Tyr Thr Thr Thr Ser Cys Ile Thr His Phe Gly Lys Gly Tyr Cys
    530                 535                 540

Phe His Ile Val Glu Ile Asn Gln Thr Ser Leu Asp Thr Leu Gln Pro
545                 550                 555                 560

Met Leu Phe Lys Thr Ser Ile Pro Lys Val Cys Lys Val Thr Ser
                565                 570                 575
```

<210> SEQ ID NO 18
<211> LENGTH: 7
<212> TYPE: PRT
<213> ORGANISM: Equine infectious anemia virus

<400> SEQUENCE: 18

```
Tyr Pro Asp Leu Ser Glu Ile
1               5
```

<210> SEQ ID NO 19

```
<211> LENGTH: 8
<212> TYPE: PRT
<213> ORGANISM: Equine infectious anemia virus

<400> SEQUENCE: 19

Tyr Pro Asp Leu Ser Glu Ile Lys
1               5

<210> SEQ ID NO 20
<211> LENGTH: 9
<212> TYPE: PRT
<213> ORGANISM: Equine infectious anemia virus

<400> SEQUENCE: 20

Tyr Pro Asp Leu Ser Glu Ile Lys Lys
1               5

<210> SEQ ID NO 21
<211> LENGTH: 10
<212> TYPE: PRT
<213> ORGANISM: Equine infectious anemia virus

<400> SEQUENCE: 21

Tyr Pro Asp Leu Ser Glu Ile Lys Lys Glu
1               5                   10

<210> SEQ ID NO 22
<211> LENGTH: 11
<212> TYPE: PRT
<213> ORGANISM: Equine infectious anemia virus

<400> SEQUENCE: 22

Tyr Pro Asp Leu Ser Glu Ile Lys Lys Glu Tyr
1               5                   10

<210> SEQ ID NO 23
<211> LENGTH: 12
<212> TYPE: PRT
<213> ORGANISM: Equine infectious anemia virus

<400> SEQUENCE: 23

Tyr Pro Asp Leu Ser Glu Ile Lys Lys Glu Tyr Asn
1               5                   10

<210> SEQ ID NO 24
<211> LENGTH: 13
<212> TYPE: PRT
<213> ORGANISM: Equine infectious anemia virus

<400> SEQUENCE: 24

Tyr Pro Asp Leu Ser Glu Ile Lys Lys Glu Tyr Asn Val
1               5                   10

<210> SEQ ID NO 25
<211> LENGTH: 14
<212> TYPE: PRT
<213> ORGANISM: Equine infectious anemia virus

<400> SEQUENCE: 25

Tyr Pro Asp Leu Ser Glu Ile Lys Lys Glu Tyr Asn Val Lys
1               5                   10

<210> SEQ ID NO 26
<211> LENGTH: 15
<212> TYPE: PRT
```

<213> ORGANISM: Equine infectious anemia virus

<400> SEQUENCE: 26

Tyr Pro Asp Leu Ser Glu Ile Lys Lys Glu Tyr Asn Val Lys Glu
1               5                   10                  15

<210> SEQ ID NO 27
<211> LENGTH: 16
<212> TYPE: PRT
<213> ORGANISM: Equine infectious anemia virus

<400> SEQUENCE: 27

Tyr Pro Asp Leu Ser Glu Ile Lys Lys Glu Tyr Asn Val Lys Glu Lys
1               5                   10                  15

<210> SEQ ID NO 28
<211> LENGTH: 17
<212> TYPE: PRT
<213> ORGANISM: Equine infectious anemia virus

<400> SEQUENCE: 28

Tyr Pro Asp Leu Ser Glu Ile Lys Lys Glu Tyr Asn Val Lys Glu Lys
1               5                   10                  15

Asp

<210> SEQ ID NO 29
<211> LENGTH: 18
<212> TYPE: PRT
<213> ORGANISM: Equine infectious anemia virus

<400> SEQUENCE: 29

Tyr Pro Asp Leu Ser Glu Ile Lys Lys Glu Tyr Asn Val Lys Glu Lys
1               5                   10                  15

Asp Gln

<210> SEQ ID NO 30
<211> LENGTH: 19
<212> TYPE: PRT
<213> ORGANISM: Equine infectious anemia virus

<400> SEQUENCE: 30

Tyr Pro Asp Leu Ser Glu Ile Lys Lys Glu Tyr Asn Val Lys Glu Lys
1               5                   10                  15

Asp Gln Val

<210> SEQ ID NO 31
<211> LENGTH: 20
<212> TYPE: PRT
<213> ORGANISM: Equine infectious anemia virus

<400> SEQUENCE: 31

Tyr Pro Asp Leu Ser Glu Ile Lys Lys Glu Tyr Asn Val Lys Glu Lys
1               5                   10                  15

Asp Gln Val Glu
            20

<210> SEQ ID NO 32
<211> LENGTH: 7
<212> TYPE: PRT
<213> ORGANISM: Equine infectious anemia virus

<400> SEQUENCE: 32

```
Leu Tyr Pro Asp Leu Ser Glu
1               5

<210> SEQ ID NO 33
<211> LENGTH: 8
<212> TYPE: PRT
<213> ORGANISM: Equine infectious anemia virus

<400> SEQUENCE: 33

Leu Tyr Pro Asp Leu Ser Glu Ile
1               5

<210> SEQ ID NO 34
<211> LENGTH: 9
<212> TYPE: PRT
<213> ORGANISM: Equine infectious anemia virus

<400> SEQUENCE: 34

Leu Tyr Pro Asp Leu Ser Glu Ile Lys
1               5

<210> SEQ ID NO 35
<211> LENGTH: 10
<212> TYPE: PRT
<213> ORGANISM: Equine infectious anemia virus

<400> SEQUENCE: 35

Leu Tyr Pro Asp Leu Ser Glu Ile Lys Lys
1               5                  10

<210> SEQ ID NO 36
<211> LENGTH: 11
<212> TYPE: PRT
<213> ORGANISM: Equine infectious anemia virus

<400> SEQUENCE: 36

Leu Tyr Pro Asp Leu Ser Glu Ile Lys Lys Glu
1               5                  10

<210> SEQ ID NO 37
<211> LENGTH: 12
<212> TYPE: PRT
<213> ORGANISM: Equine infectious anemia virus

<400> SEQUENCE: 37

Leu Tyr Pro Asp Leu Ser Glu Ile Lys Lys Glu Tyr
1               5                  10

<210> SEQ ID NO 38
<211> LENGTH: 13
<212> TYPE: PRT
<213> ORGANISM: Equine infectious anemia virus

<400> SEQUENCE: 38

Leu Tyr Pro Asp Leu Ser Glu Ile Lys Lys Glu Tyr Asn
1               5                  10

<210> SEQ ID NO 39
<211> LENGTH: 14
<212> TYPE: PRT
<213> ORGANISM: Equine infectious anemia virus

<400> SEQUENCE: 39

Leu Tyr Pro Asp Leu Ser Glu Ile Lys Lys Glu Tyr Asn Val
1               5                  10
```

-continued

```
<210> SEQ ID NO 40
<211> LENGTH: 15
<212> TYPE: PRT
<213> ORGANISM: Equine infectious anemia virus

<400> SEQUENCE: 40

Leu Tyr Pro Asp Leu Ser Glu Ile Lys Lys Glu Tyr Asn Val Lys
1               5                   10                  15

<210> SEQ ID NO 41
<211> LENGTH: 16
<212> TYPE: PRT
<213> ORGANISM: Equine infectious anemia virus

<400> SEQUENCE: 41

Leu Tyr Pro Asp Leu Ser Glu Ile Lys Lys Glu Tyr Asn Val Lys Glu
1               5                   10                  15

<210> SEQ ID NO 42
<211> LENGTH: 17
<212> TYPE: PRT
<213> ORGANISM: Equine infectious anemia virus

<400> SEQUENCE: 42

Leu Tyr Pro Asp Leu Ser Glu Ile Lys Lys Glu Tyr Asn Val Lys Glu
1               5                   10                  15

Lys

<210> SEQ ID NO 43
<211> LENGTH: 18
<212> TYPE: PRT
<213> ORGANISM: Equine infectious anemia virus

<400> SEQUENCE: 43

Leu Tyr Pro Asp Leu Ser Glu Ile Lys Lys Glu Tyr Asn Val Lys Glu
1               5                   10                  15

Lys Asp

<210> SEQ ID NO 44
<211> LENGTH: 19
<212> TYPE: PRT
<213> ORGANISM: Equine infectious anemia virus

<400> SEQUENCE: 44

Leu Tyr Pro Asp Leu Ser Glu Ile Lys Lys Glu Tyr Asn Val Lys Glu
1               5                   10                  15

Lys Asp Gln

<210> SEQ ID NO 45
<211> LENGTH: 20
<212> TYPE: PRT
<213> ORGANISM: Equine infectious anemia virus

<400> SEQUENCE: 45

Leu Tyr Pro Asp Leu Ser Glu Ile Lys Lys Glu Tyr Asn Val Lys Glu
1               5                   10                  15

Lys Asp Gln Val
            20

<210> SEQ ID NO 46
<211> LENGTH: 7
```

<212> TYPE: PRT
<213> ORGANISM: Equine infectious anemia virus

<400> SEQUENCE: 46

Asn Leu Tyr Pro Asp Leu Ser
1               5

<210> SEQ ID NO 47
<211> LENGTH: 8
<212> TYPE: PRT
<213> ORGANISM: Equine infectious anemia virus

<400> SEQUENCE: 47

Asn Leu Tyr Pro Asp Leu Ser Glu
1               5

<210> SEQ ID NO 48
<211> LENGTH: 9
<212> TYPE: PRT
<213> ORGANISM: Equine infectious anemia virus

<400> SEQUENCE: 48

Asn Leu Tyr Pro Asp Leu Ser Glu Ile
1               5

<210> SEQ ID NO 49
<211> LENGTH: 10
<212> TYPE: PRT
<213> ORGANISM: Equine infectious anemia virus

<400> SEQUENCE: 49

Asn Leu Tyr Pro Asp Leu Ser Glu Ile Lys
1               5                   10

<210> SEQ ID NO 50
<211> LENGTH: 11
<212> TYPE: PRT
<213> ORGANISM: Equine infectious anemia virus

<400> SEQUENCE: 50

Asn Leu Tyr Pro Asp Leu Ser Glu Ile Lys Lys
1               5                   10

<210> SEQ ID NO 51
<211> LENGTH: 12
<212> TYPE: PRT
<213> ORGANISM: Equine infectious anemia virus

<400> SEQUENCE: 51

Asn Leu Tyr Pro Asp Leu Ser Glu Ile Lys Lys Glu
1               5                   10

<210> SEQ ID NO 52
<211> LENGTH: 13
<212> TYPE: PRT
<213> ORGANISM: Equine infectious anemia virus

<400> SEQUENCE: 52

Asn Leu Tyr Pro Asp Leu Ser Glu Ile Lys Lys Glu Tyr
1               5                   10

<210> SEQ ID NO 53
<211> LENGTH: 14
<212> TYPE: PRT
<213> ORGANISM: Equine infectious anemia virus

```
<400> SEQUENCE: 53

Asn Leu Tyr Pro Asp Leu Ser Glu Ile Lys Lys Glu Tyr Asn
1               5                   10

<210> SEQ ID NO 54
<211> LENGTH: 15
<212> TYPE: PRT
<213> ORGANISM: Equine infectious anemia virus

<400> SEQUENCE: 54

Asn Leu Tyr Pro Asp Leu Ser Glu Ile Lys Lys Glu Tyr Asn Val
1               5                   10                  15

<210> SEQ ID NO 55
<211> LENGTH: 16
<212> TYPE: PRT
<213> ORGANISM: Equine infectious anemia virus

<400> SEQUENCE: 55

Asn Leu Tyr Pro Asp Leu Ser Glu Ile Lys Lys Glu Tyr Asn Val Lys
1               5                   10                  15

<210> SEQ ID NO 56
<211> LENGTH: 17
<212> TYPE: PRT
<213> ORGANISM: Equine infectious anemia virus

<400> SEQUENCE: 56

Asn Leu Tyr Pro Asp Leu Ser Glu Ile Lys Lys Glu Tyr Asn Val Lys
1               5                   10                  15

Glu

<210> SEQ ID NO 57
<211> LENGTH: 18
<212> TYPE: PRT
<213> ORGANISM: Equine infectious anemia virus

<400> SEQUENCE: 57

Asn Leu Tyr Pro Asp Leu Ser Glu Ile Lys Lys Glu Tyr Asn Val Lys
1               5                   10                  15

Glu Lys

<210> SEQ ID NO 58
<211> LENGTH: 19
<212> TYPE: PRT
<213> ORGANISM: Equine infectious anemia virus

<400> SEQUENCE: 58

Asn Leu Tyr Pro Asp Leu Ser Glu Ile Lys Lys Glu Tyr Asn Val Lys
1               5                   10                  15

Glu Lys Asp

<210> SEQ ID NO 59
<211> LENGTH: 20
<212> TYPE: PRT
<213> ORGANISM: Equine infectious anemia virus

<400> SEQUENCE: 59

Asn Leu Tyr Pro Asp Leu Ser Glu Ile Lys Lys Glu Tyr Asn Val Lys
1               5                   10                  15

Glu Lys Asp Gln
```

```
                        20

<210> SEQ ID NO 60
<211> LENGTH: 7
<212> TYPE: PRT
<213> ORGANISM: Equine infectious anemia virus

<400> SEQUENCE: 60

Gln Asn Leu Tyr Pro Asp Leu
1               5

<210> SEQ ID NO 61
<211> LENGTH: 8
<212> TYPE: PRT
<213> ORGANISM: Equine infectious anemia virus

<400> SEQUENCE: 61

Gln Asn Leu Tyr Pro Asp Leu Ser
1               5

<210> SEQ ID NO 62
<211> LENGTH: 9
<212> TYPE: PRT
<213> ORGANISM: Equine infectious anemia virus

<400> SEQUENCE: 62

Gln Asn Leu Tyr Pro Asp Leu Ser Glu
1               5

<210> SEQ ID NO 63
<211> LENGTH: 10
<212> TYPE: PRT
<213> ORGANISM: Equine infectious anemia virus

<400> SEQUENCE: 63

Gln Asn Leu Tyr Pro Asp Leu Ser Glu Ile
1               5                   10

<210> SEQ ID NO 64
<211> LENGTH: 11
<212> TYPE: PRT
<213> ORGANISM: Equine infectious anemia virus

<400> SEQUENCE: 64

Gln Asn Leu Tyr Pro Asp Leu Ser Glu Ile Lys
1               5                   10

<210> SEQ ID NO 65
<211> LENGTH: 12
<212> TYPE: PRT
<213> ORGANISM: Equine infectious anemia virus

<400> SEQUENCE: 65

Gln Asn Leu Tyr Pro Asp Leu Ser Glu Ile Lys Lys
1               5                   10

<210> SEQ ID NO 66
<211> LENGTH: 13
<212> TYPE: PRT
<213> ORGANISM: Equine infectious anemia virus

<400> SEQUENCE: 66

Gln Asn Leu Tyr Pro Asp Leu Ser Glu Ile Lys Lys Glu
1               5                   10
```

```
<210> SEQ ID NO 67
<211> LENGTH: 14
<212> TYPE: PRT
<213> ORGANISM: Equine infectious anemia virus

<400> SEQUENCE: 67

Gln Asn Leu Tyr Pro Asp Leu Ser Glu Ile Lys Lys Glu Tyr
1               5                   10

<210> SEQ ID NO 68
<211> LENGTH: 15
<212> TYPE: PRT
<213> ORGANISM: Equine infectious anemia virus

<400> SEQUENCE: 68

Gln Asn Leu Tyr Pro Asp Leu Ser Glu Ile Lys Lys Glu Tyr Asn
1               5                   10                  15

<210> SEQ ID NO 69
<211> LENGTH: 16
<212> TYPE: PRT
<213> ORGANISM: Equine infectious anemia virus

<400> SEQUENCE: 69

Gln Asn Leu Tyr Pro Asp Leu Ser Glu Ile Lys Lys Glu Tyr Asn Val
1               5                   10                  15

<210> SEQ ID NO 70
<211> LENGTH: 17
<212> TYPE: PRT
<213> ORGANISM: Equine infectious anemia virus

<400> SEQUENCE: 70

Gln Asn Leu Tyr Pro Asp Leu Ser Glu Ile Lys Lys Glu Tyr Asn Val
1               5                   10                  15

Lys

<210> SEQ ID NO 71
<211> LENGTH: 18
<212> TYPE: PRT
<213> ORGANISM: Equine infectious anemia virus

<400> SEQUENCE: 71

Gln Asn Leu Tyr Pro Asp Leu Ser Glu Ile Lys Lys Glu Tyr Asn Val
1               5                   10                  15

Lys Glu

<210> SEQ ID NO 72
<211> LENGTH: 19
<212> TYPE: PRT
<213> ORGANISM: Equine infectious anemia virus

<400> SEQUENCE: 72

Gln Asn Leu Tyr Pro Asp Leu Ser Glu Ile Lys Lys Glu Tyr Asn Val
1               5                   10                  15

Lys Glu Lys

<210> SEQ ID NO 73
<211> LENGTH: 20
<212> TYPE: PRT
<213> ORGANISM: Equine infectious anemia virus

<400> SEQUENCE: 73
```

Gln Asn Leu Tyr Pro Asp Leu Ser Glu Ile Lys Lys Glu Tyr Asn Val
1               5                   10                  15

Lys Glu Lys Asp
            20

<210> SEQ ID NO 74
<211> LENGTH: 8
<212> TYPE: PRT
<213> ORGANISM: Equine infectious anemia virus

<400> SEQUENCE: 74

Thr Gln Asn Leu Tyr Pro Asp Leu
1               5

<210> SEQ ID NO 75
<211> LENGTH: 9
<212> TYPE: PRT
<213> ORGANISM: Equine infectious anemia virus

<400> SEQUENCE: 75

Thr Gln Asn Leu Tyr Pro Asp Leu Ser
1               5

<210> SEQ ID NO 76
<211> LENGTH: 10
<212> TYPE: PRT
<213> ORGANISM: Equine infectious anemia virus

<400> SEQUENCE: 76

Thr Gln Asn Leu Tyr Pro Asp Leu Ser Glu
1               5                   10

<210> SEQ ID NO 77
<211> LENGTH: 11
<212> TYPE: PRT
<213> ORGANISM: Equine infectious anemia virus

<400> SEQUENCE: 77

Thr Gln Asn Leu Tyr Pro Asp Leu Ser Glu Ile
1               5                   10

<210> SEQ ID NO 78
<211> LENGTH: 12
<212> TYPE: PRT
<213> ORGANISM: Equine infectious anemia virus

<400> SEQUENCE: 78

Thr Gln Asn Leu Tyr Pro Asp Leu Ser Glu Ile Lys
1               5                   10

<210> SEQ ID NO 79
<211> LENGTH: 13
<212> TYPE: PRT
<213> ORGANISM: Equine infectious anemia virus

<400> SEQUENCE: 79

Thr Gln Asn Leu Tyr Pro Asp Leu Ser Glu Ile Lys Lys
1               5                   10

<210> SEQ ID NO 80
<211> LENGTH: 14
<212> TYPE: PRT
<213> ORGANISM: Equine infectious anemia virus -continued

```
<400> SEQUENCE: 80

Thr Gln Asn Leu Tyr Pro Asp Leu Ser Glu Ile Lys Lys Glu
1               5                   10

<210> SEQ ID NO 81
<211> LENGTH: 15
<212> TYPE: PRT
<213> ORGANISM: Equine infectious anemia virus

<400> SEQUENCE: 81

Thr Gln Asn Leu Tyr Pro Asp Leu Ser Glu Ile Lys Lys Glu Tyr
1               5                   10                  15

<210> SEQ ID NO 82
<211> LENGTH: 16
<212> TYPE: PRT
<213> ORGANISM: Equine infectious anemia virus

<400> SEQUENCE: 82

Thr Gln Asn Leu Tyr Pro Asp Leu Ser Glu Ile Lys Lys Glu Tyr Asn
1               5                   10                  15

<210> SEQ ID NO 83
<211> LENGTH: 17
<212> TYPE: PRT
<213> ORGANISM: Equine infectious anemia virus

<400> SEQUENCE: 83

Thr Gln Asn Leu Tyr Pro Asp Leu Ser Glu Ile Lys Lys Glu Tyr Asn
1               5                   10                  15

Val

<210> SEQ ID NO 84
<211> LENGTH: 18
<212> TYPE: PRT
<213> ORGANISM: Equine infectious anemia virus

<400> SEQUENCE: 84

Thr Gln Asn Leu Tyr Pro Asp Leu Ser Glu Ile Lys Lys Glu Tyr Asn
1               5                   10                  15

Val Lys

<210> SEQ ID NO 85
<211> LENGTH: 19
<212> TYPE: PRT
<213> ORGANISM: Equine infectious anemia virus

<400> SEQUENCE: 85

Thr Gln Asn Leu Tyr Pro Asp Leu Ser Glu Ile Lys Lys Glu Tyr Asn
1               5                   10                  15

Val Lys Glu

<210> SEQ ID NO 86
<211> LENGTH: 20
<212> TYPE: PRT
<213> ORGANISM: Equine infectious anemia virus

<400> SEQUENCE: 86

Thr Gln Asn Leu Tyr Pro Asp Leu Ser Glu Ile Lys Lys Glu Tyr Asn
1               5                   10                  15

Val Lys Glu Lys
            20
```

<210> SEQ ID NO 87
<211> LENGTH: 9
<212> TYPE: PRT
<213> ORGANISM: Equine infectious anemia virus

<400> SEQUENCE: 87

Gln Thr Gln Asn Leu Tyr Pro Asp Leu
1               5

<210> SEQ ID NO 88
<211> LENGTH: 10
<212> TYPE: PRT
<213> ORGANISM: Equine infectious anemia virus

<400> SEQUENCE: 88

Gln Thr Gln Asn Leu Tyr Pro Asp Leu Ser
1               5                   10

<210> SEQ ID NO 89
<211> LENGTH: 11
<212> TYPE: PRT
<213> ORGANISM: Equine infectious anemia virus

<400> SEQUENCE: 89

Gln Thr Gln Asn Leu Tyr Pro Asp Leu Ser Glu
1               5                   10

<210> SEQ ID NO 90
<211> LENGTH: 12
<212> TYPE: PRT
<213> ORGANISM: Equine infectious anemia virus

<400> SEQUENCE: 90

Gln Thr Gln Asn Leu Tyr Pro Asp Leu Ser Glu Ile
1               5                   10

<210> SEQ ID NO 91
<211> LENGTH: 13
<212> TYPE: PRT
<213> ORGANISM: Equine infectious anemia virus

<400> SEQUENCE: 91

Gln Thr Gln Asn Leu Tyr Pro Asp Leu Ser Glu Ile Lys
1               5                   10

<210> SEQ ID NO 92
<211> LENGTH: 14
<212> TYPE: PRT
<213> ORGANISM: Equine infectious anemia virus

<400> SEQUENCE: 92

Gln Thr Gln Asn Leu Tyr Pro Asp Leu Ser Glu Ile Lys Lys
1               5                   10

<210> SEQ ID NO 93
<211> LENGTH: 15
<212> TYPE: PRT
<213> ORGANISM: Equine infectious anemia virus

<400> SEQUENCE: 93

Gln Thr Gln Asn Leu Tyr Pro Asp Leu Ser Glu Ile Lys Lys Glu
1               5                   10                  15

```
<210> SEQ ID NO 94
<211> LENGTH: 16
<212> TYPE: PRT
<213> ORGANISM: Equine infectious anemia virus

<400> SEQUENCE: 94

Gln Thr Gln Asn Leu Tyr Pro Asp Leu Ser Glu Ile Lys Lys Glu Tyr
1               5                   10                  15

<210> SEQ ID NO 95
<211> LENGTH: 17
<212> TYPE: PRT
<213> ORGANISM: Equine infectious anemia virus

<400> SEQUENCE: 95

Gln Thr Gln Asn Leu Tyr Pro Asp Leu Ser Glu Ile Lys Lys Glu Tyr
1               5                   10                  15

Asn

<210> SEQ ID NO 96
<211> LENGTH: 18
<212> TYPE: PRT
<213> ORGANISM: Equine infectious anemia virus

<400> SEQUENCE: 96

Gln Thr Gln Asn Leu Tyr Pro Asp Leu Ser Glu Ile Lys Lys Glu Tyr
1               5                   10                  15

Asn Val

<210> SEQ ID NO 97
<211> LENGTH: 19
<212> TYPE: PRT
<213> ORGANISM: Equine infectious anemia virus

<400> SEQUENCE: 97

Gln Thr Gln Asn Leu Tyr Pro Asp Leu Ser Glu Ile Lys Lys Glu Tyr
1               5                   10                  15

Asn Val Lys

<210> SEQ ID NO 98
<211> LENGTH: 20
<212> TYPE: PRT
<213> ORGANISM: Equine infectious anemia virus

<400> SEQUENCE: 98

Gln Thr Gln Asn Leu Tyr Pro Asp Leu Ser Glu Ile Lys Lys Glu Tyr
1               5                   10                  15

Asn Val Lys Glu
            20

<210> SEQ ID NO 99
<211> LENGTH: 10
<212> TYPE: PRT
<213> ORGANISM: Equine infectious anemia virus

<400> SEQUENCE: 99

Pro Gln Thr Gln Asn Leu Tyr Pro Asp Leu
1               5                   10

<210> SEQ ID NO 100
<211> LENGTH: 11
<212> TYPE: PRT
<213> ORGANISM: Equine infectious anemia virus
```

<400> SEQUENCE: 100

Pro Gln Thr Gln Asn Leu Tyr Pro Asp Leu Ser
1               5                   10

<210> SEQ ID NO 101
<211> LENGTH: 12
<212> TYPE: PRT
<213> ORGANISM: Equine infectious anemia virus

<400> SEQUENCE: 101

Pro Gln Thr Gln Asn Leu Tyr Pro Asp Leu Ser Glu
1               5                   10

<210> SEQ ID NO 102
<211> LENGTH: 13
<212> TYPE: PRT
<213> ORGANISM: Equine infectious anemia virus

<400> SEQUENCE: 102

Pro Gln Thr Gln Asn Leu Tyr Pro Asp Leu Ser Glu Ile
1               5                   10

<210> SEQ ID NO 103
<211> LENGTH: 14
<212> TYPE: PRT
<213> ORGANISM: Equine infectious anemia virus

<400> SEQUENCE: 103

Pro Gln Thr Gln Asn Leu Tyr Pro Asp Leu Ser Glu Ile Lys
1               5                   10

<210> SEQ ID NO 104
<211> LENGTH: 15
<212> TYPE: PRT
<213> ORGANISM: Equine infectious anemia virus

<400> SEQUENCE: 104

Pro Gln Thr Gln Asn Leu Tyr Pro Asp Leu Ser Glu Ile Lys Lys
1               5                   10                  15

<210> SEQ ID NO 105
<211> LENGTH: 16
<212> TYPE: PRT
<213> ORGANISM: Equine infectious anemia virus

<400> SEQUENCE: 105

Pro Gln Thr Gln Asn Leu Tyr Pro Asp Leu Ser Glu Ile Lys Lys Glu
1               5                   10                  15

<210> SEQ ID NO 106
<211> LENGTH: 17
<212> TYPE: PRT
<213> ORGANISM: Equine infectious anemia virus

<400> SEQUENCE: 106

Pro Gln Thr Gln Asn Leu Tyr Pro Asp Leu Ser Glu Ile Lys Lys Glu
1               5                   10                  15

Tyr

<210> SEQ ID NO 107
<211> LENGTH: 18
<212> TYPE: PRT
<213> ORGANISM: Equine infectious anemia virus -continued

<400> SEQUENCE: 107

Pro Gln Thr Gln Asn Leu Tyr Pro Asp Leu Ser Glu Ile Lys Lys Glu
1               5                   10                  15

Tyr Asn

<210> SEQ ID NO 108
<211> LENGTH: 19
<212> TYPE: PRT
<213> ORGANISM: Equine infectious anemia virus

<400> SEQUENCE: 108

Pro Gln Thr Gln Asn Leu Tyr Pro Asp Leu Ser Glu Ile Lys Lys Glu
1               5                   10                  15

Tyr Asn Val

<210> SEQ ID NO 109
<211> LENGTH: 20
<212> TYPE: PRT
<213> ORGANISM: Equine infectious anemia virus

<400> SEQUENCE: 109

Pro Gln Thr Gln Asn Leu Tyr Pro Asp Leu Ser Glu Ile Lys Lys Glu
1               5                   10                  15

Tyr Asn Val Lys
            20

<210> SEQ ID NO 110
<211> LENGTH: 11
<212> TYPE: PRT
<213> ORGANISM: Equine infectious anemia virus

<400> SEQUENCE: 110

Thr Pro Gln Thr Gln Asn Leu Tyr Pro Asp Leu
1               5                   10

<210> SEQ ID NO 111
<211> LENGTH: 12
<212> TYPE: PRT
<213> ORGANISM: Equine infectious anemia virus

<400> SEQUENCE: 111

Thr Pro Gln Thr Gln Asn Leu Tyr Pro Asp Leu Ser
1               5                   10

<210> SEQ ID NO 112
<211> LENGTH: 13
<212> TYPE: PRT
<213> ORGANISM: Equine infectious anemia virus

<400> SEQUENCE: 112

Thr Pro Gln Thr Gln Asn Leu Tyr Pro Asp Leu Ser Glu
1               5                   10

<210> SEQ ID NO 113
<211> LENGTH: 14
<212> TYPE: PRT
<213> ORGANISM: Equine infectious anemia virus

<400> SEQUENCE: 113

Thr Pro Gln Thr Gln Asn Leu Tyr Pro Asp Leu Ser Glu Ile
1               5                   10

```
<210> SEQ ID NO 114
<211> LENGTH: 15
<212> TYPE: PRT
<213> ORGANISM: Equine infectious anemia virus

<400> SEQUENCE: 114

Thr Pro Gln Thr Gln Asn Leu Tyr Pro Asp Leu Ser Glu Ile Lys
1               5                   10                  15

<210> SEQ ID NO 115
<211> LENGTH: 16
<212> TYPE: PRT
<213> ORGANISM: Equine infectious anemia virus

<400> SEQUENCE: 115

Thr Pro Gln Thr Gln Asn Leu Tyr Pro Asp Leu Ser Glu Ile Lys Lys
1               5                   10                  15

<210> SEQ ID NO 116
<211> LENGTH: 17
<212> TYPE: PRT
<213> ORGANISM: Equine infectious anemia virus

<400> SEQUENCE: 116

Thr Pro Gln Thr Gln Asn Leu Tyr Pro Asp Leu Ser Glu Ile Lys Lys
1               5                   10                  15

Glu

<210> SEQ ID NO 117
<211> LENGTH: 18
<212> TYPE: PRT
<213> ORGANISM: Equine infectious anemia virus

<400> SEQUENCE: 117

Thr Pro Gln Thr Gln Asn Leu Tyr Pro Asp Leu Ser Glu Ile Lys Lys
1               5                   10                  15

Glu Tyr

<210> SEQ ID NO 118
<211> LENGTH: 19
<212> TYPE: PRT
<213> ORGANISM: Equine infectious anemia virus

<400> SEQUENCE: 118

Thr Pro Gln Thr Gln Asn Leu Tyr Pro Asp Leu Ser Glu Ile Lys Lys
1               5                   10                  15

Glu Tyr Asn

<210> SEQ ID NO 119
<211> LENGTH: 20
<212> TYPE: PRT
<213> ORGANISM: Equine infectious anemia virus

<400> SEQUENCE: 119

Thr Pro Gln Thr Gln Asn Leu Tyr Pro Asp Leu Ser Glu Ile Lys Lys
1               5                   10                  15

Glu Tyr Asn Val
            20

<210> SEQ ID NO 120
<211> LENGTH: 12
<212> TYPE: PRT
```

```
<213> ORGANISM: Equine infectious anemia virus

<400> SEQUENCE: 120

Glu Thr Pro Gln Thr Gln Asn Leu Tyr Pro Asp Leu
1               5                   10

<210> SEQ ID NO 121
<211> LENGTH: 13
<212> TYPE: PRT
<213> ORGANISM: Equine infectious anemia virus

<400> SEQUENCE: 121

Glu Thr Pro Gln Thr Gln Asn Leu Tyr Pro Asp Leu Ser
1               5                   10

<210> SEQ ID NO 122
<211> LENGTH: 14
<212> TYPE: PRT
<213> ORGANISM: Equine infectious anemia virus

<400> SEQUENCE: 122

Glu Thr Pro Gln Thr Gln Asn Leu Tyr Pro Asp Leu Ser Glu
1               5                   10

<210> SEQ ID NO 123
<211> LENGTH: 15
<212> TYPE: PRT
<213> ORGANISM: Equine infectious anemia virus

<400> SEQUENCE: 123

Glu Thr Pro Gln Thr Gln Asn Leu Tyr Pro Asp Leu Ser Glu Ile
1               5                   10                  15

<210> SEQ ID NO 124
<211> LENGTH: 16
<212> TYPE: PRT
<213> ORGANISM: Equine infectious anemia virus

<400> SEQUENCE: 124

Glu Thr Pro Gln Thr Gln Asn Leu Tyr Pro Asp Leu Ser Glu Ile Lys
1               5                   10                  15

<210> SEQ ID NO 125
<211> LENGTH: 17
<212> TYPE: PRT
<213> ORGANISM: Equine infectious anemia virus

<400> SEQUENCE: 125

Glu Thr Pro Gln Thr Gln Asn Leu Tyr Pro Asp Leu Ser Glu Ile Lys
1               5                   10                  15

Lys

<210> SEQ ID NO 126
<211> LENGTH: 18
<212> TYPE: PRT
<213> ORGANISM: Equine infectious anemia virus

<400> SEQUENCE: 126

Glu Thr Pro Gln Thr Gln Asn Leu Tyr Pro Asp Leu Ser Glu Ile Lys
1               5                   10                  15

Lys Glu

<210> SEQ ID NO 127
```

```
<211> LENGTH: 19
<212> TYPE: PRT
<213> ORGANISM: Equine infectious anemia virus

<400> SEQUENCE: 127

Glu Thr Pro Gln Thr Gln Asn Leu Tyr Pro Asp Leu Ser Glu Ile Lys
1               5                   10                  15
Lys Glu Tyr

<210> SEQ ID NO 128
<211> LENGTH: 20
<212> TYPE: PRT
<213> ORGANISM: Equine infectious anemia virus

<400> SEQUENCE: 128

Glu Thr Pro Gln Thr Gln Asn Leu Tyr Pro Asp Leu Ser Glu Ile Lys
1               5                   10                  15
Lys Glu Tyr Asn
            20

<210> SEQ ID NO 129
<211> LENGTH: 13
<212> TYPE: PRT
<213> ORGANISM: Equine infectious anemia virus

<400> SEQUENCE: 129

Gln Glu Thr Pro Gln Thr Gln Asn Leu Tyr Pro Asp Leu
1               5                   10

<210> SEQ ID NO 130
<211> LENGTH: 14
<212> TYPE: PRT
<213> ORGANISM: Equine infectious anemia virus

<400> SEQUENCE: 130

Gln Glu Thr Pro Gln Thr Gln Asn Leu Tyr Pro Asp Leu Ser
1               5                   10

<210> SEQ ID NO 131
<211> LENGTH: 15
<212> TYPE: PRT
<213> ORGANISM: Equine infectious anemia virus

<400> SEQUENCE: 131

Gln Glu Thr Pro Gln Thr Gln Asn Leu Tyr Pro Asp Leu Ser Glu
1               5                   10                  15

<210> SEQ ID NO 132
<211> LENGTH: 16
<212> TYPE: PRT
<213> ORGANISM: Equine infectious anemia virus

<400> SEQUENCE: 132

Gln Glu Thr Pro Gln Thr Gln Asn Leu Tyr Pro Asp Leu Ser Glu Ile
1               5                   10                  15

<210> SEQ ID NO 133
<211> LENGTH: 17
<212> TYPE: PRT
<213> ORGANISM: Equine infectious anemia virus

<400> SEQUENCE: 133

Gln Glu Thr Pro Gln Thr Gln Asn Leu Tyr Pro Asp Leu Ser Glu Ile
1               5                   10                  15
```

Lys

<210> SEQ ID NO 134
<211> LENGTH: 18
<212> TYPE: PRT
<213> ORGANISM: Equine infectious anemia virus

<400> SEQUENCE: 134

Gln Glu Thr Pro Gln Thr Gln Asn Leu Tyr Pro Asp Leu Ser Glu Ile
1               5                   10                  15

Lys Lys

<210> SEQ ID NO 135
<211> LENGTH: 19
<212> TYPE: PRT
<213> ORGANISM: Equine infectious anemia virus

<400> SEQUENCE: 135

Gln Glu Thr Pro Gln Thr Gln Asn Leu Tyr Pro Asp Leu Ser Glu Ile
1               5                   10                  15

Lys Lys Glu

<210> SEQ ID NO 136
<211> LENGTH: 20
<212> TYPE: PRT
<213> ORGANISM: Equine infectious anemia virus

<400> SEQUENCE: 136

Gln Glu Thr Pro Gln Thr Gln Asn Leu Tyr Pro Asp Leu Ser Glu Ile
1               5                   10                  15

Lys Lys Glu Tyr
            20

<210> SEQ ID NO 137
<211> LENGTH: 14
<212> TYPE: PRT
<213> ORGANISM: Equine infectious anemia virus

<400> SEQUENCE: 137

Val Gln Glu Thr Pro Gln Thr Gln Asn Leu Tyr Pro Asp Leu
1               5                   10

<210> SEQ ID NO 138
<211> LENGTH: 15
<212> TYPE: PRT
<213> ORGANISM: Equine infectious anemia virus

<400> SEQUENCE: 138

Val Gln Glu Thr Pro Gln Thr Gln Asn Leu Tyr Pro Asp Leu Ser
1               5                   10                  15

<210> SEQ ID NO 139
<211> LENGTH: 16
<212> TYPE: PRT
<213> ORGANISM: Equine infectious anemia virus

<400> SEQUENCE: 139

Val Gln Glu Thr Pro Gln Thr Gln Asn Leu Tyr Pro Asp Leu Ser Glu
1               5                   10                  15

<210> SEQ ID NO 140
<211> LENGTH: 17

```
<212> TYPE: PRT
<213> ORGANISM: Equine infectious anemia virus

<400> SEQUENCE: 140

Val Gln Glu Thr Pro Gln Thr Gln Asn Leu Tyr Pro Asp Leu Ser Glu
1               5                   10                  15

Ile

<210> SEQ ID NO 141
<211> LENGTH: 18
<212> TYPE: PRT
<213> ORGANISM: Equine infectious anemia virus

<400> SEQUENCE: 141

Val Gln Glu Thr Pro Gln Thr Gln Asn Leu Tyr Pro Asp Leu Ser Glu
1               5                   10                  15

Ile Lys

<210> SEQ ID NO 142
<211> LENGTH: 19
<212> TYPE: PRT
<213> ORGANISM: Equine infectious anemia virus

<400> SEQUENCE: 142

Val Gln Glu Thr Pro Gln Thr Gln Asn Leu Tyr Pro Asp Leu Ser Glu
1               5                   10                  15

Ile Lys Lys

<210> SEQ ID NO 143
<211> LENGTH: 20
<212> TYPE: PRT
<213> ORGANISM: Equine infectious anemia virus

<400> SEQUENCE: 143

Val Gln Glu Thr Pro Gln Thr Gln Asn Leu Tyr Pro Asp Leu Ser Glu
1               5                   10                  15

Ile Lys Lys Glu
            20

<210> SEQ ID NO 144
<211> LENGTH: 15
<212> TYPE: PRT
<213> ORGANISM: Equine infectious anemia virus

<400> SEQUENCE: 144

Val Val Gln Glu Thr Pro Gln Thr Gln Asn Leu Tyr Pro Asp Leu
1               5                   10                  15

<210> SEQ ID NO 145
<211> LENGTH: 16
<212> TYPE: PRT
<213> ORGANISM: Equine infectious anemia virus

<400> SEQUENCE: 145

Val Val Gln Glu Thr Pro Gln Thr Gln Asn Leu Tyr Pro Asp Leu Ser
1               5                   10                  15

<210> SEQ ID NO 146
<211> LENGTH: 17
<212> TYPE: PRT
<213> ORGANISM: Equine infectious anemia virus

<400> SEQUENCE: 146
```

Val Val Gln Glu Thr Pro Gln Thr Gln Asn Leu Tyr Pro Asp Leu Ser
1               5                   10                  15

Glu

<210> SEQ ID NO 147
<211> LENGTH: 18
<212> TYPE: PRT
<213> ORGANISM: Equine infectious anemia virus

<400> SEQUENCE: 147

Val Val Gln Glu Thr Pro Gln Thr Gln Asn Leu Tyr Pro Asp Leu Ser
1               5                   10                  15

Glu Ile

<210> SEQ ID NO 148
<211> LENGTH: 19
<212> TYPE: PRT
<213> ORGANISM: Equine infectious anemia virus

<400> SEQUENCE: 148

Val Val Gln Glu Thr Pro Gln Thr Gln Asn Leu Tyr Pro Asp Leu Ser
1               5                   10                  15

Glu Ile Lys

<210> SEQ ID NO 149
<211> LENGTH: 20
<212> TYPE: PRT
<213> ORGANISM: Equine infectious anemia virus

<400> SEQUENCE: 149

Val Val Gln Glu Thr Pro Gln Thr Gln Asn Leu Tyr Pro Asp Leu Ser
1               5                   10                  15

Glu Ile Lys Lys
            20

<210> SEQ ID NO 150
<211> LENGTH: 16
<212> TYPE: PRT
<213> ORGANISM: Equine infectious anemia virus

<400> SEQUENCE: 150

Ser Val Val Gln Glu Thr Pro Gln Thr Gln Asn Leu Tyr Pro Asp Leu
1               5                   10                  15

<210> SEQ ID NO 151
<211> LENGTH: 17
<212> TYPE: PRT
<213> ORGANISM: Equine infectious anemia virus

<400> SEQUENCE: 151

Ser Val Val Gln Glu Thr Pro Gln Thr Gln Asn Leu Tyr Pro Asp Leu
1               5                   10                  15

Ser

<210> SEQ ID NO 152
<211> LENGTH: 18
<212> TYPE: PRT
<213> ORGANISM: Equine infectious anemia virus

<400> SEQUENCE: 152

Ser Val Val Gln Glu Thr Pro Gln Thr Gln Asn Leu Tyr Pro Asp Leu

```
                1               5                  10                  15
Ser Glu

<210> SEQ ID NO 153
<211> LENGTH: 19
<212> TYPE: PRT
<213> ORGANISM: Equine infectious anemia virus

<400> SEQUENCE: 153

Ser Val Val Gln Glu Thr Pro Gln Thr Gln Asn Leu Tyr Pro Asp Leu
1               5                  10                  15

Ser Glu Ile

<210> SEQ ID NO 154
<211> LENGTH: 20
<212> TYPE: PRT
<213> ORGANISM: Equine infectious anemia virus

<400> SEQUENCE: 154

Ser Val Val Gln Glu Thr Pro Gln Thr Gln Asn Leu Tyr Pro Asp Leu
1               5                  10                  15

Ser Glu Ile Lys
            20

<210> SEQ ID NO 155
<211> LENGTH: 17
<212> TYPE: PRT
<213> ORGANISM: Equine infectious anemia virus

<400> SEQUENCE: 155

Lys Ser Val Val Gln Glu Thr Pro Gln Thr Gln Asn Leu Tyr Pro Asp
1               5                  10                  15

Leu

<210> SEQ ID NO 156
<211> LENGTH: 18
<212> TYPE: PRT
<213> ORGANISM: Equine infectious anemia virus

<400> SEQUENCE: 156

Lys Ser Val Val Gln Glu Thr Pro Gln Thr Gln Asn Leu Tyr Pro Asp
1               5                  10                  15

Leu Ser

<210> SEQ ID NO 157
<211> LENGTH: 19
<212> TYPE: PRT
<213> ORGANISM: Equine infectious anemia virus

<400> SEQUENCE: 157

Lys Ser Val Val Gln Glu Thr Pro Gln Thr Gln Asn Leu Tyr Pro Asp
1               5                  10                  15

Leu Ser Glu

<210> SEQ ID NO 158
<211> LENGTH: 20
<212> TYPE: PRT
<213> ORGANISM: Equine infectious anemia virus

<400> SEQUENCE: 158

Lys Ser Val Val Gln Glu Thr Pro Gln Thr Gln Asn Leu Tyr Pro Asp
```

```
                1               5                  10                 15
Leu Ser Glu Ile
            20

<210> SEQ ID NO 159
<211> LENGTH: 18
<212> TYPE: PRT
<213> ORGANISM: Equine infectious anemia virus

<400> SEQUENCE: 159

Asn Lys Ser Val Val Gln Glu Thr Pro Gln Thr Gln Asn Leu Tyr Pro
1               5                  10                 15

Asp Leu

<210> SEQ ID NO 160
<211> LENGTH: 19
<212> TYPE: PRT
<213> ORGANISM: Equine infectious anemia virus

<400> SEQUENCE: 160

Asn Lys Ser Val Val Gln Glu Thr Pro Gln Thr Gln Asn Leu Tyr Pro
1               5                  10                 15

Asp Leu Ser

<210> SEQ ID NO 161
<211> LENGTH: 20
<212> TYPE: PRT
<213> ORGANISM: Equine infectious anemia virus

<400> SEQUENCE: 161

Asn Lys Ser Val Val Gln Glu Thr Pro Gln Thr Gln Asn Leu Tyr Pro
1               5                  10                 15

Asp Leu Ser Glu
            20

<210> SEQ ID NO 162
<211> LENGTH: 19
<212> TYPE: PRT
<213> ORGANISM: Equine infectious anemia virus

<400> SEQUENCE: 162

His Asn Lys Ser Val Val Gln Glu Thr Pro Gln Thr Gln Asn Leu Tyr
1               5                  10                 15

Pro Asp Leu

<210> SEQ ID NO 163
<211> LENGTH: 20
<212> TYPE: PRT
<213> ORGANISM: Equine infectious anemia virus

<400> SEQUENCE: 163

His Asn Lys Ser Val Val Gln Glu Thr Pro Gln Thr Gln Asn Leu Tyr
1               5                  10                 15

Pro Asp Leu Ser
            20

<210> SEQ ID NO 164
<211> LENGTH: 20
<212> TYPE: PRT
<213> ORGANISM: Equine infectious anemia virus

<400> SEQUENCE: 164
```

Gln His Asn Lys Ser Val Val Gln Glu Thr Pro Gln Thr Gln Asn Leu
1               5                   10                  15

Tyr Pro Asp Leu
            20

<210> SEQ ID NO 165
<211> LENGTH: 8
<212> TYPE: PRT
<213> ORGANISM: Hepatitis C virus

<400> SEQUENCE: 165

Tyr Pro Asp Leu Gly Val Arg Val
1               5

<210> SEQ ID NO 166
<211> LENGTH: 9
<212> TYPE: PRT
<213> ORGANISM: Hepatitis C virus

<400> SEQUENCE: 166

Tyr Pro Asp Leu Gly Val Arg Val Cys
1               5

<210> SEQ ID NO 167
<211> LENGTH: 10
<212> TYPE: PRT
<213> ORGANISM: Hepatitis C virus

<400> SEQUENCE: 167

Tyr Pro Asp Leu Gly Val Arg Val Cys Glu
1               5                   10

<210> SEQ ID NO 168
<211> LENGTH: 11
<212> TYPE: PRT
<213> ORGANISM: Hepatitis C virus

<400> SEQUENCE: 168

Tyr Pro Asp Leu Gly Val Arg Val Cys Glu Lys
1               5                   10

<210> SEQ ID NO 169
<211> LENGTH: 12
<212> TYPE: PRT
<213> ORGANISM: Hepatitis C virus

<400> SEQUENCE: 169

Tyr Pro Asp Leu Gly Val Arg Val Cys Glu Lys Met
1               5                   10

<210> SEQ ID NO 170
<211> LENGTH: 13
<212> TYPE: PRT
<213> ORGANISM: Hepatitis C virus

<400> SEQUENCE: 170

Tyr Pro Asp Leu Gly Val Arg Val Cys Glu Lys Met Ala
1               5                   10

<210> SEQ ID NO 171
<211> LENGTH: 14
<212> TYPE: PRT
<213> ORGANISM: Hepatitis C virus

```
<400> SEQUENCE: 171

Tyr Pro Asp Leu Gly Val Arg Val Cys Glu Lys Met Ala Leu
1               5                   10

<210> SEQ ID NO 172
<211> LENGTH: 15
<212> TYPE: PRT
<213> ORGANISM: Hepatitis C virus

<400> SEQUENCE: 172

Tyr Pro Asp Leu Gly Val Arg Val Cys Glu Lys Met Ala Leu Tyr
1               5                   10                  15

<210> SEQ ID NO 173
<211> LENGTH: 16
<212> TYPE: PRT
<213> ORGANISM: Hepatitis C virus

<400> SEQUENCE: 173

Tyr Pro Asp Leu Gly Val Arg Val Cys Glu Lys Met Ala Leu Tyr Asp
1               5                   10                  15

<210> SEQ ID NO 174
<211> LENGTH: 17
<212> TYPE: PRT
<213> ORGANISM: Hepatitis C virus

<400> SEQUENCE: 174

Tyr Pro Asp Leu Gly Val Arg Val Cys Glu Lys Met Ala Leu Tyr Asp
1               5                   10                  15

Ile

<210> SEQ ID NO 175
<211> LENGTH: 18
<212> TYPE: PRT
<213> ORGANISM: Hepatitis C virus

<400> SEQUENCE: 175

Tyr Pro Asp Leu Gly Val Arg Val Cys Glu Lys Met Ala Leu Tyr Asp
1               5                   10                  15

Ile Thr

<210> SEQ ID NO 176
<211> LENGTH: 19
<212> TYPE: PRT
<213> ORGANISM: Hepatitis C virus

<400> SEQUENCE: 176

Tyr Pro Asp Leu Gly Val Arg Val Cys Glu Lys Met Ala Leu Tyr Asp
1               5                   10                  15

Ile Thr Gln

<210> SEQ ID NO 177
<211> LENGTH: 20
<212> TYPE: PRT
<213> ORGANISM: Hepatitis C virus

<400> SEQUENCE: 177

Tyr Pro Asp Leu Gly Val Arg Val Cys Glu Lys Met Ala Leu Tyr Asp
1               5                   10                  15

Ile Thr Gln Lys
            20
```

```
<210> SEQ ID NO 178
<211> LENGTH: 8
<212> TYPE: PRT
<213> ORGANISM: Hepatitis C virus

<400> SEQUENCE: 178

Val Tyr Pro Asp Leu Gly Val Arg
1               5

<210> SEQ ID NO 179
<211> LENGTH: 9
<212> TYPE: PRT
<213> ORGANISM: Hepatitis C virus

<400> SEQUENCE: 179

Val Tyr Pro Asp Leu Gly Val Arg Val
1               5

<210> SEQ ID NO 180
<211> LENGTH: 10
<212> TYPE: PRT
<213> ORGANISM: Hepatitis C virus

<400> SEQUENCE: 180

Val Tyr Pro Asp Leu Gly Val Arg Val Cys
1               5                   10

<210> SEQ ID NO 181
<211> LENGTH: 11
<212> TYPE: PRT
<213> ORGANISM: Hepatitis C virus

<400> SEQUENCE: 181

Val Tyr Pro Asp Leu Gly Val Arg Val Cys Glu
1               5                   10

<210> SEQ ID NO 182
<211> LENGTH: 12
<212> TYPE: PRT
<213> ORGANISM: Hepatitis C virus

<400> SEQUENCE: 182

Val Tyr Pro Asp Leu Gly Val Arg Val Cys Glu Lys
1               5                   10

<210> SEQ ID NO 183
<211> LENGTH: 13
<212> TYPE: PRT
<213> ORGANISM: Hepatitis C virus

<400> SEQUENCE: 183

Val Tyr Pro Asp Leu Gly Val Arg Val Cys Glu Lys Met
1               5                   10

<210> SEQ ID NO 184
<211> LENGTH: 14
<212> TYPE: PRT
<213> ORGANISM: Hepatitis C virus

<400> SEQUENCE: 184

Val Tyr Pro Asp Leu Gly Val Arg Val Cys Glu Lys Met Ala
1               5                   10
```

```
<210> SEQ ID NO 185
<211> LENGTH: 15
<212> TYPE: PRT
<213> ORGANISM: Hepatitis C virus

<400> SEQUENCE: 185

Val Tyr Pro Asp Leu Gly Val Arg Val Cys Glu Lys Met Ala Leu
1               5                   10                  15

<210> SEQ ID NO 186
<211> LENGTH: 16
<212> TYPE: PRT
<213> ORGANISM: Hepatitis C virus

<400> SEQUENCE: 186

Val Tyr Pro Asp Leu Gly Val Arg Val Cys Glu Lys Met Ala Leu Tyr
1               5                   10                  15

<210> SEQ ID NO 187
<211> LENGTH: 17
<212> TYPE: PRT
<213> ORGANISM: Hepatitis C virus

<400> SEQUENCE: 187

Val Tyr Pro Asp Leu Gly Val Arg Val Cys Glu Lys Met Ala Leu Tyr
1               5                   10                  15

Asp

<210> SEQ ID NO 188
<211> LENGTH: 18
<212> TYPE: PRT
<213> ORGANISM: Hepatitis C virus

<400> SEQUENCE: 188

Val Tyr Pro Asp Leu Gly Val Arg Val Cys Glu Lys Met Ala Leu Tyr
1               5                   10                  15

Asp Ile

<210> SEQ ID NO 189
<211> LENGTH: 19
<212> TYPE: PRT
<213> ORGANISM: Hepatitis C virus

<400> SEQUENCE: 189

Val Tyr Pro Asp Leu Gly Val Arg Val Cys Glu Lys Met Ala Leu Tyr
1               5                   10                  15

Asp Ile Thr

<210> SEQ ID NO 190
<211> LENGTH: 20
<212> TYPE: PRT
<213> ORGANISM: Hepatitis C virus

<400> SEQUENCE: 190

Val Tyr Pro Asp Leu Gly Val Arg Val Cys Glu Lys Met Ala Leu Tyr
1               5                   10                  15

Asp Ile Thr Gln
            20

<210> SEQ ID NO 191
<211> LENGTH: 8
<212> TYPE: PRT
<213> ORGANISM: Hepatitis C virus
```

```
<400> SEQUENCE: 191

Ile Val Tyr Pro Asp Leu Gly Val
1               5

<210> SEQ ID NO 192
<211> LENGTH: 9
<212> TYPE: PRT
<213> ORGANISM: Hepatitis C virus

<400> SEQUENCE: 192

Ile Val Tyr Pro Asp Leu Gly Val Arg
1               5

<210> SEQ ID NO 193
<211> LENGTH: 10
<212> TYPE: PRT
<213> ORGANISM: Hepatitis C virus

<400> SEQUENCE: 193

Ile Val Tyr Pro Asp Leu Gly Val Arg Val
1               5                   10

<210> SEQ ID NO 194
<211> LENGTH: 11
<212> TYPE: PRT
<213> ORGANISM: Hepatitis C virus

<400> SEQUENCE: 194

Ile Val Tyr Pro Asp Leu Gly Val Arg Val Cys
1               5                   10

<210> SEQ ID NO 195
<211> LENGTH: 12
<212> TYPE: PRT
<213> ORGANISM: Hepatitis C virus

<400> SEQUENCE: 195

Ile Val Tyr Pro Asp Leu Gly Val Arg Val Cys Glu
1               5                   10

<210> SEQ ID NO 196
<211> LENGTH: 13
<212> TYPE: PRT
<213> ORGANISM: Hepatitis C virus

<400> SEQUENCE: 196

Ile Val Tyr Pro Asp Leu Gly Val Arg Val Cys Glu Lys
1               5                   10

<210> SEQ ID NO 197
<211> LENGTH: 14
<212> TYPE: PRT
<213> ORGANISM: Hepatitis C virus

<400> SEQUENCE: 197

Ile Val Tyr Pro Asp Leu Gly Val Arg Val Cys Glu Lys Met
1               5                   10

<210> SEQ ID NO 198
<211> LENGTH: 15
<212> TYPE: PRT
<213> ORGANISM: Hepatitis C virus

<400> SEQUENCE: 198
```

```
Ile Val Tyr Pro Asp Leu Gly Val Arg Val Cys Glu Lys Met Ala
1               5                   10                  15

<210> SEQ ID NO 199
<211> LENGTH: 16
<212> TYPE: PRT
<213> ORGANISM: Hepatitis C virus

<400> SEQUENCE: 199

Ile Val Tyr Pro Asp Leu Gly Val Arg Val Cys Glu Lys Met Ala Leu
1               5                   10                  15

<210> SEQ ID NO 200
<211> LENGTH: 17
<212> TYPE: PRT
<213> ORGANISM: Hepatitis C virus

<400> SEQUENCE: 200

Ile Val Tyr Pro Asp Leu Gly Val Arg Val Cys Glu Lys Met Ala Leu
1               5                   10                  15

Tyr

<210> SEQ ID NO 201
<211> LENGTH: 18
<212> TYPE: PRT
<213> ORGANISM: Hepatitis C virus

<400> SEQUENCE: 201

Ile Val Tyr Pro Asp Leu Gly Val Arg Val Cys Glu Lys Met Ala Leu
1               5                   10                  15

Tyr Asp

<210> SEQ ID NO 202
<211> LENGTH: 19
<212> TYPE: PRT
<213> ORGANISM: Hepatitis C virus

<400> SEQUENCE: 202

Ile Val Tyr Pro Asp Leu Gly Val Arg Val Cys Glu Lys Met Ala Leu
1               5                   10                  15

Tyr Asp Ile

<210> SEQ ID NO 203
<211> LENGTH: 20
<212> TYPE: PRT
<213> ORGANISM: Hepatitis C virus

<400> SEQUENCE: 203

Ile Val Tyr Pro Asp Leu Gly Val Arg Val Cys Glu Lys Met Ala Leu
1               5                   10                  15

Tyr Asp Ile Thr
            20

<210> SEQ ID NO 204
<211> LENGTH: 8
<212> TYPE: PRT
<213> ORGANISM: Hepatitis C virus

<400> SEQUENCE: 204

Leu Ile Val Tyr Pro Asp Leu Gly
1               5
```

-continued

```
<210> SEQ ID NO 205
<211> LENGTH: 9
<212> TYPE: PRT
<213> ORGANISM: Hepatitis C virus

<400> SEQUENCE: 205

Leu Ile Val Tyr Pro Asp Leu Gly Val
1               5

<210> SEQ ID NO 206
<211> LENGTH: 10
<212> TYPE: PRT
<213> ORGANISM: Hepatitis C virus

<400> SEQUENCE: 206

Leu Ile Val Tyr Pro Asp Leu Gly Val Arg
1               5                   10

<210> SEQ ID NO 207
<211> LENGTH: 11
<212> TYPE: PRT
<213> ORGANISM: Hepatitis C virus

<400> SEQUENCE: 207

Leu Ile Val Tyr Pro Asp Leu Gly Val Arg Val
1               5                   10

<210> SEQ ID NO 208
<211> LENGTH: 12
<212> TYPE: PRT
<213> ORGANISM: Hepatitis C virus

<400> SEQUENCE: 208

Leu Ile Val Tyr Pro Asp Leu Gly Val Arg Val Cys
1               5                   10

<210> SEQ ID NO 209
<211> LENGTH: 13
<212> TYPE: PRT
<213> ORGANISM: Hepatitis C virus

<400> SEQUENCE: 209

Leu Ile Val Tyr Pro Asp Leu Gly Val Arg Val Cys Glu
1               5                   10

<210> SEQ ID NO 210
<211> LENGTH: 14
<212> TYPE: PRT
<213> ORGANISM: Hepatitis C virus

<400> SEQUENCE: 210

Leu Ile Val Tyr Pro Asp Leu Gly Val Arg Val Cys Glu Lys
1               5                   10

<210> SEQ ID NO 211
<211> LENGTH: 15
<212> TYPE: PRT
<213> ORGANISM: Hepatitis C virus

<400> SEQUENCE: 211

Leu Ile Val Tyr Pro Asp Leu Gly Val Arg Val Cys Glu Lys Met
1               5                   10                  15

<210> SEQ ID NO 212
```

```
<211> LENGTH: 16
<212> TYPE: PRT
<213> ORGANISM: Hepatitis C virus

<400> SEQUENCE: 212

Leu Ile Val Tyr Pro Asp Leu Gly Val Arg Val Cys Glu Lys Met Ala
1               5                   10                  15

<210> SEQ ID NO 213
<211> LENGTH: 17
<212> TYPE: PRT
<213> ORGANISM: Hepatitis C virus

<400> SEQUENCE: 213

Leu Ile Val Tyr Pro Asp Leu Gly Val Arg Val Cys Glu Lys Met Ala
1               5                   10                  15

Leu

<210> SEQ ID NO 214
<211> LENGTH: 18
<212> TYPE: PRT
<213> ORGANISM: Hepatitis C virus

<400> SEQUENCE: 214

Leu Ile Val Tyr Pro Asp Leu Gly Val Arg Val Cys Glu Lys Met Ala
1               5                   10                  15

Leu Tyr

<210> SEQ ID NO 215
<211> LENGTH: 19
<212> TYPE: PRT
<213> ORGANISM: Hepatitis C virus

<400> SEQUENCE: 215

Leu Ile Val Tyr Pro Asp Leu Gly Val Arg Val Cys Glu Lys Met Ala
1               5                   10                  15

Leu Tyr Asp

<210> SEQ ID NO 216
<211> LENGTH: 20
<212> TYPE: PRT
<213> ORGANISM: Hepatitis C virus

<400> SEQUENCE: 216

Leu Ile Val Tyr Pro Asp Leu Gly Val Arg Val Cys Glu Lys Met Ala
1               5                   10                  15

Leu Tyr Asp Ile
            20

<210> SEQ ID NO 217
<211> LENGTH: 8
<212> TYPE: PRT
<213> ORGANISM: Hepatitis C virus

<400> SEQUENCE: 217

Arg Leu Ile Val Tyr Pro Asp Leu
1               5

<210> SEQ ID NO 218
<211> LENGTH: 9
<212> TYPE: PRT
<213> ORGANISM: Hepatitis C virus
```

-continued

```
<400> SEQUENCE: 218

Arg Leu Ile Val Tyr Pro Asp Leu Gly
1               5

<210> SEQ ID NO 219
<211> LENGTH: 10
<212> TYPE: PRT
<213> ORGANISM: Hepatitis C virus

<400> SEQUENCE: 219

Arg Leu Ile Val Tyr Pro Asp Leu Gly Val
1               5                   10

<210> SEQ ID NO 220
<211> LENGTH: 11
<212> TYPE: PRT
<213> ORGANISM: Hepatitis C virus

<400> SEQUENCE: 220

Arg Leu Ile Val Tyr Pro Asp Leu Gly Val Arg
1               5                   10

<210> SEQ ID NO 221
<211> LENGTH: 12
<212> TYPE: PRT
<213> ORGANISM: Hepatitis C virus

<400> SEQUENCE: 221

Arg Leu Ile Val Tyr Pro Asp Leu Gly Val Arg Val
1               5                   10

<210> SEQ ID NO 222
<211> LENGTH: 13
<212> TYPE: PRT
<213> ORGANISM: Hepatitis C virus

<400> SEQUENCE: 222

Arg Leu Ile Val Tyr Pro Asp Leu Gly Val Arg Val Cys
1               5                   10

<210> SEQ ID NO 223
<211> LENGTH: 14
<212> TYPE: PRT
<213> ORGANISM: Hepatitis C virus

<400> SEQUENCE: 223

Arg Leu Ile Val Tyr Pro Asp Leu Gly Val Arg Val Cys Glu
1               5                   10

<210> SEQ ID NO 224
<211> LENGTH: 15
<212> TYPE: PRT
<213> ORGANISM: Hepatitis C virus

<400> SEQUENCE: 224

Arg Leu Ile Val Tyr Pro Asp Leu Gly Val Arg Val Cys Glu Lys
1               5                   10                  15

<210> SEQ ID NO 225
<211> LENGTH: 16
<212> TYPE: PRT
<213> ORGANISM: Hepatitis C virus

<400> SEQUENCE: 225
```

```
Arg Leu Ile Val Tyr Pro Asp Leu Gly Val Arg Val Cys Glu Lys Met
1               5                   10                  15

<210> SEQ ID NO 226
<211> LENGTH: 17
<212> TYPE: PRT
<213> ORGANISM: Hepatitis C virus

<400> SEQUENCE: 226

Arg Leu Ile Val Tyr Pro Asp Leu Gly Val Arg Val Cys Glu Lys Met
1               5                   10                  15

Ala

<210> SEQ ID NO 227
<211> LENGTH: 18
<212> TYPE: PRT
<213> ORGANISM: Hepatitis C virus

<400> SEQUENCE: 227

Arg Leu Ile Val Tyr Pro Asp Leu Gly Val Arg Val Cys Glu Lys Met
1               5                   10                  15

Ala Leu

<210> SEQ ID NO 228
<211> LENGTH: 19
<212> TYPE: PRT
<213> ORGANISM: Hepatitis C virus

<400> SEQUENCE: 228

Arg Leu Ile Val Tyr Pro Asp Leu Gly Val Arg Val Cys Glu Lys Met
1               5                   10                  15

Ala Leu Tyr

<210> SEQ ID NO 229
<211> LENGTH: 20
<212> TYPE: PRT
<213> ORGANISM: Hepatitis C virus

<400> SEQUENCE: 229

Arg Leu Ile Val Tyr Pro Asp Leu Gly Val Arg Val Cys Glu Lys Met
1               5                   10                  15

Ala Leu Tyr Asp
            20

<210> SEQ ID NO 230
<211> LENGTH: 9
<212> TYPE: PRT
<213> ORGANISM: Hepatitis C virus

<400> SEQUENCE: 230

Ala Arg Leu Ile Val Tyr Pro Asp Leu
1               5

<210> SEQ ID NO 231
<211> LENGTH: 10
<212> TYPE: PRT
<213> ORGANISM: Hepatitis C virus

<400> SEQUENCE: 231

Ala Arg Leu Ile Val Tyr Pro Asp Leu Gly
1               5                   10
```

<210> SEQ ID NO 232
<211> LENGTH: 11
<212> TYPE: PRT
<213> ORGANISM: Hepatitis C virus

<400> SEQUENCE: 232

Ala Arg Leu Ile Val Tyr Pro Asp Leu Gly Val
1               5                   10

<210> SEQ ID NO 233
<211> LENGTH: 12
<212> TYPE: PRT
<213> ORGANISM: Hepatitis C virus

<400> SEQUENCE: 233

Ala Arg Leu Ile Val Tyr Pro Asp Leu Gly Val Arg
1               5                   10

<210> SEQ ID NO 234
<211> LENGTH: 13
<212> TYPE: PRT
<213> ORGANISM: Hepatitis C virus

<400> SEQUENCE: 234

Ala Arg Leu Ile Val Tyr Pro Asp Leu Gly Val Arg Val
1               5                   10

<210> SEQ ID NO 235
<211> LENGTH: 14
<212> TYPE: PRT
<213> ORGANISM: Hepatitis C virus

<400> SEQUENCE: 235

Ala Arg Leu Ile Val Tyr Pro Asp Leu Gly Val Arg Val Cys
1               5                   10

<210> SEQ ID NO 236
<211> LENGTH: 15
<212> TYPE: PRT
<213> ORGANISM: Hepatitis C virus

<400> SEQUENCE: 236

Ala Arg Leu Ile Val Tyr Pro Asp Leu Gly Val Arg Val Cys Glu
1               5                   10                  15

<210> SEQ ID NO 237
<211> LENGTH: 16
<212> TYPE: PRT
<213> ORGANISM: Hepatitis C virus

<400> SEQUENCE: 237

Ala Arg Leu Ile Val Tyr Pro Asp Leu Gly Val Arg Val Cys Glu Lys
1               5                   10                  15

<210> SEQ ID NO 238
<211> LENGTH: 17
<212> TYPE: PRT
<213> ORGANISM: Hepatitis C virus

<400> SEQUENCE: 238

Ala Arg Leu Ile Val Tyr Pro Asp Leu Gly Val Arg Val Cys Glu Lys
1               5                   10                  15
Met

```
<210> SEQ ID NO 239
<211> LENGTH: 18
<212> TYPE: PRT
<213> ORGANISM: Hepatitis C virus

<400> SEQUENCE: 239

Ala Arg Leu Ile Val Tyr Pro Asp Leu Gly Val Arg Val Cys Glu Lys
1               5                   10                  15
Met Ala

<210> SEQ ID NO 240
<211> LENGTH: 19
<212> TYPE: PRT
<213> ORGANISM: Hepatitis C virus

<400> SEQUENCE: 240

Ala Arg Leu Ile Val Tyr Pro Asp Leu Gly Val Arg Val Cys Glu Lys
1               5                   10                  15
Met Ala Leu

<210> SEQ ID NO 241
<211> LENGTH: 20
<212> TYPE: PRT
<213> ORGANISM: Hepatitis C virus

<400> SEQUENCE: 241

Ala Arg Leu Ile Val Tyr Pro Asp Leu Gly Val Arg Val Cys Glu Lys
1               5                   10                  15
Met Ala Leu Tyr
            20

<210> SEQ ID NO 242
<211> LENGTH: 10
<212> TYPE: PRT
<213> ORGANISM: Hepatitis C virus

<400> SEQUENCE: 242

Ala Ala Arg Leu Ile Val Tyr Pro Asp Leu
1               5                   10

<210> SEQ ID NO 243
<211> LENGTH: 11
<212> TYPE: PRT
<213> ORGANISM: Hepatitis C virus

<400> SEQUENCE: 243

Ala Ala Arg Leu Ile Val Tyr Pro Asp Leu Gly
1               5                   10

<210> SEQ ID NO 244
<211> LENGTH: 12
<212> TYPE: PRT
<213> ORGANISM: Hepatitis C virus

<400> SEQUENCE: 244

Ala Ala Arg Leu Ile Val Tyr Pro Asp Leu Gly Val
1               5                   10

<210> SEQ ID NO 245
<211> LENGTH: 13
<212> TYPE: PRT
<213> ORGANISM: Hepatitis C virus

<400> SEQUENCE: 245
```

```
Ala Ala Arg Leu Ile Val Tyr Pro Asp Leu Gly Val Arg
1               5                   10
```

<210> SEQ ID NO 246
<211> LENGTH: 14
<212> TYPE: PRT
<213> ORGANISM: Hepatitis C virus

<400> SEQUENCE: 246

```
Ala Ala Arg Leu Ile Val Tyr Pro Asp Leu Gly Val Arg Val
1               5                   10
```

<210> SEQ ID NO 247
<211> LENGTH: 15
<212> TYPE: PRT
<213> ORGANISM: Hepatitis C virus

<400> SEQUENCE: 247

```
Ala Ala Arg Leu Ile Val Tyr Pro Asp Leu Gly Val Arg Val Cys
1               5                   10                  15
```

<210> SEQ ID NO 248
<211> LENGTH: 16
<212> TYPE: PRT
<213> ORGANISM: Hepatitis C virus

<400> SEQUENCE: 248

```
Ala Ala Arg Leu Ile Val Tyr Pro Asp Leu Gly Val Arg Val Cys Glu
1               5                   10                  15
```

<210> SEQ ID NO 249
<211> LENGTH: 17
<212> TYPE: PRT
<213> ORGANISM: Hepatitis C virus

<400> SEQUENCE: 249

```
Ala Ala Arg Leu Ile Val Tyr Pro Asp Leu Gly Val Arg Val Cys Glu
1               5                   10                  15

Lys
```

<210> SEQ ID NO 250
<211> LENGTH: 18
<212> TYPE: PRT
<213> ORGANISM: Hepatitis C virus

<400> SEQUENCE: 250

```
Ala Ala Arg Leu Ile Val Tyr Pro Asp Leu Gly Val Arg Val Cys Glu
1               5                   10                  15

Lys Met
```

<210> SEQ ID NO 251
<211> LENGTH: 19
<212> TYPE: PRT
<213> ORGANISM: Hepatitis C virus

<400> SEQUENCE: 251

```
Ala Ala Arg Leu Ile Val Tyr Pro Asp Leu Gly Val Arg Val Cys Glu
1               5                   10                  15

Lys Met Ala
```

<210> SEQ ID NO 252
<211> LENGTH: 20

<212> TYPE: PRT
<213> ORGANISM: Hepatitis C virus

<400> SEQUENCE: 252

```
Ala Ala Arg Leu Ile Val Tyr Pro Asp Leu Gly Val Arg Val Cys Glu
1               5                   10                  15
Lys Met Ala Leu
            20
```

<210> SEQ ID NO 253
<211> LENGTH: 11
<212> TYPE: PRT
<213> ORGANISM: Hepatitis C virus

<400> SEQUENCE: 253

```
Lys Ala Ala Arg Leu Ile Val Tyr Pro Asp Leu
1               5                   10
```

<210> SEQ ID NO 254
<211> LENGTH: 12
<212> TYPE: PRT
<213> ORGANISM: Hepatitis C virus

<400> SEQUENCE: 254

```
Lys Ala Ala Arg Leu Ile Val Tyr Pro Asp Leu Gly
1               5                   10
```

<210> SEQ ID NO 255
<211> LENGTH: 13
<212> TYPE: PRT
<213> ORGANISM: Hepatitis C virus

<400> SEQUENCE: 255

```
Lys Ala Ala Arg Leu Ile Val Tyr Pro Asp Leu Gly Val
1               5                   10
```

<210> SEQ ID NO 256
<211> LENGTH: 14
<212> TYPE: PRT
<213> ORGANISM: Hepatitis C virus

<400> SEQUENCE: 256

```
Lys Ala Ala Arg Leu Ile Val Tyr Pro Asp Leu Gly Val Arg
1               5                   10
```

<210> SEQ ID NO 257
<211> LENGTH: 15
<212> TYPE: PRT
<213> ORGANISM: Hepatitis C virus

<400> SEQUENCE: 257

```
Lys Ala Ala Arg Leu Ile Val Tyr Pro Asp Leu Gly Val Arg Val
1               5                   10                  15
```

<210> SEQ ID NO 258
<211> LENGTH: 16
<212> TYPE: PRT
<213> ORGANISM: Hepatitis C virus

<400> SEQUENCE: 258

```
Lys Ala Ala Arg Leu Ile Val Tyr Pro Asp Leu Gly Val Arg Val Cys
1               5                   10                  15
```

<210> SEQ ID NO 259

```
<211> LENGTH: 17
<212> TYPE: PRT
<213> ORGANISM: Hepatitis C virus

<400> SEQUENCE: 259

Lys Ala Ala Arg Leu Ile Val Tyr Pro Asp Leu Gly Val Arg Val Cys
1               5                   10                  15
Glu

<210> SEQ ID NO 260
<211> LENGTH: 18
<212> TYPE: PRT
<213> ORGANISM: Hepatitis C virus

<400> SEQUENCE: 260

Lys Ala Ala Arg Leu Ile Val Tyr Pro Asp Leu Gly Val Arg Val Cys
1               5                   10                  15
Glu Lys

<210> SEQ ID NO 261
<211> LENGTH: 19
<212> TYPE: PRT
<213> ORGANISM: Hepatitis C virus

<400> SEQUENCE: 261

Lys Ala Ala Arg Leu Ile Val Tyr Pro Asp Leu Gly Val Arg Val Cys
1               5                   10                  15
Glu Lys Met

<210> SEQ ID NO 262
<211> LENGTH: 20
<212> TYPE: PRT
<213> ORGANISM: Hepatitis C virus

<400> SEQUENCE: 262

Lys Ala Ala Arg Leu Ile Val Tyr Pro Asp Leu Gly Val Arg Val Cys
1               5                   10                  15
Glu Lys Met Ala
            20

<210> SEQ ID NO 263
<211> LENGTH: 12
<212> TYPE: PRT
<213> ORGANISM: Hepatitis C virus

<400> SEQUENCE: 263

Lys Lys Ala Ala Arg Leu Ile Val Tyr Pro Asp Leu
1               5                   10

<210> SEQ ID NO 264
<211> LENGTH: 13
<212> TYPE: PRT
<213> ORGANISM: Hepatitis C virus

<400> SEQUENCE: 264

Lys Lys Ala Ala Arg Leu Ile Val Tyr Pro Asp Leu Gly
1               5                   10

<210> SEQ ID NO 265
<211> LENGTH: 14
<212> TYPE: PRT
<213> ORGANISM: Hepatitis C virus
```

```
<400> SEQUENCE: 265

Lys Lys Ala Ala Arg Leu Ile Val Tyr Pro Asp Leu Gly Val
1               5                   10

<210> SEQ ID NO 266
<211> LENGTH: 15
<212> TYPE: PRT
<213> ORGANISM: Hepatitis C virus

<400> SEQUENCE: 266

Lys Lys Ala Ala Arg Leu Ile Val Tyr Pro Asp Leu Gly Val Arg
1               5                   10                  15

<210> SEQ ID NO 267
<211> LENGTH: 16
<212> TYPE: PRT
<213> ORGANISM: Hepatitis C virus

<400> SEQUENCE: 267

Lys Lys Ala Ala Arg Leu Ile Val Tyr Pro Asp Leu Gly Val Arg Val
1               5                   10                  15

<210> SEQ ID NO 268
<211> LENGTH: 17
<212> TYPE: PRT
<213> ORGANISM: Hepatitis C virus

<400> SEQUENCE: 268

Lys Lys Ala Ala Arg Leu Ile Val Tyr Pro Asp Leu Gly Val Arg Val
1               5                   10                  15

Cys

<210> SEQ ID NO 269
<211> LENGTH: 18
<212> TYPE: PRT
<213> ORGANISM: Hepatitis C virus

<400> SEQUENCE: 269

Lys Lys Ala Ala Arg Leu Ile Val Tyr Pro Asp Leu Gly Val Arg Val
1               5                   10                  15

Cys Glu

<210> SEQ ID NO 270
<211> LENGTH: 19
<212> TYPE: PRT
<213> ORGANISM: Hepatitis C virus

<400> SEQUENCE: 270

Lys Lys Ala Ala Arg Leu Ile Val Tyr Pro Asp Leu Gly Val Arg Val
1               5                   10                  15

Cys Glu Lys

<210> SEQ ID NO 271
<211> LENGTH: 20
<212> TYPE: PRT
<213> ORGANISM: Hepatitis C virus

<400> SEQUENCE: 271

Lys Lys Ala Ala Arg Leu Ile Val Tyr Pro Asp Leu Gly Val Arg Val
1               5                   10                  15

Cys Glu Lys Met
            20
```

<210> SEQ ID NO 272
<211> LENGTH: 13
<212> TYPE: PRT
<213> ORGANISM: Hepatitis C virus

<400> SEQUENCE: 272

Gly Lys Lys Ala Ala Arg Leu Ile Val Tyr Pro Asp Leu
1               5                   10

<210> SEQ ID NO 273
<211> LENGTH: 14
<212> TYPE: PRT
<213> ORGANISM: Hepatitis C virus

<400> SEQUENCE: 273

Gly Lys Lys Ala Ala Arg Leu Ile Val Tyr Pro Asp Leu Gly
1               5                   10

<210> SEQ ID NO 274
<211> LENGTH: 15
<212> TYPE: PRT
<213> ORGANISM: Hepatitis C virus

<400> SEQUENCE: 274

Gly Lys Lys Ala Ala Arg Leu Ile Val Tyr Pro Asp Leu Gly Val
1               5                   10                  15

<210> SEQ ID NO 275
<211> LENGTH: 16
<212> TYPE: PRT
<213> ORGANISM: Hepatitis C virus

<400> SEQUENCE: 275

Gly Lys Lys Ala Ala Arg Leu Ile Val Tyr Pro Asp Leu Gly Val Arg
1               5                   10                  15

<210> SEQ ID NO 276
<211> LENGTH: 17
<212> TYPE: PRT
<213> ORGANISM: Hepatitis C virus

<400> SEQUENCE: 276

Gly Lys Lys Ala Ala Arg Leu Ile Val Tyr Pro Asp Leu Gly Val Arg
1               5                   10                  15

Val

<210> SEQ ID NO 277
<211> LENGTH: 18
<212> TYPE: PRT
<213> ORGANISM: Hepatitis C virus

<400> SEQUENCE: 277

Gly Lys Lys Ala Ala Arg Leu Ile Val Tyr Pro Asp Leu Gly Val Arg
1               5                   10                  15

Val Cys

<210> SEQ ID NO 278
<211> LENGTH: 19
<212> TYPE: PRT
<213> ORGANISM: Hepatitis C virus

<400> SEQUENCE: 278

Gly Lys Lys Ala Ala Arg Leu Ile Val Tyr Pro Asp Leu Gly Val Arg
1               5                   10                  15

Val Cys Glu

<210> SEQ ID NO 279
<211> LENGTH: 20
<212> TYPE: PRT
<213> ORGANISM: Hepatitis C virus

<400> SEQUENCE: 279

Gly Lys Lys Ala Ala Arg Leu Ile Val Tyr Pro Asp Leu Gly Val Arg
1               5                   10                  15

Val Cys Glu Lys
            20

<210> SEQ ID NO 280
<211> LENGTH: 14
<212> TYPE: PRT
<213> ORGANISM: Hepatitis C virus

<400> SEQUENCE: 280

Gly Gly Lys Lys Ala Ala Arg Leu Ile Val Tyr Pro Asp Leu
1               5                   10

<210> SEQ ID NO 281
<211> LENGTH: 15
<212> TYPE: PRT
<213> ORGANISM: Hepatitis C virus

<400> SEQUENCE: 281

Gly Gly Lys Lys Ala Ala Arg Leu Ile Val Tyr Pro Asp Leu Gly
1               5                   10                  15

<210> SEQ ID NO 282
<211> LENGTH: 16
<212> TYPE: PRT
<213> ORGANISM: Hepatitis C virus

<400> SEQUENCE: 282

Gly Gly Lys Lys Ala Ala Arg Leu Ile Val Tyr Pro Asp Leu Gly Val
1               5                   10                  15

<210> SEQ ID NO 283
<211> LENGTH: 17
<212> TYPE: PRT
<213> ORGANISM: Hepatitis C virus

<400> SEQUENCE: 283

Gly Gly Lys Lys Ala Ala Arg Leu Ile Val Tyr Pro Asp Leu Gly Val
1               5                   10                  15

Arg

<210> SEQ ID NO 284
<211> LENGTH: 18
<212> TYPE: PRT
<213> ORGANISM: Hepatitis C virus

<400> SEQUENCE: 284

Gly Gly Lys Lys Ala Ala Arg Leu Ile Val Tyr Pro Asp Leu Gly Val
1               5                   10                  15

Arg Val

```
<210> SEQ ID NO 285
<211> LENGTH: 19
<212> TYPE: PRT
<213> ORGANISM: Hepatitis C virus

<400> SEQUENCE: 285

Gly Gly Lys Lys Ala Ala Arg Leu Ile Val Tyr Pro Asp Leu Gly Val
1               5                   10                  15
Arg Val Cys

<210> SEQ ID NO 286
<211> LENGTH: 20
<212> TYPE: PRT
<213> ORGANISM: Hepatitis C virus

<400> SEQUENCE: 286

Gly Gly Lys Lys Ala Ala Arg Leu Ile Val Tyr Pro Asp Leu Gly Val
1               5                   10                  15
Arg Val Cys Glu
            20

<210> SEQ ID NO 287
<211> LENGTH: 15
<212> TYPE: PRT
<213> ORGANISM: Hepatitis C virus

<400> SEQUENCE: 287

Lys Gly Gly Lys Lys Ala Ala Arg Leu Ile Val Tyr Pro Asp Leu
1               5                   10                  15

<210> SEQ ID NO 288
<211> LENGTH: 16
<212> TYPE: PRT
<213> ORGANISM: Hepatitis C virus

<400> SEQUENCE: 288

Lys Gly Gly Lys Lys Ala Ala Arg Leu Ile Val Tyr Pro Asp Leu Gly
1               5                   10                  15

<210> SEQ ID NO 289
<211> LENGTH: 17
<212> TYPE: PRT
<213> ORGANISM: Hepatitis C virus

<400> SEQUENCE: 289

Lys Gly Gly Lys Lys Ala Ala Arg Leu Ile Val Tyr Pro Asp Leu Gly
1               5                   10                  15
Val

<210> SEQ ID NO 290
<211> LENGTH: 18
<212> TYPE: PRT
<213> ORGANISM: Hepatitis C virus

<400> SEQUENCE: 290

Lys Gly Gly Lys Lys Ala Ala Arg Leu Ile Val Tyr Pro Asp Leu Gly
1               5                   10                  15
Val Arg

<210> SEQ ID NO 291
<211> LENGTH: 19
<212> TYPE: PRT
<213> ORGANISM: Hepatitis C virus
```

```
<400> SEQUENCE: 291

Lys Gly Gly Lys Lys Ala Ala Arg Leu Ile Val Tyr Pro Asp Leu Gly
1               5                   10                  15

Val Arg Val

<210> SEQ ID NO 292
<211> LENGTH: 20
<212> TYPE: PRT
<213> ORGANISM: Hepatitis C virus

<400> SEQUENCE: 292

Lys Gly Gly Lys Lys Ala Ala Arg Leu Ile Val Tyr Pro Asp Leu Gly
1               5                   10                  15

Val Arg Val Cys
            20

<210> SEQ ID NO 293
<211> LENGTH: 16
<212> TYPE: PRT
<213> ORGANISM: Hepatitis C virus

<400> SEQUENCE: 293

Thr Lys Gly Gly Lys Lys Ala Ala Arg Leu Ile Val Tyr Pro Asp Leu
1               5                   10                  15

<210> SEQ ID NO 294
<211> LENGTH: 17
<212> TYPE: PRT
<213> ORGANISM: Hepatitis C virus

<400> SEQUENCE: 294

Thr Lys Gly Gly Lys Lys Ala Ala Arg Leu Ile Val Tyr Pro Asp Leu
1               5                   10                  15

Gly

<210> SEQ ID NO 295
<211> LENGTH: 18
<212> TYPE: PRT
<213> ORGANISM: Hepatitis C virus

<400> SEQUENCE: 295

Thr Lys Gly Gly Lys Lys Ala Ala Arg Leu Ile Val Tyr Pro Asp Leu
1               5                   10                  15

Gly Val

<210> SEQ ID NO 296
<211> LENGTH: 19
<212> TYPE: PRT
<213> ORGANISM: Hepatitis C virus

<400> SEQUENCE: 296

Thr Lys Gly Gly Lys Lys Ala Ala Arg Leu Ile Val Tyr Pro Asp Leu
1               5                   10                  15

Gly Val Arg

<210> SEQ ID NO 297
<211> LENGTH: 20
<212> TYPE: PRT
<213> ORGANISM: Hepatitis C virus

<400> SEQUENCE: 297
```

```
Thr Lys Gly Gly Lys Lys Ala Ala Arg Leu Ile Val Tyr Pro Asp Leu
1               5                   10                  15

Gly Val Arg Val
            20

<210> SEQ ID NO 298
<211> LENGTH: 17
<212> TYPE: PRT
<213> ORGANISM: Hepatitis C virus

<400> SEQUENCE: 298

Pro Thr Lys Gly Gly Lys Lys Ala Ala Arg Leu Ile Val Tyr Pro Asp
1               5                   10                  15

Leu

<210> SEQ ID NO 299
<211> LENGTH: 18
<212> TYPE: PRT
<213> ORGANISM: Hepatitis C virus

<400> SEQUENCE: 299

Pro Thr Lys Gly Gly Lys Lys Ala Ala Arg Leu Ile Val Tyr Pro Asp
1               5                   10                  15

Leu Gly

<210> SEQ ID NO 300
<211> LENGTH: 19
<212> TYPE: PRT
<213> ORGANISM: Hepatitis C virus

<400> SEQUENCE: 300

Pro Thr Lys Gly Gly Lys Lys Ala Ala Arg Leu Ile Val Tyr Pro Asp
1               5                   10                  15

Leu Gly Val

<210> SEQ ID NO 301
<211> LENGTH: 20
<212> TYPE: PRT
<213> ORGANISM: Hepatitis C virus

<400> SEQUENCE: 301

Pro Thr Lys Gly Gly Lys Lys Ala Ala Arg Leu Ile Val Tyr Pro Asp
1               5                   10                  15

Leu Gly Val Arg
            20

<210> SEQ ID NO 302
<211> LENGTH: 18
<212> TYPE: PRT
<213> ORGANISM: Hepatitis C virus

<400> SEQUENCE: 302

Asp Pro Thr Lys Gly Gly Lys Lys Ala Ala Arg Leu Ile Val Tyr Pro
1               5                   10                  15

Asp Leu

<210> SEQ ID NO 303
<211> LENGTH: 19
<212> TYPE: PRT
<213> ORGANISM: Hepatitis C virus
```

-continued

```
<400> SEQUENCE: 303

Asp Pro Thr Lys Gly Gly Lys Lys Ala Ala Arg Leu Ile Val Tyr Pro
1               5                   10                  15

Asp Leu Gly

<210> SEQ ID NO 304
<211> LENGTH: 20
<212> TYPE: PRT
<213> ORGANISM: Hepatitis C virus

<400> SEQUENCE: 304

Asp Pro Thr Lys Gly Gly Lys Lys Ala Ala Arg Leu Ile Val Tyr Pro
1               5                   10                  15

Asp Leu Gly Val
            20

<210> SEQ ID NO 305
<211> LENGTH: 19
<212> TYPE: PRT
<213> ORGANISM: Hepatitis C virus

<400> SEQUENCE: 305

Val Asp Pro Thr Lys Gly Gly Lys Lys Ala Ala Arg Leu Ile Val Tyr
1               5                   10                  15

Pro Asp Leu

<210> SEQ ID NO 306
<211> LENGTH: 20
<212> TYPE: PRT
<213> ORGANISM: Hepatitis C virus

<400> SEQUENCE: 306

Val Asp Pro Thr Lys Gly Gly Lys Lys Ala Ala Arg Leu Ile Val Tyr
1               5                   10                  15

Pro Asp Leu Gly
            20

<210> SEQ ID NO 307
<211> LENGTH: 20
<212> TYPE: PRT
<213> ORGANISM: Hepatitis C virus

<400> SEQUENCE: 307

Cys Val Asp Pro Thr Lys Gly Gly Lys Lys Ala Ala Arg Leu Ile Val
1               5                   10                  15

Tyr Pro Asp Leu
            20

<210> SEQ ID NO 308
<211> LENGTH: 8
<212> TYPE: PRT
<213> ORGANISM: human herpesvirus 2

<400> SEQUENCE: 308

Tyr Pro Asp Leu Arg Arg Val Glu
1               5

<210> SEQ ID NO 309
<211> LENGTH: 9
<212> TYPE: PRT
<213> ORGANISM: human herpesvirus 2
```

-continued

<400> SEQUENCE: 309

Tyr Pro Asp Leu Arg Arg Val Glu Leu
1               5

<210> SEQ ID NO 310
<211> LENGTH: 10
<212> TYPE: PRT
<213> ORGANISM: human herpesvirus 2

<400> SEQUENCE: 310

Tyr Pro Asp Leu Arg Arg Val Glu Leu Thr
1               5                   10

<210> SEQ ID NO 311
<211> LENGTH: 11
<212> TYPE: PRT
<213> ORGANISM: human herpesvirus 2

<400> SEQUENCE: 311

Tyr Pro Asp Leu Arg Arg Val Glu Leu Thr Val
1               5                   10

<210> SEQ ID NO 312
<211> LENGTH: 12
<212> TYPE: PRT
<213> ORGANISM: human herpesvirus 2

<400> SEQUENCE: 312

Tyr Pro Asp Leu Arg Arg Val Glu Leu Thr Val Thr
1               5                   10

<210> SEQ ID NO 313
<211> LENGTH: 13
<212> TYPE: PRT
<213> ORGANISM: human herpesvirus 2

<400> SEQUENCE: 313

Tyr Pro Asp Leu Arg Arg Val Glu Leu Thr Val Thr Gly
1               5                   10

<210> SEQ ID NO 314
<211> LENGTH: 14
<212> TYPE: PRT
<213> ORGANISM: human herpesvirus 2

<400> SEQUENCE: 314

Tyr Pro Asp Leu Arg Arg Val Glu Leu Thr Val Thr Gly Gln
1               5                   10

<210> SEQ ID NO 315
<211> LENGTH: 15
<212> TYPE: PRT
<213> ORGANISM: human herpesvirus 2

<400> SEQUENCE: 315

Tyr Pro Asp Leu Arg Arg Val Glu Leu Thr Val Thr Gly Gln Ala
1               5                   10                  15

<210> SEQ ID NO 316
<211> LENGTH: 16
<212> TYPE: PRT
<213> ORGANISM: human herpesvirus 2

<400> SEQUENCE: 316

Tyr Pro Asp Leu Arg Arg Val Glu Leu Thr Val Thr Gly Gln Ala Pro
1               5                   10                  15

<210> SEQ ID NO 317
<211> LENGTH: 17
<212> TYPE: PRT
<213> ORGANISM: human herpesvirus 2

<400> SEQUENCE: 317

Tyr Pro Asp Leu Arg Arg Val Glu Leu Thr Val Thr Gly Gln Ala Pro
1               5                   10                  15
Phe

<210> SEQ ID NO 318
<211> LENGTH: 18
<212> TYPE: PRT
<213> ORGANISM: human herpesvirus 2

<400> SEQUENCE: 318

Tyr Pro Asp Leu Arg Arg Val Glu Leu Thr Val Thr Gly Gln Ala Pro
1               5                   10                  15
Phe Arg

<210> SEQ ID NO 319
<211> LENGTH: 19
<212> TYPE: PRT
<213> ORGANISM: human herpesvirus 2

<400> SEQUENCE: 319

Tyr Pro Asp Leu Arg Arg Val Glu Leu Thr Val Thr Gly Gln Ala Pro
1               5                   10                  15
Phe Arg Thr

<210> SEQ ID NO 320
<211> LENGTH: 20
<212> TYPE: PRT
<213> ORGANISM: human herpesvirus 2

<400> SEQUENCE: 320

Tyr Pro Asp Leu Arg Arg Val Glu Leu Thr Val Thr Gly Gln Ala Pro
1               5                   10                  15
Phe Arg Thr Leu
            20

<210> SEQ ID NO 321
<211> LENGTH: 8
<212> TYPE: PRT
<213> ORGANISM: human herpesvirus 2

<400> SEQUENCE: 321

Gln Tyr Pro Asp Leu Arg Arg Val
1               5

<210> SEQ ID NO 322
<211> LENGTH: 9
<212> TYPE: PRT
<213> ORGANISM: human herpesvirus 2

<400> SEQUENCE: 322

Gln Tyr Pro Asp Leu Arg Arg Val Glu
1               5

```
<210> SEQ ID NO 323
<211> LENGTH: 10
<212> TYPE: PRT
<213> ORGANISM: human herpesvirus 2

<400> SEQUENCE: 323

Gln Tyr Pro Asp Leu Arg Arg Val Glu Leu
1               5                   10

<210> SEQ ID NO 324
<211> LENGTH: 11
<212> TYPE: PRT
<213> ORGANISM: human herpesvirus 2

<400> SEQUENCE: 324

Gln Tyr Pro Asp Leu Arg Arg Val Glu Leu Thr
1               5                   10

<210> SEQ ID NO 325
<211> LENGTH: 12
<212> TYPE: PRT
<213> ORGANISM: human herpesvirus 2

<400> SEQUENCE: 325

Gln Tyr Pro Asp Leu Arg Arg Val Glu Leu Thr Val
1               5                   10

<210> SEQ ID NO 326
<211> LENGTH: 13
<212> TYPE: PRT
<213> ORGANISM: human herpesvirus 2

<400> SEQUENCE: 326

Gln Tyr Pro Asp Leu Arg Arg Val Glu Leu Thr Val Thr
1               5                   10

<210> SEQ ID NO 327
<211> LENGTH: 14
<212> TYPE: PRT
<213> ORGANISM: human herpesvirus 2

<400> SEQUENCE: 327

Gln Tyr Pro Asp Leu Arg Arg Val Glu Leu Thr Val Thr Gly
1               5                   10

<210> SEQ ID NO 328
<211> LENGTH: 15
<212> TYPE: PRT
<213> ORGANISM: human herpesvirus 2

<400> SEQUENCE: 328

Gln Tyr Pro Asp Leu Arg Arg Val Glu Leu Thr Val Thr Gly Gln
1               5                   10                  15

<210> SEQ ID NO 329
<211> LENGTH: 16
<212> TYPE: PRT
<213> ORGANISM: human herpesvirus 2

<400> SEQUENCE: 329

Gln Tyr Pro Asp Leu Arg Arg Val Glu Leu Thr Val Thr Gly Gln Ala
1               5                   10                  15

<210> SEQ ID NO 330
<211> LENGTH: 17
```

```
<212> TYPE: PRT
<213> ORGANISM: human herpesvirus 2

<400> SEQUENCE: 330

Gln Tyr Pro Asp Leu Arg Arg Val Glu Leu Thr Val Thr Gly Gln Ala
1               5                   10                  15

Pro

<210> SEQ ID NO 331
<211> LENGTH: 18
<212> TYPE: PRT
<213> ORGANISM: human herpesvirus 2

<400> SEQUENCE: 331

Gln Tyr Pro Asp Leu Arg Arg Val Glu Leu Thr Val Thr Gly Gln Ala
1               5                   10                  15

Pro Phe

<210> SEQ ID NO 332
<211> LENGTH: 19
<212> TYPE: PRT
<213> ORGANISM: human herpesvirus 2

<400> SEQUENCE: 332

Gln Tyr Pro Asp Leu Arg Arg Val Glu Leu Thr Val Thr Gly Gln Ala
1               5                   10                  15

Pro Phe Arg

<210> SEQ ID NO 333
<211> LENGTH: 20
<212> TYPE: PRT
<213> ORGANISM: human herpesvirus 2

<400> SEQUENCE: 333

Gln Tyr Pro Asp Leu Arg Arg Val Glu Leu Thr Val Thr Gly Gln Ala
1               5                   10                  15

Pro Phe Arg Thr
            20

<210> SEQ ID NO 334
<211> LENGTH: 8
<212> TYPE: PRT
<213> ORGANISM: human herpesvirus 2

<400> SEQUENCE: 334

Asn Gln Tyr Pro Asp Leu Arg Arg
1               5

<210> SEQ ID NO 335
<211> LENGTH: 9
<212> TYPE: PRT
<213> ORGANISM: human herpesvirus 2

<400> SEQUENCE: 335

Asn Gln Tyr Pro Asp Leu Arg Arg Val
1               5

<210> SEQ ID NO 336
<211> LENGTH: 10
<212> TYPE: PRT
<213> ORGANISM: human herpesvirus 2

<400> SEQUENCE: 336
```

Asn Gln Tyr Pro Asp Leu Arg Arg Val Glu
1               5                   10

<210> SEQ ID NO 337
<211> LENGTH: 11
<212> TYPE: PRT
<213> ORGANISM: human herpesvirus 2

<400> SEQUENCE: 337

Asn Gln Tyr Pro Asp Leu Arg Arg Val Glu Leu
1               5                   10

<210> SEQ ID NO 338
<211> LENGTH: 12
<212> TYPE: PRT
<213> ORGANISM: human herpesvirus 2

<400> SEQUENCE: 338

Asn Gln Tyr Pro Asp Leu Arg Arg Val Glu Leu Thr
1               5                   10

<210> SEQ ID NO 339
<211> LENGTH: 13
<212> TYPE: PRT
<213> ORGANISM: human herpesvirus 2

<400> SEQUENCE: 339

Asn Gln Tyr Pro Asp Leu Arg Arg Val Glu Leu Thr Val
1               5                   10

<210> SEQ ID NO 340
<211> LENGTH: 14
<212> TYPE: PRT
<213> ORGANISM: human herpesvirus 2

<400> SEQUENCE: 340

Asn Gln Tyr Pro Asp Leu Arg Arg Val Glu Leu Thr Val Thr
1               5                   10

<210> SEQ ID NO 341
<211> LENGTH: 15
<212> TYPE: PRT
<213> ORGANISM: human herpesvirus 2

<400> SEQUENCE: 341

Asn Gln Tyr Pro Asp Leu Arg Arg Val Glu Leu Thr Val Thr Gly
1               5                   10                  15

<210> SEQ ID NO 342
<211> LENGTH: 16
<212> TYPE: PRT
<213> ORGANISM: human herpesvirus 2

<400> SEQUENCE: 342

Asn Gln Tyr Pro Asp Leu Arg Arg Val Glu Leu Thr Val Thr Gly Gln
1               5                   10                  15

<210> SEQ ID NO 343
<211> LENGTH: 17
<212> TYPE: PRT
<213> ORGANISM: human herpesvirus 2

<400> SEQUENCE: 343

Asn Gln Tyr Pro Asp Leu Arg Arg Val Glu Leu Thr Val Thr Gly Gln

```
1               5                  10                 15
Ala

<210> SEQ ID NO 344
<211> LENGTH: 18
<212> TYPE: PRT
<213> ORGANISM: human herpesvirus 2

<400> SEQUENCE: 344

Asn Gln Tyr Pro Asp Leu Arg Arg Val Glu Leu Thr Val Thr Gly Gln
1               5                  10                 15

Ala Pro

<210> SEQ ID NO 345
<211> LENGTH: 19
<212> TYPE: PRT
<213> ORGANISM: human herpesvirus 2

<400> SEQUENCE: 345

Asn Gln Tyr Pro Asp Leu Arg Arg Val Glu Leu Thr Val Thr Gly Gln
1               5                  10                 15

Ala Pro Phe

<210> SEQ ID NO 346
<211> LENGTH: 20
<212> TYPE: PRT
<213> ORGANISM: human herpesvirus 2

<400> SEQUENCE: 346

Asn Gln Tyr Pro Asp Leu Arg Arg Val Glu Leu Thr Val Thr Gly Gln
1               5                  10                 15

Ala Pro Phe Arg
            20

<210> SEQ ID NO 347
<211> LENGTH: 8
<212> TYPE: PRT
<213> ORGANISM: human herpesvirus 2

<400> SEQUENCE: 347

Ala Asn Gln Tyr Pro Asp Leu Arg
1               5

<210> SEQ ID NO 348
<211> LENGTH: 9
<212> TYPE: PRT
<213> ORGANISM: human herpesvirus 2

<400> SEQUENCE: 348

Ala Asn Gln Tyr Pro Asp Leu Arg Arg
1               5

<210> SEQ ID NO 349
<211> LENGTH: 10
<212> TYPE: PRT
<213> ORGANISM: human herpesvirus 2

<400> SEQUENCE: 349

Ala Asn Gln Tyr Pro Asp Leu Arg Arg Val
1               5                  10

<210> SEQ ID NO 350
```

<211> LENGTH: 11
<212> TYPE: PRT
<213> ORGANISM: human herpesvirus 2

<400> SEQUENCE: 350

Ala Asn Gln Tyr Pro Asp Leu Arg Arg Val Glu
1               5                   10

<210> SEQ ID NO 351
<211> LENGTH: 12
<212> TYPE: PRT
<213> ORGANISM: human herpesvirus 2

<400> SEQUENCE: 351

Ala Asn Gln Tyr Pro Asp Leu Arg Arg Val Glu Leu
1               5                   10

<210> SEQ ID NO 352
<211> LENGTH: 13
<212> TYPE: PRT
<213> ORGANISM: human herpesvirus 2

<400> SEQUENCE: 352

Ala Asn Gln Tyr Pro Asp Leu Arg Arg Val Glu Leu Thr
1               5                   10

<210> SEQ ID NO 353
<211> LENGTH: 14
<212> TYPE: PRT
<213> ORGANISM: human herpesvirus 2

<400> SEQUENCE: 353

Ala Asn Gln Tyr Pro Asp Leu Arg Arg Val Glu Leu Thr Val
1               5                   10

<210> SEQ ID NO 354
<211> LENGTH: 15
<212> TYPE: PRT
<213> ORGANISM: human herpesvirus 2

<400> SEQUENCE: 354

Ala Asn Gln Tyr Pro Asp Leu Arg Arg Val Glu Leu Thr Val Thr
1               5                   10                  15

<210> SEQ ID NO 355
<211> LENGTH: 16
<212> TYPE: PRT
<213> ORGANISM: human herpesvirus 2

<400> SEQUENCE: 355

Ala Asn Gln Tyr Pro Asp Leu Arg Arg Val Glu Leu Thr Val Thr Gly
1               5                   10                  15

<210> SEQ ID NO 356
<211> LENGTH: 17
<212> TYPE: PRT
<213> ORGANISM: human herpesvirus 2

<400> SEQUENCE: 356

Ala Asn Gln Tyr Pro Asp Leu Arg Arg Val Glu Leu Thr Val Thr Gly
1               5                   10                  15

Gln

<210> SEQ ID NO 357

-continued

<211> LENGTH: 18
<212> TYPE: PRT
<213> ORGANISM: human herpesvirus 2

<400> SEQUENCE: 357

Ala Asn Gln Tyr Pro Asp Leu Arg Arg Val Glu Leu Thr Val Thr Gly
1               5                   10                  15

Gln Ala

<210> SEQ ID NO 358
<211> LENGTH: 19
<212> TYPE: PRT
<213> ORGANISM: human herpesvirus 2

<400> SEQUENCE: 358

Ala Asn Gln Tyr Pro Asp Leu Arg Arg Val Glu Leu Thr Val Thr Gly
1               5                   10                  15

Gln Ala Pro

<210> SEQ ID NO 359
<211> LENGTH: 20
<212> TYPE: PRT
<213> ORGANISM: human herpesvirus 2

<400> SEQUENCE: 359

Ala Asn Gln Tyr Pro Asp Leu Arg Arg Val Glu Leu Thr Val Thr Gly
1               5                   10                  15

Gln Ala Pro Phe
            20

<210> SEQ ID NO 360
<211> LENGTH: 8
<212> TYPE: PRT
<213> ORGANISM: human herpesvirus 2

<400> SEQUENCE: 360

Arg Ala Asn Gln Tyr Pro Asp Leu
1               5

<210> SEQ ID NO 361
<211> LENGTH: 9
<212> TYPE: PRT
<213> ORGANISM: human herpesvirus 2

<400> SEQUENCE: 361

Arg Ala Asn Gln Tyr Pro Asp Leu Arg
1               5

<210> SEQ ID NO 362
<211> LENGTH: 10
<212> TYPE: PRT
<213> ORGANISM: human herpesvirus 2

<400> SEQUENCE: 362

Arg Ala Asn Gln Tyr Pro Asp Leu Arg Arg
1               5                   10

<210> SEQ ID NO 363
<211> LENGTH: 11
<212> TYPE: PRT
<213> ORGANISM: human herpesvirus 2

<400> SEQUENCE: 363

-continued

Arg Ala Asn Gln Tyr Pro Asp Leu Arg Arg Val
1               5                   10

<210> SEQ ID NO 364
<211> LENGTH: 12
<212> TYPE: PRT
<213> ORGANISM: human herpesvirus 2

<400> SEQUENCE: 364

Arg Ala Asn Gln Tyr Pro Asp Leu Arg Arg Val Glu
1               5                   10

<210> SEQ ID NO 365
<211> LENGTH: 13
<212> TYPE: PRT
<213> ORGANISM: human herpesvirus 2

<400> SEQUENCE: 365

Arg Ala Asn Gln Tyr Pro Asp Leu Arg Arg Val Glu Leu
1               5                   10

<210> SEQ ID NO 366
<211> LENGTH: 14
<212> TYPE: PRT
<213> ORGANISM: human herpesvirus 2

<400> SEQUENCE: 366

Arg Ala Asn Gln Tyr Pro Asp Leu Arg Arg Val Glu Leu Thr
1               5                   10

<210> SEQ ID NO 367
<211> LENGTH: 15
<212> TYPE: PRT
<213> ORGANISM: human herpesvirus 2

<400> SEQUENCE: 367

Arg Ala Asn Gln Tyr Pro Asp Leu Arg Arg Val Glu Leu Thr Val
1               5                   10                  15

<210> SEQ ID NO 368
<211> LENGTH: 16
<212> TYPE: PRT
<213> ORGANISM: human herpesvirus 2

<400> SEQUENCE: 368

Arg Ala Asn Gln Tyr Pro Asp Leu Arg Arg Val Glu Leu Thr Val Thr
1               5                   10                  15

<210> SEQ ID NO 369
<211> LENGTH: 17
<212> TYPE: PRT
<213> ORGANISM: human herpesvirus 2

<400> SEQUENCE: 369

Arg Ala Asn Gln Tyr Pro Asp Leu Arg Arg Val Glu Leu Thr Val Thr
1               5                   10                  15
Gly

<210> SEQ ID NO 370
<211> LENGTH: 18
<212> TYPE: PRT
<213> ORGANISM: human herpesvirus 2

<400> SEQUENCE: 370

-continued

Arg Ala Asn Gln Tyr Pro Asp Leu Arg Val Glu Leu Thr Val Thr
1               5                   10                  15

Gly Gln

<210> SEQ ID NO 371
<211> LENGTH: 19
<212> TYPE: PRT
<213> ORGANISM: human herpesvirus 2

<400> SEQUENCE: 371

Arg Ala Asn Gln Tyr Pro Asp Leu Arg Val Glu Leu Thr Val Thr
1               5                   10                  15

Gly Gln Ala

<210> SEQ ID NO 372
<211> LENGTH: 20
<212> TYPE: PRT
<213> ORGANISM: human herpesvirus 2

<400> SEQUENCE: 372

Arg Ala Asn Gln Tyr Pro Asp Leu Arg Val Glu Leu Thr Val Thr
1               5                   10                  15

Gly Gln Ala Pro
            20

<210> SEQ ID NO 373
<211> LENGTH: 9
<212> TYPE: PRT
<213> ORGANISM: human herpesvirus 2

<400> SEQUENCE: 373

Phe Arg Ala Asn Gln Tyr Pro Asp Leu
1               5

<210> SEQ ID NO 374
<211> LENGTH: 10
<212> TYPE: PRT
<213> ORGANISM: human herpesvirus 2

<400> SEQUENCE: 374

Phe Arg Ala Asn Gln Tyr Pro Asp Leu Arg
1               5                   10

<210> SEQ ID NO 375
<211> LENGTH: 11
<212> TYPE: PRT
<213> ORGANISM: human herpesvirus 2

<400> SEQUENCE: 375

Phe Arg Ala Asn Gln Tyr Pro Asp Leu Arg Arg
1               5                   10

<210> SEQ ID NO 376
<211> LENGTH: 12
<212> TYPE: PRT
<213> ORGANISM: human herpesvirus 2

<400> SEQUENCE: 376

Phe Arg Ala Asn Gln Tyr Pro Asp Leu Arg Arg Val
1               5                   10

<210> SEQ ID NO 377
<211> LENGTH: 13

-continued

<212> TYPE: PRT
<213> ORGANISM: human herpesvirus 2

<400> SEQUENCE: 377

Phe Arg Ala Asn Gln Tyr Pro Asp Leu Arg Arg Val Glu
1               5                   10

<210> SEQ ID NO 378
<211> LENGTH: 14
<212> TYPE: PRT
<213> ORGANISM: human herpesvirus 2

<400> SEQUENCE: 378

Phe Arg Ala Asn Gln Tyr Pro Asp Leu Arg Arg Val Glu Leu
1               5                   10

<210> SEQ ID NO 379
<211> LENGTH: 15
<212> TYPE: PRT
<213> ORGANISM: human herpesvirus 2

<400> SEQUENCE: 379

Phe Arg Ala Asn Gln Tyr Pro Asp Leu Arg Arg Val Glu Leu Thr
1               5                   10                  15

<210> SEQ ID NO 380
<211> LENGTH: 16
<212> TYPE: PRT
<213> ORGANISM: human herpesvirus 2

<400> SEQUENCE: 380

Phe Arg Ala Asn Gln Tyr Pro Asp Leu Arg Arg Val Glu Leu Thr Val
1               5                   10                  15

<210> SEQ ID NO 381
<211> LENGTH: 17
<212> TYPE: PRT
<213> ORGANISM: human herpesvirus 2

<400> SEQUENCE: 381

Phe Arg Ala Asn Gln Tyr Pro Asp Leu Arg Arg Val Glu Leu Thr Val
1               5                   10                  15

Thr

<210> SEQ ID NO 382
<211> LENGTH: 18
<212> TYPE: PRT
<213> ORGANISM: human herpesvirus 2

<400> SEQUENCE: 382

Phe Arg Ala Asn Gln Tyr Pro Asp Leu Arg Arg Val Glu Leu Thr Val
1               5                   10                  15

Thr Gly

<210> SEQ ID NO 383
<211> LENGTH: 19
<212> TYPE: PRT
<213> ORGANISM: human herpesvirus 2

<400> SEQUENCE: 383

Phe Arg Ala Asn Gln Tyr Pro Asp Leu Arg Arg Val Glu Leu Thr Val
1               5                   10                  15

Thr Gly Gln

<210> SEQ ID NO 384
<211> LENGTH: 20
<212> TYPE: PRT
<213> ORGANISM: human herpesvirus 2

<400> SEQUENCE: 384

Phe Arg Ala Asn Gln Tyr Pro Asp Leu Arg Arg Val Glu Leu Thr Val
1               5                   10                  15

Thr Gly Gln Ala
            20

<210> SEQ ID NO 385
<211> LENGTH: 10
<212> TYPE: PRT
<213> ORGANISM: human herpesvirus 2

<400> SEQUENCE: 385

Val Phe Arg Ala Asn Gln Tyr Pro Asp Leu
1               5                   10

<210> SEQ ID NO 386
<211> LENGTH: 11
<212> TYPE: PRT
<213> ORGANISM: human herpesvirus 2

<400> SEQUENCE: 386

Val Phe Arg Ala Asn Gln Tyr Pro Asp Leu Arg
1               5                   10

<210> SEQ ID NO 387
<211> LENGTH: 12
<212> TYPE: PRT
<213> ORGANISM: human herpesvirus 2

<400> SEQUENCE: 387

Val Phe Arg Ala Asn Gln Tyr Pro Asp Leu Arg Arg
1               5                   10

<210> SEQ ID NO 388
<211> LENGTH: 13
<212> TYPE: PRT
<213> ORGANISM: human herpesvirus 2

<400> SEQUENCE: 388

Val Phe Arg Ala Asn Gln Tyr Pro Asp Leu Arg Arg Val
1               5                   10

<210> SEQ ID NO 389
<211> LENGTH: 14
<212> TYPE: PRT
<213> ORGANISM: human herpesvirus 2

<400> SEQUENCE: 389

Val Phe Arg Ala Asn Gln Tyr Pro Asp Leu Arg Arg Val Glu
1               5                   10

<210> SEQ ID NO 390
<211> LENGTH: 15
<212> TYPE: PRT
<213> ORGANISM: human herpesvirus 2

<400> SEQUENCE: 390

Val Phe Arg Ala Asn Gln Tyr Pro Asp Leu Arg Arg Val Glu Leu

-continued

```
1               5                   10                  15
```

<210> SEQ ID NO 391
<211> LENGTH: 16
<212> TYPE: PRT
<213> ORGANISM: human herpesvirus 2

<400> SEQUENCE: 391

```
Val Phe Arg Ala Asn Gln Tyr Pro Asp Leu Arg Arg Val Glu Leu Thr
1               5                   10                  15
```

<210> SEQ ID NO 392
<211> LENGTH: 17
<212> TYPE: PRT
<213> ORGANISM: human herpesvirus 2

<400> SEQUENCE: 392

```
Val Phe Arg Ala Asn Gln Tyr Pro Asp Leu Arg Arg Val Glu Leu Thr
1               5                   10                  15

Val
```

<210> SEQ ID NO 393
<211> LENGTH: 18
<212> TYPE: PRT
<213> ORGANISM: human herpesvirus 2

<400> SEQUENCE: 393

```
Val Phe Arg Ala Asn Gln Tyr Pro Asp Leu Arg Arg Val Glu Leu Thr
1               5                   10                  15

Val Thr
```

<210> SEQ ID NO 394
<211> LENGTH: 19
<212> TYPE: PRT
<213> ORGANISM: human herpesvirus 2

<400> SEQUENCE: 394

```
Val Phe Arg Ala Asn Gln Tyr Pro Asp Leu Arg Arg Val Glu Leu Thr
1               5                   10                  15

Val Thr Gly
```

<210> SEQ ID NO 395
<211> LENGTH: 20
<212> TYPE: PRT
<213> ORGANISM: human herpesvirus 2

<400> SEQUENCE: 395

```
Val Phe Arg Ala Asn Gln Tyr Pro Asp Leu Arg Arg Val Glu Leu Thr
1               5                   10                  15

Val Thr Gly Gln
            20
```

<210> SEQ ID NO 396
<211> LENGTH: 11
<212> TYPE: PRT
<213> ORGANISM: human herpesvirus 2

<400> SEQUENCE: 396

```
Ser Val Phe Arg Ala Asn Gln Tyr Pro Asp Leu
1               5                   10
```

<210> SEQ ID NO 397

```
<211> LENGTH: 12
<212> TYPE: PRT
<213> ORGANISM: human herpesvirus 2

<400> SEQUENCE: 397

Ser Val Phe Arg Ala Asn Gln Tyr Pro Asp Leu Arg
1               5                   10

<210> SEQ ID NO 398
<211> LENGTH: 13
<212> TYPE: PRT
<213> ORGANISM: human herpesvirus 2

<400> SEQUENCE: 398

Ser Val Phe Arg Ala Asn Gln Tyr Pro Asp Leu Arg Arg
1               5                   10

<210> SEQ ID NO 399
<211> LENGTH: 14
<212> TYPE: PRT
<213> ORGANISM: human herpesvirus 2

<400> SEQUENCE: 399

Ser Val Phe Arg Ala Asn Gln Tyr Pro Asp Leu Arg Arg Val
1               5                   10

<210> SEQ ID NO 400
<211> LENGTH: 15
<212> TYPE: PRT
<213> ORGANISM: human herpesvirus 2

<400> SEQUENCE: 400

Ser Val Phe Arg Ala Asn Gln Tyr Pro Asp Leu Arg Arg Val Glu
1               5                   10                  15

<210> SEQ ID NO 401
<211> LENGTH: 16
<212> TYPE: PRT
<213> ORGANISM: human herpesvirus 2

<400> SEQUENCE: 401

Ser Val Phe Arg Ala Asn Gln Tyr Pro Asp Leu Arg Arg Val Glu Leu
1               5                   10                  15

<210> SEQ ID NO 402
<211> LENGTH: 17
<212> TYPE: PRT
<213> ORGANISM: human herpesvirus 2

<400> SEQUENCE: 402

Ser Val Phe Arg Ala Asn Gln Tyr Pro Asp Leu Arg Arg Val Glu Leu
1               5                   10                  15
Thr

<210> SEQ ID NO 403
<211> LENGTH: 18
<212> TYPE: PRT
<213> ORGANISM: human herpesvirus 2

<400> SEQUENCE: 403

Ser Val Phe Arg Ala Asn Gln Tyr Pro Asp Leu Arg Arg Val Glu Leu
1               5                   10                  15
Thr Val
```

<210> SEQ ID NO 404
<211> LENGTH: 19
<212> TYPE: PRT
<213> ORGANISM: human herpesvirus 2

<400> SEQUENCE: 404

Ser Val Phe Arg Ala Asn Gln Tyr Pro Asp Leu Arg Arg Val Glu Leu
1               5                   10                  15

Thr Val Thr

<210> SEQ ID NO 405
<211> LENGTH: 20
<212> TYPE: PRT
<213> ORGANISM: human herpesvirus 2

<400> SEQUENCE: 405

Ser Val Phe Arg Ala Asn Gln Tyr Pro Asp Leu Arg Arg Val Glu Leu
1               5                   10                  15

Thr Val Thr Gly
            20

<210> SEQ ID NO 406
<211> LENGTH: 12
<212> TYPE: PRT
<213> ORGANISM: human herpesvirus 2

<400> SEQUENCE: 406

Leu Ser Val Phe Arg Ala Asn Gln Tyr Pro Asp Leu
1               5                   10

<210> SEQ ID NO 407
<211> LENGTH: 13
<212> TYPE: PRT
<213> ORGANISM: human herpesvirus 2

<400> SEQUENCE: 407

Leu Ser Val Phe Arg Ala Asn Gln Tyr Pro Asp Leu Arg
1               5                   10

<210> SEQ ID NO 408
<211> LENGTH: 14
<212> TYPE: PRT
<213> ORGANISM: human herpesvirus 2

<400> SEQUENCE: 408

Leu Ser Val Phe Arg Ala Asn Gln Tyr Pro Asp Leu Arg Arg
1               5                   10

<210> SEQ ID NO 409
<211> LENGTH: 15
<212> TYPE: PRT
<213> ORGANISM: human herpesvirus 2

<400> SEQUENCE: 409

Leu Ser Val Phe Arg Ala Asn Gln Tyr Pro Asp Leu Arg Arg Val
1               5                   10                  15

<210> SEQ ID NO 410
<211> LENGTH: 16
<212> TYPE: PRT
<213> ORGANISM: human herpesvirus 2

<400> SEQUENCE: 410

Leu Ser Val Phe Arg Ala Asn Gln Tyr Pro Asp Leu Arg Arg Val Glu
1               5                   10                  15

<210> SEQ ID NO 411
<211> LENGTH: 17
<212> TYPE: PRT
<213> ORGANISM: human herpesvirus 2

<400> SEQUENCE: 411

Leu Ser Val Phe Arg Ala Asn Gln Tyr Pro Asp Leu Arg Arg Val Glu
1               5                   10                  15

Leu

<210> SEQ ID NO 412
<211> LENGTH: 18
<212> TYPE: PRT
<213> ORGANISM: human herpesvirus 2

<400> SEQUENCE: 412

Leu Ser Val Phe Arg Ala Asn Gln Tyr Pro Asp Leu Arg Arg Val Glu
1               5                   10                  15

Leu Thr

<210> SEQ ID NO 413
<211> LENGTH: 19
<212> TYPE: PRT
<213> ORGANISM: human herpesvirus 2

<400> SEQUENCE: 413

Leu Ser Val Phe Arg Ala Asn Gln Tyr Pro Asp Leu Arg Arg Val Glu
1               5                   10                  15

Leu Thr Val

<210> SEQ ID NO 414
<211> LENGTH: 20
<212> TYPE: PRT
<213> ORGANISM: human herpesvirus 2

<400> SEQUENCE: 414

Leu Ser Val Phe Arg Ala Asn Gln Tyr Pro Asp Leu Arg Arg Val Glu
1               5                   10                  15

Leu Thr Val Thr
            20

<210> SEQ ID NO 415
<211> LENGTH: 13
<212> TYPE: PRT
<213> ORGANISM: human herpesvirus 2

<400> SEQUENCE: 415

Leu Leu Ser Val Phe Arg Ala Asn Gln Tyr Pro Asp Leu
1               5                   10

<210> SEQ ID NO 416
<211> LENGTH: 14
<212> TYPE: PRT
<213> ORGANISM: human herpesvirus 2

<400> SEQUENCE: 416

Leu Leu Ser Val Phe Arg Ala Asn Gln Tyr Pro Asp Leu Arg
1               5                   10

```
<210> SEQ ID NO 417
<211> LENGTH: 15
<212> TYPE: PRT
<213> ORGANISM: human herpesvirus 2

<400> SEQUENCE: 417

Leu Leu Ser Val Phe Arg Ala Asn Gln Tyr Pro Asp Leu Arg Arg
1               5                   10                  15

<210> SEQ ID NO 418
<211> LENGTH: 16
<212> TYPE: PRT
<213> ORGANISM: human herpesvirus 2

<400> SEQUENCE: 418

Leu Leu Ser Val Phe Arg Ala Asn Gln Tyr Pro Asp Leu Arg Arg Val
1               5                   10                  15

<210> SEQ ID NO 419
<211> LENGTH: 17
<212> TYPE: PRT
<213> ORGANISM: human herpesvirus 2

<400> SEQUENCE: 419

Leu Leu Ser Val Phe Arg Ala Asn Gln Tyr Pro Asp Leu Arg Arg Val
1               5                   10                  15

Glu

<210> SEQ ID NO 420
<211> LENGTH: 18
<212> TYPE: PRT
<213> ORGANISM: human herpesvirus 2

<400> SEQUENCE: 420

Leu Leu Ser Val Phe Arg Ala Asn Gln Tyr Pro Asp Leu Arg Arg Val
1               5                   10                  15

Glu Leu

<210> SEQ ID NO 421
<211> LENGTH: 19
<212> TYPE: PRT
<213> ORGANISM: human herpesvirus 2

<400> SEQUENCE: 421

Leu Leu Ser Val Phe Arg Ala Asn Gln Tyr Pro Asp Leu Arg Arg Val
1               5                   10                  15

Glu Leu Thr

<210> SEQ ID NO 422
<211> LENGTH: 20
<212> TYPE: PRT
<213> ORGANISM: human herpesvirus 2

<400> SEQUENCE: 422

Leu Leu Ser Val Phe Arg Ala Asn Gln Tyr Pro Asp Leu Arg Arg Val
1               5                   10                  15

Glu Leu Thr Val
            20

<210> SEQ ID NO 423
<211> LENGTH: 14
<212> TYPE: PRT
<213> ORGANISM: human herpesvirus 2
```

-continued

<400> SEQUENCE: 423

Ser Leu Leu Ser Val Phe Arg Ala Asn Gln Tyr Pro Asp Leu
1               5                   10

<210> SEQ ID NO 424
<211> LENGTH: 15
<212> TYPE: PRT
<213> ORGANISM: human herpesvirus 2

<400> SEQUENCE: 424

Ser Leu Leu Ser Val Phe Arg Ala Asn Gln Tyr Pro Asp Leu Arg
1               5                   10                  15

<210> SEQ ID NO 425
<211> LENGTH: 16
<212> TYPE: PRT
<213> ORGANISM: human herpesvirus 2

<400> SEQUENCE: 425

Ser Leu Leu Ser Val Phe Arg Ala Asn Gln Tyr Pro Asp Leu Arg Arg
1               5                   10                  15

<210> SEQ ID NO 426
<211> LENGTH: 17
<212> TYPE: PRT
<213> ORGANISM: human herpesvirus 2

<400> SEQUENCE: 426

Ser Leu Leu Ser Val Phe Arg Ala Asn Gln Tyr Pro Asp Leu Arg Arg
1               5                   10                  15

Val

<210> SEQ ID NO 427
<211> LENGTH: 18
<212> TYPE: PRT
<213> ORGANISM: human herpesvirus 2

<400> SEQUENCE: 427

Ser Leu Leu Ser Val Phe Arg Ala Asn Gln Tyr Pro Asp Leu Arg Arg
1               5                   10                  15

Val Glu

<210> SEQ ID NO 428
<211> LENGTH: 19
<212> TYPE: PRT
<213> ORGANISM: human herpesvirus 2

<400> SEQUENCE: 428

Ser Leu Leu Ser Val Phe Arg Ala Asn Gln Tyr Pro Asp Leu Arg Arg
1               5                   10                  15

Val Glu Leu

<210> SEQ ID NO 429
<211> LENGTH: 20
<212> TYPE: PRT
<213> ORGANISM: human herpesvirus 2

<400> SEQUENCE: 429

Ser Leu Leu Ser Val Phe Arg Ala Asn Gln Tyr Pro Asp Leu Arg Arg
1               5                   10                  15

Val Glu Leu Thr

-continued

```
<210> SEQ ID NO 430
<211> LENGTH: 15
<212> TYPE: PRT
<213> ORGANISM: human herpesvirus 2

<400> SEQUENCE: 430
```

Arg Ser Leu Leu Ser Val Phe Arg Ala Asn Gln Tyr Pro Asp Leu
1               5                   10                  15

```
<210> SEQ ID NO 431
<211> LENGTH: 16
<212> TYPE: PRT
<213> ORGANISM: human herpesvirus 2

<400> SEQUENCE: 431
```

Arg Ser Leu Leu Ser Val Phe Arg Ala Asn Gln Tyr Pro Asp Leu Arg
1               5                   10                  15

```
<210> SEQ ID NO 432
<211> LENGTH: 17
<212> TYPE: PRT
<213> ORGANISM: human herpesvirus 2

<400> SEQUENCE: 432
```

Arg Ser Leu Leu Ser Val Phe Arg Ala Asn Gln Tyr Pro Asp Leu Arg
1               5                   10                  15

Arg

```
<210> SEQ ID NO 433
<211> LENGTH: 18
<212> TYPE: PRT
<213> ORGANISM: human herpesvirus 2

<400> SEQUENCE: 433
```

Arg Ser Leu Leu Ser Val Phe Arg Ala Asn Gln Tyr Pro Asp Leu Arg
1               5                   10                  15

Arg Val

```
<210> SEQ ID NO 434
<211> LENGTH: 19
<212> TYPE: PRT
<213> ORGANISM: human herpesvirus 2

<400> SEQUENCE: 434
```

Arg Ser Leu Leu Ser Val Phe Arg Ala Asn Gln Tyr Pro Asp Leu Arg
1               5                   10                  15

Arg Val Glu

```
<210> SEQ ID NO 435
<211> LENGTH: 20
<212> TYPE: PRT
<213> ORGANISM: human herpesvirus 2

<400> SEQUENCE: 435
```

Arg Ser Leu Leu Ser Val Phe Arg Ala Asn Gln Tyr Pro Asp Leu Arg
1               5                   10                  15

Arg Val Glu Leu
            20

```
<210> SEQ ID NO 436
```

```
<211> LENGTH: 16
<212> TYPE: PRT
<213> ORGANISM: human herpesvirus 2

<400> SEQUENCE: 436

Lys Arg Ser Leu Leu Ser Val Phe Arg Ala Asn Gln Tyr Pro Asp Leu
1               5                   10                  15

<210> SEQ ID NO 437
<211> LENGTH: 17
<212> TYPE: PRT
<213> ORGANISM: human herpesvirus 2

<400> SEQUENCE: 437

Lys Arg Ser Leu Leu Ser Val Phe Arg Ala Asn Gln Tyr Pro Asp Leu
1               5                   10                  15

Arg

<210> SEQ ID NO 438
<211> LENGTH: 18
<212> TYPE: PRT
<213> ORGANISM: human herpesvirus 2

<400> SEQUENCE: 438

Lys Arg Ser Leu Leu Ser Val Phe Arg Ala Asn Gln Tyr Pro Asp Leu
1               5                   10                  15

Arg Arg

<210> SEQ ID NO 439
<211> LENGTH: 19
<212> TYPE: PRT
<213> ORGANISM: human herpesvirus 2

<400> SEQUENCE: 439

Lys Arg Ser Leu Leu Ser Val Phe Arg Ala Asn Gln Tyr Pro Asp Leu
1               5                   10                  15

Arg Arg Val

<210> SEQ ID NO 440
<211> LENGTH: 20
<212> TYPE: PRT
<213> ORGANISM: human herpesvirus 2

<400> SEQUENCE: 440

Lys Arg Ser Leu Leu Ser Val Phe Arg Ala Asn Gln Tyr Pro Asp Leu
1               5                   10                  15

Arg Arg Val Glu
            20

<210> SEQ ID NO 441
<211> LENGTH: 17
<212> TYPE: PRT
<213> ORGANISM: human herpesvirus 2

<400> SEQUENCE: 441

Gln Lys Arg Ser Leu Leu Ser Val Phe Arg Ala Asn Gln Tyr Pro Asp
1               5                   10                  15

Leu

<210> SEQ ID NO 442
<211> LENGTH: 18
<212> TYPE: PRT
```

-continued

<213> ORGANISM: human herpesvirus 2

<400> SEQUENCE: 442

Gln Lys Arg Ser Leu Leu Ser Val Phe Arg Ala Asn Gln Tyr Pro Asp
1               5                   10                  15
Leu Arg

<210> SEQ ID NO 443
<211> LENGTH: 19
<212> TYPE: PRT
<213> ORGANISM: human herpesvirus 2

<400> SEQUENCE: 443

Gln Lys Arg Ser Leu Leu Ser Val Phe Arg Ala Asn Gln Tyr Pro Asp
1               5                   10                  15
Leu Arg Arg

<210> SEQ ID NO 444
<211> LENGTH: 20
<212> TYPE: PRT
<213> ORGANISM: human herpesvirus 2

<400> SEQUENCE: 444

Gln Lys Arg Ser Leu Leu Ser Val Phe Arg Ala Asn Gln Tyr Pro Asp
1               5                   10                  15
Leu Arg Arg Val
            20

<210> SEQ ID NO 445
<211> LENGTH: 18
<212> TYPE: PRT
<213> ORGANISM: human herpesvirus 2

<400> SEQUENCE: 445

Asp Gln Lys Arg Ser Leu Leu Ser Val Phe Arg Ala Asn Gln Tyr Pro
1               5                   10                  15
Asp Leu

<210> SEQ ID NO 446
<211> LENGTH: 19
<212> TYPE: PRT
<213> ORGANISM: human herpesvirus 2

<400> SEQUENCE: 446

Asp Gln Lys Arg Ser Leu Leu Ser Val Phe Arg Ala Asn Gln Tyr Pro
1               5                   10                  15
Asp Leu Arg

<210> SEQ ID NO 447
<211> LENGTH: 20
<212> TYPE: PRT
<213> ORGANISM: human herpesvirus 2

<400> SEQUENCE: 447

Asp Gln Lys Arg Ser Leu Leu Ser Val Phe Arg Ala Asn Gln Tyr Pro
1               5                   10                  15
Asp Leu Arg Arg
            20

<210> SEQ ID NO 448
<211> LENGTH: 19

```
<212> TYPE: PRT
<213> ORGANISM: human herpesvirus 2

<400> SEQUENCE: 448

Val Asp Gln Lys Arg Ser Leu Leu Ser Val Phe Arg Ala Asn Gln Tyr
1               5                   10                  15

Pro Asp Leu

<210> SEQ ID NO 449
<211> LENGTH: 20
<212> TYPE: PRT
<213> ORGANISM: human herpesvirus 2

<400> SEQUENCE: 449

Val Asp Gln Lys Arg Ser Leu Leu Ser Val Phe Arg Ala Asn Gln Tyr
1               5                   10                  15

Pro Asp Leu Arg
            20

<210> SEQ ID NO 450
<211> LENGTH: 20
<212> TYPE: PRT
<213> ORGANISM: human herpesvirus 2

<400> SEQUENCE: 450

Leu Val Asp Gln Lys Arg Ser Leu Leu Ser Val Phe Arg Ala Asn Gln
1               5                   10                  15

Tyr Pro Asp Leu
            20

<210> SEQ ID NO 451
<211> LENGTH: 8
<212> TYPE: PRT
<213> ORGANISM: Variola virus

<400> SEQUENCE: 451

Tyr Pro Asp Leu Asn Phe Asp Asn
1               5

<210> SEQ ID NO 452
<211> LENGTH: 9
<212> TYPE: PRT
<213> ORGANISM: Variola virus

<400> SEQUENCE: 452

Tyr Pro Asp Leu Asn Phe Asp Asn Thr
1               5

<210> SEQ ID NO 453
<211> LENGTH: 10
<212> TYPE: PRT
<213> ORGANISM: Variola virus

<400> SEQUENCE: 453

Tyr Pro Asp Leu Asn Phe Asp Asn Thr Tyr
1               5                   10

<210> SEQ ID NO 454
<211> LENGTH: 11
<212> TYPE: PRT
<213> ORGANISM: Variola virus

<400> SEQUENCE: 454
```

-continued

Tyr Pro Asp Leu Asn Phe Asp Asn Thr Tyr Leu
1               5                   10

<210> SEQ ID NO 455
<211> LENGTH: 12
<212> TYPE: PRT
<213> ORGANISM: Variola virus

<400> SEQUENCE: 455

Tyr Pro Asp Leu Asn Phe Asp Asn Thr Tyr Leu Phe
1               5                   10

<210> SEQ ID NO 456
<211> LENGTH: 13
<212> TYPE: PRT
<213> ORGANISM: Variola virus

<400> SEQUENCE: 456

Tyr Pro Asp Leu Asn Phe Asp Asn Thr Tyr Leu Phe Asn
1               5                   10

<210> SEQ ID NO 457
<211> LENGTH: 14
<212> TYPE: PRT
<213> ORGANISM: Variola virus

<400> SEQUENCE: 457

Tyr Pro Asp Leu Asn Phe Asp Asn Thr Tyr Leu Phe Asn Ile
1               5                   10

<210> SEQ ID NO 458
<211> LENGTH: 15
<212> TYPE: PRT
<213> ORGANISM: Variola virus

<400> SEQUENCE: 458

Tyr Pro Asp Leu Asn Phe Asp Asn Thr Tyr Leu Phe Asn Ile Leu
1               5                   10                  15

<210> SEQ ID NO 459
<211> LENGTH: 16
<212> TYPE: PRT
<213> ORGANISM: Variola virus

<400> SEQUENCE: 459

Tyr Pro Asp Leu Asn Phe Asp Asn Thr Tyr Leu Phe Asn Ile Leu Tyr
1               5                   10                  15

<210> SEQ ID NO 460
<211> LENGTH: 17
<212> TYPE: PRT
<213> ORGANISM: Variola virus

<400> SEQUENCE: 460

Tyr Pro Asp Leu Asn Phe Asp Asn Thr Tyr Leu Phe Asn Ile Leu Tyr
1               5                   10                  15
Lys

<210> SEQ ID NO 461
<211> LENGTH: 18
<212> TYPE: PRT
<213> ORGANISM: Variola virus

<400> SEQUENCE: 461

-continued

Tyr Pro Asp Leu Asn Phe Asp Asn Thr Tyr Leu Phe Asn Ile Leu Tyr
1               5                   10                  15

Lys Asp

<210> SEQ ID NO 462
<211> LENGTH: 19
<212> TYPE: PRT
<213> ORGANISM: Variola virus

<400> SEQUENCE: 462

Tyr Pro Asp Leu Asn Phe Asp Asn Thr Tyr Leu Phe Asn Ile Leu Tyr
1               5                   10                  15

Lys Asp Val

<210> SEQ ID NO 463
<211> LENGTH: 20
<212> TYPE: PRT
<213> ORGANISM: Variola virus

<400> SEQUENCE: 463

Tyr Pro Asp Leu Asn Phe Asp Asn Thr Tyr Leu Phe Asn Ile Leu Tyr
1               5                   10                  15

Lys Asp Val Ile
            20

<210> SEQ ID NO 464
<211> LENGTH: 8
<212> TYPE: PRT
<213> ORGANISM: Variola virus

<400> SEQUENCE: 464

Lys Tyr Pro Asp Leu Asn Phe Asp
1               5

<210> SEQ ID NO 465
<211> LENGTH: 9
<212> TYPE: PRT
<213> ORGANISM: Variola virus

<400> SEQUENCE: 465

Lys Tyr Pro Asp Leu Asn Phe Asp Asn
1               5

<210> SEQ ID NO 466
<211> LENGTH: 10
<212> TYPE: PRT
<213> ORGANISM: Variola virus

<400> SEQUENCE: 466

Lys Tyr Pro Asp Leu Asn Phe Asp Asn Thr
1               5                   10

<210> SEQ ID NO 467
<211> LENGTH: 11
<212> TYPE: PRT
<213> ORGANISM: Variola virus

<400> SEQUENCE: 467

Lys Tyr Pro Asp Leu Asn Phe Asp Asn Thr Tyr
1               5                   10

<210> SEQ ID NO 468
<211> LENGTH: 12

```
<212> TYPE: PRT
<213> ORGANISM: Variola virus

<400> SEQUENCE: 468

Lys Tyr Pro Asp Leu Asn Phe Asp Asn Thr Tyr Leu
1               5                   10

<210> SEQ ID NO 469
<211> LENGTH: 13
<212> TYPE: PRT
<213> ORGANISM: Variola virus

<400> SEQUENCE: 469

Lys Tyr Pro Asp Leu Asn Phe Asp Asn Thr Tyr Leu Phe
1               5                   10

<210> SEQ ID NO 470
<211> LENGTH: 14
<212> TYPE: PRT
<213> ORGANISM: Variola virus

<400> SEQUENCE: 470

Lys Tyr Pro Asp Leu Asn Phe Asp Asn Thr Tyr Leu Phe Asn
1               5                   10

<210> SEQ ID NO 471
<211> LENGTH: 15
<212> TYPE: PRT
<213> ORGANISM: Variola virus

<400> SEQUENCE: 471

Lys Tyr Pro Asp Leu Asn Phe Asp Asn Thr Tyr Leu Phe Asn Ile
1               5                   10                  15

<210> SEQ ID NO 472
<211> LENGTH: 16
<212> TYPE: PRT
<213> ORGANISM: Variola virus

<400> SEQUENCE: 472

Lys Tyr Pro Asp Leu Asn Phe Asp Asn Thr Tyr Leu Phe Asn Ile Leu
1               5                   10                  15

<210> SEQ ID NO 473
<211> LENGTH: 17
<212> TYPE: PRT
<213> ORGANISM: Variola virus

<400> SEQUENCE: 473

Lys Tyr Pro Asp Leu Asn Phe Asp Asn Thr Tyr Leu Phe Asn Ile Leu
1               5                   10                  15

Tyr

<210> SEQ ID NO 474
<211> LENGTH: 18
<212> TYPE: PRT
<213> ORGANISM: Variola virus

<400> SEQUENCE: 474

Lys Tyr Pro Asp Leu Asn Phe Asp Asn Thr Tyr Leu Phe Asn Ile Leu
1               5                   10                  15

Tyr Lys
```

-continued

```
<210> SEQ ID NO 475
<211> LENGTH: 19
<212> TYPE: PRT
<213> ORGANISM: Variola virus

<400> SEQUENCE: 475

Lys Tyr Pro Asp Leu Asn Phe Asp Asn Thr Tyr Leu Phe Asn Ile Leu
1               5                   10                  15

Tyr Lys Asp

<210> SEQ ID NO 476
<211> LENGTH: 20
<212> TYPE: PRT
<213> ORGANISM: Variola virus

<400> SEQUENCE: 476

Lys Tyr Pro Asp Leu Asn Phe Asp Asn Thr Tyr Leu Phe Asn Ile Leu
1               5                   10                  15

Tyr Lys Asp Val
            20

<210> SEQ ID NO 477
<211> LENGTH: 8
<212> TYPE: PRT
<213> ORGANISM: Variola virus

<400> SEQUENCE: 477

Lys Lys Tyr Pro Asp Leu Asn Phe
1               5

<210> SEQ ID NO 478
<211> LENGTH: 9
<212> TYPE: PRT
<213> ORGANISM: Variola virus

<400> SEQUENCE: 478

Lys Lys Tyr Pro Asp Leu Asn Phe Asp
1               5

<210> SEQ ID NO 479
<211> LENGTH: 10
<212> TYPE: PRT
<213> ORGANISM: Variola virus

<400> SEQUENCE: 479

Lys Lys Tyr Pro Asp Leu Asn Phe Asp Asn
1               5                   10

<210> SEQ ID NO 480
<211> LENGTH: 11
<212> TYPE: PRT
<213> ORGANISM: Variola virus

<400> SEQUENCE: 480

Lys Lys Tyr Pro Asp Leu Asn Phe Asp Asn Thr
1               5                   10

<210> SEQ ID NO 481
<211> LENGTH: 12
<212> TYPE: PRT
<213> ORGANISM: Variola virus

<400> SEQUENCE: 481

Lys Lys Tyr Pro Asp Leu Asn Phe Asp Asn Thr Tyr
```

<210> SEQ ID NO 482
<211> LENGTH: 13
<212> TYPE: PRT
<213> ORGANISM: Variola virus

<400> SEQUENCE: 482

Lys Lys Tyr Pro Asp Leu Asn Phe Asp Asn Thr Tyr Leu
1               5                   10

<210> SEQ ID NO 483
<211> LENGTH: 14
<212> TYPE: PRT
<213> ORGANISM: Variola virus

<400> SEQUENCE: 483

Lys Lys Tyr Pro Asp Leu Asn Phe Asp Asn Thr Tyr Leu Phe
1               5                   10

<210> SEQ ID NO 484
<211> LENGTH: 15
<212> TYPE: PRT
<213> ORGANISM: Variola virus

<400> SEQUENCE: 484

Lys Lys Tyr Pro Asp Leu Asn Phe Asp Asn Thr Tyr Leu Phe Asn
1               5                   10                  15

<210> SEQ ID NO 485
<211> LENGTH: 16
<212> TYPE: PRT
<213> ORGANISM: Variola virus

<400> SEQUENCE: 485

Lys Lys Tyr Pro Asp Leu Asn Phe Asp Asn Thr Tyr Leu Phe Asn Ile
1               5                   10                  15

<210> SEQ ID NO 486
<211> LENGTH: 17
<212> TYPE: PRT
<213> ORGANISM: Variola virus

<400> SEQUENCE: 486

Lys Lys Tyr Pro Asp Leu Asn Phe Asp Asn Thr Tyr Leu Phe Asn Ile
1               5                   10                  15

Leu

<210> SEQ ID NO 487
<211> LENGTH: 18
<212> TYPE: PRT
<213> ORGANISM: Variola virus

<400> SEQUENCE: 487

Lys Lys Tyr Pro Asp Leu Asn Phe Asp Asn Thr Tyr Leu Phe Asn Ile
1               5                   10                  15

Leu Tyr

<210> SEQ ID NO 488
<211> LENGTH: 19
<212> TYPE: PRT
<213> ORGANISM: Variola virus

<400> SEQUENCE: 488

```
Lys Lys Tyr Pro Asp Leu Asn Phe Asp Asn Thr Tyr Leu Phe Asn Ile
1               5                   10                  15

Leu Tyr Lys

<210> SEQ ID NO 489
<211> LENGTH: 20
<212> TYPE: PRT
<213> ORGANISM: Variola virus

<400> SEQUENCE: 489

Lys Lys Tyr Pro Asp Leu Asn Phe Asp Asn Thr Tyr Leu Phe Asn Ile
1               5                   10                  15

Leu Tyr Lys Asp
            20

<210> SEQ ID NO 490
<211> LENGTH: 8
<212> TYPE: PRT
<213> ORGANISM: Variola virus

<400> SEQUENCE: 490

Glu Lys Lys Tyr Pro Asp Leu Asn
1               5

<210> SEQ ID NO 491
<211> LENGTH: 9
<212> TYPE: PRT
<213> ORGANISM: Variola virus

<400> SEQUENCE: 491

Glu Lys Lys Tyr Pro Asp Leu Asn Phe
1               5

<210> SEQ ID NO 492
<211> LENGTH: 10
<212> TYPE: PRT
<213> ORGANISM: Variola virus

<400> SEQUENCE: 492

Glu Lys Lys Tyr Pro Asp Leu Asn Phe Asp
1               5                   10

<210> SEQ ID NO 493
<211> LENGTH: 11
<212> TYPE: PRT
<213> ORGANISM: Variola virus

<400> SEQUENCE: 493

Glu Lys Lys Tyr Pro Asp Leu Asn Phe Asp Asn
1               5                   10

<210> SEQ ID NO 494
<211> LENGTH: 12
<212> TYPE: PRT
<213> ORGANISM: Variola virus

<400> SEQUENCE: 494

Glu Lys Lys Tyr Pro Asp Leu Asn Phe Asp Asn Thr
1               5                   10

<210> SEQ ID NO 495
<211> LENGTH: 13
<212> TYPE: PRT
```

<213> ORGANISM: Variola virus

<400> SEQUENCE: 495

Glu Lys Lys Tyr Pro Asp Leu Asn Phe Asp Asn Thr Tyr
1               5                   10

<210> SEQ ID NO 496
<211> LENGTH: 14
<212> TYPE: PRT
<213> ORGANISM: Variola virus

<400> SEQUENCE: 496

Glu Lys Lys Tyr Pro Asp Leu Asn Phe Asp Asn Thr Tyr Leu
1               5                   10

<210> SEQ ID NO 497
<211> LENGTH: 15
<212> TYPE: PRT
<213> ORGANISM: Variola virus

<400> SEQUENCE: 497

Glu Lys Lys Tyr Pro Asp Leu Asn Phe Asp Asn Thr Tyr Leu Phe
1               5                   10                  15

<210> SEQ ID NO 498
<211> LENGTH: 16
<212> TYPE: PRT
<213> ORGANISM: Variola virus

<400> SEQUENCE: 498

Glu Lys Lys Tyr Pro Asp Leu Asn Phe Asp Asn Thr Tyr Leu Phe Asn
1               5                   10                  15

<210> SEQ ID NO 499
<211> LENGTH: 17
<212> TYPE: PRT
<213> ORGANISM: Variola virus

<400> SEQUENCE: 499

Glu Lys Lys Tyr Pro Asp Leu Asn Phe Asp Asn Thr Tyr Leu Phe Asn
1               5                   10                  15

Ile

<210> SEQ ID NO 500
<211> LENGTH: 18
<212> TYPE: PRT
<213> ORGANISM: Variola virus

<400> SEQUENCE: 500

Glu Lys Lys Tyr Pro Asp Leu Asn Phe Asp Asn Thr Tyr Leu Phe Asn
1               5                   10                  15

Ile Leu

<210> SEQ ID NO 501
<211> LENGTH: 19
<212> TYPE: PRT
<213> ORGANISM: Variola virus

<400> SEQUENCE: 501

Glu Lys Lys Tyr Pro Asp Leu Asn Phe Asp Asn Thr Tyr Leu Phe Asn
1               5                   10                  15

Ile Leu Tyr

<210> SEQ ID NO 502
<211> LENGTH: 20
<212> TYPE: PRT
<213> ORGANISM: Variola virus

<400> SEQUENCE: 502

Glu Lys Lys Tyr Pro Asp Leu Asn Phe Asp Asn Thr Tyr Leu Phe Asn
1               5                   10                  15

Ile Leu Tyr Lys
            20

<210> SEQ ID NO 503
<211> LENGTH: 8
<212> TYPE: PRT
<213> ORGANISM: Variola virus

<400> SEQUENCE: 503

Ala Glu Lys Lys Tyr Pro Asp Leu
1               5

<210> SEQ ID NO 504
<211> LENGTH: 9
<212> TYPE: PRT
<213> ORGANISM: Variola virus

<400> SEQUENCE: 504

Ala Glu Lys Lys Tyr Pro Asp Leu Asn
1               5

<210> SEQ ID NO 505
<211> LENGTH: 10
<212> TYPE: PRT
<213> ORGANISM: Variola virus

<400> SEQUENCE: 505

Ala Glu Lys Lys Tyr Pro Asp Leu Asn Phe
1               5                   10

<210> SEQ ID NO 506
<211> LENGTH: 11
<212> TYPE: PRT
<213> ORGANISM: Variola virus

<400> SEQUENCE: 506

Ala Glu Lys Lys Tyr Pro Asp Leu Asn Phe Asp
1               5                   10

<210> SEQ ID NO 507
<211> LENGTH: 12
<212> TYPE: PRT
<213> ORGANISM: Variola virus

<400> SEQUENCE: 507

Ala Glu Lys Lys Tyr Pro Asp Leu Asn Phe Asp Asn
1               5                   10

<210> SEQ ID NO 508
<211> LENGTH: 13
<212> TYPE: PRT
<213> ORGANISM: Variola virus

<400> SEQUENCE: 508

Ala Glu Lys Lys Tyr Pro Asp Leu Asn Phe Asp Asn Thr
1               5                   10

<210> SEQ ID NO 509
<211> LENGTH: 14
<212> TYPE: PRT
<213> ORGANISM: Variola virus

<400> SEQUENCE: 509

Ala Glu Lys Lys Tyr Pro Asp Leu Asn Phe Asp Asn Thr Tyr
1               5                   10

<210> SEQ ID NO 510
<211> LENGTH: 15
<212> TYPE: PRT
<213> ORGANISM: Variola virus

<400> SEQUENCE: 510

Ala Glu Lys Lys Tyr Pro Asp Leu Asn Phe Asp Asn Thr Tyr Leu
1               5                   10                  15

<210> SEQ ID NO 511
<211> LENGTH: 16
<212> TYPE: PRT
<213> ORGANISM: Variola virus

<400> SEQUENCE: 511

Ala Glu Lys Lys Tyr Pro Asp Leu Asn Phe Asp Asn Thr Tyr Leu Phe
1               5                   10                  15

<210> SEQ ID NO 512
<211> LENGTH: 17
<212> TYPE: PRT
<213> ORGANISM: Variola virus

<400> SEQUENCE: 512

Ala Glu Lys Lys Tyr Pro Asp Leu Asn Phe Asp Asn Thr Tyr Leu Phe
1               5                   10                  15

Asn

<210> SEQ ID NO 513
<211> LENGTH: 18
<212> TYPE: PRT
<213> ORGANISM: Variola virus

<400> SEQUENCE: 513

Ala Glu Lys Lys Tyr Pro Asp Leu Asn Phe Asp Asn Thr Tyr Leu Phe
1               5                   10                  15

Asn Ile

<210> SEQ ID NO 514
<211> LENGTH: 19
<212> TYPE: PRT
<213> ORGANISM: Variola virus

<400> SEQUENCE: 514

Ala Glu Lys Lys Tyr Pro Asp Leu Asn Phe Asp Asn Thr Tyr Leu Phe
1               5                   10                  15

Asn Ile Leu

<210> SEQ ID NO 515
<211> LENGTH: 20
<212> TYPE: PRT
<213> ORGANISM: Variola virus -continued

<400> SEQUENCE: 515

Ala Glu Lys Lys Tyr Pro Asp Leu Asn Phe Asp Asn Thr Tyr Leu Phe
1               5                   10                  15

Asn Ile Leu Tyr
            20

<210> SEQ ID NO 516
<211> LENGTH: 9
<212> TYPE: PRT
<213> ORGANISM: Variola virus

<400> SEQUENCE: 516

Leu Ala Glu Lys Lys Tyr Pro Asp Leu
1               5

<210> SEQ ID NO 517
<211> LENGTH: 10
<212> TYPE: PRT
<213> ORGANISM: Variola virus

<400> SEQUENCE: 517

Leu Ala Glu Lys Lys Tyr Pro Asp Leu Asn
1               5                   10

<210> SEQ ID NO 518
<211> LENGTH: 11
<212> TYPE: PRT
<213> ORGANISM: Variola virus

<400> SEQUENCE: 518

Leu Ala Glu Lys Lys Tyr Pro Asp Leu Asn Phe
1               5                   10

<210> SEQ ID NO 519
<211> LENGTH: 12
<212> TYPE: PRT
<213> ORGANISM: Variola virus

<400> SEQUENCE: 519

Leu Ala Glu Lys Lys Tyr Pro Asp Leu Asn Phe Asp
1               5                   10

<210> SEQ ID NO 520
<211> LENGTH: 13
<212> TYPE: PRT
<213> ORGANISM: Variola virus

<400> SEQUENCE: 520

Leu Ala Glu Lys Lys Tyr Pro Asp Leu Asn Phe Asp Asn
1               5                   10

<210> SEQ ID NO 521
<211> LENGTH: 14
<212> TYPE: PRT
<213> ORGANISM: Variola virus

<400> SEQUENCE: 521

Leu Ala Glu Lys Lys Tyr Pro Asp Leu Asn Phe Asp Asn Thr
1               5                   10

<210> SEQ ID NO 522
<211> LENGTH: 15
<212> TYPE: PRT
<213> ORGANISM: Variola virus

<400> SEQUENCE: 522

Leu Ala Glu Lys Lys Tyr Pro Asp Leu Asn Phe Asp Asn Thr Tyr
1               5                   10                  15

<210> SEQ ID NO 523
<211> LENGTH: 16
<212> TYPE: PRT
<213> ORGANISM: Variola virus

<400> SEQUENCE: 523

Leu Ala Glu Lys Lys Tyr Pro Asp Leu Asn Phe Asp Asn Thr Tyr Leu
1               5                   10                  15

<210> SEQ ID NO 524
<211> LENGTH: 17
<212> TYPE: PRT
<213> ORGANISM: Variola virus

<400> SEQUENCE: 524

Leu Ala Glu Lys Lys Tyr Pro Asp Leu Asn Phe Asp Asn Thr Tyr Leu
1               5                   10                  15

Phe

<210> SEQ ID NO 525
<211> LENGTH: 18
<212> TYPE: PRT
<213> ORGANISM: Variola virus

<400> SEQUENCE: 525

Leu Ala Glu Lys Lys Tyr Pro Asp Leu Asn Phe Asp Asn Thr Tyr Leu
1               5                   10                  15

Phe Asn

<210> SEQ ID NO 526
<211> LENGTH: 19
<212> TYPE: PRT
<213> ORGANISM: Variola virus

<400> SEQUENCE: 526

Leu Ala Glu Lys Lys Tyr Pro Asp Leu Asn Phe Asp Asn Thr Tyr Leu
1               5                   10                  15

Phe Asn Ile

<210> SEQ ID NO 527
<211> LENGTH: 20
<212> TYPE: PRT
<213> ORGANISM: Variola virus

<400> SEQUENCE: 527

Leu Ala Glu Lys Lys Tyr Pro Asp Leu Asn Phe Asp Asn Thr Tyr Leu
1               5                   10                  15

Phe Asn Ile Leu
            20

<210> SEQ ID NO 528
<211> LENGTH: 10
<212> TYPE: PRT
<213> ORGANISM: Variola virus

<400> SEQUENCE: 528

Val Leu Ala Glu Lys Lys Tyr Pro Asp Leu

-continued

```
1               5                  10

<210> SEQ ID NO 529
<211> LENGTH: 11
<212> TYPE: PRT
<213> ORGANISM: Variola virus

<400> SEQUENCE: 529

Val Leu Ala Glu Lys Lys Tyr Pro Asp Leu Asn
1               5                  10

<210> SEQ ID NO 530
<211> LENGTH: 12
<212> TYPE: PRT
<213> ORGANISM: Variola virus

<400> SEQUENCE: 530

Val Leu Ala Glu Lys Lys Tyr Pro Asp Leu Asn Phe
1               5                  10

<210> SEQ ID NO 531
<211> LENGTH: 13
<212> TYPE: PRT
<213> ORGANISM: Variola virus

<400> SEQUENCE: 531

Val Leu Ala Glu Lys Lys Tyr Pro Asp Leu Asn Phe Asp
1               5                  10

<210> SEQ ID NO 532
<211> LENGTH: 14
<212> TYPE: PRT
<213> ORGANISM: Variola virus

<400> SEQUENCE: 532

Val Leu Ala Glu Lys Lys Tyr Pro Asp Leu Asn Phe Asp Asn
1               5                  10

<210> SEQ ID NO 533
<211> LENGTH: 15
<212> TYPE: PRT
<213> ORGANISM: Variola virus

<400> SEQUENCE: 533

Val Leu Ala Glu Lys Lys Tyr Pro Asp Leu Asn Phe Asp Asn Thr
1               5                  10                 15

<210> SEQ ID NO 534
<211> LENGTH: 16
<212> TYPE: PRT
<213> ORGANISM: Variola virus

<400> SEQUENCE: 534

Val Leu Ala Glu Lys Lys Tyr Pro Asp Leu Asn Phe Asp Asn Thr Tyr
1               5                  10                 15

<210> SEQ ID NO 535
<211> LENGTH: 17
<212> TYPE: PRT
<213> ORGANISM: Variola virus

<400> SEQUENCE: 535

Val Leu Ala Glu Lys Lys Tyr Pro Asp Leu Asn Phe Asp Asn Thr Tyr
1               5                  10                 15
```

Leu

<210> SEQ ID NO 536
<211> LENGTH: 18
<212> TYPE: PRT
<213> ORGANISM: Variola virus

<400> SEQUENCE: 536

Val Leu Ala Glu Lys Lys Tyr Pro Asp Leu Asn Phe Asp Asn Thr Tyr
1               5                   10                  15

Leu Phe

<210> SEQ ID NO 537
<211> LENGTH: 19
<212> TYPE: PRT
<213> ORGANISM: Variola virus

<400> SEQUENCE: 537

Val Leu Ala Glu Lys Lys Tyr Pro Asp Leu Asn Phe Asp Asn Thr Tyr
1               5                   10                  15

Leu Phe Asn

<210> SEQ ID NO 538
<211> LENGTH: 20
<212> TYPE: PRT
<213> ORGANISM: Variola virus

<400> SEQUENCE: 538

Val Leu Ala Glu Lys Lys Tyr Pro Asp Leu Asn Phe Asp Asn Thr Tyr
1               5                   10                  15

Leu Phe Asn Ile
            20

<210> SEQ ID NO 539
<211> LENGTH: 11
<212> TYPE: PRT
<213> ORGANISM: Variola virus

<400> SEQUENCE: 539

Asp Val Leu Ala Glu Lys Lys Tyr Pro Asp Leu
1               5                   10

<210> SEQ ID NO 540
<211> LENGTH: 12
<212> TYPE: PRT
<213> ORGANISM: Variola virus

<400> SEQUENCE: 540

Asp Val Leu Ala Glu Lys Lys Tyr Pro Asp Leu Asn
1               5                   10

<210> SEQ ID NO 541
<211> LENGTH: 13
<212> TYPE: PRT
<213> ORGANISM: Variola virus

<400> SEQUENCE: 541

Asp Val Leu Ala Glu Lys Lys Tyr Pro Asp Leu Asn Phe
1               5                   10

<210> SEQ ID NO 542
<211> LENGTH: 14
<212> TYPE: PRT

<213> ORGANISM: Variola virus

<400> SEQUENCE: 542

Asp Val Leu Ala Glu Lys Lys Tyr Pro Asp Leu Asn Phe Asp
1               5                   10

<210> SEQ ID NO 543
<211> LENGTH: 15
<212> TYPE: PRT
<213> ORGANISM: Variola virus

<400> SEQUENCE: 543

Asp Val Leu Ala Glu Lys Lys Tyr Pro Asp Leu Asn Phe Asp Asn
1               5                   10                  15

<210> SEQ ID NO 544
<211> LENGTH: 16
<212> TYPE: PRT
<213> ORGANISM: Variola virus

<400> SEQUENCE: 544

Asp Val Leu Ala Glu Lys Lys Tyr Pro Asp Leu Asn Phe Asp Asn Thr
1               5                   10                  15

<210> SEQ ID NO 545
<211> LENGTH: 17
<212> TYPE: PRT
<213> ORGANISM: Variola virus

<400> SEQUENCE: 545

Asp Val Leu Ala Glu Lys Lys Tyr Pro Asp Leu Asn Phe Asp Asn Thr
1               5                   10                  15

Tyr

<210> SEQ ID NO 546
<211> LENGTH: 18
<212> TYPE: PRT
<213> ORGANISM: Variola virus

<400> SEQUENCE: 546

Asp Val Leu Ala Glu Lys Lys Tyr Pro Asp Leu Asn Phe Asp Asn Thr
1               5                   10                  15

Tyr Leu

<210> SEQ ID NO 547
<211> LENGTH: 19
<212> TYPE: PRT
<213> ORGANISM: Variola virus

<400> SEQUENCE: 547

Asp Val Leu Ala Glu Lys Lys Tyr Pro Asp Leu Asn Phe Asp Asn Thr
1               5                   10                  15

Tyr Leu Phe

<210> SEQ ID NO 548
<211> LENGTH: 20
<212> TYPE: PRT
<213> ORGANISM: Variola virus

<400> SEQUENCE: 548

Asp Val Leu Ala Glu Lys Lys Tyr Pro Asp Leu Asn Phe Asp Asn Thr
1               5                   10                  15

-continued

Tyr Leu Phe Asn
            20

<210> SEQ ID NO 549
<211> LENGTH: 12
<212> TYPE: PRT
<213> ORGANISM: Variola virus

<400> SEQUENCE: 549

Met Asp Val Leu Ala Glu Lys Lys Tyr Pro Asp Leu
1               5                   10

<210> SEQ ID NO 550
<211> LENGTH: 13
<212> TYPE: PRT
<213> ORGANISM: Variola virus

<400> SEQUENCE: 550

Met Asp Val Leu Ala Glu Lys Lys Tyr Pro Asp Leu Asn
1               5                   10

<210> SEQ ID NO 551
<211> LENGTH: 14
<212> TYPE: PRT
<213> ORGANISM: Variola virus

<400> SEQUENCE: 551

Met Asp Val Leu Ala Glu Lys Lys Tyr Pro Asp Leu Asn Phe
1               5                   10

<210> SEQ ID NO 552
<211> LENGTH: 15
<212> TYPE: PRT
<213> ORGANISM: Variola virus

<400> SEQUENCE: 552

Met Asp Val Leu Ala Glu Lys Lys Tyr Pro Asp Leu Asn Phe Asp
1               5                   10                  15

<210> SEQ ID NO 553
<211> LENGTH: 16
<212> TYPE: PRT
<213> ORGANISM: Variola virus

<400> SEQUENCE: 553

Met Asp Val Leu Ala Glu Lys Lys Tyr Pro Asp Leu Asn Phe Asp Asn
1               5                   10                  15

<210> SEQ ID NO 554
<211> LENGTH: 17
<212> TYPE: PRT
<213> ORGANISM: Variola virus

<400> SEQUENCE: 554

Met Asp Val Leu Ala Glu Lys Lys Tyr Pro Asp Leu Asn Phe Asp Asn
1               5                   10                  15
Thr

<210> SEQ ID NO 555
<211> LENGTH: 18
<212> TYPE: PRT
<213> ORGANISM: Variola virus

<400> SEQUENCE: 555

-continued

Met Asp Val Leu Ala Glu Lys Lys Tyr Pro Asp Leu Asn Phe Asp Asn
1               5                   10                  15

Thr Tyr

<210> SEQ ID NO 556
<211> LENGTH: 19
<212> TYPE: PRT
<213> ORGANISM: Variola virus

<400> SEQUENCE: 556

Met Asp Val Leu Ala Glu Lys Lys Tyr Pro Asp Leu Asn Phe Asp Asn
1               5                   10                  15

Thr Tyr Leu

<210> SEQ ID NO 557
<211> LENGTH: 20
<212> TYPE: PRT
<213> ORGANISM: Variola virus

<400> SEQUENCE: 557

Met Asp Val Leu Ala Glu Lys Lys Tyr Pro Asp Leu Asn Phe Asp Asn
1               5                   10                  15

Thr Tyr Leu Phe
            20

<210> SEQ ID NO 558
<211> LENGTH: 13
<212> TYPE: PRT
<213> ORGANISM: Variola virus

<400> SEQUENCE: 558

Ser Met Asp Val Leu Ala Glu Lys Lys Tyr Pro Asp Leu
1               5                   10

<210> SEQ ID NO 559
<211> LENGTH: 14
<212> TYPE: PRT
<213> ORGANISM: Variola virus

<400> SEQUENCE: 559

Ser Met Asp Val Leu Ala Glu Lys Lys Tyr Pro Asp Leu Asn
1               5                   10

<210> SEQ ID NO 560
<211> LENGTH: 15
<212> TYPE: PRT
<213> ORGANISM: Variola virus

<400> SEQUENCE: 560

Ser Met Asp Val Leu Ala Glu Lys Lys Tyr Pro Asp Leu Asn Phe
1               5                   10                  15

<210> SEQ ID NO 561
<211> LENGTH: 16
<212> TYPE: PRT
<213> ORGANISM: Variola virus

<400> SEQUENCE: 561

Ser Met Asp Val Leu Ala Glu Lys Lys Tyr Pro Asp Leu Asn Phe Asp
1               5                   10                  15

<210> SEQ ID NO 562
<211> LENGTH: 17

```
<212> TYPE: PRT
<213> ORGANISM: Variola virus

<400> SEQUENCE: 562

Ser Met Asp Val Leu Ala Glu Lys Lys Tyr Pro Asp Leu Asn Phe Asp
1               5                   10                  15
Asn

<210> SEQ ID NO 563
<211> LENGTH: 18
<212> TYPE: PRT
<213> ORGANISM: Variola virus

<400> SEQUENCE: 563

Ser Met Asp Val Leu Ala Glu Lys Lys Tyr Pro Asp Leu Asn Phe Asp
1               5                   10                  15
Asn Thr

<210> SEQ ID NO 564
<211> LENGTH: 19
<212> TYPE: PRT
<213> ORGANISM: Variola virus

<400> SEQUENCE: 564

Ser Met Asp Val Leu Ala Glu Lys Lys Tyr Pro Asp Leu Asn Phe Asp
1               5                   10                  15
Asn Thr Tyr

<210> SEQ ID NO 565
<211> LENGTH: 20
<212> TYPE: PRT
<213> ORGANISM: Variola virus

<400> SEQUENCE: 565

Ser Met Asp Val Leu Ala Glu Lys Lys Tyr Pro Asp Leu Asn Phe Asp
1               5                   10                  15
Asn Thr Tyr Leu
            20

<210> SEQ ID NO 566
<211> LENGTH: 14
<212> TYPE: PRT
<213> ORGANISM: Variola virus

<400> SEQUENCE: 566

Asp Ser Met Asp Val Leu Ala Glu Lys Lys Tyr Pro Asp Leu
1               5                   10

<210> SEQ ID NO 567
<211> LENGTH: 15
<212> TYPE: PRT
<213> ORGANISM: Variola virus

<400> SEQUENCE: 567

Asp Ser Met Asp Val Leu Ala Glu Lys Lys Tyr Pro Asp Leu Asn
1               5                   10                  15

<210> SEQ ID NO 568
<211> LENGTH: 16
<212> TYPE: PRT
<213> ORGANISM: Variola virus

<400> SEQUENCE: 568
```

Asp Ser Met Asp Val Leu Ala Glu Lys Lys Tyr Pro Asp Leu Asn Phe
1               5                   10                  15

<210> SEQ ID NO 569
<211> LENGTH: 17
<212> TYPE: PRT
<213> ORGANISM: Variola virus

<400> SEQUENCE: 569

Asp Ser Met Asp Val Leu Ala Glu Lys Lys Tyr Pro Asp Leu Asn Phe
1               5                   10                  15

Asp

<210> SEQ ID NO 570
<211> LENGTH: 18
<212> TYPE: PRT
<213> ORGANISM: Variola virus

<400> SEQUENCE: 570

Asp Ser Met Asp Val Leu Ala Glu Lys Lys Tyr Pro Asp Leu Asn Phe
1               5                   10                  15

Asp Asn

<210> SEQ ID NO 571
<211> LENGTH: 19
<212> TYPE: PRT
<213> ORGANISM: Variola virus

<400> SEQUENCE: 571

Asp Ser Met Asp Val Leu Ala Glu Lys Lys Tyr Pro Asp Leu Asn Phe
1               5                   10                  15

Asp Asn Thr

<210> SEQ ID NO 572
<211> LENGTH: 20
<212> TYPE: PRT
<213> ORGANISM: Variola virus

<400> SEQUENCE: 572

Asp Ser Met Asp Val Leu Ala Glu Lys Lys Tyr Pro Asp Leu Asn Phe
1               5                   10                  15

Asp Asn Thr Tyr
            20

<210> SEQ ID NO 573
<211> LENGTH: 15
<212> TYPE: PRT
<213> ORGANISM: Variola virus

<400> SEQUENCE: 573

Ser Asp Ser Met Asp Val Leu Ala Glu Lys Lys Tyr Pro Asp Leu
1               5                   10                  15

<210> SEQ ID NO 574
<211> LENGTH: 16
<212> TYPE: PRT
<213> ORGANISM: Variola virus

<400> SEQUENCE: 574

Ser Asp Ser Met Asp Val Leu Ala Glu Lys Lys Tyr Pro Asp Leu Asn
1               5                   10                  15

-continued

<210> SEQ ID NO 575
<211> LENGTH: 17
<212> TYPE: PRT
<213> ORGANISM: Variola virus

<400> SEQUENCE: 575

Ser Asp Ser Met Asp Val Leu Ala Glu Lys Lys Tyr Pro Asp Leu Asn
1               5                   10                  15

Phe

<210> SEQ ID NO 576
<211> LENGTH: 18
<212> TYPE: PRT
<213> ORGANISM: Variola virus

<400> SEQUENCE: 576

Ser Asp Ser Met Asp Val Leu Ala Glu Lys Lys Tyr Pro Asp Leu Asn
1               5                   10                  15

Phe Asp

<210> SEQ ID NO 577
<211> LENGTH: 19
<212> TYPE: PRT
<213> ORGANISM: Variola virus

<400> SEQUENCE: 577

Ser Asp Ser Met Asp Val Leu Ala Glu Lys Lys Tyr Pro Asp Leu Asn
1               5                   10                  15

Phe Asp Asn

<210> SEQ ID NO 578
<211> LENGTH: 20
<212> TYPE: PRT
<213> ORGANISM: Variola virus

<400> SEQUENCE: 578

Ser Asp Ser Met Asp Val Leu Ala Glu Lys Lys Tyr Pro Asp Leu Asn
1               5                   10                  15

Phe Asp Asn Thr
            20

<210> SEQ ID NO 579
<211> LENGTH: 16
<212> TYPE: PRT
<213> ORGANISM: Variola virus

<400> SEQUENCE: 579

Gly Ser Asp Ser Met Asp Val Leu Ala Glu Lys Lys Tyr Pro Asp Leu
1               5                   10                  15

<210> SEQ ID NO 580
<211> LENGTH: 17
<212> TYPE: PRT
<213> ORGANISM: Variola virus

<400> SEQUENCE: 580

Gly Ser Asp Ser Met Asp Val Leu Ala Glu Lys Lys Tyr Pro Asp Leu
1               5                   10                  15

Asn

<210> SEQ ID NO 581

-continued

```
<211> LENGTH: 18
<212> TYPE: PRT
<213> ORGANISM: Variola virus

<400> SEQUENCE: 581

Gly Ser Asp Ser Met Asp Val Leu Ala Glu Lys Lys Tyr Pro Asp Leu
 1               5                  10                  15

Asn Phe

<210> SEQ ID NO 582
<211> LENGTH: 19
<212> TYPE: PRT
<213> ORGANISM: Variola virus

<400> SEQUENCE: 582

Gly Ser Asp Ser Met Asp Val Leu Ala Glu Lys Lys Tyr Pro Asp Leu
 1               5                  10                  15

Asn Phe Asp

<210> SEQ ID NO 583
<211> LENGTH: 20
<212> TYPE: PRT
<213> ORGANISM: Variola virus

<400> SEQUENCE: 583

Gly Ser Asp Ser Met Asp Val Leu Ala Glu Lys Lys Tyr Pro Asp Leu
 1               5                  10                  15

Asn Phe Asp Asn
             20

<210> SEQ ID NO 584
<211> LENGTH: 17
<212> TYPE: PRT
<213> ORGANISM: Variola virus

<400> SEQUENCE: 584

Asp Gly Ser Asp Ser Met Asp Val Leu Ala Glu Lys Lys Tyr Pro Asp
 1               5                  10                  15

Leu

<210> SEQ ID NO 585
<211> LENGTH: 18
<212> TYPE: PRT
<213> ORGANISM: Variola virus

<400> SEQUENCE: 585

Asp Gly Ser Asp Ser Met Asp Val Leu Ala Glu Lys Lys Tyr Pro Asp
 1               5                  10                  15

Leu Asn

<210> SEQ ID NO 586
<211> LENGTH: 19
<212> TYPE: PRT
<213> ORGANISM: Variola virus

<400> SEQUENCE: 586

Asp Gly Ser Asp Ser Met Asp Val Leu Ala Glu Lys Lys Tyr Pro Asp
 1               5                  10                  15

Leu Asn Phe

<210> SEQ ID NO 587
```

```
<211> LENGTH: 20
<212> TYPE: PRT
<213> ORGANISM: Variola virus

<400> SEQUENCE: 587

Asp Gly Ser Asp Ser Met Asp Val Leu Ala Glu Lys Lys Tyr Pro Asp
1               5                   10                  15

Leu Asn Phe Asp
            20

<210> SEQ ID NO 588
<211> LENGTH: 18
<212> TYPE: PRT
<213> ORGANISM: Variola virus

<400> SEQUENCE: 588

Pro Asp Gly Ser Asp Ser Met Asp Val Leu Ala Glu Lys Lys Tyr Pro
1               5                   10                  15

Asp Leu

<210> SEQ ID NO 589
<211> LENGTH: 19
<212> TYPE: PRT
<213> ORGANISM: Variola virus

<400> SEQUENCE: 589

Pro Asp Gly Ser Asp Ser Met Asp Val Leu Ala Glu Lys Lys Tyr Pro
1               5                   10                  15

Asp Leu Asn

<210> SEQ ID NO 590
<211> LENGTH: 20
<212> TYPE: PRT
<213> ORGANISM: Variola virus

<400> SEQUENCE: 590

Pro Asp Gly Ser Asp Ser Met Asp Val Leu Ala Glu Lys Lys Tyr Pro
1               5                   10                  15

Asp Leu Asn Phe
            20

<210> SEQ ID NO 591
<211> LENGTH: 19
<212> TYPE: PRT
<213> ORGANISM: Variola virus

<400> SEQUENCE: 591

Lys Pro Asp Gly Ser Asp Ser Met Asp Val Leu Ala Glu Lys Lys Tyr
1               5                   10                  15

Pro Asp Leu

<210> SEQ ID NO 592
<211> LENGTH: 20
<212> TYPE: PRT
<213> ORGANISM: Variola virus

<400> SEQUENCE: 592

Lys Pro Asp Gly Ser Asp Ser Met Asp Val Leu Ala Glu Lys Lys Tyr
1               5                   10                  15

Pro Asp Leu Asn
            20
```

```
<210> SEQ ID NO 593
<211> LENGTH: 20
<212> TYPE: PRT
<213> ORGANISM: Variola virus

<400> SEQUENCE: 593

Ile Lys Pro Asp Gly Ser Asp Ser Met Asp Val Leu Ala Glu Lys Lys
1               5                   10                  15
Tyr Pro Asp Leu
            20

<210> SEQ ID NO 594
<211> LENGTH: 8
<212> TYPE: PRT
<213> ORGANISM: Human parainfluenza virus 1

<400> SEQUENCE: 594

Tyr Pro Asp Leu Asn Pro Val Ile
1               5

<210> SEQ ID NO 595
<211> LENGTH: 9
<212> TYPE: PRT
<213> ORGANISM: Human parainfluenza virus 1

<400> SEQUENCE: 595

Tyr Pro Asp Leu Asn Pro Val Ile Ser
1               5

<210> SEQ ID NO 596
<211> LENGTH: 10
<212> TYPE: PRT
<213> ORGANISM: Human parainfluenza virus 1

<400> SEQUENCE: 596

Tyr Pro Asp Leu Asn Pro Val Ile Ser His
1               5                   10

<210> SEQ ID NO 597
<211> LENGTH: 11
<212> TYPE: PRT
<213> ORGANISM: Human parainfluenza virus 1

<400> SEQUENCE: 597

Tyr Pro Asp Leu Asn Pro Val Ile Ser His Thr
1               5                   10

<210> SEQ ID NO 598
<211> LENGTH: 12
<212> TYPE: PRT
<213> ORGANISM: Human parainfluenza virus 1

<400> SEQUENCE: 598

Tyr Pro Asp Leu Asn Pro Val Ile Ser His Thr Tyr
1               5                   10

<210> SEQ ID NO 599
<211> LENGTH: 13
<212> TYPE: PRT
<213> ORGANISM: Human parainfluenza virus 1

<400> SEQUENCE: 599

Tyr Pro Asp Leu Asn Pro Val Ile Ser His Thr Tyr Asp
1               5                   10
```

<210> SEQ ID NO 600
<211> LENGTH: 14
<212> TYPE: PRT
<213> ORGANISM: Human parainfluenza virus 1

<400> SEQUENCE: 600

Tyr Pro Asp Leu Asn Pro Val Ile Ser His Thr Tyr Asp Ile
1               5                   10

<210> SEQ ID NO 601
<211> LENGTH: 15
<212> TYPE: PRT
<213> ORGANISM: Human parainfluenza virus 1

<400> SEQUENCE: 601

Tyr Pro Asp Leu Asn Pro Val Ile Ser His Thr Tyr Asp Ile Asn
1               5                   10                  15

<210> SEQ ID NO 602
<211> LENGTH: 16
<212> TYPE: PRT
<213> ORGANISM: Human parainfluenza virus 1

<400> SEQUENCE: 602

Tyr Pro Asp Leu Asn Pro Val Ile Ser His Thr Tyr Asp Ile Asn Asp
1               5                   10                  15

<210> SEQ ID NO 603
<211> LENGTH: 17
<212> TYPE: PRT
<213> ORGANISM: Human parainfluenza virus 1

<400> SEQUENCE: 603

Tyr Pro Asp Leu Asn Pro Val Ile Ser His Thr Tyr Asp Ile Asn Asp
1               5                   10                  15

Asn

<210> SEQ ID NO 604
<211> LENGTH: 18
<212> TYPE: PRT
<213> ORGANISM: Human parainfluenza virus 1

<400> SEQUENCE: 604

Tyr Pro Asp Leu Asn Pro Val Ile Ser His Thr Tyr Asp Ile Asn Asp
1               5                   10                  15

Asn Arg

<210> SEQ ID NO 605
<211> LENGTH: 19
<212> TYPE: PRT
<213> ORGANISM: Human parainfluenza virus 1

<400> SEQUENCE: 605

Tyr Pro Asp Leu Asn Pro Val Ile Ser His Thr Tyr Asp Ile Asn Asp
1               5                   10                  15

Asn Arg Lys

<210> SEQ ID NO 606
<211> LENGTH: 20
<212> TYPE: PRT
<213> ORGANISM: Human parainfluenza virus 1

-continued

```
<400> SEQUENCE: 606

Tyr Pro Asp Leu Asn Pro Val Ile Ser His Thr Tyr Asp Ile Asn Asp
1               5                   10                  15

Asn Arg Lys Ser
            20

<210> SEQ ID NO 607
<211> LENGTH: 8
<212> TYPE: PRT
<213> ORGANISM: Human parainfluenza virus 1

<400> SEQUENCE: 607

Met Tyr Pro Asp Leu Asn Pro Val
1               5

<210> SEQ ID NO 608
<211> LENGTH: 9
<212> TYPE: PRT
<213> ORGANISM: Human parainfluenza virus 1

<400> SEQUENCE: 608

Met Tyr Pro Asp Leu Asn Pro Val Ile
1               5

<210> SEQ ID NO 609
<211> LENGTH: 10
<212> TYPE: PRT
<213> ORGANISM: Human parainfluenza virus 1

<400> SEQUENCE: 609

Met Tyr Pro Asp Leu Asn Pro Val Ile Ser
1               5                   10

<210> SEQ ID NO 610
<211> LENGTH: 11
<212> TYPE: PRT
<213> ORGANISM: Human parainfluenza virus 1

<400> SEQUENCE: 610

Met Tyr Pro Asp Leu Asn Pro Val Ile Ser His
1               5                   10

<210> SEQ ID NO 611
<211> LENGTH: 12
<212> TYPE: PRT
<213> ORGANISM: Human parainfluenza virus 1

<400> SEQUENCE: 611

Met Tyr Pro Asp Leu Asn Pro Val Ile Ser His Thr
1               5                   10

<210> SEQ ID NO 612
<211> LENGTH: 13
<212> TYPE: PRT
<213> ORGANISM: Human parainfluenza virus 1

<400> SEQUENCE: 612

Met Tyr Pro Asp Leu Asn Pro Val Ile Ser His Thr Tyr
1               5                   10

<210> SEQ ID NO 613
<211> LENGTH: 14
<212> TYPE: PRT
<213> ORGANISM: Human parainfluenza virus 1
```

-continued

<400> SEQUENCE: 613

Met Tyr Pro Asp Leu Asn Pro Val Ile Ser His Thr Tyr Asp
1               5                   10

<210> SEQ ID NO 614
<211> LENGTH: 15
<212> TYPE: PRT
<213> ORGANISM: Human parainfluenza virus 1

<400> SEQUENCE: 614

Met Tyr Pro Asp Leu Asn Pro Val Ile Ser His Thr Tyr Asp Ile
1               5                   10                  15

<210> SEQ ID NO 615
<211> LENGTH: 16
<212> TYPE: PRT
<213> ORGANISM: Human parainfluenza virus 1

<400> SEQUENCE: 615

Met Tyr Pro Asp Leu Asn Pro Val Ile Ser His Thr Tyr Asp Ile Asn
1               5                   10                  15

<210> SEQ ID NO 616
<211> LENGTH: 17
<212> TYPE: PRT
<213> ORGANISM: Human parainfluenza virus 1

<400> SEQUENCE: 616

Met Tyr Pro Asp Leu Asn Pro Val Ile Ser His Thr Tyr Asp Ile Asn
1               5                   10                  15

Asp

<210> SEQ ID NO 617
<211> LENGTH: 18
<212> TYPE: PRT
<213> ORGANISM: Human parainfluenza virus 1

<400> SEQUENCE: 617

Met Tyr Pro Asp Leu Asn Pro Val Ile Ser His Thr Tyr Asp Ile Asn
1               5                   10                  15

Asp Asn

<210> SEQ ID NO 618
<211> LENGTH: 19
<212> TYPE: PRT
<213> ORGANISM: Human parainfluenza virus 1

<400> SEQUENCE: 618

Met Tyr Pro Asp Leu Asn Pro Val Ile Ser His Thr Tyr Asp Ile Asn
1               5                   10                  15

Asp Asn Arg

<210> SEQ ID NO 619
<211> LENGTH: 20
<212> TYPE: PRT
<213> ORGANISM: Human parainfluenza virus 1

<400> SEQUENCE: 619

Met Tyr Pro Asp Leu Asn Pro Val Ile Ser His Thr Tyr Asp Ile Asn
1               5                   10                  15

Asp Asn Arg Lys

<210> SEQ ID NO 620
<211> LENGTH: 8
<212> TYPE: PRT
<213> ORGANISM: Human parainfluenza virus 1

<400> SEQUENCE: 620

Asp Met Tyr Pro Asp Leu Asn Pro
1               5

<210> SEQ ID NO 621
<211> LENGTH: 9
<212> TYPE: PRT
<213> ORGANISM: Human parainfluenza virus 1

<400> SEQUENCE: 621

Asp Met Tyr Pro Asp Leu Asn Pro Val
1               5

<210> SEQ ID NO 622
<211> LENGTH: 10
<212> TYPE: PRT
<213> ORGANISM: Human parainfluenza virus 1

<400> SEQUENCE: 622

Asp Met Tyr Pro Asp Leu Asn Pro Val Ile
1               5                   10

<210> SEQ ID NO 623
<211> LENGTH: 11
<212> TYPE: PRT
<213> ORGANISM: Human parainfluenza virus 1

<400> SEQUENCE: 623

Asp Met Tyr Pro Asp Leu Asn Pro Val Ile Ser
1               5                   10

<210> SEQ ID NO 624
<211> LENGTH: 12
<212> TYPE: PRT
<213> ORGANISM: Human parainfluenza virus 1

<400> SEQUENCE: 624

Asp Met Tyr Pro Asp Leu Asn Pro Val Ile Ser His
1               5                   10

<210> SEQ ID NO 625
<211> LENGTH: 13
<212> TYPE: PRT
<213> ORGANISM: Human parainfluenza virus 1

<400> SEQUENCE: 625

Asp Met Tyr Pro Asp Leu Asn Pro Val Ile Ser His Thr
1               5                   10

<210> SEQ ID NO 626
<211> LENGTH: 14
<212> TYPE: PRT
<213> ORGANISM: Human parainfluenza virus 1

<400> SEQUENCE: 626

Asp Met Tyr Pro Asp Leu Asn Pro Val Ile Ser His Thr Tyr
1               5                   10

-continued

<210> SEQ ID NO 627
<211> LENGTH: 15
<212> TYPE: PRT
<213> ORGANISM: Human parainfluenza virus 1

<400> SEQUENCE: 627

Asp Met Tyr Pro Asp Leu Asn Pro Val Ile Ser His Thr Tyr Asp
1               5                   10                  15

<210> SEQ ID NO 628
<211> LENGTH: 16
<212> TYPE: PRT
<213> ORGANISM: Human parainfluenza virus 1

<400> SEQUENCE: 628

Asp Met Tyr Pro Asp Leu Asn Pro Val Ile Ser His Thr Tyr Asp Ile
1               5                   10                  15

<210> SEQ ID NO 629
<211> LENGTH: 17
<212> TYPE: PRT
<213> ORGANISM: Human parainfluenza virus 1

<400> SEQUENCE: 629

Asp Met Tyr Pro Asp Leu Asn Pro Val Ile Ser His Thr Tyr Asp Ile
1               5                   10                  15

Asn

<210> SEQ ID NO 630
<211> LENGTH: 18
<212> TYPE: PRT
<213> ORGANISM: Human parainfluenza virus 1

<400> SEQUENCE: 630

Asp Met Tyr Pro Asp Leu Asn Pro Val Ile Ser His Thr Tyr Asp Ile
1               5                   10                  15

Asn Asp

<210> SEQ ID NO 631
<211> LENGTH: 19
<212> TYPE: PRT
<213> ORGANISM: Human parainfluenza virus 1

<400> SEQUENCE: 631

Asp Met Tyr Pro Asp Leu Asn Pro Val Ile Ser His Thr Tyr Asp Ile
1               5                   10                  15

Asn Asp Asn

<210> SEQ ID NO 632
<211> LENGTH: 20
<212> TYPE: PRT
<213> ORGANISM: Human parainfluenza virus 1

<400> SEQUENCE: 632

Asp Met Tyr Pro Asp Leu Asn Pro Val Ile Ser His Thr Tyr Asp Ile
1               5                   10                  15

Asn Asp Asn Arg
            20

<210> SEQ ID NO 633
<211> LENGTH: 8
<212> TYPE: PRT

<213> ORGANISM: Human parainfluenza virus 1

<400> SEQUENCE: 633

Ser Asp Met Tyr Pro Asp Leu Asn
1               5

<210> SEQ ID NO 634
<211> LENGTH: 9
<212> TYPE: PRT
<213> ORGANISM: Human parainfluenza virus 1

<400> SEQUENCE: 634

Ser Asp Met Tyr Pro Asp Leu Asn Pro
1 5

<210> SEQ ID NO 635
<211> LENGTH: 10
<212> TYPE: PRT
<213> ORGANISM: Human parainfluenza virus 1

<400> SEQUENCE: 635

Ser Asp Met Tyr Pro Asp Leu Asn Pro Val
1 5 10

<210> SEQ ID NO 636
<211> LENGTH: 11
<212> TYPE: PRT
<213> ORGANISM: Human parainfluenza virus 1

<400> SEQUENCE: 636

Ser Asp Met Tyr Pro Asp Leu Asn Pro Val Ile
1 5 10

<210> SEQ ID NO 637
<211> LENGTH: 12
<212> TYPE: PRT
<213> ORGANISM: Human parainfluenza virus 1

<400> SEQUENCE: 637

Ser Asp Met Tyr Pro Asp Leu Asn Pro Val Ile Ser
1 5 10

<210> SEQ ID NO 638
<211> LENGTH: 13
<212> TYPE: PRT
<213> ORGANISM: Human parainfluenza virus 1

<400> SEQUENCE: 638

Ser Asp Met Tyr Pro Asp Leu Asn Pro Val Ile Ser His
1 5 10

<210> SEQ ID NO 639
<211> LENGTH: 14
<212> TYPE: PRT
<213> ORGANISM: Human parainfluenza virus 1

<400> SEQUENCE: 639

Ser Asp Met Tyr Pro Asp Leu Asn Pro Val Ile Ser His Thr
1 5 10

<210> SEQ ID NO 640
<211> LENGTH: 15
<212> TYPE: PRT
<213> ORGANISM: Human parainfluenza virus 1

-continued

```
<400> SEQUENCE: 640

Ser Asp Met Tyr Pro Asp Leu Asn Pro Val Ile Ser His Th

<210> SEQ ID NO 647
<211> LENGTH: 9
<212> TYPE: PRT
<213> ORGANISM: Human parainfluenza virus 1

<400> SEQUENCE: 647

Asn Ser Asp Met Tyr Pro Asp Leu Asn
1               5

<210> SEQ ID NO 648
<211> LENGTH: 10
<212> TYPE: PRT
<213> ORGANISM: Human parainfluenza virus 1

<400> SEQUENCE: 648

Asn Ser Asp Met Tyr Pro Asp Leu Asn Pro
1               5                   10

<210> SEQ ID NO 649
<211> LENGTH: 11
<212> TYPE: PRT
<213> ORGANISM: Human parainfluenza virus 1

<400> SEQUENCE: 649

Asn Ser Asp Met Tyr Pro Asp Leu Asn Pro Val
1               5                   10

<210> SEQ ID NO 650
<211> LENGTH: 12
<212> TYPE: PRT
<213> ORGANISM: Human parainfluenza virus 1

<400> SEQUENCE: 650

Asn Ser Asp Met Tyr Pro Asp Leu Asn Pro Val Ile
1               5                   10

<210> SEQ ID NO 651
<211> LENGTH: 13
<212> TYPE: PRT
<213> ORGANISM: Human parainfluenza virus 1

<400> SEQUENCE: 651

Asn Ser Asp Met Tyr Pro Asp Leu Asn Pro Val Ile Ser
1               5                   10

<210> SEQ ID NO 652
<211> LENGTH: 14
<212> TYPE: PRT
<213> ORGANISM: Human parainfluenza virus 1

<400> SEQUENCE: 652

Asn Ser Asp Met Tyr Pro Asp Leu Asn Pro Val Ile Ser His
1               5                   10

<210> SEQ ID NO 653
<211> LENGTH: 15
<212> TYPE: PRT
<213> ORGANISM: Human parainfluenza virus 1

<400> SEQUENCE: 653

Asn Ser Asp Met Tyr Pro Asp Leu Asn Pro Val Ile Ser His Thr
1               5                   10                  15

-continued

<210> SEQ ID NO 654
<211> LENGTH: 16
<212> TYPE: PRT
<213> ORGANISM: Human parainfluenza virus 1

<400> SEQUENCE: 654

Asn Ser Asp Met Tyr Pro Asp Leu Asn Pro Val Ile Ser His Thr Tyr
1               5                   10                  15

<210> SEQ ID NO 655
<211> LENGTH: 17
<212> TYPE: PRT
<213> ORGANISM: Human parainfluenza virus 1

<400> SEQUENCE: 655

Asn Ser Asp Met Tyr Pro Asp Leu Asn Pro Val Ile Ser His Thr Tyr
1               5                   10                  15

Asp

<210> SEQ ID NO 656
<211> LENGTH: 18
<212> TYPE: PRT
<213> ORGANISM: Human parainfluenza virus 1

<400> SEQUENCE: 656

Asn Ser Asp Met Tyr Pro Asp Leu Asn Pro Val Ile Ser His Thr Tyr
1               5                   10                  15

Asp Ile

<210> SEQ ID NO 657
<211> LENGTH: 19
<212> TYPE: PRT
<213> ORGANISM: Human parainfluenza virus 1

<400> SEQUENCE: 657

Asn Ser Asp Met Tyr Pro Asp Leu Asn Pro Val Ile Ser His Thr Tyr
1               5                   10                  15

Asp Ile Asn

<210> SEQ ID NO 658
<211> LENGTH: 20
<212> TYPE: PRT
<213> ORGANISM: Human parainfluenza virus 1

<400> SEQUENCE: 658

Asn Ser Asp Met Tyr Pro Asp Leu Asn Pro Val Ile Ser His Thr Tyr
1               5                   10                  15

Asp Ile Asn Asp
            20

<210> SEQ ID NO 659
<211> LENGTH: 9
<212> TYPE: PRT
<213> ORGANISM: Human parainfluenza virus 1

<400> SEQUENCE: 659

Leu Asn Ser Asp Met Tyr Pro Asp Leu
1               5

<210> SEQ ID NO 660
<211> LENGTH: 10
<212> TYPE: PRT
<213> ORGANISM: Human parainfluenza virus 1

-continued

```
<400> SEQUENCE: 660

Leu Asn Ser Asp Met Tyr Pro Asp Leu Asn
1               5                   10

<210> SEQ ID NO 661
<211> LENGTH: 11
<212> TYPE: PRT
<213> ORGANISM: Human parainfluenza virus 1

<400> SEQUENCE: 661

Leu Asn Ser Asp Met Tyr Pro Asp Leu Asn Pro
1               5                   10

<210> SEQ ID NO 662
<211> LENGTH: 12
<212> TYPE: PRT
<213> ORGANISM: Human parainfluenza virus 1

<400> SEQUENCE: 662

Leu Asn Ser Asp Met Tyr Pro Asp Leu Asn Pro Val
1               5                   10

<210> SEQ ID NO 663
<211> LENGTH: 13
<212> TYPE: PRT
<213> ORGANISM: Human parainfluenza virus 1

<400> SEQUENCE: 663

Leu Asn Ser Asp Met Tyr Pro Asp Leu Asn Pro Val Ile
1               5                   10

<210> SEQ ID NO 664
<211> LENGTH: 14
<212> TYPE: PRT
<213> ORGANISM: Human parainfluenza virus 1

<400> SEQUENCE: 664

Leu Asn Ser Asp Met Tyr Pro Asp Leu Asn Pro Val Ile Ser
1               5                   10

<210> SEQ ID NO 665
<211> LENGTH: 15
<212> TYPE: PRT
<213> ORGANISM: Human parainfluenza virus 1

<400> SEQUENCE: 665

Leu Asn Ser Asp Met Tyr Pro Asp Leu Asn Pro Val Ile Ser His
1               5                   10                  15

<210> SEQ ID NO 666
<211> LENGTH: 16
<212> TYPE: PRT
<213> ORGANISM: Human parainfluenza virus 1

<400> SEQUENCE: 666

Leu Asn Ser Asp Met Tyr Pro Asp Leu Asn Pro Val Ile Ser His Thr
1               5                   10                  15

<210> SEQ ID NO 667
<211> LENGTH: 17
<212> TYPE: PRT
<213> ORGANISM: Human parainfluenza virus 1

<400> SEQUENCE: 667
```

```
Leu Asn Ser Asp Met Tyr Pro Asp Leu Asn Pro Val Ile Ser His Thr
1               5                   10                  15

Tyr

<210> SEQ ID NO 668
<211> LENGTH: 18
<212> TYPE: PRT
<213> ORGANISM: Human parainfluenza virus 1

<400> SEQUENCE: 668

Leu Asn Ser Asp Met Tyr Pro Asp Leu Asn Pro Val Ile Ser His Thr
1               5                   10                  15

Tyr Asp

<210> SEQ ID NO 669
<211> LENGTH: 19
<212> TYPE: PRT
<213> ORGANISM: Human parainfluenza virus 1

<400> SEQUENCE: 669

Leu Asn Ser Asp Met Tyr Pro Asp Leu Asn Pro Val Ile Ser His Thr
1               5                   10                  15

Tyr Asp Ile

<210> SEQ ID NO 670
<211> LENGTH: 20
<212> TYPE: PRT
<213> ORGANISM: Human parainfluenza virus 1

<400> SEQUENCE: 670

Leu Asn Ser Asp Met Tyr Pro Asp Leu Asn Pro Val Ile Ser His Thr
1               5                   10                  15

Tyr Asp Ile Asn
            20

<210> SEQ ID NO 671
<211> LENGTH: 10
<212> TYPE: PRT
<213> ORGANISM: Human parainfluenza virus 1

<400> SEQUENCE: 671

Ser Leu Asn Ser Asp Met Tyr Pro Asp Leu
1               5                   10

<210> SEQ ID NO 672
<211> LENGTH: 11
<212> TYPE: PRT
<213> ORGANISM: Human parainfluenza virus 1

<400> SEQUENCE: 672

Ser Leu Asn Ser Asp Met Tyr Pro Asp Leu Asn
1               5                   10

<210> SEQ ID NO 673
<211> LENGTH: 12
<212> TYPE: PRT
<213> ORGANISM: Human parainfluenza virus 1

<400> SEQUENCE: 673

Ser Leu Asn Ser Asp Met Tyr Pro Asp Leu Asn Pro
1               5                   10
```

```
<210> SEQ ID NO 674
<211> LENGTH: 13
<212> TYPE: PRT
<213> ORGANISM: Human parainfluenza virus 1

<400> S

```
                1               5                  10                 15

Thr Tyr Asp

<210> SEQ ID NO 681
<211> LENGTH: 20
<212> TYPE: PRT
<213> ORGANISM: Human parainfluenza virus 1

<400> SEQUENCE: 681

Ser Leu Asn Ser Asp Met Tyr Pro Asp Leu Asn Pro Val Ile Ser His
1               5                  10                 15

Thr Tyr Asp Ile
            20

<210> SEQ ID NO 682
<211> LENGTH: 11
<212> TYPE: PRT
<213> ORGANISM: Human parainfluenza virus 1

<400> SEQUENCE: 682

Ile Ser Leu Asn Ser Asp Met Tyr Pro Asp Leu
1               5                  10

<210> SEQ ID NO 683
<211> LENGTH: 12
<212> TYPE: PRT
<213> ORGANISM: Human parainfluenza virus 1

<400> SEQUENCE: 683

Ile Ser Leu Asn Ser Asp Met Tyr Pro Asp Leu Asn
1               5                  10

<210> SEQ ID NO 684
<211> LENGTH: 13
<212> TYPE: PRT
<213> ORGANISM: Human parainfluenza virus 1

<400> SEQUENCE: 684

Ile Ser Leu Asn Ser Asp Met Tyr Pro Asp Leu Asn Pro
1               5                  10

<210> SEQ ID NO 685
<211> LENGTH: 14
<212> TYPE: PRT
<213> ORGANISM: Human parainfluenza virus 1

<400> SEQUENCE: 685

Ile Ser Leu Asn Ser Asp Met Tyr Pro Asp Leu Asn Pro Val
1               5                  10

<210> SEQ ID NO 686
<211> LENGTH: 15
<212> TYPE: PRT
<213> ORGANISM: Human parainfluenza virus 1

<400> SEQUENCE: 686

Ile Ser Leu Asn Ser Asp Met Tyr Pro Asp Leu Asn Pro Val Ile
1               5                  10                 15

<210> SEQ ID NO 687
<211> LENGTH: 16
<212> TYPE: PRT
<213> ORGANISM: Human parainfluenza virus 1
```

-continued

```
<400> SEQUENCE: 687

Ile Ser Leu Asn Ser Asp Met Tyr Pro Asp Leu Asn Pro Val Ile Ser
1

<210> SEQ ID NO 694
<211> LENGTH: 14
<212> TYPE: PRT
<213> ORGANISM: Human parainfluenza virus 1

<400> SEQUENCE: 694

Tyr Ile Ser Leu Asn Ser Asp Met Tyr Pro Asp Leu Asn Pro
1               5                   10

<210> SEQ ID NO 695
<211> LENGTH: 15
<212> TYPE: PRT
<213> ORGANISM: Human parainfluenza virus 1

<400> SEQUENCE: 695

Tyr Ile Ser Leu Asn Ser Asp Met Tyr Pro Asp Leu Asn Pro Val
1               5                   10                  15

<210> SEQ ID NO 696
<211> LENGTH: 16
<212> TYPE: PRT
<213> ORGANISM: Human parainfluenza virus 1

<400> SEQUENCE: 696

Tyr Ile Ser Leu Asn Ser Asp Met Tyr Pro Asp Leu Asn Pro Val Ile
1               5                   10                  15

<210> SEQ ID NO 697
<211> LENGTH: 17
<212> TYPE: PRT
<213> ORGANISM: Human parainfluenza virus 1

<400> SEQUENCE: 697

Tyr Ile Ser Leu Asn Ser Asp Met Tyr Pro Asp Leu Asn Pro Val Ile
1               5                   10                  15

Ser

<210> SEQ ID NO 698
<211> LENGTH: 18
<212> TYPE: PRT
<213> ORGANISM: Human parainfluenza virus 1

<400> SEQUENCE: 698

Tyr Ile Ser Leu Asn Ser Asp Met Tyr Pro Asp Leu Asn Pro Val Ile
1               5                   10                  15

Ser His

<210> SEQ ID NO 699
<211> LENGTH: 19
<212> TYPE: PRT
<213> ORGANISM: Human parainfluenza virus 1

<400> SEQUENCE: 699

Tyr Ile Ser Leu Asn Ser Asp Met Tyr Pro Asp Leu Asn Pro Val Ile
1               5                   10                  15

Ser His Thr

<210> SEQ ID NO 700
<211> LENGTH: 20
<212> TYPE: PRT
<213> ORGANISM: Human parainfluenza virus 1

-continued

```
<400> SEQUENCE: 700

Tyr Ile Ser Leu Asn Ser Asp Met Tyr Pro Asp Leu Asn Pro Val Ile
1               5                   10                  15

Ser His Thr Tyr
            20

<210> SEQ ID NO 701
<211> LENGTH: 13
<212> TYPE: PRT
<213> ORGANISM: Human parainfluenza virus 1

<400> SEQUENCE: 701

Gly Tyr Ile Ser Leu Asn Ser Asp Met Tyr Pro Asp Leu
1               5                   10

<210> SEQ ID NO 702
<211> LENGTH: 14
<212> TYPE: PRT
<213> ORGANISM: Human parainfluenza virus 1

<400> SEQUENCE: 702

Gly Tyr Ile Ser Leu Asn Ser Asp Met Tyr Pro Asp Leu Asn
1               5                   10

<210> SEQ ID NO 703
<211> LENGTH: 15
<212> TYPE: PRT
<213> ORGANISM: Human parainfluenza virus 1

<400> SEQUENCE: 703

Gly Tyr Ile Ser Leu Asn Ser Asp Met Tyr Pro Asp Leu Asn Pro
1               5                   10                  15

<210> SEQ ID NO 704
<211> LENGTH: 16
<212> TYPE: PRT
<213> ORGANISM: Human parainfluenza virus 1

<400> SEQUENCE: 704

Gly Tyr Ile Ser Leu Asn Ser Asp Met Tyr Pro Asp Leu Asn Pro Val
1               5                   10                  15

<210> SEQ ID NO 705
<211> LENGTH: 17
<212> TYPE: PRT
<213> ORGANISM: Human parainfluenza virus 1

<400> SEQUENCE: 705

Gly Tyr Ile Ser Leu Asn Ser Asp Met Tyr Pro Asp Leu Asn Pro Val
1               5                   10                  15

Ile

<210> SEQ ID NO 706
<211> LENGTH: 18
<212> TYPE: PRT
<213> ORGANISM: Human parainfluenza virus 1

<400> SEQUENCE: 706

Gly Tyr Ile Ser Leu Asn Ser Asp Met Tyr Pro Asp Leu Asn Pro Val
1               5                   10                  15

Ile Ser
```

```
<210> SEQ ID NO 707
<211> LENGTH: 19
<212> TYPE: PRT
<213> ORGANISM: Human parainfluenza virus 1

<400> SEQUENCE: 707

Gly Tyr Ile Ser Leu Asn Ser Asp Met Tyr Pro Asp Leu Asn Pro Val
1               5                   10                  15

Ile Ser His

<210> SEQ ID NO 708
<211> LENGTH: 20
<212> TYPE: PRT
<213> ORGANISM: Human parainfluenza virus 1

<400> SEQUENCE: 708

Gly Tyr Ile Ser Leu Asn Ser Asp Met Tyr Pro Asp Leu Asn Pro Val
1               5                   10                  15

Ile Ser His Thr
            20

<210> SEQ ID NO 709
<211> LENGTH: 14
<212> TYPE: PRT
<213> ORGANISM: Human parainfluenza virus 1

<400> SEQUENCE: 709

Leu Gly Tyr Ile Ser Leu Asn Ser Asp Met Tyr Pro Asp Leu
1               5                   10

<210> SEQ ID NO 710
<211> LENGTH: 15
<212> TYPE: PRT
<213> ORGANISM: Human parainfluenza virus 1

<400> SEQUENCE: 710

Leu Gly Tyr Ile Ser Leu Asn Ser Asp Met Tyr Pro Asp Leu Asn
1               5                   10                  15

<210> SEQ ID NO 711
<211> LENGTH: 16
<212> TYPE: PRT
<213> ORGANISM: Human parainfluenza virus 1

<400> SEQUENCE: 711

Leu Gly Tyr Ile Ser Leu Asn Ser Asp Met Tyr Pro Asp Leu Asn Pro
1               5                   10                  15

<210> SEQ ID NO 712
<211> LENGTH: 17
<212> TYPE: PRT
<213> ORGANISM: Human parainfluenza virus 1

<400> SEQUENCE: 712

Leu Gly Tyr Ile Ser Leu Asn Ser Asp Met Tyr Pro Asp Leu Asn Pro
1               5                   10                  15

Val

<210> SEQ ID NO 713
<211> LENGTH: 18
<212> TYPE: PRT
<213> ORGANISM: Human parainfluenza virus 1

<400> SEQUENCE: 713
```

-continued

Leu Gly Tyr Ile Ser Leu Asn Ser Asp Met Tyr Pro Asp Leu Asn Pro
1               5                   10                  15

Val Ile

<210> SEQ ID NO 714
<211> LENGTH: 19
<212> TYPE: PRT
<213> ORGANISM: Human parainfluenza virus 1

<400> SEQUENCE: 714

Leu Gly Tyr Ile Ser Leu Asn Ser Asp Met Tyr Pro Asp Leu Asn Pro
1               5                   10                  15

Val Ile Ser

<210> SEQ ID NO 715
<211> LENGTH: 20
<212> TYPE: PRT
<213> ORGANISM: Human parainfluenza virus 1

<400> SEQUENCE: 715

Leu Gly Tyr Ile Ser Leu Asn Ser Asp Met Tyr Pro Asp Leu Asn Pro
1               5                   10                  15

Val Ile Ser His
            20

<210> SEQ ID NO 716
<211> LENGTH: 15
<212> TYPE: PRT
<213> ORGANISM: Human parainfluenza virus 1

<400> SEQUENCE: 716

Gln Leu Gly Tyr Ile Ser Leu Asn Ser Asp Met Tyr Pro Asp Leu
1               5                   10                  15

<210> SEQ ID NO 717
<211> LENGTH: 16
<212> TYPE: PRT
<213> ORGANISM: Human parainfluenza virus 1

<400> SEQUENCE: 717

Gln Leu Gly Tyr Ile Ser Leu Asn Ser Asp Met Tyr Pro Asp Leu Asn
1               5                   10                  15

<210> SEQ ID NO 718
<211> LENGTH: 17
<212> TYPE: PRT
<213> ORGANISM: Human parainfluenza virus 1

<400> SEQUENCE: 718

Gln Leu Gly Tyr Ile Ser Leu Asn Ser Asp Met Tyr Pro Asp Leu Asn
1               5                   10                  15

Pro

<210> SEQ ID NO 719
<211> LENGTH: 18
<212> TYPE: PRT
<213> ORGANISM: Human parainfluenza virus 1

<400> SEQUENCE: 719

Gln Leu Gly Tyr Ile Ser Leu Asn Ser Asp Met Tyr Pro Asp Leu Asn
1               5                   10                  15

-continued

Pro Val

<210> SEQ ID NO 720
<211> LENGTH: 19
<212> TYPE: PRT
<213> ORGANISM: Human parainfluenza virus 1

<400> SEQUENCE: 720

Gln Leu Gly Tyr Ile Ser Leu Asn Ser Asp Met Tyr Pro Asp Leu Asn
1               5                   10                  15

Pro Val Ile

<210> SEQ ID NO 721
<211> LENGTH: 20
<212> TYPE: PRT
<213> ORGANISM: Human parainfluenza virus 1

<400> SEQUENCE: 721

Gln Leu Gly Tyr Ile Ser Leu Asn Ser Asp Met Tyr Pro Asp Leu Asn
1               5                   10                  15

Pro Val Ile Ser
            20

<210> SEQ ID NO 722
<211> LENGTH: 16
<212> TYPE: PRT
<213> ORGANISM: Human parainfluenza virus 1

<400> SEQUENCE: 722

Leu Gln Leu Gly Tyr Ile Ser Leu Asn Ser Asp Met Tyr Pro Asp Leu
1               5                   10                  15

<210> SEQ ID NO 723
<211> LENGTH: 17
<212> TYPE: PRT
<213> ORGANISM: Human parainfluenza virus 1

<400> SEQUENCE: 723

Leu Gln Leu Gly Tyr Ile Ser Leu Asn Ser Asp Met Tyr Pro Asp Leu
1               5                   10                  15

Asn

<210> SEQ ID NO 724
<211> LENGTH: 18
<212> TYPE: PRT
<213> ORGANISM: Human parainfluenza virus 1

<400> SEQUENCE: 724

Leu Gln Leu Gly Tyr Ile Ser Leu Asn Ser Asp Met Tyr Pro Asp Leu
1               5                   10                  15

Asn Pro

<210> SEQ ID NO 725
<211> LENGTH: 19
<212> TYPE: PRT
<213> ORGANISM: Human parainfluenza virus 1

<400> SEQUENCE: 725

Leu Gln Leu Gly Tyr Ile Ser Leu Asn Ser Asp Met Tyr Pro Asp Leu
1               5                   10                  15

Asn Pro Val

```
<210> SEQ ID NO 726
<211> LENGTH: 20
<212> TYPE: PRT
<213> ORGANISM: Human parainfluenza virus 1

<400> SEQUENCE: 726

Leu Gln Leu Gly Tyr Ile Ser Leu Asn Ser Asp Met Tyr Pro Asp Leu
1               5                   10                  15

Asn Pro Val Ile
            20

<210> SEQ ID NO 727
<211> LENGTH: 17
<212> TYPE: PRT
<213> ORGANISM: Human parainfluenza virus 1

<400> SEQUENCE: 727

Val Leu Gln Leu Gly Tyr Ile Ser Leu Asn Ser Asp Met Tyr Pro Asp
1               5                   10                  15

Leu

<210> SEQ ID NO 728
<211> LENGTH: 18
<212> TYPE: PRT
<213> ORGANISM: Human parainfluenza virus 1

<400> SEQUENCE: 728

Val Leu Gln Leu Gly Tyr Ile Ser Leu Asn Ser Asp Met Tyr Pro Asp
1               5                   10                  15

Leu Asn

<210> SEQ ID NO 729
<211> LENGTH: 19
<212> TYPE: PRT
<213> ORGANISM: Human parainfluenza virus 1

<400> SEQUENCE: 729

Val Leu Gln Leu Gly Tyr Ile Ser Leu Asn Ser Asp Met Tyr Pro Asp
1               5                   10                  15

Leu Asn Pro

<210> SEQ ID NO 730
<211> LENGTH: 20
<212> TYPE: PRT
<213> ORGANISM: Human parainfluenza virus 1

<400> SEQUENCE: 730

Val Leu Gln Leu Gly Tyr Ile Ser Leu Asn Ser Asp Met Tyr Pro Asp
1               5                   10                  15

Leu Asn Pro Val
            20

<210> SEQ ID NO 731
<211> LENGTH: 18
<212> TYPE: PRT
<213> ORGANISM: Human parainfluenza virus 1

<400> SEQUENCE: 731

Gln Val Leu Gln Leu Gly Tyr Ile Ser Leu Asn Ser Asp Met Tyr Pro
1               5                   10                  15

Asp Leu
```

```
<210> SEQ ID NO 732
<211> LENGTH: 19
<212> TYPE: PRT
<213> ORGANISM: Human parainfluenza virus 1

<400> SEQUENCE: 732

Gln Val Leu Gln Leu Gly Tyr Ile Ser Leu Asn Ser Asp Met Tyr Pro
1               5                   10                  15

Asp Leu Asn

<210> SEQ ID NO 733
<211> LENGTH: 20
<212> TYPE: PRT
<213> ORGANISM: Human parainfluenza virus 1

<400> SEQUENCE: 733

Gln Val Leu Gln Leu Gly Tyr Ile Ser Leu Asn Ser Asp Met Tyr Pro
1               5                   10                  15

Asp Leu Asn Pro
            20

<210> SEQ ID NO 734
<211> LENGTH: 19
<212> TYPE: PRT
<213> ORGANISM: Human parainfluenza virus 1

<400> SEQUENCE: 734

Tyr Gln Val Leu Gln Leu Gly Tyr Ile Ser Leu Asn Ser Asp Met Tyr
1               5                   10                  15

Pro Asp Leu

<210> SEQ ID NO 735
<211> LENGTH: 20
<212> TYPE: PRT
<213> ORGANISM: Human parainfluenza virus 1

<400> SEQUENCE: 735

Tyr Gln Val Leu Gln Leu Gly Tyr Ile Ser Leu Asn Ser Asp Met Tyr
1               5                   10                  15

Pro Asp Leu Asn
            20

<210> SEQ ID NO 736
<211> LENGTH: 20
<212> TYPE: PRT
<213> ORGANISM: Human parainfluenza virus 1

<400> SEQUENCE: 736

Ser Tyr Gln Val Leu Gln Leu Gly Tyr Ile Ser Leu Asn Ser Asp Met
1               5                   10                  15

Tyr Pro Asp Leu
            20
```

THERAPEUTIC COMPOSITIONS AND METHODS FOR TREATING VIRAL INFECTION

RELATED U.S. APPLICATIONS

This application claims priority under 35 U.S.C. §119(e) to U.S. Provisional Application Ser. No. 60/314,182 filed on Aug. 22, 2001, which is incorporated herein by reference in its entirety.

FIELD OF THE INVENTION

The present invention generally relates to pharmaceuticals and methods of treating diseases, particularly to methods and pharmaceutical compositions for treating viral infection.

BACKGROUND OF THE INVENTION

Viruses are the smallest of parasites, and are completely dependent on the cells they infect for their reproduction. Viruses are composed of an outer coat of protein, which is sometimes surrounded by a lipid envelope, and an inner nucleic acid core consisting of either RNA or DNA. Generally, after docking with the plasma membrane of a susceptible cell, the viral core penetrates the cell membrane to initiate the viral infection. After infecting cells, viruses commandeer the cell's molecular machinery to direct their own replication and packaging. The "replicative phase" of the viral lifecycle may begin immediately upon entry into the cell, or may occur after a period of dormancy or latency. After the infected cell synthesizes sufficient amounts of viral components, the "packaging phase" of the viral life cycle begins and new viral particles are assembled. Some viruses reproduce without killing their host cells, and many of these bud from host cell membranes. Other viruses cause their host cells to lyse or burst, releasing the newly assembled viral particles into the surrounding environment, where they can begin the next round of their infectious cycle.

Several hundred different types of viruses are known to infect humans, however, since many of these have only recently been recognized, their clinical significance is not fully understood. Of these viruses that infect humans, many infect their hosts without producing overt symptoms, while others (e.g., influenza) produce a well-characterized set of symptoms. Importantly, although symptoms can vary with the virulence of the infecting strain, identical viral strains can have drastically different effects depending upon the health and immune response of the host. Despite remarkable achievements in the development of vaccines for certain viral infections (i.e., polio and measles), and the eradication of specific viruses from the human population (e.g., smallpox), viral diseases remain as important medical and public health problems. Indeed, viruses are responsible for several "emerging" (or reemerging) diseases (e.g., West Nile encephalitis & Dengue fever), and also for the largest pandemic in the history of mankind (HIV and AIDS).

Viruses that primarily infect humans are spread mainly via respiratory and enteric excretions. These viruses are found worldwide, but their spread is limited by inborn resistance, prior immunizing infections or vaccines, sanitary and other public health control measures, and prophylactic antiviral drugs. Zoonotic viruses pursue their biologic cycles chiefly in animals, and humans are secondary or accidental hosts. These viruses are limited to areas and environments able to support their nonhuman natural cycles of infection (vertebrates or arthropods or both). However, with increased global travel by humans, and the likely accidental co-transport of arthropod vectors bearing viral payloads, many zoonotic viruses are appearing in new areas and environments as emerging diseases. For example, West Nile virus, which is spread by the bite of an infected mosquito, and can infect people, horses, many types of birds, and other animals, was first isolated from a febrile adult woman in the West Nile District of Uganda in 1937. The virus made its first appearance in the Western Hemisphere, in the New York City area in the autumn of 1999, and during its first year in North America, caused the deaths of 7 people and the hospitalization of 62. At the time of this writing (August, 2002) the virus has been detected in birds in 37 states and the District of Columbia, and confirmed human infections have occurred in Alabama, the District of Columbia, Florida, Illinois, Indiana, Louisiana, Massachusetts, Mississippi, Missouri, New York City, Ohio, and Texas. (See: http://www.cdc.gov/od/oc/media/wncount.htm).

Additionally, some viruses are known to have oncogenic properties. Human T-cell lymphotropic virus type 1 (a retrovirus) is associated with human leukemia and lymphoma. Epstein-Barr virus has been associated with malignancies such as nasopharyngeal carcinoma, Burkitt's lymphoma, Hodgkin's disease, and lymphomas in immuno-suppressed organ transplant recipients. Kaposi's sarcoma-associated virus is associated with Kaposi's sarcoma, primary effusion lymphomas, and Castleman's disease (a lymphoproliferative disorder).

Treatment of viral diseases presents unique challenges to modern medicine. Since viruses depend on host cells to provide many functions necessary for their multiplication, it is difficult to inhibit viral replication without at the same time affecting the host cell itself. Consequently, antiviral treatments are often directed at the functions of specific enzymes of particular viruses. However, such antiviral treatments that specifically target viral enzymes (e.g., HIV protease, or HIV reverse transcriptase) often have limited usefulness, because resistant strains of viruses readily arise through genetic drift and mutation.

SUMMARY OF THE INVENTION

The present invention provides a method for inhibiting viral propagation in infected cells. The method includes administering to the cells a compound comprising an amino acid sequence motif of $YX_1X_2L$, where $X_1$ and $X_2$ are any amino acids. Preferably, the compound is capable of binding the cellular protein AP-50, in the region including amino acid residues 121 to 435. The method can be used in treating viral infections, in particular infections caused by enveloped viruses, and preferably viruses such as hepatitis C virus, human herpesvirus 2, variola (smallpox) virus, vaccinia virus, and human parainfluenza virus 1. In addition, the method can also be useful in treating and preventing symptoms caused by and/or associated with these viral infections.

In one embodiment, the compound comprises an amino acid sequence motif $YX_1X_2L$, wherein $X_1$ is proline (P), and $X_2$ is any amino acid, and the peptide is capable of binding the cellular protein AP-50, in the region including amino acid residues 121 to 435. In a preferred embodiment, $X_1$ is P and $X_2$ is selected from the group consisting of aspartatic acid (D), alanine (A), or glutamic acid (E), or analogs thereof. In a most preferred embodiment, $YX_1X_2L$ is YPDL, or an analog thereof. Preferably, the peptide consists of from about 8 to about 100 amino acid residues, more preferably from 9 to about 50, or from 10 to about 20 amino acid residues.

In specific aspects of the embodiment, the peptide includes a contiguous amino acid sequence of at least 6, preferably at least 7 or 8 amino acid residues, and more preferably from about 8 to about 30 or from about 9 to 20 amino acid residues of a viral protein selected from the group consisting of HCV polyprotein, HSV UL42 protein, variola virus A10L protein, vaccinia virus virion core protein P4a, human parainfluenza virus hemagglutinin-neuramimidase and EIAV GAGp9; wherein said contiguous amino acid sequence encompasses the YPXL motif of the viral protein. For example, the peptide can include an amino acid sequence selected from the group consisting of SEQ ID NOs:18–164, SEQ ID NOs:165–307, SEQ ID NOs:308–450, SEQ ID NOs:451–593, and SEQ ID NOs:594–736.

In preferred embodiments, the peptide in the composition is associated with, or more preferably covalently linked to, a transporter that is capable of increasing the uptake of the peptide by a mammalian cell. In highly preferred embodiments the transporter increases uptake by at least 100%, preferably at least 300%. Advantageously, the transporter is selected from the group consisting of penetratins, l-$Tat_{49-57}$, d-$Tat_{49-57}$, retro-inverso isomers of l- or d-$Tat_{49-57}$, L-arginine oligomers, D-arginine oligomers, L-lysine oligomers, D-lysine oligomers, L-histidine oligomers, D-histidine oligomers, L-ornithine oligomers, D-ornithine oligomers, and HSV-1 structural protein VP22 and fragments thereof, and peptides having at least six contiguous amino acid residues that are L-arginine, D-arginine, L-lysine, D-lysine, L-histidine, D-histidine, L-ornithine, D-ornithine, or a combination thereof; and peptoid analogs thereof. Alternatively, the transporter can be non-peptidic molecules or structures such as liposomes, dendrimers, and siderophores.

When a transporter covalently linked to a peptide of the present invention is peptidic transporter, a hybrid polypeptide is provided. In one embodiment, the hybrid polypeptide consists of from about 8 to about 100 amino acid residues, preferably from about 9 to about 50 amino acid residues. In preferred embodiments, the hybrid polypeptide consists of from about 12 to about 30 amino acid residues. In specific embodiments, the peptide in the hybrid polypeptide includes a YPXL motif, wherein X is either a aspartate (D), alanine (A), glutamic acid (E), or glycine (G).

Advantageously, the peptidic transporter in the hybrid polypeptide is capable of increasing the uptake of the peptide by a mammalian cell by at least 100%, preferably at least 300%. Examples of the peptidic transporter include penetratins, l-$Tat_{49-57}$, retro-inverso isomers of l-$Tat_{49-57}$, L-arginine oligomers, L-lysine oligomers, HSV-1 structural protein VP22 and fragments thereof, and peptides consisting of at least six contiguous amino acid residues that include two or more of the group consisting of L-arginine, L-lysine and L-histidine. However, in certain embodiments, the hybrid polypeptide does not contain a terminal L-histidine oligomer. In one embodiment, the transporter includes from 6 to about 14 argnines residues.

Various modifications may be made to improve the stability and solubility of the compound, and/or optimize its binding affinity to AP-50—especially to the region including amino acid residues 121 to 435. In particular, various protective groups can be incorporated into the amino acid residues of the compounds. In addition, the compounds according to the present invention can also be in various pharmaceutically acceptable salt forms.

In another aspect, present invention also provides isolated nucleic acids encoding the various hybrid polypeptides of the present invention. Additionally, host cells containing such isolated nucleic acid and/or expressing the hybrid polypeptides encoded thereof are also provided.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

As used herein, the term "viral infection" generally encompasses infection of an animal host, particularly a human host, by one or more viruses. Thus, treating viral infection will encompass the treatment of a person who is a carrier of one or more specific viruses or a person who is diagnosed of active symptoms caused by and/or associated with infection by the viruses. A carrier of virus may be identified by any methods known in the art. For example, a person can be identified as virus carrier on the basis that the person is antiviral antibody positive, or is virus-positive, or has symptoms of viral infection. That is, "treating viral infection" should be understood as treating a patient who is at any one of the several stages of viral infection progression. In addition, "treating or preventing viral infection" will also encompass treating suspected infection by a particular virus after suspected past exposure to virus by e.g., blood transfusion, exchange of body fluids, bites, accidental needle stick, or exposure to patient blood during surgery, or other contacts with a person with viral infection that may result in transmission of the virus.

Specifically, as used herein, the term "HCV infection" generally encompasses infection of a human by any types or subtypes of hepatitis C virus, including acute hepatitis C infection and chronic hepatitis C infection. Thus, treating HCV infection means the treatment of a person who is a carrier of any types or subtypes of hepatitis C virus or a person who is diagnosed of active hepatitis C to reduce the HCV viral load in the person or to alleviate one or more symptoms associated with HCV infection and/or hepatitis C. A carrier of HCV may be identified by any methods known in the art. For example, a person can be identified as HCV carrier on the basis that the person is anti-HCV antibody positive, or is HCV-positive (e.g., based on HCV RNA or DNA) or has symptoms of hepatitis C infection or hepatitis C (e.g., elevated serum transaminases). That is, "treating HCV infection" should be understood as treating a patient who is at any one of the several stages of HCV infection progression. In addition, the term "treating HCV infection" will also encompass treating suspected infection by HCV after suspected past exposure to HCV by, e.g., contact with HCV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HCV infection" will also encompass treating a person who is free of HCV infection but is believed to be at risk of infection by HCV. The term of "preventing HCV" as used herein means preventing in a patient who has HCV infection or is suspected to have HCV infection or is at risk of HCV infection from developing hepatitis C (which is characterized by more serious hepatitis-defining symptoms), cirrhosis, or hepatocellular carcinoma.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, etc. Modified forms also encompass pharmaceutically acceptable salt forms. In addition, modifications also include intramolecular crosslinking and covalent attachment to various moieties such as lipids, flavin, biotin, polyethylene glycol or derivatives thereof, etc. In addition, modifications may also include cyclization, and branching. Further, amino acids other than the conventional twenty amino acids encoded by genes may also be included in a polypeptide.

As used herein, the term "AP-50" means human AP-50 protein, unless otherwise specified.

The recruitment of cellular machinery to facilitate virus budding appears to be a general phenomenon, and distinct late domains have been identified in the structural proteins of several other enveloped viruses. See Vogt, *Proc. Natl. Acad. Sci. USA*, 97:12945–12947 (2000). Three well characterized late domains are found in membrane-associated proteins from certain enveloped viruses. See Craven et al., *J. Virol.*, 73:3359–3365 (1999); Harty et al., *Proc. Natl. Acad. Sci. USA*, 97:13871–13876 (2000); Harty et al., *J. Virol.*, 73:2921–2929 (1999); and Jayakar et al., *J. Virol.*, 74:9818–9827 (2000). These include the "P(T/S)AP" motif found in HIV GAG p6 region, "PY" motif (consensus sequence: PPXY/W; X=any amino acid) found in e.g., the matrix proteins of filoviruses, and the "YXXL" motif. The cellular target for the PY motif is Nedd4, which also contains a Hect ubiquitin E3 ligase domain. The "YL" motif (YXXL) was found in the Gag protein of equine infectious anemia virus (EIAV). Puffer et al., *J. Virol.*, 71:6541–6546 (1997); Puffer et al., *J. Virol.*, 72:10218–10221 (1998). The YXXL motif of the EIAV p9 protein binds the cellular AP-50 medium chain subunit of the plasma membrane-localized AP-2 clathrin-associated adapter protein complex (hereinafter AP-50). See Puffer et al., *J. Virol.*, 72:10218–10221 (1998). The AP-2 complex is known to be involved in endocytosis. In particular, the YXXL motif of the EIAV p9 protein binds to a truncated AP-50 having amino acid residues 121 to 435. See id. Interestingly, the late domains such as the P(T/S)AP motif, PY motif and the YL motif can still function when moved to different positions within retroviral Gag proteins, which suggests that they are docking sites for cellular factors rather than structural elements. Parent et al., *J. Virol.*, 69:5455–5460 (1995); Yuan et al., *EMBO J.*, 18:4700–4710 (2000). Moreover, the late domains such as the P(T/S)AP motif, PY motif and the YL motif can function interchangeably. That is, one late domain motif can be used in place of another late domain motif without affecting viral budding. Parent et al., *J. Virol.*, 69:5455–5460 (1995); Yuan et al., *EMBO J.*, 18:4700–4710 (2000); Strack et al., *Proc. Natl. Acad. Sci. USA*, 97:13063–13068 (2000).

Accordingly, while not wishing to be bound by any theory, it is believed that although the three late domain motifs bind to different cellular targets, they utilize common cellular pathways to effect viral budding. In particular, it is believed that the different cellular receptors for viral late domain motifs feed into common downstream steps of the vacuolar protein sorting (VPS) and MVB pathway. As is known in the art, all three cellular targets, i.e., Tsg101, Nedd4 and AP-2, function in the VPS pathway. Another protein, Vps4, functions in Tsg101 cycling and endosomal trafficking. Particularly, Vps4 mutants prevent normal Tsg101 trafficking and induce formation of aberrant, highly vacuolated endosomes that are defective in the sorting and recycling of endocytosed substrates. See See Babst et al, *Traffic*, 1:248–258 (2000); Bishop and Woodman, *J. Biol. Chem.*, 276:11735 (2001).

While not wishing to be bound by any theory, it is believed that the YL motif or a variant thereof enables a protein containing the YL motif to bind the cellular protein AP-50, and that the binding of the YL motif in viral proteins to AP-50 or another cellular protein enables viruses having the YL motif to usurp cellular machinery normally used for MVB formation to allow viral budding from the plasma membrane. AP-50 and/or other AP-50-like proteins may serve as the common docking site(s) for all viruses that utilize the YL motif to bud off host cell cytoplasm membrane. It is also believed that depletion of AP-50 or interfering with the interaction between AP-50 and the YL motif in virus-infected cells will prevent viral budding from the cells, particularly those viruses that utilize YL motif for budding. In addition, disruption of the interaction between AP-50 and the YL motif in virus-infected cells may also interfere with the entry of viruses into cells inhibit the viruses' infectivity.

In accordance with the present invention, a number of viral proteins of viruses other than EIAV have been found to also contain the YL motif. The proteins are summarized in Table 1 below.

TABLE 1

Viral Proteins Containing the YPDL Motif

| Virus | YPDL-Containing Protein | GenBank Accession No. | SEQ ID NO: |
|---|---|---|---|
| Equine Infectious Anemia Virus | Gag p9 | AAA43011 | 12 |
| Hepatitis C Virus | Polyprotein | AAF01178 | 13 |
| Human Herpesvirus 2 | UL42 | BAA00746 | 14 |
| Variola (Smallpox) Virus | A10L | NP_042158 | 15 |
| Vaccinia Virus | Major core protein P4a precursor (Virion core protein P4a) | P16715 | 16 |
| Human Parainfluenza Virus 1 | Hemagglutinin-Neuraminidase | AAA18296 | 17 |

The inventors therefore propose using peptides containing a YL motif in treating viral infection, particularly infections caused by viruses that utilize their YL motif in viral budding. In particular, the peptides are capable of binding a region including the amino acid residues 121 to 435 of AP-50.

Thus, in accordance with a first aspect of the present invention, a method is provided for inhibiting viral budding from virus-infected cells and/or inhibiting viral infectivity, and thus inhibiting viral propagation in the cells. The method includes administering to the cells a compound containing a YL motif in treating viral infection. Preferably, the compound is capable of binding to a region including the amino acid residues 121 to 435 of AP-50.

A compound is "capable of binding to a region including the amino acid residues 121 to 435 of AP-50" when the compound is shown to bind the region of AP-50 using a fluorescence polarization (FP) based binding assay as described below, and the dissociation constant ($K_d$) is comparable to that exhibited between EIAV p9 protein and the same region of AP-50. That is, the $K_d$ determined for AP-50 and the compound, is not more than ten-fold greater than the $K_d$ determined for AP-50 and p9 protein, and is at least ten-fold lower than the $K_d$ determined for AP-50 and a p9 protein lacking the late domain (YPDL) motif.

The binding of test compounds to AP-50 can be assessed by an assay that exploits a physical property known as FP. This method has been described in detail for both the binding, and the disruption of binding, of peptides to the human Src-SH2 domain (Lynch et al., Anal. Biochem. 247:77–82 (1997)). FP is based upon the observation that fluorescent molecules in solution, when excited with polarized light, will emit light back in a fixed plane (i.e., polarized fluorescent emission). This polarized emission can be depolarized by a number of factors, the most significant being rotational diffusion of the fluorescent group. Measurements of polarized emissions reflect the average angular displacement of the fluorophore that occurs between the moment of absorption and the moment of emission of photons. The angular displacement of the fluorophore is dependent upon the rate and extent of rotational diffusion during the lifetime of the excited state.

In practice, fluorophores that have a low molecular weight, or are very flexible, and hence show greater rotational diffusion, have lower polarization values than those that have a high molecular weight, or are inflexible. This intrinsic property of fluorophores can be utilized in a peptide binding assay by attaching the fluorophore to the peptide, thereby generating a binding probe. Probes with low molecular weights (i.e., peptides with attached fluorophores such as 5-carboxyfluorescein) will have low polarization values when free in solution. However, upon binding to a larger target molecule (i.e., a protein), the polarization of the probe increases, due to reduced rotational diffusion. The difference between the two values reflects the bound and unbound states of the probe, and saturation binding studies conducted with such probes readily allow for the determination of dissociation constants ($K_d$s) for the probe(peptide)/protein interaction.

The relative strengths of binding interactions occurring between the peptides of the present invention and their target (amino acid residues 121–435 of AP-50) can be readily determined using the methods described by Lynch and coworkers (See Lynch et al., Anal. Biochem. 247:77–82 (1997)). The $K_d$ values thus determined can be directly compared to assess relative strengths of interactions. Additionally, if desired, binding competition assays can be conducted with a labeled peptide probe, and an unlabeled peptide inhibitor, and $IC_{50}$ values can be determined.

Specifically, the method comprises administering cells in vitro or in vivo a compound having an amino acid sequence motif of $X_1X_2X_3X_4$, wherein $X_1$ is Y or W or an analog thereof, $X_4$ is either L or I or an analog thereof. In some embodiments, $X_2$ in the motif is P or an analog thereof. In one embodiment, $X_3$ is aspartate (D), alanine (A) or glutamic acid (E), or an analog thereof. In preferred embodiments, the compound administered has the amino acid sequence motif of $YX_2X_3L$. In a more preferred embodiment, the compound has an amino acid sequence motif YPXL. In specific aspects of these embodiments, X is preferably aspartate (D), alanine (A) or glutamic acid (E), or an analog thereof. In a most preferred embodiment, the compound has an amino acid sequence motif YPDL or YPAL.

Preferably, the compound of the present invention is capable of binding a region including the amino acid residues 121 to 435 of AP-50.

Specifically, the present invention encompasses compounds having the Y $X_2X_3$L motif wherein the Y is either unphosphorylated or phosphorylated.

The compounds can be administered to cells in vitro or cells in vivo in a human or animal body. The method of the present invention can be used for inhibiting viral budding and/or suppressing viral infectivity of an enveloped virus. Advantageously, the method is used for inhibiting viral budding and/or suppressing viral entry into cells by viruses such as hepatitis C virus ("HCV"), human herpers virus 2 (HSV2), variola virus, vaccinia virus, human parainfluenza virus, etc. By inhibiting viral budding and suppressing viral infectivity in a patient, the viral load in the patient body can be prevented from increasing and can even be reduced. Accordingly, the method of the present invention can also be used in treating viral infection as well as symptoms caused by and/or associated with the viral infection. In addition, when applied at an early stage before a patient develops a full-blown disease caused by viral infection, the method can be used to prevent such a disease by inhibiting viral propagation and decreasing the viral load in the patient. For example, human hepatitis C virus is known to cause hepatitis C which may increase the risk of liver cancer. Thus, if the compounds of the present invention is applied to a patient at an early stage of the hepatitis C virus infection before the full development of hepatitis, hepatitis may be prevented and the likelihood of liver cancer in the patient may be reduced.

The compounds according to the present invention can be of any type of chemical compounds. For example, the compound can be a peptide, a modified peptide, an oligonucleotide-peptide hybrid (e.g., PNA), etc. In a preferred embodiment, the compound administered is capable of binding a region including the amino acid residues 121 to 435 of AP-50. In a specific aspect of this embodiment, the compound is a peptide having a YPXL motif. Advantageously, X is selected from the group consisting of alanine (A), glutamic acid (E), or aspartatic acid (D).

Thus, the compounds can be a tetrapeptide, e.g., having an amino acid sequence of $X_1X_2X_3X_4$, wherein $X_1$ is Y or W or an analog thereof, $X_4$ is either L or I or an analog thereof. For example, the compounds can have an amino acid sequence of YPDL (SEQ ID NO:1) or YPEL (SEQ ID NO:2).

The compound can also include a longer peptide comprising the amino acid sequence motif of YXXL. For example, the compound may include a peptide of 5, 6, 7, 8 or 9 amino acids, preferably 10, 11, 12, 13, 14, 15, 16, 17, 18, 19, 20 or more amino acids. Advantageously, the compound is a peptide that contains an amino acid sequence of less than about 400, 375, 350, 325, 300, 275, 250, 225 or 200 residues. Preferably, the peptide contains an amino acid sequence of less than about 175, 150, 125, 115, 100, 95, 90, 85, 80, 75, 70, 65, 60 or 55 residues. More preferably, the peptide contains an amino acid sequence of less than about 50, 48, 45, 42, 40, 38, 35, 33, 32, 31, 30, 29, 28, 27, 26, 25, 24, 23, 22, 21 or 20 residues. In preferred embodiments, the peptide contains an amino acid sequence of from about 4 to about 200, 6 to about 150, 7 to about 100, preferably from about 8 to about 50, more preferably from about 9 to about 50, from about 9 to 45, 9 to 40, 9 to 37, 9 to 35, 9 to 30, 9 to 25 residues. More advantageously, the peptide contains an amino acid sequence of from 9 to about 10, 11, 12, 13, 14, 15, 16, 17, 18, 19, 20, 21, 22, 23 or 24 residues, even more advantageously, from 10 to about 11, 12, 13, 14, 15, 16, 17, 18, 19, 20, 21, 22, 23 or 24 residues. Preferably, the YXXL motif in the sequence is the YPXL motif.

For example, the compound may include a peptide of 5, 6, 7, 8 or 9 amino acids, preferably 10, 11, 12, 13, 14, 15, 16, 17, 18, 19, 20 or more amino acids. Preferably, the peptide has less than 100, more preferably no more than 50 amino acids. Preferred examples of pentapeptides include but are not limited to YPDLG (SEQ ID NO:3), YPDLR (SEQ ID NO:4), YPDLN (SEQ ID NO:5), YPDLS (SEQ ID NO:6), VYPDL (SEQ ID NO:7), QYPDL (SEQ ID NO:8), KYPDL (SEQ ID NO:9), MYPDL (SEQ ID NO:10) and LYPDL (SEQ ID NO:11).

In one embodiment, the compound includes a contiguous amino acid sequence of a viral protein selected from the group consisting of HCV polyprotein, HSV UL42 protein, variola virus A10L protein, vaccinia virus virion core protein P4a, human parainfluenza virus hemagglutinin-neuramimidase and EIAV GAGp9, wherein the contiguous amino acid sequence encompasses the YPXL motif of the viral protein.

In a specific embodiment, the compound includes a contiguous amino acid sequence of HCV polyprotein that encompasses the YPXL motif of the protein. In another specific embodiment, the compound includes a contiguous amino acid sequence of EIAV GAGp9 that encompasses the YPXL motif of the protein.

Advantageously, the compound is a peptide that contains a contiguous amino acid sequence of less than about 400, 375, 350, 325, 300, 275, 250, 225 or 200 residues of one of the viral proteins in Table 1, which encompasses the YPXL motif of the viral protein, and is capable of binding a region including the amino acid residues 121 to 435 of AP-50. Preferably, the peptide contains a contiguous amino acid sequence of less than about 175, 150, 125, 115, 100, 95, 90, 85, 80, 75, 70, 65, 60 or 55 residues of one of the viral proteins in Table 1, which encompasses the YPXL motif of the viral protein, and is capable of binding a region including the amino acid residues 121 to 435 of AP-50. More preferably, the peptide contains a contiguous amino acid sequence of less than about 50, 48, 45, 42, 40, 38, 35, 33, 32, 31, 30, 29, 28, 27, 26, 25, 24, 23, 22, 21 or 20 residues of one of the viral proteins in Table 1, which encompasses the YPXL motif of the viral protein, and is capable of binding a region including the amino acid residues 121 to 435 of AP-50. In preferred embodiments, the peptide contains a contiguous amino acid sequence of from about 4 to about 50, preferably from about 6 to about 50, from about 8 to about 50, more preferably from about 9 to about 50, from about 9 to 45, 9 to 40, 9 to 37, 9 to 35, 9 to 30, 9 to 25 residues of one of the viral proteins in Table 1, which encompasses the YPXL motif of the viral protein, and is capable of binding a a region including the amino acid residues 121 to 435 of AP-50. More advantageously, the peptide contains a contiguous amino acid sequence of from 9 to about 10, 11, 12, 13, 14, 15, 16, 17, 18, 19, 20, 21, 22, 23 or 24 residues of a viral protein in Table 1, even more advantageously, from 10 to about 11, 12, 13, 14, 15, 16, 17, 18, 19, 20, 21, 22, 23 or 24 residues of one of the viral proteins in Table 1, which encompasses the YPXL motif of the viral protein, and is capable of binding a region including the amino acid residues 121 to 435 of AP-50.

In specific embodiments, a peptide according to the present invention has a contiguous amino acid sequence of a viral protein in Table 1 as provided in SEQ ID NOs:18–164, SEQ ID NOs:165–307, SEQ ID NOs:308–450, SEQ ID NOs:451–593, and SEQ ID NOs:594–736.

In another embodiment, the compound according to the present invention has an amino acid sequence that is at least 70 percent, preferably at least 80 percent or 85 percent, more preferably at least 90 percent or 95 percent identical to a contiguous amino acid sequence of at least 5, 6, 7, 8 or 9 amino acid residues, preferably 10, 11, 12, 13, 14, 15, 16, 17, 18, 19, 20 or more amino acid residues, but preferably less than 100 and more preferably no more than 50 amino acid residues of one of the proteins in Table 1, which contiguous amino acids sequence spans the late domain motif YPXL. In other embodiments, the compound according to the present invention is within an amino acid sequence that is at least 70 percent, preferably at least 80 percent or 85 percent, more preferably at least 90 percent or 95 percent identical to a contiguous amino acid sequence of at least 5, 6, 7, 8 or 9 amino acid residues, preferably 10, 11, 12, 13, 14, 15, 16, 17, 18, 19, 20 or more amino acid residues, but preferably less than 100 amino acid residues, and more preferably no more than 50 amino acid residues, of a naturally occuring EIAV p9 peptide, which contiguous amino acid sequence spans the late domain motif YPDL of p9.

In a specific embodiment, the compound according to the present invention is within an amino acid sequence that is at least 70 percent, preferably at least 80 percent or 85 percent, more preferably at least 90 percent or 95 percent identical to a contiguous amino acid sequence of at least 5, 6, 7, 8 or 9 amino acid residues, preferably 10, 11, 12, 13, 14, 15, 16, 17, 18, 19, 20 or more amino acid residues, but preferably less than 100 amino acids, and more preferably no more than 50 amino acid residues, of a naturally occuring hepatitis C virus polyprotein, which contiguous amino acid sequence spans the late domain motif YPDL of the polyprotein. In another specific embodiment, the compound according to the present invention is within an amino acid sequence that is at least 70 percent, preferably at least 80 percent or 85 percent, more preferably at least 90 percent or 95 percent identical to a contiguous amino acid sequence of at least 5, 6, 7, 8 or 9 amino acid residues, preferably 10, 11, 12, 13, 14, 15, 16, 17, 18, 19, 20 or more amino acid residues, but preferably less than 100 amino acid residues, and more preferably no more than 50 amino acid residues, of a naturally occuring human parainfluenza virus 1 hemagglutinin-neuramimidase, which contiguous amino acid sequence spans the late domain motif YPDL in the hemagglutinin-neuramimidase protein. In yet another specific embodiment, the compound according to the present invention is within an amino acid sequence that is at least 70 percent, preferably at least 80 percent or 85 percent, more preferably at least 90 percent or 95 percent identical to a contiguous amino acid sequence of at least 5, 6, 7, 8 or 9 amino acid residues, preferably 10, 11, 12, 13, 14, 15, 16, 17, 18, 19, 20 or more amino acid residues, but preferably less than 100 amino acid residues, and more preferably no more than 50 amino acid residues, of a naturally occuring UL42 protein of human herpes virus 2, which contiguous amino acid sequence spans the late domain motif YPDL in the UL42 protein. In this respect, the percentage identity is determined by the algorithm of Karlin and Altschul, *Proc. Natl. Acad. Sci. USA*, 90:5873–77 (1993), which is incorporated into the various BLAST programs. Specifically, the percentage identity is determined by the "BLAST 2 Sequences" tool, which is available at http://www.ncbi.nlm.nih.gov/gorf/bl2.html. See Tatusova and Madden, *FEMS Microbiol. Lett.*, 174(2):247–50 (1999). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter). In preferred embodiments, such homologue peptides retain the ability to bind a region including the amino acid residues 121 to 435 of AP-50.

The homologues can be made by site-directed mutagenesis based on, e.g., a late domain motif-containing EIAV p9 peptide or another known YL late domain motif-containing viral protein, or on a YL late domain motif-containing sequence of a protein in Table 1. The site-directed mutagenesis can be designed to generate amino acid substitutions, insertions, or deletions. Methods for conducting such mutagenesis should be apparent to skilled artisans in the field of molecular biology. The resultant homologues can be tested for their binding affinity to a region including the amino acid residues 121 to 435 of AP-50.

The peptide portion in the compounds according to the present invention can also be in a modified form. Various modifications may be made to improve the stability and solubility of the compound, and/or optimize its binding affinity to a region including the amino acid residues 121 to 435 of AP-50. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, and branching. Amino acids other than the conventional twenty amino acids encoded by genes may also be included in a polypeptide sequence in the compound of the present invention. For example, the compounds may include D-amino acids in place of L-amino acids.

To increase the stability of the compounds according to the present invention, various protection groups can also be incorporated into the amino acid residues of the compounds. In particular, terminal residues are preferably protected. Carboxyl groups may be protected by esters (e.g., methyl, ethyl, benzyl, p-nitrobenzyl, t-butyl or t-amyl esters, etc.), lower alkoxyl groups (e.g., methoxy, ethoxy, propoxy, butoxy, etc.), aralkyloxy groups (e.g., benzyloxy, etc.), amino groups, lower alkylamino or di(lower alkyl)amino groups. The term "lower alkoxy" is intended to mean an alkoxy group having a straight, branched or cyclic hydrocarbon moiety of up to six carbon atoms. Protection groups for amino groups may include lower alkyl, benzyloxycarbonyl, t-butoxycarbonyl, and sobornyloxycarbonyl. "Lower alkyl" is intended to mean an alkyl group having a straight, branched or cyclic hydrocarbon moiety of up to six carbon atoms. In one example, a 5-oxo-L-prolyl residue may be used in place of a prolyl residue. A 5-oxo-L-prolyl residue is especially desirable at the N-terminus of a peptide compound. In another example, when a proline residue is at the C-terminus of a peptide compound, a N-ethyl-L-prolinamide residue may be desirable in place of the proline residue. Various other protection groups known in the art useful in increasing the stability of peptide compounds can also be employed.

In addition, the compounds according to the present invention can also be in various pharmaceutically acceptable salt forms. "Pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, hydrobromide salts, sulfate salts, bisulfate salts, nitrate salts, acetate salts, phosphate salts, nitrate salts, oxalate salts, valerate salts, oleate salts, borate salts, benzoate salts, laurate saltes, stearate salts, palmitate salts, lactate salts, tosylate salts, citrate salts, maleate, salts, succinate salts, tartrate salts, naththylate salts, fumarate salts, mesylate salts, laurylsuphonate salts, glucoheptonate salts, and the like. See, e.g., Berge, et al. *J. Pharm. Sci.*, 66:1–19 (1977).

Suitable pharmaceutically acceptable salts also include, but are not limited to, alkali metal salts, alkaline earth salts, and ammonium salts. Thus, suitable salts may be salts of aluminum, calcium, lithium, magnesium, potassium, sodium and zinc. In addition, organic salts may also be used including, e.g., salts of lysine, N,N'-dibenzylethylenediamine, chloroprocaine, choline, diethanolamine, ethylenediamine, meglumine (N-methylglucamine), procaine and tris. In addition, metal complex forms (e.g. copper complex compounds, zinc complex compounds, etc.) of the compounds of the present invention may also exhibit improved stability.

Additionally, as will be apparent to skilled artisans apprised of the present disclosure, peptide mimetics can be designed based on the above-described compounds according to the present invention. However, it is noted that the mimetics preferably are capable of binding a region including the amino acid residues 121 to 435 of AP-50. For example, peptoid analogs of the YPDL motif can be prepared using known methods. Peptoids are oligomeric N-substituted glycines. Typically, various side chain groups can be included when forming an N-substituted glycine (peptoid monomer) that mimics a particular amino acid. Peptoid monomers can be linked together to form an oligomeric N-substituted glycines—peptoid. Peptoids are easy to synthesize in large amounts. In contrast to peptides, the backbone linkage of peptoids are resistant to hydrolytic enzymes. In addition, since a variety of functional groups can be presented as side chains off of the oligomeric backbone, peptoid analogs corresponding to any peptides can be produced with improved characterics. See Simon et al., *Proc. Natl. Acad. Sci. USA*, 89:9367–9371 (1992); Figliozzi et al., *Methods Enzymol.*, 267:437–447 (1996); Horwell, *Trends Biotechnol.*, 13:132–134 (1995); and Horwell, *Drug Des. Discov.*, 12:63–75 (1994), all of which are incorporated herein by reference.

Thus, peptoid analogs of the above-described compounds of the present invention can be made using methods known in the art. The thus prepared peptoid analogs can be tested for their binding affinity to a region including the amino acid residues 121 to 435 of AP-50. They can also be tested in anti-viral assays for their ability to inhibit virus budding from infected host cells and ability to inhibit virus propagation.

Mimetics of the compounds of the present invention can also be selected by rational drug design and/or virtual screening. Methods known in the art for rational drug design can be used in the present invention. See, e.g., Hodgson et al., *Bio/Technology*, 9:19–21 (1991); U.S. Pat. Nos. 5,800, 998 and 5,891,628, all of which are incorporated herein by reference. An example of rational drug design is the development of HIV protease inhibitors. See Erickson et al., *Science*, 249:527–533 (1990). Structural information on AP-50 in complex with a YL motif-containing EIAV p9 peptide is preferably elucidated. Structural information on the binding complex formed by AP-50 and the YL motif in a protein in Table 1 can also be obtained. The interacting complex can be studied using various biophysics techniques including, e.g., X-ray crystallography, NMR, computer modeling, mass spectrometry, and the like. Likewise, structural information can also be obtained from protein complexes formed by AP-50 and a variation of the YL motif.

Computer programs are employed to select compounds based on structural models. In addition, once an effective compound is identified, structural analogs or mimetics thereof can be produced based on rational drug design with the aim of improving drug efficacy and stability, and reducing side effects.

In addition, understanding of the interaction between AP-50 and compounds of the present invention can also be derived from mutagenesis analysis using yeast two-hybrid system or other methods for detection protein-protein interaction. In this respect, various mutations can be introduced into the interacting proteins and the effect of the mutations on protein-protein interaction is examined by a suitable method such as in vitro binding assay or the yeast two-hybrid system.

Various mutations including amino acid substitutions, deletions and insertions can be introduced into the protein sequence of AP-50 and/or a compound of the present invention using conventional recombinant DNA technologies. Generally, it is particularly desirable to decipher the protein binding sites. Thus, it is important that the mutations introduced only affect protein-protein interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.*, 202:301–306 (1991); Bass et al., *Proc. Natl. Acad. Sci. USA*, 88:4498–4502 (1991); Bennet et al., *J. Biol. Chem.*, 266:5191–5201 (1991); Diamond et al., *J. Virol.*, 68:863–876 (1994). Using this technique, charged or hydrophobic amino acid residues of the interacting proteins are replaced by alanine, and the effect on the interaction between the proteins is analyzed using e.g., an in vitro binding assay. In this manner, the domains or residues of the proteins important to compound-target interaction can be identified.

Based on the structural information obtained, structural relationships between AP-50 and a compound of the present invention are elucidated. The moieties and the three-dimensional structures critical to the interaction are revealed. Medicinal chemists can then design analog compounds having similar moieties and structures.

The residues or domains critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., in *OSAR: Quantitative Structure-Activity Relationships in Drug Design*, pp.189–193, Alan R. Liss, Inc., 1989; Rotivinen et al., *Acta Pharmaceutical Fennica*, 97:159–166 (1988); Lewis et al., *Proc. R. Soc. Lond.*, 236:125–140 (1989); McKinaly et al., *Annu. Rev. Pharmacol. Toxiciol.*, 29:111–122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

The mimetics including peptoid analogs can exhibit optimal binding affinity to AP-50 or animal orthologs thereof. Various known methods can be utilized to test the AP-50-binding characteristics of a mimetics. For example, the entire AP-50 protein or a fragment thereof may be recombinantly expressed, purified, and contacted with the mimetics to be tested. Binding can be determined using a surface plasmon resonance biosensor. See e.g., Panayotou et al., *Mol. Cell. Biol.*, 13:3567–3576 (1993). Other methods known in the art for estimating and determining binding constants in protein-protein interactions can also be employed. See Phizicky and Fields, et al., *Microbiol. Rev.*, 59:94–123 (1995). For example, protein affinity chromatography may be used. First, columns are prepared with different concentrations of an interacting member, which is covalently bound to the columns. Then a preparation of its interacting partner is run through the column and washed with buffer. The interacting partner bound to the interacting member linked to the column is then eluted. Binding constant is then estimated based on the concentrations of the bound protein and the eluted protein. Alternatively, the method of sedimentation through gradients monitors the rate of sedimentation of a mixture of proteins through gradients of glycerol or sucrose. At concentrations above the binding constant, the two interacting members sediment as a complex. Thus, binding constant can be calculated based on the concentrations. Other suitable methods known in the art for estimating binding constant include but are not limited to gel filtration column such as nonequilibrium "small-zone" gel filtration columns (See e.g., Gill et al., *J. Mol. Biol.*, 220:307–324 (1991)), the Hummel-Dreyer method of equilibrium gel filtration (See e.g., Hummel and Dreyer, *Biochim. Biophys. Acta*, 63:530–532 (1962)) and large-zone equilibrium gel filtration (See e.g., Gilbert and Kellett, *J. Biol. Chem.*, 246:6079–6086 (1971)), sedimentation equilibrium (See e.g., Rivas and Minton, *Trends Biochem.*, 18:284–287 (1993)), fluorescence methods such as fluorescence spectrum (See e.g., Otto-Bruc et al, *Biochemistry*, 32:8632–8645 (1993)) and fluorescence polarization or anisotropy with tagged molecules (See e.g., Weiel and Hershey, *Biochemistry*, 20:5859–5865 (1981)), and solution equilibrium measured with immobilized binding protein (See e.g., Nelson and Long, *Biochemistry*, 30:2384–2390 (1991)).

The compounds according the present invention can be delivered into cells by direct cell internalization, receptor mediated endocytosis, or via a "transporter." It is noted that the compound administered to cells in vitro or in vivo in the method of the present invention preferably is delivered into the cells in order to achieve optimal results. Thus, preferably, the compound to be delivered is associated with a transporter capable of increasing the uptake of the compound by a mammalian cell, preferably a human cell, susceptible to infection by a virus, particularly a virus selected from those in Table 1. As used herein, the term "associated with" means a compound to be delivered is physically associated with a transporter. The compound and the transporter can be covalently linked together, or associated with each other as a result of physical affinities such as forces caused by electrical charge differences, hydrophobicity, hydrogen bonds, van der Waals force, ionic force, or a combination thereof. For example, the compound can be encapsulated within a transporter such as a cationic liposome.

As used herein, the term "transporter" refers to an entity (e.g., a compound or a composition or a physical structure formed from multiple copies of a compound or multiple different compounds) that is capable of facilitating the uptake of a compound of the present invention by a mammalian cell, particularly a human cell. Typically, the cell uptake of a compound of the present invention in the presence of a "transporter" is at least 50% higher than the cell uptake of the compound in the absence of the "transporter." Preferably, the cell uptake of a compound of the present invention in the presence of a "transporter" is at least 75% higher, preferably at least 100% or 200% higher, and more preferably at least 300%, 400% or 500% higher than the cell uptake of the compound in the absence of the "transporter." Methods of assaying cell uptake of a compound should be apparent to skilled artisans. For example, the compound to be delivered can be labeled with a radioactive isotope or another detectable marker (e.g., a fluorescence marker), and added to cultured cells in the presence or absence of a transporter, and incubated for a time period sufficient to allow maximal uptake. Cells can then be separated from the culture medium and the detectable signal (e.g., radioactivity) caused by the compound inside the cells can be measured. The result obtained in the presence of a transporter can be compared to that obtained in the absence of a transporter.

Many molecules and structures known in the art can be used as "transporter." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., *Trends Cell Biol.*, 8:84–87 (1998), which is incorporated herein by reference. Penetratins transport molecules attached thereto across cytoplasm membranes or nucleus membranes efficiently in a receptor-independent, energy-independent, and cell type-independent manner. Methods for using a penetratin as a carrier to deliver oligonucleotides and polypeptides are also disclosed in U.S. Pat. No. 6,080,724; Pooga et al., *Nat. Biotech.*, 16:857 (1998); and Schutze et al., *J. Immunol.*, 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminal is tryptophan, while the amino acids at positions 3 and 5 counting from either the N- or C-terminal are not both valine. Preferably, the helix 3 of the homeodomain of *Drosophila* Antennapedia is used as a transporter. More preferably, a peptide having a sequence of the amino acids 43–58 of the homeodomain Antp is employed as a transporter. In addition, other naturally occurring homologs of the helix 3 of the homeodomain of *Drosophila* Antennapedia can also be used. For example, homeodomains of Fushi-tarazu and Engrailed have been shown to be capable of transporting peptides into cells. See Han et al., *Mol. Cells*, 10:728–32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound.

In another embodiment, the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, *Cell*, 55:1179 (1988); Frankel and Pabo, *Cell*, 55:1189 (1988); Vives et al., *J. Biol. Chem.*, 272:16010–16017 (1997); Schwarze et al., *Science*, 285:1569–1572 (1999). It is known that the sequence responsible for cellular uptake consists of the highly basic region, amino acid residues 49–57. See e.g., Vives et al., *J. Biol. Chem.*, 272:16010–16017 (1997); Wender et al., *Proc. Nat'l. Acad. Sci. USA*, 97:13003–13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., *Science*, 285:1569–1572 (1999). Any HIV tat-derived peptides or peptoid analogs thereof capable of transporting macromolecules such as peptides can be used for purposes of the present invention. For example, any native tat peptides having the highly basic region, amino acid residues 49–57 can be used as a transporter by covalently linking it to the compound to be delivered. In addition, various analogs of the tat peptide of amino acid residues 49–57 can also be useful transporters for purposes of this invention. Examples of various such analogs are disclosed in Wender et al., *Proc. Nat'l Acad. Sci. USA*, 97:13003–13008 (2000) (which is incorporated herein by reference) including, e.g., d-Tat$_{49-57}$, retro-inverso isomers of l- or d-Tat$_{49-57}$ (i.e., l-Tat$_{57-49}$ and d-Tat$_{57-49}$), L-arginine oligomers, D-arginine oligomers, L-lysine oligomers, D-lysine oligomers, L-histine oligomers, D-histine oligomers, L-ornithine oligomers, D-ornithine oligomers, and various homologues, derivatives (e.g., modified forms with conjugates linked to the small peptides) and peptoid analogs thereof. Preferably, arginine oligomers are preferred to the other oligomers, since arginine oligomers are much more efficient in promoting cellular uptake. As used herein, the term "oligomer" means a molecule that includes a covalently linked chain of amino acid residues of the same amino acids having a large enough number of such amino acid residues to confer transporter activities on the molecule. Typically, an oligomer contains at least 6, preferably at least 7, 8, or at least 9 such amino acid residues. In one embodiment, the transporter is a peptide that includes at least six contiguous amino acid residues that are a combination of two or more of L-arginine, D-arginine, L-lysine, D-lysine, L-histidine, D-histine, L-ornithine, and D-ornithine.

Other useful transporters known in the art include, but are not limited to, short peptide sequences derived from fibroblast growth factor (See Lin et al., *J. Biol. Chem.*, 270:14255–14258 (1998)), Galparan (See Pooga et al., *FASEB J.* 12:67–77 (1998)), and HSV-1 structural protein VP22 (See Elliott and O'Hare, *Cell*, 88:223–233 (1997)).

As the above-described various transporters are generally peptides, fusion proteins can be conveniently made by recombinant expression to contain a transporter peptide covalently linked by a peptide bond to a peptide compound according to the present invention. Alternatively, conventional methods can be used to chemically synthesize a transporter peptide or a peptide of the present invention or both.

In addition to peptide-based transporters, various other types of transporters can also be used, including but not limited to cationic liposomes (see Rui et al., *J. Am. Chem. Soc.*, 120:11213–11218 (1998)), dendrimers (Kono et al., *Bioconjugate Chem.*, 10:1115–1121 (1999)), siderophores (Ghosh et al., *Chem. Biol.*, 3:1011–1019 (1996)), etc. In a specific embodiment, the compound according to the present invention is encapsulated into liposomes for delivery into cells.

Additionally, when a compound according to the present invention is a peptide, it can be introduced into cells by a gene therapy method. That is, a nucleic acid encoding the peptide can be administered to in vitro cells or to cells in vivo in a human or animal body. The nucleic acid encoding the peptide may or may not also encode a peptidic transporter as described above. Various gene therapy methods are well known in the art. Successes in gene therapy have been reported recently. See e.g., Kay et al., *Nature Genet.*, 24:257–61 (2000); Cavazzana-Calvo et al., *Science*, 288:669 (2000); and Blaese et al., *Science*, 270: 475 (1995); Kantoff, et al., *J. Exp. Med.*, 166:219 (1987).

In one embodiment, the peptide consists of a contiguous amino acid sequence of from 7 to about 30 amino acid residues of a viral protein selected from the group consisting of a viral protein selected from the group consisting of HCV polyprotein, HSV UL42 protein, variola virus A10L protein, vaccinia virus virion core protein P4a, human parainfluenza virus hemagglutinin-neuramimidase and EIAV GAGp9, and wherein the contiguous amino acid sequence encompasses the YPXL motif of the viral protein.

Preferably, the peptide consists of at least 7, 8, 9, 10, 11, 12, 13, 14, or 15 amino acids. Also preferably, the peptide consists of no greater than 25, 24, 23, 22, 21, 20, 19, 18, 17, 16 or 15 amino acids. More preferably, the peptide consists of from 9 to 20, 23 or 25 amino acids, or from 10 or 11 to 20, 23 or 25 amino acids.

For example, the peptide can include an amino acid sequence selected from the group consisting of SEQ ID NOs:18–164, SEQ ID NOs:165–307, SEQ ID NOs:308–450, SEQ ID NOs:451–593, and SEQ ID NOs:594–736.

Any suitable gene therapy methods may be used for purposes of the present invention. Generally, an exogenous nucleic acid encoding a peptide compound of the present invention is incorporated into a suitable expression vector and is operably linked to a promoter in the vector. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Where tissue-specific expression of the exogenous gene is desirable, tissue-specific promoters may be operably linked to the exogenous gene. In addition, selection markers may also be included in the vector for purposes of selecting, in vitro, those cells that contain the exogenous nucleic acid encoding the peptide compound of the present invention. Various selection markers known in the art may be used including, but not limited to, e.g., genes conferring resistance to neomycin, hygromycin, zeocin, and the like.

In one embodiment, the exogenous nucleic acid is incorporated into a plasmid DNA vector. Many commercially available expression vectors may be useful for the present invention, including, e.g., pCEP4, pcDNAI, pIND, pSecTag2, pVAX1, pcDNA3.1, and pBI-EGFP, and pDisplay.

Various viral vectors may also be used. Typically, in a viral vector, the viral genome is engineered to eliminate the disease-causing capability, e.g., the ability to replicate in the host cells. The exogenous nucleic acid to be introduced into a patient may be incorporated into the engineered viral genome, e.g., by inserting it into a viral gene that is non-essential to the viral infectivity. Viral vectors are convenient to use as they can be easily introduced into tissue cells by way of infection. Once in the host cell, the recombinant virus typically is integrated into the genome of the host cell. In rare instances, the recombinant virus may also replicate and remain as extrachromosomal elements.

A large number of retroviral vectors have been developed for gene therapy. These include vectors derived from oncoretroviruses (e.g., MLV), viruses (e.g., HIV and SIV) and other retroviruses. For example, gene therapy vectors have been developed based on murine leukemia virus (See, Cepko, et al., *Cell*, 37:1053–1062 (1984), Cone and Mulligan, *Proc. Natl. Acad. Sci. U.S.A.*, 81:6349–6353 (1984)), mouse mammary tumor virus (See, Salmons et al., *Biochem. Biophys. Res. Commun.*, 159:1191–1198 (1984)), gibbon ape leukemia virus (See, Miller et al., *J. Virology*, 65:2220–2224 (1991)), HIV, (See Shimada et al., *J. Clin. Invest.*, 88:1043–1047 (1991)), and avian retroviruses (See Cosset et al., *J. Virology*, 64:1070–1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et al., *Nature Genet.* 24:257–61 (2000). AAV is a naturally occurring defective virus that requires other viruses such as adenoviruses or herpes viruses as helper viruses. See Muzyczka, *Curr. Top. Microbiol. Immun.*, 158:97 (1992). A recombinant AAV virus useful as a gene therapy vector is disclosed in U.S. Pat. No. 6,153,436, which is incorporated herein by reference.

Adenoviral vectors can also be useful for purposes of gene therapy in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., *Science*, 252:431–434 (1991); and Rosenfeld et al., *Cell*, 68:143–155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258).

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or taken up by cells.

The exogenous nucleic acid fragment or plasmid DNA vector containing the exogenous nucleic acid may also be introduced into cells by way of receptor-mediated endocytosis. See e.g., U.S. Pat. No. 6,090,619; Wu and Wu, *J. Biol. Chem.*, 263:14621 (1988); Curiel et al., *Proc. Natl. Acad. Sci. USA*, 88:8850 (1991). For example, U.S. Pat. No. 6,083,741 discloses introducing an exogenous nucleic acid into mammalian cells by associating the nucleic acid to a polycation moiety (e.g., poly-L-lysine, having 3–100 lysine residues), which is itself coupled to an integrin receptor binding moiety (e.g., a cyclic peptide having the amino acid sequence RGD).

Alternatively, the exogenous nucleic acid or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Mammalian cells contacted with the complex can readily absorb the complex.

The exogenous nucleic acid can be introduced into a patient for purposes of gene therapy by various methods known in the art. For example, the exogenous nucleic acid alone or in a conjugated or complex form described above, or incorporated into viral or DNA vectors, may be administered directly by injection into an appropriate tissue or organ of a patient. Alternatively, catheters or like devices may be used for delivery into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

In addition, the exogenous nucleic acid encoding a peptide compound of the present invention or vectors containing the nucleic acid can be introduced into isolated cells using any known techniques such as calcium phosphate precipitation, microinjection, lipofection, electroporation, gene gun, receptor-mediated endocytosis, and the like. Cells expressing the exogenous gene may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., obtained from the patient being treated.

When the transporter used in the method of the present invention is a peptidic transporter, a hybrid polypeptide or fusion polypeptide is provided. In preferred embodiments, the hybrid polypeptide includes (a) a first portion comprising an amino acid sequence motif YPXL, and capable of binding a region including the amino acid residues 121 to 435 of AP-50, wherein X is an amino acid, preferably is aspartate, alanine, glutamic acid, or glycine, and (b) a second portion which is a peptidic transporter capable of increasing the uptake of the first portion by a human cell.

In one embodiment, the hybrid polypeptide includes from about 8 to about 100 amino acid residues, preferably 9 to 50 amino acid residues, more preferably 12 to 30 amino acid residues, and even more preferably from about 14 to 20 amino acid residues.

In a specific embodiment, the hybrid polypeptide does not contain a terminal L-histidine oligomer. As used herein, the term "terminal L-histidine oligomer" means an L-histidine oligomer at either of the two termini of the hybrid polypeptide, or at no more than one, two or three amino acid residues from either terminus of the hybrid polypeptide.

Preferably, the peptidic transporter is capable of increasing the uptake of the first portion by a mammalian cell by at least 100%, more preferably by at least 300%, 400% or 500%. In one embodiment, the transporter includes from at least 6 to about 14 arginine residues.

The hybrid polypeptide can be produced in a patient's body by administering to the patient a nucleic acid encoding the hybrid polypeptide by a gene therapy method as described above. Alternatively, the hybrid polypeptide can be chemically synthesized or produced by recombinant expression.

Thus, the present invention also provides isolated nucleic acids encoding the hybrid polypeptides and host cells containing one of the nucleic acids and recombinantly expressing one of the hybrid polypeptides. Such a host cell can be prepared by introducing into a suitable cell an exogenous nucleic acid encoding one of the hybrid polypeptides by standard molecular cloning techniques as described above. The nucleic acids can be prepared by linking a nucleic acid encoding the first portion and a nucleic acid encoding the second portion. Methods for preparing such nucleic acids and for using them in recombinant expression should be apparent to skilled artisans.

The compounds according to the present invention are a novel class of anti-viral compounds distinct from other commercially available compounds. While not wishing to be bound by any theory or hypothesis, it is believed that the compounds according to the present invention inhibit virus through a mechanism distinct from those of the anti-viral compounds known in the art. Therefore, it may be desirable to employ combination therapies to administer to a patient both a compound according to the present invention, with or without a transporter, and another anti-viral compound of a different class. However, it is to be understood that such other anti-viral compounds should be pharmaceutically compatible with the compound of the present invention. By "pharmaceutically compatible" it is intended that the other anti-viral agent(s) will not interact or react with the above composition, directly or indirectly, in such a way as to adversely affect the effect of the treatment, or to cause any significant adverse side reaction in the patient. In this combination therapy approach, the two different pharmaceutically active compounds can be administered separately or in the same pharmaceutical composition. Compounds suitable for use in combination therapies with the compounds according to the present invention include, but are not limited to, small molecule drugs, antibodies, immunomodulators, and vaccines. For example, compounds useful in treating HCV infection may include interferon (Intron A®, or PEG-Intron®), and various nucleoside analogs.

Typically, compounds of the present invention are administered to a patient in a pharmaceutical composition, which typically includes one or more pharmaceutically acceptable carriers that are inherently nontoxic and non-therapeutic. That is, the compounds are used in the manufacture of medicaments for use in the methods of treating viral infection provided in the present invention.

The pharmaceutical composition according to the present invention may be administered to a subject needing treatment or prevention through any appropriate routes such as parenteral, oral, or topical administration. The active compounds of this invention are administered at a therapeutically effective amount to achieve the desired therapeutic effect without causing any serious adverse effects in the patient treated. Generally, the toxicity profile and therapeutic efficacy of therapeutic agents can be determined by standard pharmaceutical procedures in suitable cell models or animal models or human clinical trials. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the $ED_{50}$ and/or $IC_{50}$, but significantly below the $LD_{50}$ obtained from cell or animal models.

Typically, the compounds of the present invention can be effective at an amount of from about 0.01 microgram to about 5000 mg per day, preferably from about 1 microgram to about 2500 mg per day. However, the amount can vary with the body weight of the patient treated and the state of disease conditions. The active ingredient may be administered at once, or may be divided into a number of smaller doses to be administered at predetermined intervals of time. The suitable dosage unit for each administration of the compounds of the present invention can be, e.g., from about 0.01 microgram to about 2000 mg, preferably from about 1 microgram to about 1000 mg.

In the case of combination therapy, a therapeutically effective amount of another anti-viral compound can be administered in a separate pharmaceutical composition, or alternatively included in the pharmaceutical composition that contains a compound according to the present invention. The pharmacology and toxicology of many of such other anti-viral compounds are known in the art. See e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can also be adjusted as the various factors change over time.

The active compounds according to this invention can be administered to patients to be treated through any suitable routes of administration. Advantageously, the active compounds are delivered to the patient parenterally, i.e., by intravenous, intramuscular, intraperitoneal, intracisternal, subcutaneous, or intraarticular injection or infusion.

For parenteral administration, the active compounds can be formulated into solutions or suspensions, or in lyophilized forms for conversion into solutions or suspensions before use. Lyophilized compositions may include pharmaceutically acceptable carriers such as gelatin, DL-lactic and glycolic acids copolymer, D-mannitol, etc. To convert the lyophilized forms into solutions or suspensions, diluent containing, e.g., carboxymethylcellulose sodium, D-mannitol, polysorbate 80, and water may be employed. Lyophilized forms may be stored in, e.g., a dual chamber syringe with one chamber containing the lyophilized composition and the other chamber containing the diluent. In addition, the active ingredient(s) can also be incorporated into sterile lyophilized microspheres for sustained release. Methods for making such microspheres are generally known in the art. See U.S. Pat. Nos. 4,652,441; 4,728,721; 4,849,228; 4,917,893; 4,954,298; 5,330,767; 5,476,663; 5,480,656; 5,575,987; 5,631,020; 5,631,021; 5,643,607; and 5,716,640.

In a solution or suspension form suitable for parenteral administration, the pharmaceutical composition can include, in addition to a therapeutically or prophylactically effective amount of a compound of the present invention, a buffering agent, an isotonicity adjusting agent, a preservative, and/or an anti-absorbent. Examples of suitable buffering agent include, but are not limited to, citrate, phosphate, tartrate, succinate, adipate, maleate, lactate and acetate buffers, sodium bicarbonate, and sodium carbonate, or a mixture thereof. Preferably, the buffering agent adjusts the pH of the solution to within the range of 5–8. Examples of suitable isotonicity adjusting agents include sodium chloride, glycerol, mannitol, and sorbitol, or a mixture thereof. A preservative (e.g., anti-microbial agent) may be desirable as it can inhibit microbial contamination or growth in the liquid forms of the pharmaceutical composition. Useful preservatives may include benzyl alcohol, a paraben and phenol or a mixture thereof. Materials such as human serum albumin, gelatin or a mixture thereof may be used as anti-absorbents. In addition, conventional solvents, surfactants, stabilizers, pH balancing buffers, and antioxidants can all be used in the parenteral formulations, including but not limited to dextrose, fixed oils, glycerine, polyethylene glycol, propylene glycol, ascorbic acid, sodium bisulfite, and the like. The parenteral formulation can be stored in any conventional containers such as vials, ampoules, and syringes.

The active compounds can also be delivered orally in enclosed gelatin capsules or compressed tablets. Capsules and tablets can be prepared in any conventional techniques. For example, the active compounds can be incorporated into a formulation which includes pharmaceutically acceptable carriers such as excipients (e.g., starch, lactose), binders (e.g., gelatin, cellulose, gum tragacanth), disintegrating agents (e.g., alginate, Primogel, and corn starch), lubricants (e.g., magnesium stearate, silicon dioxide), and sweetening or flavoring agents (e.g., glucose, sucrose, saccharin, methyl salicylate, and peppermint). Various coatings can also be prepared for the capsules and tablets to modify the flavors, tastes, colors, and shapes of the capsules and tablets. In addition, liquid carriers such as fatty oil can also be included in capsules.

Other forms of oral formulations such as chewing gum, suspension, syrup, wafer, elixir, and the like can also be prepared containing the active compounds used in this invention. Various modifying agents for flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered topically through rectal, vaginal, nasal, bucal, or mucosal applications. Topical formulations are generally known in the art including creams, gels, ointments, lotions, powders, pastes, suspensions, sprays, drops and aerosols. Typically, topical formulations include one or more thickening agents, humectants, and/or emollients including but not limited to xanthan gum, petrolatum, beeswax, or polyethylene glycol, sorbitol, mineral oil, lanolin, squalene, and the like.

A special form of topical administration is delivery by a transdermal patch. Methods for preparing transdermal patches are disclosed, e.g., in Brown, et al., *Annual Review of Medicine*, 39:221–229 (1988), which is incorporated herein by reference.

The active compounds can also be delivered by subcutaneous implantation for sustained release. This may be accomplished by using aseptic techniques to surgically implant the active compounds in any suitable formulation into the subcutaneous space of the anterior abdominal wall. See, e.g., Wilson et al., *J. Clin. Psych.* 45:242–247 (1984). Sustained release can be achieved by incorporating the active ingredients into a special carrier such as a hydrogel. Typically, a hydrogel is a network of high molecular weight biocompatible polymers, which can swell in water to form a gel like material. Hydrogels are generally known in the art. For example, hydrogels made of polyethylene glycols, or collagen, or poly(glycolic-co-L-lactic acid) are suitable for this invention. See, e.g., Phillips et al., *J. Pharmaceut. Sci.*, 73:1718–1720 (1984).

The active compounds can also be conjugated, i.e., covalently linked, to a water soluble non-immunogenic high molecular weight polymer to form a polymer conjugate. Preferably, such polymers do not undesirably interfere with the cellular uptake of the active compounds. Advantageously, such polymers, e.g., polyethylene glycol, can impart solubility, stability, and reduced immunogenicity to the active compounds. As a result, the active compound in the conjugate when administered to a patient, can have a longer half-life in the body, and exhibit better efficacy. In one embodiment, the polymer is a peptide such as albumin or antibody fragment Fc. PEGylated proteins are currently being used in protein replacement therapies and for other therapeutic uses. For example, PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). A general review of PEG-protein conjugates with clinical efficacy can be found in, e.g., Burnham, *Am. J. Hosp. Pharm.*, 15:210–218 (1994). Preferably, the covalent linkage between the polymer and the active compound is hydrolytically degradable and is susceptible to hydrolysis under physiological conditions. Such conjugates are known as "prodrugs" and the polymer in the conjugate can be readily cleaved off inside the body, releasing the free active compounds.

Alternatively, other forms controlled release or protection including microcapsules and nanocapsules generally known in the art, and hydrogels described above can all be utilized in oral, parenteral, topical, and subcutaneous administration of the active compounds.

Another preferable delivery form is using liposomes as carrier. Liposomes are micelles formed from various lipids such as cholesterol, phospholipids, fatty acids, and derivatives thereof. Active compounds can be enclosed within such micelles. Methods for preparing liposomal suspensions containing active ingredients therein are generally known in the art and are disclosed in, e.g., U.S. Pat. No. 4,522,811, and Prescott, Ed., *Methods in Cell Biology*, Volume XIV, Academic Press, New York, N.Y. (1976), p. 33 et seq., both of which are incorporated herein by reference. Several anticancer drugs delivered in the form of liposomes are known in the art and are commercially available from Liposome Inc. of Princeton, N.J., U.S.A. It has been shown that liposomes can reduce the toxicity of the active compounds, and increase their stability.

EXAMPLE 1

Fragments of the viral proteins selected from those in Table 1 are tested for their interaction with human AP-50 protein using yeast two-hybrid system. That is, to prepare a yeast two-hybrid activation domain-AP-50 construct, a DNA fragment encompassing the full-length coding sequence for AP-50 is obtained by PCR from a human fetal brain cDNA library and cloned into the EcoRI/Pst1 sites of the activation domain parent plasmid GADpN2 (LEU2, CEN4, ARS1, ADH1p-SV40NLS-GAL4 (768–881)-MCS (multiple cloning site)-PGK1t, AmpR, ColE1_ori). To prepare the yeast two-hybrid DNA binding domain-YL motif-containing viral peptide construct, a DNA fragment corresponding to a contiguous amino acid sequence of a viral protein in Table 1 that spans the YL motif therein is obtained and is cloned into the EcoRI/Sal1 sites of the binding domain parent plasmid pGBT.Q.

To perform the yeast two-hybrid assays, yeast cells of the strain Y189 purchased from Clontech (ura3–52 his3*200 ade2-101 trp1-901 leu2-3,112 met gal4 gal80 URA3:GAL1p-lacZ) are co-transformed with the activation domain-AP-50 construct and a binding domain-YPDL-containing viral peptide construct or the binding domain-wild type EIAV p9 construct. Filter lift assays for β-Gal activity are conducted by lifting the transformed yeast colonies with filters, lysing the yeast cells by freezing and thawing, and contacting the lysed cells with X-Gal. Positive β-Gal activity indicates that the p9 wild type or YPDL-containing viral peptide interacts with AP-50. All binding domain constructs are also tested for self-activation of β-Gal activity.

EXAMPLE 2

A fusion protein with a GST tag fused to the EIAV p9 domain is recombinantly expressed and purified by chromatography. In addition, a series of fusion peptides containing a short peptide compound according to the present invention fused to a peptidic transporter are synthesized chemically by standard peptide synthesis methods or recombinantly expressed in a standard protein expression system. The short peptides are fused to a peptidic transporter such as an L-arginine oligomer containing 9 arginines. A number of short peptide compounds according to the present invention are also prepared by chemical synthesis or recombinant expression, e.g., free and unfused peptides having a sequence selected from the group of SEQ ID NOs:1–11, 18–736. The peptides are purified by conventional protein purification techniques, e.g., by chromatography.

Nunc/Nalgene Maxisorp plates are incubated overnight at 4° C. or for 1–2 hrs at room temperature in 100 µl of a protein coupling solution containing purified GST-p9 and 50 mM Carbonate, pH=9.6. This allows the attachment of the GST-p9 fusion protein to the plates. Liquids in the plates are then emptied and wells filled with 400 µl/well of a blocking buffer (SuperBlock; Pierce-Endogen, Rockford, Ill.). After incubating for 1 hour at room temperature, 100 µl of a mixture containing Drosophila S2 cell lysate myc-tagged AP-50 and a short peptide compound of the present invention is applied to the wells of the plate. This mixture is allowed to react for 2 hours at room temperature to form p9:AP-50 protein-protein complexes.

Plates are then washed 4×100 μl with 1×PBST solution (Invitrogen; Carlsbad, Calif.). After washing, 100 μl of 1 μg/ml solution of anti-myc monoclonal antibody (Clone 9E10; Roche Molecular Biochemicals; Indianapolis, Ind.) in 1×PBST is added to the wells of the plate to detect the myc-epitope tag on the AP-50 protein. Plates are then washed again with 4×100 μl with 1×PBST solution and 100 μl of 1 μg/ml solution of horseradish peroxidase (HRP) conjugated Goat anti-mouse IgG (Jackson Immunoresearch Labs; West Grove, Pa.) in 1×PBST is added to the wells of the plate to detect bound mouse anti-myc antibodies. Plates are then washed again with 4×100 μl with 1×PBST solution and 100 μl of fluorescent substrate (QuantaBlu; Pierce-Endogen, Rockford, Ill.) is added to all wells. After 30 minutes, 100 μl of stop solution is added to each well to inhibit the function of HRP. Plates are then read on a Packard Fusion instrument at an excitation wavelength of 325 nm and an emission wavelength of 420 nm. The presence of fluorescent signals indicates binding of AP-50 to the fixed GST-p9. In contrast, the absence of fluorescent signals indicates that the short peptide compound according to the present invention is capable of disrupting the interaction between AP-50 and EIAV p9.

EXAMPLE 3

The following examples demonstrate the anti-viral effect of the peptides according to the present invention which are tested in Example 2. Approximately 1 million PC12 cells in a T25 flask are either mock-infected or infected with HSV-2 in 1.5 ml of Medium 199 at a multiplicity of infection of 0.1. In addition, the test peptides according to the present invention are also added to the medium at various concentrations. At 8 hour after infection, cells are harvested and RNA and protein extracts are prepared as described in Liu & Roizman, *J. Virol.*, 65:5149–5156 (1991). A PCR protocol (see Koenig et al., Diagn. Microbiol. Infect. Dis., 40(3):107–10 (2001) or enzyme-linked immunoassay can then be used to detect the extent of viral infection and determine the efficacy of the test peptides.

```
(Equine Infectious Anemia Virus Gag p9 (AAA43011)
DPRDSRGELTEVFWRCSWPEHRRTGKMGDPLTWSKALKKLEKVTVQGSQKLTTGNCNWAL   SEQ ID NO: 12

SLVDLFHDTNFVKEKDWQLRDVIPLLEDVTQTLSGQEREAFERTWWATSAVKMGLQINNV

VDGKASFQLLRAKYEKKTANKKQSEPSEEYPIMIDGAGNRNFRPLTPRGYTTWVNTIQTN

GLLNEASQNLFGILSVDCTSEEMNAFLDVVPGQAGQKQILLDATDKTADDWDNRHPLPNA

PLVAPPQGPTPMTARFIRGLGVPRERQMEPAFDQFRQTYRQWIIEAMSEGTKVMIGKPKA

QNIRQGAKEPYPEFVDRLLSQIKSEGHPQEISKFLTDTLTIQNANEECRNAMRHLRPEDT

LEEKMYACRDIGTTKQKMMLLAKALQTGLAGPFKGGALKGGPLKAAQTCYNCGKPGHLSS

QCRAPKVCFKCKQPGHFSKQCRSVPKNGKQGAQGRPQKQTFPIQQKSQHNKSVVQETPQT

QNLYPDLSEIKKEYNVKEKDQVEDLNLDSLWE (Hepatitis C Virus Polyprotein (AAF01178)):
MSTNPKPQRKTKRNTNRRPQDVKFPGGGQTVGGVYLLPRRGPRLGVPATRKTSERSQPRG  SEQ ID NO: 13

RRQPTPKDRRSTGKSWGKPGYPWPLYGNEGLGWAGWLLSPRGSRPSWGPNDPRHRSRNVG

KVIDTLTCGFADLMGYIPVVGAPLGGVARALAHGVRVLEDGXmFATGNLPGCSFSIELLA

LLSCITTPVSAAEVKNISTGYMVTNDCTNDSTTWQLQAAVLHVPGCVPCEKVGNASQCWT

PVSPNVAVQRPGALTQGLRTHIDNMSATLCSALYVGDLCGGVIVILAAQMFIVSPQHHWF

VQDCNCSIYPGTITGHRMAWDMMMNWSPTATMILAYAMRVPEVIIDIISGAHWGVMFGLA

YFSMQGAWAKVVVILLLAAGVDARTHTVGGSAAQTTGRLTSLFDMGPRQKTQLVNTNGSW

HINRTALNCNDSLHTGFIASLFYTHSFNSSGCPERMSACRSIEAFRVGWGALOYEDNVTN

PEDMRPYCWHYPPRQCGVVSAKTVCGPVYCFTPSPVVVGTTDRLGAPTYTWGENETDVFL

LNSTRPPLGSWFGCTWMNSSGYTKTCGAPPCRTPADFNASTDLLCPTDCFRKHPDTTYLK

CGSGPWLTPRCLIDYPYRLWHYPCTVNYTIFKIPMYVGGVEHRLTAACNFTRGDRCNLED

RDRSQLSPLLHSTTEWAILPCSYSDLPALSTGLLHLHQNIVDVQFMYGLSPALTKYIVRW

EWVILLFLLLADARVCACLWMLILLGQAEAALEKLVILHAASAASCNGFLYFVIFFVAAW

YIKGRVVPLATYSLTGLWSFSLLLLALPQQAYAYDASVHGQIGAALLVMITLFTLTPGYK

TLLSRFLWWLCYLLTLGEAMVQEWAPPMQVRFFRDGIIWAVAIFYPGVVFDITKWLLAVL

GPAYLLKGALTRVPYFVRAHALLRMCTMARHLAGGRYVQMALLALGRWTGTYIYDHLTPM
```

-continued

SDWAASGLRDLAVAVEPIIFSPMEKKVIVWGAETAACGDILHGLPVSARLGREVLLGPAD

GYTSKGWSLLAPITAYAQQTRGLLGTIVVSMTGRDKTEQAGEIQVLSTVTQSFLGTSISG

VLWTVYHGAGNKTLAGSRGPVTQMYSSAEGDLVGWPSPPGTKSLEPCTCGAVDLYLVTRN

ADVIPARRRGDKRGALLSPRPLSTLKGSSGGPVLCPRGHAVGVFRAAVCSRGVAKSIDFI

PVETLDIVTRSPTFSDNSTPPAVPQTYQVGYLHAPTGSGKSTKVPVAYAAQGYKVLVLNP

SVAATLGFGAYLSKAHGINPNIRTGVRTVTTGAPITYSTYGKFLADGGCAGGAYDIIICD

ECHAVDSTTILGIGTVLDQAETAGVRLTVLATATPPGSVTTPHPNIEEVALGQEGEIPFY

GRAIPLSYIKGGRHLIFCHSKKKCDELAAALRGMGLNSVAYYRGLDVSVIPTQGDVVVVA

TDALMTGYTGDFDSVIDCNVAVTQVVDFSLDPTFTITTQIVPQDAVSRSQRRGRTGRGRL

GIYRYVSTGEPASGMFDSVVLCECYDAGAAWYELTPSETTVRLPAYFNTPGLPVCQDHLE

FWEAVFTGLTHIDAHFLSQTKQSGENFAYLTAYQATVCARAKAPPPSWDVMWKCLTRLKP

TLVGPTPLLYRLGSVTNEVTLTHPVTKYIATCMQADLEVMTSTWVLAGGVLAAVAAYCLA

TGCVCIIGRLHINQRAVVAPDKEVLYEAFDEMEECASRAALIEEGQRIAEMLKSKIQGLL

QQASKQAQDIQPTVQASWPKVEQFWAKHMWNFISGIQYLAGLSTLPGNPAVASMMAFSAA

LTSPLSTSTTILLNILGGWLASQIAPPAGATGFVVSGLVGAAVGSIGLGKVLVDILAGYG

AGISGALVAFKIMSGEKPSMEDVVNLLPGILSPGALVVGVICAAILRRHVGPGEGAVQWM

NRLIAFASRGNHVAPTHYVTESDASQRVTQLLGSLTITSLLRRLHNWITEDCPIPCGGSW

LRDVWDWVCTILTDFKNWLTSKLFPKMPGLPFVSCQKGYKGVWAGTGIMTTRCPCGANIS

GNVRLGSMRITGPKTCMNIWQGTFPINCYTEGQCBPKPAPNFKVAIWRVAASEYAEVTQH

GSYHYITGLTTDNLKVPCQLPSPEFFSWVDGVQIHRFAPTPKPFFRDEVSFCVGLNSFVV

GSQLPCDPEPDTDVLMSMLTDPSHITAETAARRLARGSPPSEASSSASQLSAPSLRATCT

THGKAYDVDMVDANLFMGGDVTRIESGSKVVVLDSLDPWVEERSDLEPSIPSEYMLPKKR

FPPALPAWARPDYNPPLVESWKRPDYQPATVAGCALPPPRKTPTPPPRRRRTVGLSEDST

GDALQQLATKSFGQPPPSGDSGLSTGAGAADSGSQTPPDELALSETGSISSMPPLEGELG

DPDLEPEQVEPQPPPQGGVAAPGSDSGSWSTCSEEDDSWSTCSMSYSWTGALITPCSPEE

EKLPINPLSNSLLRYHNKVYCTTTKSASLRAKKVTFDRMQVLDSYYDSVLKDIKLAASKV

TARLLTMEEACQLTPPHSARSKYGFGAKEVRSLSGRAVNHIKSVWKDLLEDSETPIPTTI

MAKNEVFCVDPTKGGKKAARLTVYPDLGVRVCEKMALYDTTQKLPQAVMGASYGFQYSPA

QRVEFLLKAWAEKKDPMGFSYDTRCFDSTVTERDTRTEESIYRACSLPEEAHTAIHSLTE

RLYVGGPMFNSKGQTCHTRRCRASGVLTTSMGNTITCYVKALAACKAAGIIAPTMLVCGD

DLVVISESQGTEEDERNLRAFTEAMTRYSAPPGDPPRPEYDLELITSCSSNVSVALGPQG

RRRYYLTRDPTTPIARAAWETVRHSPVNSWLGNIIQYAPTIWARMVLMTHFFSILMAQDT

LDQNLNFEMYGAVYSVSPLDLPAIIERLHGLDAFSLHTYTPHELTRVASALRKLGAPPLR (Human Herpesvirus 2 UL42 (DAA00746)):
MAHLPGGAAAAPLSEDAIPSPRERTEDWPPCQIVLQGAELNGILQAFAPLRTSLLDSLLV    SEQ ID NO: 14

VGDRGILVHNAIFGEQVFLPLDHSQFSRYRWGGPTAAFLSLVDQKRSLLSVFRANQYPDL

RRVELTVTGQAPFRTLVQRIWTTASDGEAVELASETLMKRELTSFAVLLPQGDPDVQLRL

TKPQLTKVVNAVGDETAKPTTFEL (Variola (Smallpox) Virus A10L (NP_042158))
MMPIKSIVTLDQLEDSEYLFRIVSTVLPHLCLDYKVCDQLKTTFVHPFDVFLNNSLGSVT SEQ ID NO: 15

KQDELQAATSKLGINYLIDTTSRELKLFTNTLNAGNIDIINTPINISSETNPIINTHSFY

-continued

DLPPFTQHLLNTRLTDTEYRARFIGGYIKPDGSDSMDVLAEKKYPDLNFDNTYLFNILYK
DVINAPIKEFKAKIVNGVLSRQDFDNLIGVRQYITAQDQPRFDNTYAIADAARHYGVNLN
TLPLPNVDLTTMPTYKHLIMYEQYFVDDYDRVPIYYNGNRVTFDDEIINFCTSMRYQSLT
PRLVEFFPDIPVNNNIVLHTRDPQNAAVNVTVGLPNMQFVDINRNNKFFINFFNLLAKEQ
RSTAIKVTKSMFWDGMDYEEYKSKNLQDMMFINSTCYVFGLYNHNNTTYCSILSDIISAE
KTPIRVCLLPRVVGGKTVTDLISETLKSISSMTIREFPKKDKSSIMHIGLSETGFMRFFQ
LLRLMADKPHETAIKEVVMAYVGIKLGDKGSPYYIRKESYQDFIYLLFASMGFKVTTRRS
IMGSNNISIISIRPRVTKQYIVTTLMKTSCSKNEAEKLITSAFDLLNFMVSVSDFRDYQS
YRQYRNYCPRYFYAGSPEGEETIICDSEPISILDRIDTRGIFSAYTINEMMDTDIFSPEN
KAFKNNLSRFIESGDITGEDIFCAMPYNILDRIITNAGTCTVSIGDMLDNITTQSDCNMT
NEITDMINASLKNTISKDNNMLVSQALDSVANHSKQKIGDLRQSSCKMALLFKNLATSIY
TIERIFNAKVGDDVKASMLEKYKVFTDISMSLYKDLIAMENLKAMLYIIRRSGCRIDDAQ
ITTDDLVKSYSLIRPKILSMINYYNEMSRGYFEHMKKNLNMTGDSVSFDDE (Vaccinia Virus Major Core Protein P4a Precursor (P16715))
MMPIKSIVTLDQLEDSEYLFRIVSTVLPHLCLDYKVCDQLKTTFTHPFDILLNNSLGSVT    SEQ ID NO: 16
KQDELQAAISKLGINYLIDTTSRELKLFNVTLNAGNIDIINTPINISSETNPIINTHSFY
DLPPFTQHLLNIRLTDTEYRARFIGGYIKPDGSDSMDVLAEKKYPDLNFDNTYLFNILYK
DVINAPIKEFKAKIVNGVLSRQDFDNLIGVRQYITIQDRPRFDDAYNIADAARHYGVNLN
TLPLPNVDLTTMPTYKHLIMFEQYFIYTYDRVDIYYNGNKMLFDDEIINFTISMRYQSLI
PRLVDFFPDIPVNNNIVLHTRDPQNAAVNVTVALPNVQFVDINRNNKFFINFFNLLAKEQ
RSTAIKVTKSMFWDGMDYEEYKSKNLQDMMFINSTCYVFGLYNHNNTTYCSILSDIISAE
KTPIRVCLLPRVVGGKTVTNLISETLKSISSMTIREFPRKDKSIMHIGLSETGFMRFFQL
LRLMADKPHETAIKEVVMAYVGIKLGDKGSPYYIRKESYQDFIYLLFASMGFKVTTRRSI
MGSNNISITSIRPRVTKQYIVATLMKTSCSKNEAEKLITSAFDLLNFMVSVSDFRDYQSY
RQYRNYCPRYFYAGSPEGEETITCDSEPISILDRIDTRGTFSAYTINEMMDTDIFSPENK
AFKNNLSRFTESGDITGEDIFCAMPYNILDRTITNAGTCTVSIGDMLDNTTQSDCNMTN
EITDMINASLKNTISKDNNNLVSQALNSVANRSKQKIGDLRQSSCKMALLFKNLATSIYT
IERIFNAKVGDDVKSAMLEKYKVFTDISMSLYKDLIAMENLKAMLYIIRRSGCRIDDAQI
TTDDLVKSYSLIRPKILSMTNYYNEMSRGYFEHMKKNLNTVITDGDSVSFDDE (Human Parainfluenza Virus Hemagglutinin-Neuraminidase
(AAA18296))
MADKGKTISSYWSTTRNDNSTVNTHINTPGRIHIWLLIATTMHTVLSFIIMILCIDLLII    SEQ ID NO: 17
KQDTCMKTNIMTVSSMNESAKTIKETITELIRQEVISRTINIQSSVQSGIPILLNKQSRD
LTQLIEKSCNRQELAQICENTIAIHHADGISPLDPHDFWRCPVGEPLLSNNPNTSLLPGP
SLLSGSTTTSGCVRLPSLSIGDAIYAYSSNLITQGCADIGKSYQVLQLGYISLNSDMYPD
LNPVISHTYDINDNRKSCSVIAAGTRGYQLCSLPTVNETTDYSSEGIEDLVFDILDLKGK
TKSHRYKNEDITFDHPFSAMYPSVGSGIKIENTLVFLGYGGLTTPLQGDTKCVINRCPNI
NQSVCNDALKITWLKKRQVVNVLIRINNYLSDRPKIVVETIPITQNYLGAEGRLLKLGKK
IYITTRSSGWHSNLQIGSLDINNPMTINWAPHKVLSRPGNPDCNWFNKCPRECISGVYTD
AYPLSPDAVNVATTTLYANTSRVNPTIMYSSTSKITNNLRLKNGQLEAAYTTTSCTTHFG
KGYCFHIVEINQTSLDTLQPMLFKTSIPKVCKVTS

TABLE 2

YPXL Motif Containing Peptides from Equine Infectious Virus Gag p9 (Gen Bank Accession No. AAA43011)

| | |
|---|---|
| SEQ ID NO: 18 | YPDLSEI |
| SEQ ID NO: 19 | YPDLSEIK |
| SEQ ID NO: 20 | YPDLSEIKK |
| SEQ ID NO: 21 | YPDLSEIKKE |
| SEQ ID NO: 22 | YPDLSEIKKEY |
| SEQ ID NO: 23 | YPDLSEIKKEYN |
| SEQ ID NO: 24 | YPDLSEIKKEYNV |
| SEQ ID NO: 25 | YPDLSEIKKEYNVK |
| SEQ ID NO: 26 | YPDLSEIKKEYNVKE |
| SEQ ID NO: 27 | YPDLSEIKKEYNVKEK |
| SEQ ID NO: 28 | YPDLSEIKKEYNVKEKD |
| SEQ ID NO: 29 | YPDLSEIKKEYNVKEKDQ |
| SEQ ID NO: 30 | YPDLSEIKKEYNVKEKDQV |
| SEQ ID NO: 31 | YPDLSEIKKEYNVKEKDQVE |
| SEQ ID NO: 32 | LYPDLSE |
| SEQ ID NO: 33 | LYPDLSEI |
| SEQ ID NO: 34 | LYPDLSEIK |
| SEQ ID NO: 35 | LYPDLSEIKK |
| SEQ ID NO: 36 | LYPDLSEIKKE |
| SEQ ID NO: 37 | LYPDLSEIKKEY |
| SEQ ID NO: 38 | LYPDLSEIKKEYN |
| SEQ ID NO: 39 | LYPDLSEIKKEYNV |
| SEQ ID NO: 40 | LYPDLSEIKKEYNVK |
| SEQ ID NO: 41 | LYPDLSEIKKEYNVKE |
| SEQ ID NO: 42 | LYPDLSEIKKEYNVKEK |
| SEQ ID NO: 43 | LYPDLSEIKKEYNVKEKD |
| SEQ ID NO: 44 | LYPDLSEIKKEYNVKEKDQ |
| SEQ ID NO: 45 | LYPDLSEIKKEYNVKEKDQV |
| SEQ ID NO: 46 | NLYPDLS |
| SEQ ID NO: 47 | NLYPDLSE |
| SEQ ID NO: 48 | NLYPDLSEI |
| SEQ ID NO: 49 | NLYPDLSEIK |
| SEQ ID NO: 50 | NLYPDLSEIKK |
| SEQ ID NO: 51 | NLYPDLSEIKKE |
| SEQ ID NO: 52 | NLYPDLSEIKKEY |
| SEQ ID NO: 53 | NLYPDLSEIKKEYN |
| SEQ ID NO: 54 | NLYPDLSEIKKEYNV |
| SEQ ID NO: 55 | NLYPDLSEIKKEYNVK |
| SEQ ID NO: 56 | NLYPDLSEIKKEYNVKE |
| SEQ ID NO: 57 | NLYPDLSEIKKEYNVKEK |
| SEQ ID NO: 58 | NLYPDLSEIKKEYNVKEKD |
| SEQ ID NO: 59 | NLYPDLSEIKKEYNVKEKDQ |
| SEQ ID NO: 60 | QNLYPDL |
| SEQ ID NO: 61 | QNLYPDLS |
| SEQ ID NO: 62 | QNLYPDLSE |
| SEQ ID NO: 63 | QNLYPDLSEI |
| SEQ ID NO: 64 | QNLYPDLSEIK |
| SEQ ID NO: 65 | QNLYPDLSEIKK |
| SEQ ID NO: 66 | QNLYPDLSEIKKE |
| SEQ ID NO: 67 | QNLYPDLSEIKKEY |
| SEQ ID NO: 68 | QNLYPDLSEIKKEYN |
| SEQ ID NO: 69 | QNLYPDLSEIKKEYNV |
| SEQ ID NO: 70 | QNLYPDLSEIKKEYNVK |
| SEQ ID NO: 71 | QNLYPDLSEIKKEYNVKE |
| SEQ ID NO: 72 | QNLYPDLSEIKKEYNVKEK |
| SEQ ID NO: 73 | QNLYPDLSEIKKEYNVKEKD |
| SEQ ID NO: 74 | TQNLYPDL |
| SEQ ID NO: 75 | TQNLYPDLS |
| SEQ ID NO: 76 | TQNLYPDLSE |
| SEQ ID NO: 77 | TQNLYPDLSEI |
| SEQ ID NO: 78 | TQNLYPDLSEIK |
| SEQ ID NO: 79 | TQNLYPDLSEIKK |
| SEQ ID NO: 80 | TQNLYPDLSEIKKE |
| SEQ ID NO: 81 | TQNLYPDLSEIKKEY |
| SEQ ID NO: 82 | TQNLYPDLSEIKKEYN |
| SEQ ID NO: 83 | TQNLYPDLSEIKKEYNV |
| SEQ ID NO: 84 | TQNLYPDLSEIKKEYNVK |
| SEQ ID NO: 85 | TQNLYPDLSEIKKEYNVKE |
| SEQ ID NO: 86 | TQNLYPDLSEIKKEYNVKEK |
| SEQ ID NO: 87 | QTQNLYPDL |
| SEQ ID NO: 88 | QTQNLYPDLS |
| SEQ ID NO: 89 | QTQNLYPDLSE |
| SEQ ID NO: 90 | QTQNLYPDLSEI |
| SEQ ID NO: 91 | QTQNLYPDLSEIK |
| SEQ ID NO: 92 | QTQNLYPDLSEIKK |

TABLE 2-continued

YPXL Motif Containing Peptides from Equine Infectious Virus Gag p9
(Gen Bank Accession No. AAA43011)

| | |
|---|---|
| SEQ ID NO: 93 | QTQNLYPDLSELKKE |
| SEQ ID NO: 94 | QTQNLYPDLSEIKKEY |
| SEQ ID NO: 95 | QTQNLYPDLSELKKEYN |
| SEQ ID NO: 96 | QTQNLYPDLSEIKKEYNV |
| SEQ ID NO: 97 | QTQNLYPDLSEIKKEYNVK |
| SEQ ID NO: 98 | QTQNLYPDLSEIKKEYNVKE |
| SEQ ID NO: 99 | PQTQNLYPDL |
| SEQ ID NO: 100 | PQTQNLYPDLS |
| SEQ ID NO: 101 | PQTQNLYPDLSE |
| SEQ ID NO: 102 | PQTQNLYPDLSEI |
| SEQ ID NO: 103 | PQTQNLYPDLSEIK |
| SEQ ID NO: 104 | PQTQNLYPDLSEIKK |
| SEQ ID NO: 105 | PQTQNLYPDLSEIKKE |
| SEQ ID NO: 106 | PQTQNLYPDLSEIKKEY |
| SEQ ID NO: 107 | PQTQNLYPDLSEIKKEYN |
| SEQ ID NO: 108 | PQTQNLYPDLSEIKKEYNV |
| SEQ ID NO: 109 | PQTQNLYPDLSEIKKEYNVK |
| SEQ ID NO: 110 | TPQTQNLYPDL |
| SEQ ID NO: 111 | TPQTQNLYPDLS |
| SEQ ID NO: 112 | TPQTQNLYPDLSE |
| SEQ ID NO: 113 | TPQTQNLYPDLSEI |
| SEQ ID NO: 114 | TPQTQNLYPDLSEIK |
| SEQ ID NO: 115 | TPQTQNLYPDLSEIKK |
| SEQ ID NO: 116 | TPQTQNLYPDLSEIKKE |
| SEQ ID NO: 117 | TPQTQNLYPDLSEIKKEY |
| SEQ ID NO: 118 | TPQTQNLYPDLSEIKKEYN |
| SEQ ID NO: 119 | TPQTQNLYPDLSEIKKEYNV |
| SEQ ID NO: 120 | ETPQTQNLYPDL |
| SEQ ID NO: 121 | ETPQTQNLYPDLS |
| SEQ ID NO: 122 | ETPQTQNLYPDLSE |
| SEQ ID NO: 123 | ETPQTQNLYPDLSEI |
| SEQ ID NO: 124 | ETPQTQNLYPDLSEIK |
| SEQ ID NO: 125 | ETPQTQNLYPDLSEIKK |
| SEQ ID NO: 126 | ETPQTQNLYPDLSEIKKE |
| SEQ ID NO: 127 | ETPQTQNLYPDLSEIKKEY |
| SEQ ID NO: 128 | ETPQTQNLYPDLSEIKKEYN |
| SEQ ID NO: 129 | QETPQTQNLYPDL |
| SEQ ID NO: 130 | QETPQTQNLYPDLS |
| SEQ ID NO: 131 | QETPQTQNLYPDLSE |
| SEQ ID NO: 132 | QETPQTQNLYPDLSEI |
| SEQ ID NO: 133 | QETPQTQNLYPDLSEIK |
| SEQ ID NO: 134 | QETPQTQNLYPDLSEIKK |
| SEQ ID NO: 135 | QETPQTQNLYPDLSEIKKE |
| SEQ ID NO: 136 | QETPQTQNLYPDLSEIKKEY |
| SEQ ID NO: 137 | VQETPQTQNLYPDL |
| SEQ ID NO: 138 | VQETPQTQNLYPDLS |
| SEQ ID NO: 139 | VQETPQTQNLYPDLSE |
| SEQ ID NO: 140 | VQETPQTQNLYPDLSEI |
| SEQ ID NO: 141 | VQETPQTQNLYPDLSEIK |
| SEQ ID NO: 142 | VQETPQTQNLYPDLSEIKK |
| SEQ ID NO: 143 | VQETPQTQNLYPDLSEIKKE |
| SEQ ID NO: 144 | VVQETPQTQNLYPDL |
| SEQ ID NO: 145 | VVQETPQTQNLYPDLS |
| SEQ ID NO: 146 | VVQETPQTQNLYPDLSE |
| SEQ ID NO: 147 | VVQETPQTQNLYPDLSEI |
| SEQ ID NO: 148 | VVQETPQTQNLYPDLSEIK |
| SEQ ID NO: 149 | VVQETPQTQNLYPDLSEIKK |
| SEQ ID NO: 150 | SVVQETPQTQNLYPDL |
| SEQ ID NO: 151 | SVVQETPQTQNLYPDLS |
| SEQ ID NO: 152 | SVVQETPQTQNLYPDLSE |
| SEQ ID NO: 153 | SVVQETPQTQNLYPDLSEI |
| SEQ ID NO: 154 | SVVQETPQTQNLYPDLSEIK |
| SEQ ID NO: 155 | KSVVQETPQTQNLYPDL |
| SEQ ID NO: 156 | KSVVQETPQTQNLYPDLS |
| SEQ ID NO: 157 | KSVVQETPQTQNLYPDLSE |
| SEQ ID NO: 158 | KSVVQETPQTQNLYPDLSEI |
| SEQ ID NO: 159 | NKSVVQETPQTQNLYPDL |
| SEQ ID NO: 160 | NKSVVQETPQTQNLYPDLS |
| SEQ ID NO: 161 | NKSVVQETPQTQNLYPDLSE |
| SEQ ID NO: 162 | HNKSVVQETPQTQNLYPDL |
| SEQ ID NO: 163 | HNKSVVQETPQTQNLYPDLS |
| SEQ ID NO: 164 | QHNKSVVQETPQTQNLYPDL |

TABLE 3

YPXL Motif Containing Peptides from Hepatitis C
Virus Polyprotein
(GenBank Accession No. AAF01178)

| | |
|---|---|
| SEQ ID NO: 165 | YPDLGVRV |
| SEQ ID NO: 166 | YPDLGVRVC |
| SEQ ID NO: 167 | YPDLGVRVCE |
| SEQ ID NO: 168 | YPDLGVRVCEK |
| SEQ ID NO: 169 | YPDLGVRVCEKM |
| SEQ ID NO: 170 | YPDLGVRVCEKMA |
| SEQ ID NO: 171 | YPDLGVRVCEKMAI |
| SEQ ID NO: 172 | YPDLGVRVCEKMAIY |
| SEQ ID NO: 173 | YPDLGVRVCEKMAIYD |
| SEQ ID NO: 174 | YPDLGVRVCEKMAIYDI |
| SEQ ID NO: 175 | YPDLGVRVCEKMAIYDIT |
| SEQ ID NO: 176 | YPDLGVRVCEKMALYDITQ |
| SEQ ID NO: 177 | YPDLGVRVCEKMALYDITQK |
| SEQ ID NO: 178 | VYPDLGVR |
| SEQ ID NO: 179 | VYPDLGVRV |
| SEQ ID NO: 180 | VYPDLGVRVC |
| SEQ ID NO: 181 | VYPDLGVRVCE |
| SEQ ID NO: 182 | VYPDLGVRVCEK |
| SEQ ID NO: 183 | VYPDLOVRVCEKM |
| SEQ ID NO: 184 | VYPDLGVRVCEKMA |
| SEQ ID NO: 185 | VYPDLGVRVCEKMAL |
| SEQ ID NO: 186 | VYPDLGVRVCEKMALY |
| SEQ ID NO: 187 | VYPDLGVRVCEKMALYD |
| SEQ ID NO: 188 | VYPDLGVRVCEKMALYDI |
| SEQ ID NO: 189 | VYPDLGVRVCEKMAIYDIT |
| SEQ ID NO: 190 | VYPDLGVRVCEKMALYDITQ |
| SEQ ID NO: 191 | IVYPDLGV |
| SEQ ID NO: 192 | IVYPDLGVR |
| SEQ ID NO: 193 | IVYPDLGVRV |
| SEQ ID NO: 194 | IVYPDLGVRVC |
| SEQ ID NO: 195 | IVYPDLGVRVCE |
| SEQ ID NO: 196 | IVYPDLGVRVCEK |
| SEQ ID NO: 197 | IVYPDLGVRVCEKM |
| SEQ ID NO: 198 | IVYPDLGVRVCEKMA |
| SEQ ID NO: 199 | IVYPDLGVRVCEKMAL |
| SEQ ID NO: 200 | IVYPDLGVRVCEKMALY |
| SEQ ID NO: 201 | IVYPDLGVRVCEKMALYD |
| SEQ ID NO: 202 | IVYPDLGVRVCEKMALYDI |
| SEQ ID NO: 203 | IVYPDLGVRVCEKMALYDIT |
| SEQ ID NO: 204 | LIVYPDLG |
| SEQ ID NO: 205 | LIVYPDLGV |
| SEQ ID NO: 206 | LIVYPDLGVR |
| SEQ ID NO: 207 | LIVYPDLGVRV |
| SEQ ID NO: 208 | LIVYPDLGVRVC |
| SEQ ID NO: 209 | LIVYPDLGVRVCE |
| SEQ ID NO: 210 | LIVYPDLGVRVCEK |
| SEQ ID NO: 211 | LIVYPDLGVRVCEKM |
| SEQ ID NO: 212 | LIVYPDLGVRVCEKIMA |
| SEQ ID NO: 213 | LIVYPDLGVRVCEKMAL |
| SEQ ID NO: 214 | LIVYPDLGVRVCEKMALY |
| SEQ ID NO: 215 | LIVYPDLGVRVCEKMALYD |
| SEQ ID NO: 216 | LIVYPDLOVRVCEKMALYDI |
| SEQ ID NO: 217 | RLIVYPDL |
| SEQ ID NO: 218 | RLIVYPDLG |
| SEQ ID NO: 219 | RLIVYPDLGV |
| SEQ ID NO: 220 | RLIVYPDLGVR |
| SEQ ID NO: 221 | RLIVYPDLGVRV |
| SEQ ID NO: 222 | RLIVYPDLGVRVC |
| SEQ ID NO: 223 | RLIVYPDLGVRVCE |
| SEQ ID NO: 224 | RLIVYPDLGVRVCEK |
| SEQ ID NO: 225 | RLIVYPDLGVRVCEKM |
| SEQ ID NO: 226 | RLIVYPDLGVRVCEKMA |
| SEQ ID NO: 227 | RLIVYPDLGVRVCEKMAL |
| SEQ ID NO: 228 | RLIVYPDLGVRVCEKMALY |
| SEQ ID NO: 229 | RLIVYPDLGVRVCEKMALYD |
| SEQ ID NO: 230 | ARLIVYPDL |
| SEQ ID NO: 231 | ARLIVYPDLG |
| SEQ ID NO: 232 | ARLIVYPDLGV |
| SEQ ID NO: 233 | ARLIVYPDLGVR |
| SEQ ID NO: 234 | ARLIVYPDLGVRV |
| SEQ ID NO: 235 | ARLIVYPDLGVRVC |
| SEQ ID NO: 236 | ARLIVYPDLGVRVCE |
| SEQ ID NO: 237 | ARLIVYPDLGVRVCEK |
| SEQ ID NO: 238 | ARLIVYPDLGVRVCEKM |
| SEQ ID NO: 239 | ARLIVYPDLGVRVCEKMA |

TABLE 3-continued

YPXL Motif Containing Peptides from Hepatitis C Virus Polyprotein
(GenBank Accession No. AAF01178)

| | |
|---|---|
| SEQ ID NO: 240 | ARLIVYPDLGVRVCEKMAL |
| SEQ ID NO: 241 | ARLIVYPDLGVRVCEKMALY |
| SEQ ID NO: 242 | AARLIVYPDL |
| SEQ ID NO: 243 | AARLIVYPDLG |
| SEQ ID NO: 244 | AARLIVYPDLGV |
| SEQ ID NO: 245 | AARLIVYPDLGVR |
| SEQ ID NO: 246 | AARLIVYPDLGVRV |
| SEQ ID NO: 247 | AARLIVYPDLGVRVC |
| SEQ ID NO: 248 | AARLIVYPDLGVRVCE |
| SEQ ID NO: 249 | AARLIVYPDLGVRVCEK |
| SEQ ID NO: 250 | AARLIVYPDLGVRVCEKM |
| SEQ ID NO: 251 | AARLIVYPDLGVRVCEKMA |
| SEQ ID NO: 252 | AARLIVYPDLGVRVCEKMAL |
| SEQ ID NO: 253 | KAARLIVYPDL |
| SEQ ID NO: 254 | KAARLIVYPDLG |
| SEQ ID NO: 255 | KAARLIVYPDLGV |
| SEQ ID NO: 256 | KAARLIVYPDLGVR |
| SEQ ID NO: 257 | KAARLIVYPDLGVRV |
| SEQ ID NO: 258 | KAARLIVYPDLGVRVC |
| SEQ ID NO: 259 | KAARLIVYPDLGVRVCE |
| SEQ ID NO: 260 | KAARLIVYPDLGVRVCEK |
| SEQ ID NO: 261 | KAARLIVYPDLGVRVCEKM |
| SEQ ID NO: 262 | KAARLIVYPDLGVRVCEKMA |
| SEQ ID NO: 263 | KKAARLIVYPDL |
| SEQ ID NO: 264 | KKAARLIVYPDLG |
| SEQ ID NO: 265 | KKAARLIVYPDLGV |
| SEQ ID NO: 266 | KKAARLIVYPDLGVR |
| SEQ ID NO: 267 | KKAARLIVYPDLGVRV |
| SEQ ID NO: 268 | KKAARLIVYPDLGVRVC |
| SEQ ID NO: 269 | KKAARLIVYPDLGVRVCE |
| SEQ ID NO: 270 | KKAARLIVYPDLGVRVCEK |
| SEQ ID NO: 271 | KKAARLIVYPDLGVRVCEKM |
| SEQ ID NO: 272 | GKKAARLIVYPDL |
| SEQ ID NO: 273 | GKKAARLIVYPDLG |
| SEQ ID NO: 274 | GKKAARLIVYPDLGV |
| SEQ ID NO: 275 | GKKAARLIVYPDLGVR |
| SEQ ID NO: 276 | GKKAARLIVYPDLGVRV |
| SEQ ID NO: 277 | GKKAARLIVYPDLGVRVC |
| SEQ ID NO: 278 | GKKAARLIVYPDLGVRVCE |
| SEQ ID NO: 279 | GKKAARLIVYPDLGVRVCEK |
| SEQ ID NO: 280 | GGKKAARLIVYPDL |
| SEQ ID NO: 281 | GGKKAARLIVYPDLO |
| SEQ ID NO: 282 | GGKKAARLIVYPDLGV |
| SEQ ID NO: 283 | GGKKAARLIVYPDLGVR |
| SEQ ID NO: 284 | GGKKAARLIVYPDLGVRV |
| SEQ ID NO: 285 | GGKKAARLIVYPDLGVRVC |
| SEQ ID NO: 286 | GGKKAARLIVYPDLGVRVCE |
| SEQ ID NO: 287 | KGGKKAARLIVYPDL |
| SEQ ID NO: 288 | KGGKKAARLIVYPDLG |
| SEQ ID NO: 289 | KGGKKAARLIVYPDLGV |
| SEQ ID NO: 290 | KGGKKAARLIVYPDLGVR |
| SEQ ID NO: 291 | KGGKKAARLIVYPDLGVRV |
| SEQ ID NO: 292 | KGGKKAARLIVYPDLGVRVC |
| SEQ ID NO: 293 | TKGGKKAARLIVYPDL |
| SEQ ID NO: 294 | TKGGKKAARLIVYPDLG |
| SEQ ID NO: 295 | TKGGKKAARLIVYPDLGV |
| SEQ ID NO: 296 | TKGGKKAARLIVYPDLGVR |
| SEQ ID NO: 297 | TKGGKKAARLIVYPDLGVRV |
| SEQ ID NO: 298 | PTKGGKKAARLIVYPDL |
| SEQ ID NO: 299 | PTKGGKKAARLIVYPDLG |
| SEQ ID NO: 300 | PTKGGKKAARLIVYPDLGV |
| SEQ ID NO: 301 | PTKGGKKAARLIVYPDLGVR |
| SEQ ID NO: 302 | DPTKGGKKAARLIVYPDL |
| SEQ ID NO: 303 | DPTKGGKKAARLIVYPDLG |
| SEQ ID NO: 304 | DPTKGGKKAARLIVYPDLGV |
| SEQ ID NO: 305 | VDPTKGGKKAARLIVYPDL |
| SEQ ID NO: 306 | VDPTKGGKKAARLIVYPDLG |
| SEQ ID NO: 307 | CVDPTKGGKKAARLIVYPDL |

TABLE 4

YPXL Motif Containing Peptides from Human Herpes Virus 2 UL42
(GenBank Accession No. BAA00746)

| | |
|---|---|
| SEQ ID NO: 308 | YPDLRRVE |
| SEQ ID NO: 309 | YPDLRRVEL |
| SEQ ID NO: 310 | YPDLRRVELT |

TABLE 4-continued

YPXL Motif Containing Peptides from Human Herpes Virus 2 UL42 (GenBank Accession No. BAA00746)

| | |
|---|---|
| SEQ ID NO: 311 | YPDLRRVELTV |
| SEQ ID NO: 312 | YPDLRRVELTVT |
| SEQ ID NO: 313 | YPDLRRVELTVTG |
| SEQ ID NO: 314 | YPDLRRVELTVTGQ |
| SEQ ID NO: 315 | YPDLRRVELTVTGQA |
| SEQ ID NO: 316 | YPDLRRVELTVTGQAP |
| SEQ ID NO: 317 | YPDLRRVELTVTGQAPF |
| SEQ ID NO: 318 | YPDLRRVELTVTGQAPFR |
| SEQ ID NO: 319 | YPDLRRVELTVTGQAPFRT |
| SEQ ID NO: 320 | YPDLRRVELTVTGQAPFRTL |
| SEQ ID NO: 321 | QYPDLRRV |
| SEQ ID NO: 322 | QYPDLRRVE |
| SEQ ID NO: 323 | QYPDLRRVEL |
| SEQ ID NO: 324 | QYPDLRRVELT |
| SEQ ID NO: 325 | QYPDLRRVELTV |
| SEQ ID NO: 326 | QYPDLRRVELTVT |
| SEQ ID NO: 327 | QYPDLRRVELTVTG |
| SEQ ID NO: 328 | QYPDLRRVELTVTGQ |
| SEQ ID NO: 329 | QYPDLRRVELTVTGQA |
| SEQ ID NO: 330 | QYPDLRRVELTVTGQAP |
| SEQ ID NO: 331 | QYPDLRRVELTVTGQAPF |
| SEQ ID NO: 332 | QYPDLRRVELTVTGQAPFR |
| SEQ ID NO: 333 | QYPDLRRVELTVTGQAPFRT |
| SEQ ID NO: 334 | NQYPDLRR |
| SEQ ID NO: 335 | NQYPDLRRV |
| SEQ ID NO: 336 | NQYPDLRRVE |
| SEQ ID NO: 337 | NQYPDLRRVEL |
| SEQ ID NO: 338 | NQYPDLRRVELT |
| SEQ ID NO: 339 | NQYPDLRRVELTV |
| SEQ ID NO: 340 | NQYPDLRRVELTVT |
| SEQ ID NO: 341 | NQYPDLRRVELTVTG |
| SEQ ID NO: 342 | NQYPDLRRVELTVTGQ |
| SEQ ID NO: 343 | NQYPDLRRVELTVTGQA |
| SEQ ID NO: 344 | NQYPDLRRVELTVTGQAP |
| SEQ ID NO: 345 | NQYPDLRRVELTVTGQAPF |
| SEQ ID NO: 346 | NQYPDLRRVELTVTGQAPFR |
| SEQ ID NO: 347 | ANQYPDLR |
| SEQ ID NO: 348 | ANQYPDLRR |
| SEQ ID NO: 349 | ANQYPDLRRV |
| SEQ ID NO: 350 | ANQYPDLRRVE |
| SEQ ID NO: 351 | ANQYPDLRRVEL |
| SEQ ID NO: 352 | ANQYPDLRRVELT |
| SEQ ID NO: 353 | ANQYPDLRRVELTV |
| SEQ ID NO: 354 | ANQYPDLRRVELTVT |
| SEQ ID NO: 355 | ANQYPDLRRVELTVTG |
| SEQ ID NO: 356 | ANQYPDLRRVELTVTGQ |
| SEQ ID NO: 357 | ANQYPDLRRVELTVTGQA |
| SEQ ID NO: 358 | ANQYPDLRRVELTVTGQAP |
| SEQ ID NO: 359 | ANQYPDLRRVELTVTGQAPF |
| SEQ ID NO: 360 | RANQYPDL |
| SEQ ID NO: 361 | RANQYPDLR |
| SEQ ID NO: 362 | RANQYPDLRR |
| SEQ ID NO: 363 | RANQYPDLRRV |
| SEQ ID NO: 364 | RANQYPDLRRVE |
| SEQ ID NO: 365 | RANQYPDLRRVEL |
| SEQ ID NO: 366 | RANQYPDLRRVELT |
| SEQ ID NO: 367 | RANQYPDLRRVELTV |
| SEQ ID NO: 368 | RANQYPDLRRVELTVT |
| SEQ ID NO: 369 | RANQYPDLRRVELTVTG |
| SEQ ID NO: 370 | RANQYPDLRRVELTVTGQ |
| SEQ ID NO: 371 | RANQYPDLRRVELTVTGQA |
| SEQ ID NO: 372 | RANQYPDLRRVELTVTGQAP |
| SEQ ID NO: 373 | FRANQYPDL |
| SEQ ID NO: 374 | FRANQYPDLR |
| SEQ ID NO: 375 | FRANQYPDLRR |
| SEQ ID NO: 376 | FRANQYPDLRRV |
| SEQ ID NO: 377 | FRANQYPDLRRVE |
| SEQ ID NO: 378 | FRANQYPDLRRVEL |
| SEQ ID NO: 379 | FRANQYPDLRRVELT |
| SEQ ID NO: 380 | FRANQYPDLRRVELTV |
| SEQ ID NO: 381 | FRANQYPDLRRVELTVT |
| SEQ ID NO: 382 | FRANQYPDLRRVELTVTG |
| SEQ ID NO: 383 | FRANQYPDLRRVELTVTGQ |
| SEQ ID NO: 384 | FRANQYPDLRRVELTVTGQA |
| SEQ ID NO: 385 | VFRANQYPDL |

TABLE 4-continued

YPXL Motif Containing Peptides from Human Herpes Virus 2 UL42
(GenBank Accession No. BAA00746)

| | |
|---|---|
| SEQ ID NO: 386 | VFRANQYPDLR |
| SEQ ID NO: 387 | VFRANQYPDLRR |
| SEQ ID NO: 388 | VFRANQYPDLRRV |
| SEQ ID NO: 389 | VFRANQYPDLRRVE |
| SEQ ID NO: 390 | VFRANQYPDLRRVEL |
| SEQ ID NO: 391 | VFRANQYPDLRRVELT |
| SEQ ID NO: 392 | VFRANQYPDLRRVELTV |
| SEQ ID NO: 393 | VFRANQYPDLRRVELTVT |
| SEQ ID NO: 394 | VFRANQYPDLRRVELTVTG |
| SEQ ID NO: 395 | VFRANQYPDLRRVELTVTGQ |
| SEQ ID NO: 396 | SVFRANQYPDL |
| SEQ ID NO: 397 | SVFRANQYPDLR |
| SEQ ID NO: 398 | SVFRANQYPDLRR |
| SEQ ID NO: 399 | SVFRANQYPDLRRV |
| SEQ ID NO: 400 | SVFRANQYPDLRRVE |
| SEQ ID NO: 401 | SVFRANQYPDLRRVEL |
| SEQ ID NO: 402 | SVFRANQYPDLRRVELT |
| SEQ ID NO: 403 | SVFRANQYPDLRRVELTV |
| SEQ ID NO: 404 | SVFRANQYPDLRRVELTVT |
| SEQ ID NO: 405 | SVFRANQYPDLRRVELTVTG |
| SEQ ID NO: 406 | LSVFRANQYPDL |
| SEQ ID NO: 407 | LSVFRANQYPDLR |
| SEQ ID NO: 408 | LSVFRANQYPDLRR |
| SEQ ID NO: 409 | LSVFRANQYPDLRRV |
| SEQ ID NO: 410 | LSVFRANQYPDLRRVE |
| SEQ ID NO: 411 | LSVFRANQYPDLRRVEL |
| SEQ ID NO: 412 | LSVFRANQYPDLRRVELT |
| SEQ ID NO: 413 | LSVFRANQYPDLRRVELTV |
| SEQ ID NO: 414 | LSVFRANQYPDLRRVELTVT |
| SEQ ID NO: 415 | LLSVFRANQYPDL |
| SEQ ID NO: 416 | LLSVFRANQYPDLR |
| SEQ ID NO: 417 | LLSVFRANQYPDLRR |
| SEQ ID NO: 418 | LLSVFRANQYPDLRRV |
| SEQ ID NO: 419 | LLSVFRANQYPDLRRVE |
| SEQ ID NO: 420 | LLSVFRANQYPDLRRVEL |
| SEQ ID NO: 421 | LLSVFRANQYPDLRRVELT |
| SEQ ID NO: 422 | LLSVFRANQYPDLRRVELTV |
| SEQ ID NO: 423 | SLLSVFRANQYPDL |
| SEQ ID NO: 424 | SLLSVFRANQYPDLR |
| SEQ ID NO: 425 | SLLSVFRANQYPDLRR |
| SEQ ID NO: 426 | SLLSVFRANQYPDLRRV |
| SEQ ID NO: 427 | SLLSVFRANQYPDLRRVE |
| SEQ ID NO: 428 | SLLSVFRANQYPDLRRVEL |
| SEQ ID NO: 429 | SLLSVFRANQYPDLRRVELT |
| SEQ ID NO: 430 | RSLLSVFRANQYPDL |
| SEQ ID NO: 431 | RSLLSVFRANQYPDLR |
| SEQ ID NO: 432 | RSLLSVFRANQYPDLRR |
| SEQ ID NO: 433 | RSLLSVFRANQYPDLRRV |
| SEQ ID NO: 434 | RSLLSVFRANQYPDLRRVE |
| SEQ ID NO: 435 | RSLLSVFRANQYPDLRRVEL |
| SEQ ID NO: 436 | KRSLLSVFRANQYPDL |
| SEQ ID NO: 437 | KRSLLSVFRANQYPDLR |
| SEQ ID NO: 438 | KRSLLSVFRANQYPDLRR |
| SEQ ID NO: 439 | KRSLLSVFRANQYPDLRRV |
| SEQ ID NO: 440 | KRSLLSVFRANQYPDLRRVE |
| SEQ ID NO: 441 | QKRSLLSVFRANQYPDL |
| SEQ ID NO: 442 | QKRSLLSVFRANQYPDLR |
| SEQ ID NO: 443 | QKRSLLSVFRANQYPDLRR |
| SEQ ID NO: 444 | QKRSLLSVFRANQYPDLRRV |
| SEQ ID NO: 445 | DQKRSLLSVFRANQYPDL |
| SEQ ID NO: 446 | DQKRSLLSVFRANQYPDLR |
| SEQ ID NO: 447 | DQKRSLLSVFRANQYPDLRR |
| SEQ ID NO: 448 | VDQKRSLLSVFRANQYPDL |
| SEQ ID NO: 449 | VDQKRSLLSVFRANQYPDLR |
| SEQ ID NO: 450 | LVDQKRSLLSVFRANQYPDL |

TABLE 5

YPXL Motif Containing Peptides from Variola (Smallpox) Virus A10L
(GenBank Accession No. NP_042158) and
Vaccinia Virus Major Core Protein P4a Precursor
(Virion Core Protein P4a)
(GenBank Accession No. P16715)

| | |
|---|---|
| SEQ ID NO: 451 | YPDLNFDN |
| SEQ ID NO: 452 | YPDLNFDNT |
| SEQ ID NO: 453 | YPDLNFDNTY |
| SEQ ID NO: 454 | YPDLNFDNTYL |

TABLE 5-continued

YPXL Motif Containing Peptides from Variola
(Smallpox) Virus A10L
(GenBank Accession No. NP_042158) and
Vaccinia Virus Major Core Protein P4a Precursor
(Virion Core Protein P4a)
(GenBank Accession No. P16715)

| | |
|---|---|
| SEQ ID NO: 455 | YPDLNFDNTYLF |
| SEQ ID NO: 456 | YPDLNFDNTYLFN |
| SEQ ID NO: 457 | YPDLNFDNTYLFNI |
| SEQ ID NO: 458 | YPDLNFDNTYLFNIL |
| SEQ ID NO: 459 | YPDLNFDNTYLFNILY |
| SEQ ID NO: 460 | YPDLNEDNTYLFNILYK |
| SEQ ID NO: 461 | YPDLNFDNTYLFNILYKD |
| SEQ ID NO: 462 | YPDLNIFDNTYLFNILYKDV |
| SEQ ID NO: 463 | YPDLNFDNTYLFNILYKDVI |
| SEQ ID NO: 464 | KYPDLNFD |
| SEQ ID NO: 465 | KYPDLNFDN |
| SEQ ID NO: 466 | KYPDLNFDNT |
| SEQ ID NO: 467 | KYPDLNFDNTY |
| SEQ ID NO: 468 | KYPDLNFDNTYL |
| SEQ ID NO: 469 | KYPDLNFDNTYLF |
| SEQ ID NO: 470 | KYPDLNFDNTYLFN |
| SEQ ID NO: 471 | KYPDLNFDNTYLFNI |
| SEQ ID NO: 472 | KYPDLNFDNTYLFNIL |
| SEQ ID NO: 473 | KYPDLNFDNTYLFNILY |
| SEQ ID NO: 474 | KYPDLNFDNTYLFNILYK |
| SEQ ID NO: 475 | KYPDLNFDNTYLFNILYKD |
| SEQ ID NO: 476 | KYPDLNFDNTYLFNILYKDV |
| SEQ ID NO: 477 | KKYPDLNF |
| SEQ ID NO: 478 | KKYPDLNFD |
| SEQ ID NO: 479 | KKYPDLNFDN |
| SEQ ID NO: 480 | KKYPDLNFDNT |
| SEQ ID NO: 481 | KKYPDLNFDNTY |
| SEQ ID NO: 482 | KKYPDLNFDNTYL |
| SEQ ID NO: 483 | KKYPDLNFDNTYLF |
| SEQ ID NO: 484 | KKYPDLNFDNTYLFN |
| SEQ ID NO: 485 | KKYPDLNFDNTYLFNI |
| SEQ ID NO: 486 | KKYPDLNEDNTYLFNJL |
| SEQ ID NO: 487 | KKYPDLNFDNTYLFNILY |
| SEQ ID NO: 488 | KKYPDLNFDNTYLFNWYK |
| SEQ ID NO: 489 | KKYPDLNFDNTYLFNILYKD |
| SEQ ID NO: 490 | EKYPDLN |
| SEQ ID NO: 491 | EKKYPDLNF |
| SEQ ID NO: 492 | EKKYPDLNFD |
| SEQ ID NO: 493 | EKKYPDLEDN |
| SEQ ID NO: 494 | EKKYPDLNFDNT |
| SEQ ID NO: 495 | EKKYPDLNFDNTY |
| SEQ ID NO: 496 | EKKYPDLNFDNTYL |
| SEQ ID NO: 497 | EKKYPDLNEDNTYLF |
| SEQ ID NO: 498 | EKKYPDLNFDNTYLFN |
| SEQ ID NO: 499 | EKKYPDLNFDNTYLFNI |
| SEQ ID NO: 500 | EKKYPDLNFDNTYLFNIL |
| SEQ ID NO: 501 | EKKYPDLNFDNTYLFNILY |
| SEQ ID NO: 502 | EKKYPDLNFDNTYLFNILYK |
| SEQ ID NO: 503 | AEKKYPDL |
| SEQ ID NO: 504 | AEKKYPDLN |
| SEQ ID NO: 505 | AEKKYPDLNF |
| SEQ ID NO: 506 | AEKKYPDLNFD |
| SEQ ID NO: 507 | AEKKYPDLNFDN |
| SEQ ID NO: 508 | AEKKYPDLNFDNT |
| SEQ ID NO: 509 | AEKKYPDLNFDNTY |
| SEQ ID NO: 510 | AEKKYPDLNFDNTYL |
| SEQ ID NO: 511 | AEKKYPDLNFDNTYLF |
| SEQ ID NO: 512 | AEKKYPDLNEDNTYLFN |
| SEQ ID NO: 513 | AEKKYPDLNFDNTYLFNI |
| SEQ ID NO: 514 | AEKKYPDLNFDNTYLFNIL |
| SEQ ID NO: 515 | AEKKYPDLNFDNTYLFNILY |
| SEQ ID NO: 516 | LAEKKYPDL |
| SEQ ID NO: 517 | LAEKKYPDLN |
| SEQ ID NO: 518 | LAEKKYPDLNF |
| SEQ ID NO: 519 | LAEKKYPDLNFD |
| SEQ ID NO: 520 | LAEKKYPDLNFDN |
| SEQ ID NO: 521 | LAEKKYPDLNFDNT |
| SEQ ID NO: 522 | LAEKKYPDLNFDNTY |
| SEQ ID NO: 523 | LAEKKYPDLNFDNTYL |
| SEQ ID NO: 524 | LAEKKYPDLNFDNTYLF |
| SEQ ID NO: 525 | LAEKKYPDLNFDNTYLFN |
| SEQ ID NO: 526 | LAEKKYPDLNFDNTYLFNI |

TABLE 5-continued

YPXL Motif Containing Peptides from Variola
(Smallpox) Virus A10L
(GenBank Accession No. NP_042158) and
Vaccinia Virus Major Core Protein P4a Precursor
(Virion Core Protein P4a)
(GenBank Accession No. P16715)

| | |
|---|---|
| SEQ ID NO: 527 | LAEKKYPDLNFDNTYLFNIL |
| SEQ ID NO: 528 | VLAEKKYPDL |
| SEQ ID NO: 529 | VLAEKKYPDLN |
| SEQ ID NO: 530 | VLAEKKYPDLNF |
| SEQ ID NO: 531 | VLAEKKYPDLNFD |
| SEQ ID NO: 532 | VLAEKKYPDLNFDN |
| SEQ ID NO: 533 | VLAEKKYPDLNFDNT |
| SEQ ID NO: 534 | VLAEKKYPDLNFDNTY |
| SEQ ID NO: 535 | VLAEKKYPDLNFDNTYL |
| SEQ ID NO: 536 | VLAEKKYPDLNFDNTYLF |
| SEQ ID NO: 537 | VLAEKKYPDLNFDNTYLFN |
| SEQ ID NO: 538 | VLAEKKYPDLNFDNTYLFNI |
| SEQ ID NO: 539 | DVLAEKKYPDL |
| SEQ ID NO: 540 | DVLAEKKYPDLN |
| SEQ ID NO: 541 | DVLAEKKYPDLNF |
| SEQ ID NO: 542 | DVLAEKKYPDLNFD |
| SEQ ID NO: 543 | DVLAEKKYPDLNFDN |
| SEQ ID NO: 544 | DVLAEKKYPDLNFDNT |
| SEQ ID NO: 545 | DVLAEKKYPDLNFDNTY |
| SEQ ID NO: 546 | DVLAEKKYPDLNFDNTYL |
| SEQ ID NO: 547 | DVLAEKKYPDLNFDNTYLF |
| SEQ ID NO: 548 | DVLAEKKYPDLNFDNTYLFN |
| SEQ ID NO: 549 | MDVLAEKKYPDL |
| SEQ ID NO: 550 | MDVLAEKKYPDLN |
| SEQ ID NO: 551 | MDVLAEKKYPDLNF |
| SEQ ID NO: 552 | MDVLAEKKYPDLNFD |
| SEQ ID NO: 553 | MDVLAEKKYPDLNFDN |
| SEQ ID NO: 554 | MDVLAEKKYPDLNFDNT |
| SEQ ID NO: 555 | MDVLAEKKYPDLNEDNTY |
| SEQ ID NO: 556 | MDVLAEKKYPDLNFDNTYL |
| SEQ ID NO: 557 | MDVLAEKKYPDLNFDNTYLF |
| SEQ ID NO: 558 | SMDVLAEKKYPDL |
| SEQ ID NO: 559 | SMDVLAEKKYPDLN |
| SEQ ID NO: 560 | SMDVLAEKKYPDLNF |
| SEQ ID NO: 561 | SMDVLAEKKYPDLNFD |
| SEQ ID NO: 562 | SMDVLAEKKYPDLNFDN |
| SEQ ID NO: 563 | SMDVLAEKKYPDLNFDNT |
| SEQ ID NO: 564 | SMDVLAEKKYPDLNFDNTY |
| SEQ ID NO: 565 | SMDVLAEKKYPDLNFDNTYL |
| SEQ ID NO: 566 | DSMDVLAEKKYPDL |
| SEQ ID NO: 567 | DSMDVLAEKKYPDLN |
| SEQ ID NO: 568 | DSMDVLAEKKYPDLNF |
| SEQ ID NO: 569 | DSMDVLAEKKYPDLNFD |
| SEQ ID NO: 570 | DSMDVLAEKKYPDLNFDN |
| SEQ ID NO: 571 | DSMDVLAEKKYPDLNFDNT |
| SEQ ID NO: 572 | DSMDVLAEKKYPDLNFDNTY |
| SEQ ID NO: 573 | SDSMDVLAEKKYPDL |
| SEQ ID NO: 574 | SDSMDVLAEKKYPDLN |
| SEQ ID NO: 575 | SDSMDVLAEKKYPDLNF |
| SEQ ID NO: 576 | SDSMDVLAEKKYPDLNFD |
| SEQ ID NO: 577 | SDSMDVLAEKKYPDLNFDN |
| SEQ ID NO: 578 | SDSMDVLAEKKYPDLNFDNT |
| SEQ ID NO: 579 | GSDSMDVLAEKKYPDL |
| SEQ ID NO: 580 | GSDSMDVLAEKKYPDLN |
| SEQ ID NO: 581 | GSDSMDVLAEKKYPDLNF |
| SEQ ID NO: 582 | GSDSMDVLAEKKYPDLNFD |
| SEQ ID NO: 583 | GSDSMDVLAEKKYPDLNFDN |
| SEQ ID NO: 584 | DGSDSMDVLAEKKYPDL |
| SEQ ID NO: 585 | DGSDSMDVLAEKKYPDLN |
| SEQ ID NO: 586 | DOSDSMDVLAEKKYPDLNF |
| SEQ ID NO: 587 | DOSDSMDVLAEKKYPDLNFD |
| SEQ ID NO: 588 | PDGSDSMDVLAEKKYPDL |
| SEQ ID NO: 589 | PDGSDSMDVLAEKKYPDLN |
| SEQ ID NO: 590 | PDGSDSMDVLAEKKYPDLNF |
| SEQ ID NO: 591 | KPDGSDSMDVLAEKKYPDL |
| SEQ ID NO: 592 | KPDGSDSMDVLAEKKYPDLN |
| SEQ ID NO: 593 | IKPDGSDSMDVLAEKKYPDL |

TABLE 6

YPXL Motif Containing Peptides from Human Parainfluenza Virus Hemagglutinin-Neuraminidase (GenBank Accession No. AAA18296)

| | |
|---|---|
| SEQ ID NO: 594 | YPDLNPVI |
| SEQ ID NO: 595 | YPDLNPVIS |
| SEQ ID NO: 596 | YPDLNPVISH |
| SEQ ID NO: 597 | YPDLNPVISHT |
| SEQ ID NO: 598 | YPDLNPVISHTY |
| SEQ ID NO: 599 | YPDLNPVISHTYD |
| SEQ ID NO: 600 | YPDLNPVISHTYDI |
| SEQ ID NO: 601 | YPDLNPVISHTYDIN |
| SEQ ID NO: 602 | YPDLNPVISHTYDIND |
| SEQ ID NO: 603 | YPDLNPVISHTYDINDN |
| SEQ ID NO: 604 | YPDLNPVISHTYDINDNR |
| SEQ ID NO: 605 | YPDLNPVISHTYDINDNRK |
| SEQ ID NO: 606 | YPDLNPVISHTYDINDNRKS |
| SEQ ID NO: 607 | MYPDLNPV |
| SEQ ID NO: 608 | MYPDLNPVI |
| SEQ ID NO: 609 | MYPDLNPVIS |
| SEQ ID NO: 610 | MYPDLNPVISH |
| SEQ ID NO: 611 | MYPDLNPVISHT |
| SEQ ID NO: 612 | MYPDLNPVISHTY |
| SEQ ID NO: 613 | MYPDLNPVISHTYD |
| SEQ ID NO: 614 | MYPDLNPVLSHTYDI |
| SEQ ID NO: 615 | MYPDLNPVISHTYDIN |
| SEQ ID NO: 616 | MYPDLNPVISIITYDIND |
| SEQ ID NO: 617 | MYPDLNPVISHTYDINDN |
| SEQ ID NO: 618 | MYPDLNPVISHTYDINDNR |
| SEQ ID NO: 619 | MYPDLNPVISHTYDINDNRK |
| SEQ ID NO: 620 | DMYPDLNP |
| SEQ ID NO: 621 | DMYPDLNPV |
| SEQ ID NO: 622 | DMYPDLNPVI |
| SEQ ID NO: 623 | DMYPDLNPVIS |
| SEQ ID NO: 624 | DMYPDLNPVISH |
| SEQ ID NO: 625 | DMYPDLNPVISHT |
| SEQ ID NO: 626 | DMYPDLNPVISHTY |
| SEQ ID NO: 627 | DMYPDLNPVISHTYD |
| SEQ ID NO: 628 | DMYPDLNPVISHTYDI |
| SEQ ID NO: 629 | DMYPDLNPVISHTYDIN |
| SEQ ID NO: 630 | DMYPDLNPVISHTYDIND |
| SEQ ID NO: 631 | DMYPDLNPVISHTYDINDN |
| SEQ ID NO: 632 | DMYPDLNPVISHTYDINDNR |
| SEQ ID NO: 633 | SDMYPDLN |
| SEQ ID NO: 634 | SDMYPDLNP |
| SEQ ID NO: 635 | SDMYPDLNPV |
| SEQ ID NO: 636 | SDMYPDLNPVI |
| SEQ ID NO: 637 | SDMYPDLNPVIS |
| SEQ ID NO: 638 | SDMYPDLNPVISH |
| SEQ ID NO: 639 | SDMYPDLNPVISHT |
| SEQ ID NO: 640 | SDMYPDLNPVISHTY |
| SEQ ID NO: 641 | SDMYPDLNPVISHTYD |
| SEQ ID NO: 642 | SDMYPDLNPVISHTYDI |
| SEQ ID NO: 643 | SDMYPDLNPVISHTYDIN |
| SEQ ID NO: 644 | SDMYPDLNPVISHTYDIND |
| SEQ ID NO: 645 | SDMYPDLNPVLSHTYDINDN |
| SEQ ID NO: 646 | NSDMYPDL |
| SEQ ID NO: 647 | NSDMYPDLN |
| SEQ ID NO: 648 | NSDMYPDLNP |
| SEQ ID NO: 649 | NSDMYPDLNPV |
| SEQ ID NO: 650 | NSDMYPDLNPVI |
| SEQ ID NO: 651 | NSDMYPDLNPVIS |
| SEQ ID NO: 652 | NSDMYPDLNPVISH |
| SEQ ID NO: 653 | NSDMYPDLNPVLSHT |
| SEQ ID NO: 654 | NSDMYPDLNPVISHTY |
| SEQ ID NO: 655 | NSDMYPDLNPVISHTYD |
| SEQ ID NO: 656 | NSDMYPDLNPVISHTYDI |
| SEQ ID NO: 657 | NSDMYPDLNPVISHTYDIN |
| SEQ ID NO: 658 | NSDMYPDLNIPVISHTYDIND |
| SEQ ID NO: 659 | LNSDMYPDL |
| SEQ ID NO: 660 | LNSDMYPDLN |
| SEQ ID NO: 661 | LNSDMYPDLNP |
| SEQ ID NO: 662 | LNSDMYPDLNPV |
| SEQ ID NO: 663 | LNSDMYPDLNPVI |
| SEQ ID NO: 664 | LNSDMYPDLNPVIS |
| SEQ ID NO: 665 | LNSDMYPDLNPVISH |
| SEQ ID NO: 666 | LNSDMYPDLNPVISHT |
| SEQ ID NO: 667 | LNSDMYPDLNPVISHTY |
| SEQ ID NO: 668 | LNSDMYPDLNPVISHTYD |

TABLE 6-continued

YPXL Motif Containing Peptides from Human Parainfluenza Virus Hemagglutinin-Neuraminidase (GenBank Accession No. AAA18296)

| | |
|---|---|
| SEQ ID NO: 669 | LNSDMYPDLNPVISHTYDI |
| SEQ ID NO: 670 | LNSDMYPDLNIPVISHTYDIN |
| SEQ ID NO: 671 | SLNSDMYPDL |
| SEQ ID NO: 672 | SLNSDMYPDLN |
| SEQ ID NO: 673 | SLNSDMYPDLNP |
| SEQ ID NO: 674 | SLNSDMYPDLNPV |
| SEQ ID NO: 675 | SLNSDMYPDLNPVI |
| SEQ ID NO: 676 | SLNSDMYPDLNPVIS |
| SEQ ID NO: 677 | SLNSDMYPDLNPVISH |
| SEQ ID NO: 678 | SLNSDMYPDLNPVISHT |
| SEQ ID NO: 679 | SLNSDMYPDLNPVISHTY |
| SEQ ID NO: 680 | SLNSDMYPDLNPVISHTYD |
| SEQ ID NO: 681 | SLNSDMYPDLNPVISHTYDI |
| SEQ ID NO: 682 | ISLNSDMYPDL |
| SEQ ID NO: 683 | ISLNSDMYPDLN |
| SEQ ID NO: 684 | ISLNSDMYPDLNP |
| SEQ ID NO: 685 | ISLNSDMYPDLNPV |
| SEQ ID NO: 686 | ISLNSDMYPDLNPVI |
| SEQ ID NO: 687 | ISLNSDMYPDLNPVIS |
| SEQ ID NO: 688 | ISLNSDMYPDLNPVISH |
| SEQ ID NO: 689 | ISLNSDMYPDLNPVISHT |
| SEQ ID NO: 690 | ISLNSDMYPDLNPVISHTY |
| SEQ ID NO: 691 | ISLNSDMYPDLNPVISHTYD |
| SEQ ID NO: 692 | YISLNSDMYPDL |
| SEQ ID NO: 693 | YISLNSDMYPDLN |
| SEQ ID NO: 694 | YISLNSDMYPDLNP |
| SEQ ID NO: 695 | YISLNSDMYPDLNPV |
| SEQ ID NO: 696 | YISLNSDMYPDLNPVI |
| SEQ ID NO: 697 | YISLNSDMYPDLNPVIS |
| SEQ ID NO: 698 | YISLNSDMYPDLNPVISH |
| SEQ ID NO: 699 | YISLNSDMYPDLNPVISHT |
| SEQ ID NO: 700 | YISLNSDMYPDLNPVISHTY |
| SEQ ID NO: 701 | GYISLNSDMYPDL |
| SEQ ID NO: 702 | GYISLNSDMYPDLN |
| SEQ ID NO: 703 | GYISLNSDMYPDLNP |
| SEQ ID NO: 704 | GYISLNSDMYPDLNPV |
| SEQ ID NO: 705 | GYISLNSDMYPDLNPVI |
| SEQ ID NO: 706 | GYISLNSDMYPDLNPVIS |
| SEQ ID NO: 707 | GYISLNSDMYPDLNPVISH |
| SEQ ID NO: 708 | GYISLNSDMYPDLNPVISHT |
| SEQ ID NO: 709 | LGYISLNSDMYPDL |
| SEQ ID NO: 710 | LGYISLNSDMYPDLN |
| SEQ ID NO: 711 | LGYISLNSDMYPDLNP |
| SEQ ID NO: 712 | LGYISLNSDMYPDLNPV |
| SEQ ID NO: 713 | LGYISLNSDMYPDLNPVI |
| SEQ ID NO: 714 | LGYISLNSDMYPDLNPVIS |
| SEQ ID NO: 715 | LGYISLNSDMYPDLNPVISH |
| SEQ ID NO: 716 | QLGYISLNSDMYPDL |
| SEQ ID NO: 717 | QLGYISLNSDMYPDLN |
| SEQ ID NO: 718 | QLGYISLNSDMYPDLNP |
| SEQ ID NO: 719 | QLGYISLNSDMYPDLNPV |
| SEQ ID NO: 720 | QLGYISLNSDMYPDLNPVI |
| SEQ ID NO: 721 | QLGYISLNSDMYPDLNPVIS |
| SEQ ID NO: 722 | LQLGYISLNSDMYPDL |
| SEQ ID NO: 723 | LQLGYISLNSDMYPDLN |
| SEQ ID NO: 724 | LQLGYISLNSDMYPDLNP |
| SEQ ID NO: 725 | LQLGYISLNSDMYPDLNPV |
| SEQ ID NO: 726 | LQLGYISLNSDMYPDLNPVI |
| SEQ ID NO: 727 | VLQLGYISLNSDMYPDL |
| SEQ ID NO: 728 | VLQLGYISLNSDMYPDLN |
| SEQ ID NO: 729 | VLQLGYISLNSDMYPDLNP |
| SEQ ID NO: 730 | VLQLGYISLNSDMYPDLNPV |
| SEQ ID NO: 731 | QVLQLGYISLNSDMYPDL |
| SEQ ID NO: 732 | QVLQLGYISLNSDMYPDLN |
| SEQ ID NO: 733 | QVLQLGYISLNSDMYPDLNP |
| SEQ ID NO: 734 | YQVLQLGYISLNSDMYPDL |
| SEQ ID NO: 735 | YQVLQLGYISLNSDMYPDLN |
| SEQ ID NO: 736 | SYQVLQLGYISLNSDMYPDL |

What is claimed is:

1. A composition comprising a peptide associated with a transporter that is capable of increasing the uptake of said peptide by a mammalian cell,
wherein said peptide includes an amino acid sequence motif YPXL and is capable of binding a region including the amino acid residues 121 to 435 of AD-50, wherein X is an amino acid.

2. The composition according to claim 1, wherein X is selected from the group consisting of aspartate (D), alanine (A), and glutamic acid (E).

3. The composition of claim 1, wherein said transporter is capable of increasing the uptake of said peptide by a mammalian cell by at least 100%.

4. The composition of claim 1, wherein said transporter is capable of increasing the uptake of said peptide by a mammalian cell by at least 300%.

5. The composition of claim 1, wherein said peptide is covalently linked to said transporter.

6. The composition of claim 5, wherein said transporter is selected from the group consisting of penetratins, l-Tat$_{49-57}$, d-Tat$_{49-57}$, retro-inverso isomers of l- or d-Tat$_{49-57}$, L-arginine oligomers, D-arginine oligomers, L-lysine oligomers, D-lysine oligomers, L-histidine oligomers, D-histidine oligomers, L-ornithine oligomers, D-ornithine oligomers, and HSV-1 structural protein VP22 and fragments thereof, and peptides having at least six contiguous amino acid residues that are L-arginine, D-arginine, L-lysine, D-lysine, L-histidine, D-histidine, L-ornithine, D-ornithine, or a combination thereof; and peptoid analogs thereof.

7. The composition according to claim 1, wherein said transporter is selected from the group consisting of liposomes, dendrimers, and siderophores.

8. The composition according to claim 1, wherein said peptide includes a contiguous amino acid sequence of at least 6 amino acid residues of a viral protein selected from the group consisting of HCV polyprotein, HSV UL42 protein, variola virus A10L protein, vaccinia virus virion core protein P4a, human parainfluenza virus hemagglutinin-neuraminidase, and EIAV GAGp9, and wherein said contiguous amino acid sequence encompasses the YPXL motif of said viral protein.

9. The composition according to claim 1, wherein said peptide includes a contiguous amino acid sequence of at least 6 amino acid residues of EIAV GAGp9, and wherein said contiguous amino acid sequence encompasses the YPXL motif of EIAV GAGp9.

10. A composition comprising a hybrid polypeptide, said hybrid polypeptide consists of a peptide covalently linked to a peptidic transporter that is capable of increasing the uptake of said peptide by a mammalian cell by at least 100%,
wherein said hybrid polypeptide consists of from about 8 to about 100 amino acid residues, and wherein said peptide comprises an amino acid sequence motif YPXL and is capable of binding a region including the amino acid residues 121 to 435 of AP-50, wherein X is an amino acid.

11. The composition according to claim 10, wherein said hybrid polypeptide consists of from about 9 to about 50 amino acid residues.

12. The composition according to claim 10, wherein said hybrid polypeptide consists of from about 12 to about 30 amino acid residues.

13. The composition according to claim 10, wherein X is selected from the group consisting of aspartate (D), alanine (A), or glutamic acid (E).

14. The composition according to claim 10, wherein said peptide includes a contiguous amino acid sequence of at least 6 amino acid residues of a viral protein selected from the group consisting of HCV polyprotein, HSV UL42 protein, variola virus A10L protein, vaccinia virus virion core protein P4a, human parainfluenza virus hemagglutinin-neuraminidase and EIAV GAGp9, and wherein said contiguous amino acid sequence encompasses the YPXL motif of said viral protein.

15. The composition according to claim 10, wherein said peptide includes a contiguous amino acid sequence of at least 6 amino acid residues of EIAV GAGp9, and wherein said contiguous amino acid sequence encompasses the YPXL motif of EIAV GAGp9.

16. The composition according to claim 10, wherein said transporter that is capable of increasing the uptake of said peptide by a mammalian cell by at least 300%.

17. The composition according to claim 10, wherein said transporter is selected from the group consisting of penetratins, l-Tat$_{49-57}$, retro-inverso isomers of l-Tat$_{49-57}$, L-arginine oligomers, L-lysine oligomers, HSV-1 structural protein VP22 and fragments thereof, and peptides consisting of at least six contiguous amino acid residues that are a combination of two or more of L-arginine, L-lysine and L-histidine.

18. The composition according to claim 12, wherein said transporter includes from 6 to about 12 arginines.

19. The composition according to claim 11, wherein said peptide comprises an amino acid sequence selected from the group consisting of SEQ ID NOs:18–164, SEQ ID NOs:165–307, SEQ ID NOs:308–450, SEQ ID NOs:451–593, and SEQ ID NOs:594–736.

20. The composition according to claim 10, wherein said hybrid polypeptide does not contain a terminal L-histidine oligomer.

21. A composition comprising a hybrid polypeptide, said hybrid polypeptide consists of a peptide covalently linked to a peptidic transporter that is capable of increasing the uptake of said peptide by a mammalian cell by at least 200%,
wherein said hybrid polypeptide consists of from about 10 to about 30 amino acid residues, and wherein said peptide comprises an amino acid sequence motif YPXL and is capable of binding a region including the amino acid residues 121 to 435 of AP-50, wherein X is an amino acid.

22. The composition of claim 21, wherein said hybrid polypeptide does not contain a terminal L-histidine oligomer of at least 6 histidine residues.

23. An isolated nucleic acid encoding the hybrid polypeptide according to claim 10.

24. An isolated nucleic acid encoding the hybrid polypeptide according to claim 11.

25. An isolated nucleic acid encoding the hybrid polypeptide according to claim 22.

26. A host cell comprising the isolated nucleic acid according to claim 23.

27. A host cell comprising the isolated nucleic acid according to claim 24.

28. A host cell comprising the isolated nucleic acid according to claim 25.

29. An isolated peptide consisting of a contiguous amino acid sequence of from 7 to about 30 amino acid residues of a viral protein selected from the group consisting of HCV polyprotein, HSV UL42 protein, variola virus A10L protein, vaccinia virus virion core protein P4a, and human parainfluenza virus hemagglutinin-neuraminidase, wherein said contiguous amino acid sequence encompasses the YPXL motif of said viral protein, and wherein said peptide is capable of binding a region including the amino acid residues 121 to 435 of AP-50.

30. The isolated peptide according to claim 29, wherein said isolated peptide consists of from 9 to about 20 amino acid residues.

31. The isolated peptide of claim 29, wherein said peptide comprises of an amino acid sequence selected from the group consisting of SEQ ID NOs:18–164, SEQ ID NOs:165–307, SEQ ID NOs:308–450, SEQ ID NOs:451–593, and SEQ ID NOs:594–736.

32. An isolated nucleic acid encoding the isolated peptide according to claim 29.

33. An isolated nucleic acid encoding the isolated peptide according to claim 30.

34. An isolated nucleic acid encoding the isolated peptide according to claim 31.

35. A method for treating an infection caused by a virus selected from the group consisting of HCV, HSV1 and variola virus, said method comprising:
introducing into a patient in need of such treatment a peptide consisting of from 8 to about 30 amino acid residues and having an amino acid sequence motif YPXL, wherein X is an amino acid, and wherein said peptide is capable of binding a region including the amino acid residues 121 to 435 of AP-50.

36. The method of claim 35, wherein said introducing step comprises administering to the cells a nucleic acid encoding said peptide.

37. The method of claim 35, wherein X is selected from the group consisting of aspartate (D), alanine (A), and glutamic acid (E).

38. The method of claim 35, wherein said peptide includes a contiguous amino acid sequence of at least 8 residues of a viral protein selected from the group consisting of HCV polyprotein, HSV UL42 protein, variola virus A10L protein, vaccinia virus virion core protein P4a, human parainfluenza virus hemagglutinin-neuraminidase, and EIAV GAGp9, and wherein said contiguous amino acid sequence encompasses the YPXL motif of said viral protein.

39. A method for treating an infection caused by a virus selected from the group consisting of HCV, HSV1 and variola virus, said method comprising:
administering to a patient in need of such treatment a composition comprising a peptide associated with a transporter that is capable of increasing the uptake of said peptide by a mammalian cell,
wherein said peptide includes an amino acid sequence motif YPXL and is capable of binding a region including the amino acid residues 121 to 435 of AP-50, wherein X is an amino acid.

40. The method according to claim 39, wherein X is selected from the group consisting of aspartate (D), alanine (A), and glutamic acid (E).

41. The method according to claim 39, wherein said transporter is capable of increasing the uptake of said peptide by a mammalian cell by at least 100%.

42. The method according to claim 39, wherein said transporter is capable of increasing the uptake of said peptide by a mammalian cell by at least 300%.

43. The method according to claim 39, wherein said peptide is covalently linked to said transporter.

44. The method according to claim 43, wherein said transporter is selected from the group consisting of penetratins, l-Tat$_{49-57}$, d-Tat$_{49-57}$, retro-inverso isomers of l- or d-Tat$_{49-57}$, L-arginine oligomers, D-arginine oligomers, L-lysine oligomers, D-lysine oligomers, L-histidine oligomers, D-histidine oligomers, L-ornithine oligomers, D-ornithine oligomers, and HSV-1 structural protein VP22 and fragments thereof, and peptides having at least six contiguous amino acid residues that are L-arginine, D-arginine, L-lysine, D-lysine, L-histidine, D-histidine, L-ornithine, D-ornithine, or a combination thereof; and peptoid analogs thereof.

45. The method according to claim 39, wherein said transporter is selected from the group consisting of liposomes, dendrimers, and siderophores.

46. The method according to claim 39, wherein said peptide includes a contiguous amino acid sequence of at least 6 amino acid residues of a viral protein selected from the group consisting of HCV polyprotein, HSV UL42 protein, variola virus A10L protein, vaccinia virus virion core protein P4a, human parainfluenza virus hemagglutinin-neuraminidase, and EIAV GAGp9, and wherein said contiguous amino acid sequence encompasses the YPXL motif of said viral protein.

47. The method according to claim 39, wherein said peptide includes a contiguous amino acid sequence of at least 6 amino acid residues of EIAV GAGp9, and wherein said contiguous amino acid sequence encompasses the YPXL motif of EIAV GAGp9.

48. A method for treating an infection caused by a virus selected from the group consisting of HCV, HSV1 and variola virus, said method comprising:
administering to a patient in need of such treatment a hybrid polypeptide, said hybrid polypeptide consists of a peptide covalently linked to a peptidic transporter that is capable of increasing the uptake of said peptide by a mammalian cell by at least 100%,
wherein said hybrid polypeptide consists of from about 8 to about 100 amino acid residues, and wherein said peptide comprises an amino acid sequence motif YPXL and is capable of binding a region including the amino acid residues 121 to 435 of AP-50, wherein X is an amino acid.

49. The method according to claim 48, wherein said hybrid polypeptide consists of from about 9 to about 50 amino acid residues.

50. The method according to claim 48, wherein said hybrid polypeptide consists of from about 12 to about 30 amino acid residues.

51. The method according to claim 48, wherein X is selected from the group consisting of aspartate (D), alanine (A), and glutamic acid (E).

52. The method according to claim 48, wherein said peptide includes a contiguous amino acid sequence of at least 6 amino acid residues of a viral protein selected from the group consisting of HCV polyprotein, HSV UL42 protein, variola virus A10L protein, vaccinia virus virion core protein P4a, human parainfluenza virus hemagglutinin-neuraminidase, and EIAV GAGp9, and wherein said contiguous amino acid sequence encompasses the YPXL motif of said viral protein.

53. The method according to claim 48, wherein said peptide includes a contiguous amino acid sequence of at least 6 amino acid residues of EIAV GAGp9, and wherein said contiguous amino acid sequence encompasses the YPXL motif of EIAV GAGp9.

54. The method according to claim 48, wherein said transporter includes from 6 to 14 arginine residues.

55. The method according to claim 48, wherein said transporter is capable of increasing the uptake of said peptide by a mammalian cell by at least 300%.

56. The method according to claim 48, wherein said transporter is selected from the group consisting of penetratins, l-Tat$_{49-57}$, retro-inverso isomers of l-Tat$_{49-57}$, L-arginine oligomers, L-lysine oligomers, HSV-1 structural protein VP22 and fragments thereof, and peptides consisting of at least six contiguous amino acid residues that include two or more of the group consisting of L-arginine, L-lysine and L-histidine.

57. The method according to claim 48, wherein said peptide comprises an amino acid sequence selected from the group consisting of SEQ ID NOs:18–164, SEQ ID NOs:165–307, SEQ ID NOs:308–450, SEQ ID NOs:451–593, and SEQ ID NOs:594–736.

58. The method according to claim 48, wherein said hybrid polypeptide does not contain a terminal L-histidine oligomer.

59. A method for treating an infection caused by a virus selected from the group consisting of HCV, HSV1 and variola virus, said method comprising:

administering to a patient in need of such treatment a composition comprising a hybrid polypeptide, said hybrid polypeptide consists of a peptide covalently linked to a peptidic transporter that is capable of increasing the uptake of said peptide by a mammalian cell by at least 200%, wherein said hybrid polypeptide consists of from about 10 to about 30 amino acid residues, and wherein said peptide comprises an amino acid sequence motif YPXL and is capable of binding a region including the amino acid residues 121 to 435 of AP-50, wherein X is an amino acid.

* * * * *